(12) United States Patent
Ludwig et al.

(10) Patent No.: US 10,274,487 B2
(45) Date of Patent: Apr. 30, 2019

(54) MICROPROCESSOR-CONTROLLED MICROFLUIDIC PLATFORM FOR PATHOGEN, TOXIN, BIOMARKER, AND CHEMICAL DETECTION WITH REMOVABLE UPDATABLE SENSOR ARRAY FOR FOOD AND WATER SAFETY, MEDICAL, AND LABORATORY APPLICATIONS

(71) Applicant: Lester F. Ludwig, San Antonio, TX (US)

(72) Inventors: Lester F. Ludwig, San Antonio, TX (US); Pooncharas Tipgunlakant, Belmont, CA (US)

(73) Assignee: NRI R&D PATENT LICENSING, LLC, San Antonio, TX (US)

( * ) Notice: Subject to any disclaimer, the term of this patent is extended or adjusted under 35 U.S.C. 154(b) by 244 days.

(21) Appl. No.: 13/761,142

(22) Filed: Feb. 6, 2013

(65) Prior Publication Data
US 2013/0217598 A1    Aug. 22, 2013

Related U.S. Application Data

(60) Provisional application No. 61/595,651, filed on Feb. 6, 2012, provisional application No. 61/595,681, filed
(Continued)

(51) Int. Cl.
*G01N 15/06* (2006.01)
*G01N 33/00* (2006.01)
(Continued)

(52) U.S. Cl.
CPC .............. *G01N 33/54373* (2013.01)

(58) Field of Classification Search
CPC .......... B01L 9/00; G01N 15/06; G01N 33/00; G01N 33/48
(Continued)

(56) References Cited

U.S. PATENT DOCUMENTS

2002/0197390 A1* 12/2002 Lewis .................... C07K 17/14
427/2.11
2005/0017190 A1* 1/2005 Eversmann ........ G01N 27/4145
250/370.14
(Continued)

*Primary Examiner* — Brian J. Sines
(74) *Attorney, Agent, or Firm* — Procopio, Cory, Hargreaves & Savitch LLP

(57) ABSTRACT

The invention provides a platform technology with rich ability to flexibly perform, create, deploy, maintain, and update a wide range of panels, assay, array, and/or sequence of tests for a wide range of substances and pathogens. The invention provides a unifying framework for widely-ranging miniature sensor implementation, fluidic/gas interfacing, electrical interfaces and optical interfaces, and further by collocating, allowing the integration a large number highly-selective sensors and chemical sensors—together as needed with appropriately selected supplemental sensors (for example temperature, pH, selective ions, etc.), into a common readily-manufacturable framework. The diverse sensor arrays give rise to statistical enhancing through novel statistical processing approaches. The invention is deployable and useable in a wide range of situations previously unavailable, and addresses many otherwise problematic aspects of field testing for food safety, water safety, epidemic outbreaks, routine diagnosis, and disease monitoring.

17 Claims, 113 Drawing Sheets

Related U.S. Application Data on Feb. 6, 2012, provisional application No. 61/595,692, filed on Feb. 7, 2012, provisional application No. 61/595,973, filed on Feb. 7, 2012, provisional application No. 61/596,016, filed on Feb. 7, 2012, provisional application No. 61/614,229, filed on Mar. 22, 2012, provisional application No. 61/614,253, filed on Mar. 22, 2012.

(51) Int. Cl.
*G01N 33/48* (2006.01)
*B01L 9/00* (2006.01)
*G01N 33/543* (2006.01)

(58) Field of Classification Search
USPC ............... 422/50, 68.1, 502, 503, 504, 554; 436/43, 164, 174, 180, 89
See application file for complete search history.

(56) References Cited

U.S. PATENT DOCUMENTS

| | | | |
|---|---|---|---|
| 2007/0292855 A1* | 12/2007 | Dubin et al. | 435/6 |
| 2007/0292941 A1* | 12/2007 | Handique et al. | 435/288.7 |
| 2009/0242405 A1* | 10/2009 | Mayer | B81C 1/00214 204/435 |
| 2010/0248209 A1* | 9/2010 | Datta | G01N 27/4145 435/5 |
| 2014/0292318 A1* | 10/2014 | Wang | B82Y 25/00 324/228 |

* cited by examiner

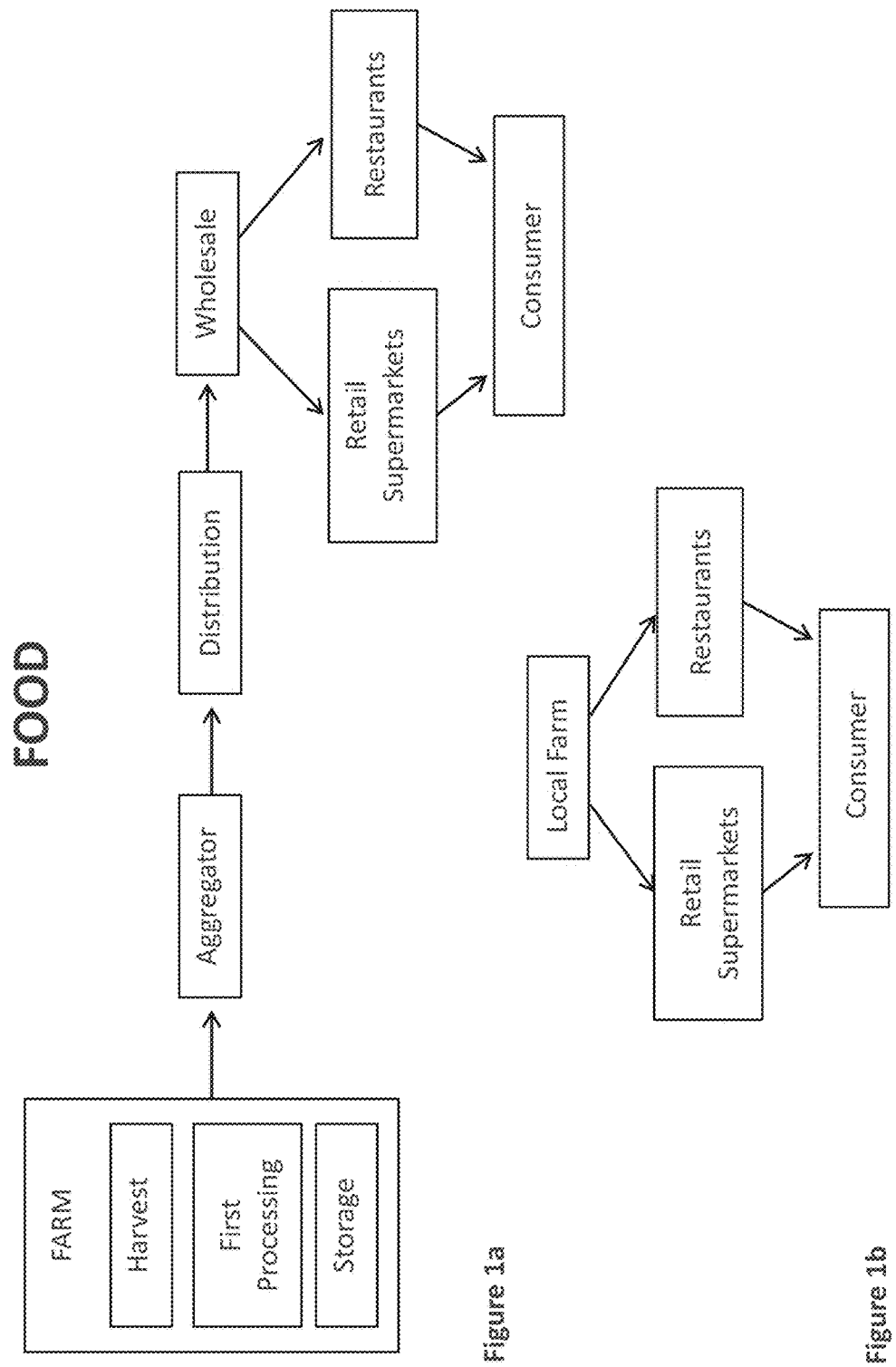

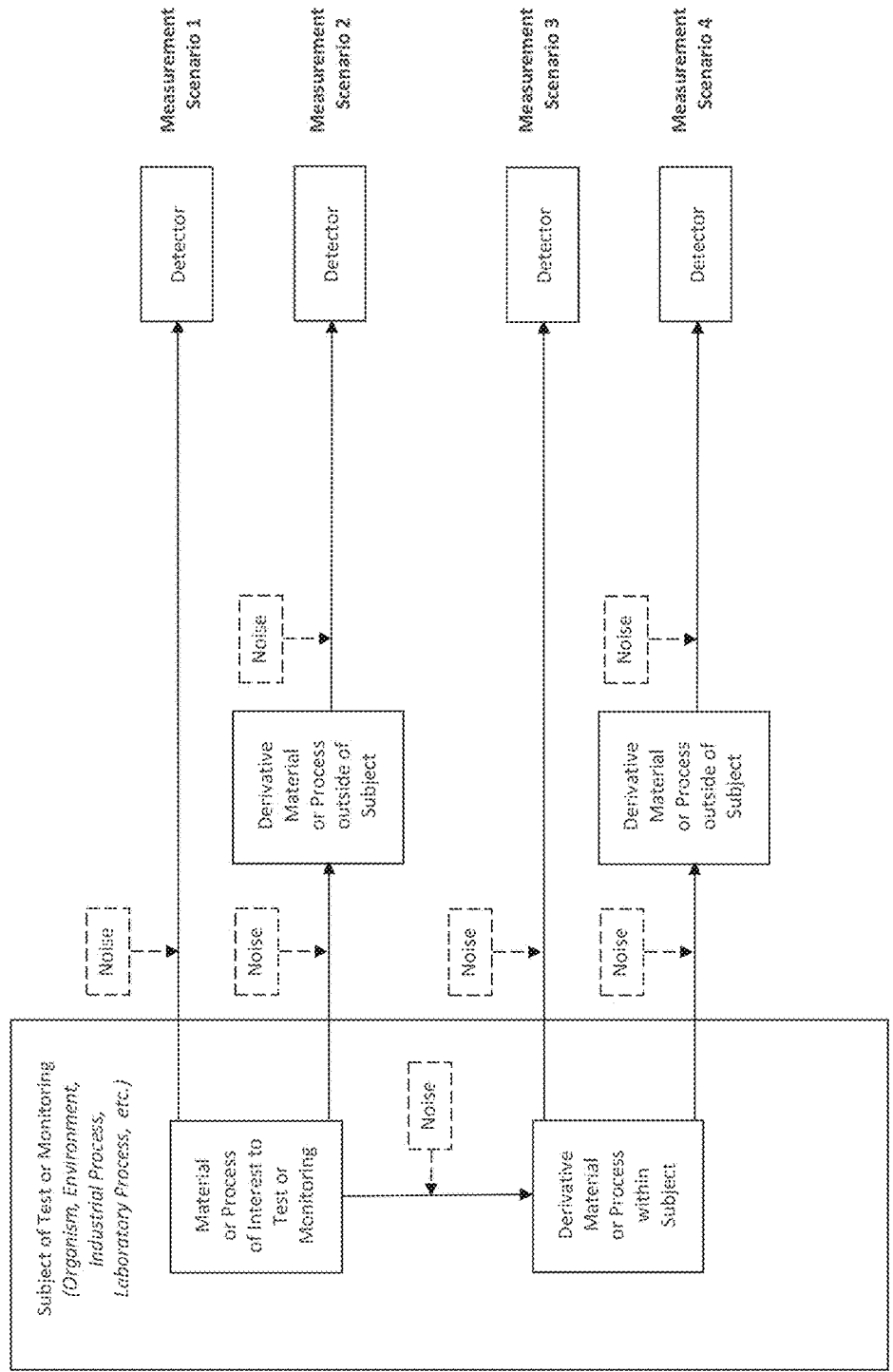

Adapted from K.K. Jain, *The Handbook of Biomarkers*, ISBN 160761684X, Springer 2010.

| Probe | Excitation Wavelength (nm) | Emission Wavelength (nm) | Molecular Weight |
|---|---|---|---|
| *Reactive and conjugated probes* | | | |
| Hydroxycoumarin | 325 | 386 | 331 |
| Aminocoumarin | 350 | 445 | 330 |
| Methoxycoumarin | 360 | 410 | 317 |
| Cascade Blue | (375); 401 | 423 | 596 |
| Pacific Blue | 403 | 455 | 406 |
| Pacific Orange | 403 | 551 | |
| Lucifer yellow | 425 | 528 | |
| NBD | 466 | 539 | 294 |
| R-Phycoerythrin (PE) | 480; 565 | 578 | 240 |
| PE-Cy5 conjugates | 480; 565, 650 | 670 | |
| PE-Cy7 conjugates | 480; 565, 743 | 767 | |
| Red 613 | 480; 565 | 613 | |
| PerCP | 490 | 675 | |
| TruRed | 490,675 | 695 | |
| FluorX | 494 | 520 | 587 |
| Fluorescein | 495 | 519 | 389 |
| BODIPY-FL | 503 | 512 | |
| TRITC | 547 | 572 | 444 |
| X-Rhodamine | 570 | 576 | 548 |
| Lissamine Rhodamine B | 570 | 590 | |
| Texas Red | 589 | 615 | 625 |
| Allophycocyanin (APC) | 650 | 660 | 104 |
| APC-Cy7 conjugates | 650; 755 | 767 | |
| *Alexa Fluor dyes (antibody conjugates)* | | | |
| Alexa Fluor 350 | 343 | 442 | 410 |
| Alexa Fluor 405 | 401 | 421 | 1028 |
| Alexa Fluor 430 | 434 | 540 | 702 |
| Alexa Fluor 488 | 499 | 519 | 643 |
| Alexa Fluor 500 | 503 | 525 | 700 |
| Alexa Fluor 514 | 517 | 542 | 714 |
| Alexa Fluor 532 | 530 | 555 | 724 |
| Alexa Fluor 546 | 561 | 572 | 1079 |
| Alexa Fluor 555 | 553 | 568 | 1250 |
| Alexa Fluor 568 | 579 | 603 | 792 |
| Alexa Fluor 594 | 591 | 618 | 820 |
| Alexa Fluor 610 | 610 | 629 | 1285 |
| Alexa Fluor 633 | 632 | 648 | 1200 |
| Alexa Fluor 647 | 652 | 668 | 1300 |
| Alexa Fluor 660 | 663 | 691 | 1100 |
| Alexa Fluor 680 | 680 | 702 | 1150 |
| Alexa Fluor 700 | 696 | 719 | 1400 |
| Alexa Fluor 750 | 752 | 776 | 1300 |
| Alexa Fluor 790 | 782 | 804 | 1750 |

Figure 14

| | | | |
|---|---|---|---|
| Alexa Fluor 610 | 610 | 629 | 1285 |
| Alexa Fluor 633 | 632 | 648 | 1200 |
| Alexa Fluor 647 | 652 | 668 | 1300 |
| Alexa Fluor 660 | 663 | 691 | 1100 |
| Alexa Fluor 680 | 680 | 702 | 1150 |
| Alexa Fluor 700 | 696 | 719 | 1400 |
| Alexa Fluor 750 | 752 | 776 | 1300 |
| Alexa Fluor 790 | 782 | 804 | 1750 |

| Probe | Excitation Wavelength (nm) | Emission Wavelength (nm) | Molecular Weight |
|---|---|---|---|
| *DyLight dyes [Pierce]* | | | |
| DyLight 350 | 353 | 432 | |
| DyLight 405 | 400 | 420 | |
| DyLight 488 | 493 | 518 | |
| DyLight 549 | 562 | 576 | |
| DyLight 594 | 593 | 618 | |
| DyLight 633 | 638 | 658 | |
| DyLight 649 | 654 | 673 | |
| DyLight 680 | 692 | 712 | |
| DyLight 750 | 752 | 778 | |
| DyLight 800 | 777 | 794 | |
| *Nucleic acid probes* | | | |
| Hoechst 33342 | 343 | 483 | 616 |
| DAPI | 345 | 455 | |
| Hoechst 33258 | 345 | 478 | 624 |
| SYTOX Blue | 431 | 480 | ~400 |
| Chromomycin A3 | 445 | 575 | |
| Mithramycin | 445 | 575 | |
| YOYO-1 | 491 | 509 | 1271 |
| Ethidium Bromide | 493 | 620 | 394 |
| Acridine Orange | 503 | 530/640 | |
| SYTOX Green | 504 | 523 | ~600 |
| TOTO-1, TO-PRO-1 | 509 | 533 | |
| Thiazole Orange | 510 | 530 | |
| Propidium Iodide (PI) | 536 | 617 | 668.4 |
| LDS 751 | 543; 590 | 712; 607 | 472 |
| 7-AAD | 546 | 647 | |

Figure 14 (continued)

Examples of polyclonal and monoclonal antibody-based sensors and their associated analytes and transducers.

| Transducer | Analyte detected | Antibody type |
|---|---|---|
| Electrochemical | | |
| Potentiometric | Terbuthylazine | Monoclonal |
| | Hepatitis B surface antigen | Not specified |
| | Diphtherotoxin | Monoclonal |
| Amperometric | E. coli O157:H7 | Polyclonal |
| | Carcinoembryonic antigen (CEA) | Not specified |
| | Afloxin M1 | Monoclonal |
| | Progesterone | Monoclonal |
| | Listeria monocytogenes (Internatlin B) | Polyclonal |
| Piezoelectric | | |
| | E. coli O157:H7 | Polyclonal |
| | Canine IgG Isoforms | Monoclonal |
| | Cocaine/derivative (BZE-DADOO) | Polyclonal |
| | Atrazine | Monoclonal |
| | Bacillus anthracis | Polyclonal |
| | Francisella tularensis | Polyclonal |
| Optical | | |
| SPR | Urediniospores | Monoclonal |
| | Polychlorinated biphenyls | Monoclonal |
| | Vitellogenin (Carp) | Monoclonal |
| | Campylobacter jejuni | Polyclonal |
| | Listeria monocytogenes | Monoclonal |
| | Okadaic acid | Polyclonal |
| | L. monocytogenes | Monoclonal |
| Resonant mirror | Testosterone (also RifS) | Monoclonal |
| TIRF | Carbohydrates (maltose and panose) | Monoclonal |
| | Estrone | Polyclonal |
| RifS | Tuberculosis (also interferometry) | Monoclonal |
| | Cell adhesion | Monoclonal |
| | Trifluralin | Polyclonal |
| OWLS | Sulfamethazine | Not specified |
| | Atrazine | Monoclonal |
| Interferometry | Hepatitis B virus surface antigen | Not specified |
| | Mycotoxin T-2 (TIRE also QCM) | Mono- and polyclonal |
| Ellipsometry | Salmonella typhimurium | Monoclonal |
| | L. monocytogenes (Imaging) | Polyclonal |
| Fibre optic | B. anthracis (Evanescent wave FO) | Not specified |
| | Raptor™ - biothreat (e.g. B. anthracis) | Various monoclonal |

Adapted from Table 1 of P. Conroy, S. Hearty, P. Leonard, R. O'Kennedy, "Antibody Production, Design and Use for Biosensor-Based Applications," *Seminars in Cell & Developmental Biology* 20 (2009), pp.10–26.

Figure 15

| Species as Antigen | Antibody | Isotype |
|---|---|---|
| E. coli O157 | E. coli O157 (1.B.250B) Antibody | mouse IgG$_3$ |
| | E. coli O157 (1031) Antibody | mouse IgG$_3$ |
| | E. coli O157 (8.F.101) Antibody | mouse IgG$_3$ |
| | E. coli O157 (1041) Antibody | mouse IgM |
| | E. coli O157 (1.B.248) Antibody | mouse IgG$_3$ |
| L. monocytogenes | Listeria monocytogenes (LX32) Antibody | mouse IgG$_1$ |
| | Listeria monocytogenes (LZA2) Antibody | mouse IgM |
| | Listeria monocytogenes (LZH1) Antibody | mouse IgG$_3$ |
| | Listeria monocytogenes (LX99) Antibody | mouse IgG$_4$ |
| Shigella dysenteriae | Shigella dysenteriae (0911) Antibody | mouse IgG |
| Shigella flexneri | Shigella flexneri (306/305) Antibody | mouse IgG$_1$ |
| Salmonella enteriditis D | Salmonella enteriditis 0-9 (4G7C) Antibody | mouse IgG$_1$ |
| Salmonella typhimurium | Salmonella typhimurium (IFR0402) Antibody | mouse IgM |
| | Salmonella typhimurium (6331) Antibody | mouse IgG |
| | Salmonella typhimurium 0-4 (1E6) Antibody | mouse IgG$_1$ |
| | Salmonella typhimurium 0-4 (8C11C) Antibody | mouse IgG$_2$ |
| Clostridium botulinum | BoNT/D (5131) Antibody sc-57637 | mouse IgG1 |
| | BoNT/A (KBA211) Antibody sc-51774 | mouse IgG1 |
| | BoNT/A (KBA468) Antibody sc-51775 | mouse IgG2a |
| | BoNT/B (GR-3G7) Antibody sc-101376 | mouse IgG1 |
| | BoNT/B (KBB18) Antibody | mouse IgG1 |
| | BoNT/B (KBB36) Antibody | mouse IgG1 |
| | BoNT/D (KB21) Antibody | mouse IgG1 |
| | BoNT/D (KB22) Antibody | mouse IgG1 |
| | BoNT/D (KB23) Antibody | mouse IgG1 |
| | BoNT/E (11D4) Antibody | mouse IgG1 |
| | BoNT/E (8B9) Antibody | mouse IgG1 |
| | BoNT/E (BE2) Antibody | mouse IgG1 |
| | BoNT/E (BE3) Antibody | mouse IgG1 |
| | BoNT/E (KB144) Antibody | mouse IgG1 |
| | BoNT/E (KBE169) Antibody | mouse IgG1 |
| | BoNT/E (KBE42) Antibody | mouse IgG1 |
| | BoNT/D (1.B.204) Antibody | mouse IgG1 |
| | BoNT/A (24A29) Antibody | mouse IgM |
| | BoNT/A (2A33) Antibody | mouse IgG1 |

Figure 16

| Species as Antigen | Antibody | Isotype |
|---|---|---|
| E. coli O157 | E. coli O157 (1.B.250B) Antibody | mouse IgG$_3$ |
| | E. coli O157 (1031) Antibody | mouse IgG$_3$ |
| | E. coli O157 (8.F.101) Antibody | mouse IgG$_3$ |
| | E. coli O157 (1041) Antibody | mouse IgM |
| | E. coli O157 (1.B.248) Antibody | mouse IgG$_3$ |
| L. monocytogenes | Listeria monocytogenes (LX32) Antibody | mouse IgG$_1$ |
| | Listeria monocytogenes (LZA2) Antibody | mouse IgM |
| | Listeria monocytogenes (LZH1) Antibody | mouse IgG$_3$ |
| | Listeria monocytogenes (LX99) Antibody | mouse IgG$_4$ |
| Shigella dysenteriae | Shigella dysenteriae (0911) Antibody | mouse IgG |
| Shigella flexneri | Shigella flexneri (306/305) Antibody | mouse IgG$_1$ |
| Salmonella enteriditis D | Salmonella enteriditis 0-9 (4G7C) Antibody | mouse IgG$_1$ |
| Salmonella typhimurium | Salmonella typhimurium (IFR0402) Antibody | mouse IgM |
| | Salmonella typhimurium (6331) Antibody | mouse IgG |
| | Salmonella typhimurium 0-4 (1E6) Antibody | mouse IgG$_1$ |
| | Salmonella typhimurium 0-4 (8C11C) Antibody | mouse IgG$_2$ |
| Clostridium botulinum | BoNT/D (5131) Antibody sc-57637 | mouse IgG1 |
| | BoNT/A (KBA211) Antibody sc-51774 | mouse IgG1 |
| | BoNT/A (KBA468) Antibody sc-51775 | mouse IgG2a |
| | BoNT/B (GR-3G7) Antibody sc-101376 | mouse IgG1 |
| | BoNT/B (KBB18) Antibody | mouse IgG1 |
| | BoNT/B (KBB36) Antibody | mouse IgG1 |
| | BoNT/D (KB21) Antibody | mouse IgG1 |
| | BoNT/D (KB22) Antibody | mouse IgG1 |
| | BoNT/D (KB23) Antibody | mouse IgG1 |
| | BoNT/E (11D4) Antibody | mouse IgG1 |
| | BoNT/E (8B9) Antibody | mouse IgG1 |
| | BoNT/E (BE2) Antibody | mouse IgG1 |
| | BoNT/E (BE3) Antibody | mouse IgG1 |
| | BoNT/E (KB144) Antibody | mouse IgG1 |
| | BoNT/E (KBE169) Antibody | mouse IgG1 |
| | BoNT/E (KBE42) Antibody | mouse IgG1 |
| | BoNT/D (1.B.204) Antibody | mouse IgG1 |
| | BoNT/A (24A29) Antibody | mouse IgM |
| | BoNT/A (2A33) Antibody | mouse IgG1 |

Figure 16a

| Species as Antigen | Antibody | Isotype |
|---|---|---|
| Campylobacter jejuni | Campylobacter jejuni (57-24) Antibody | mouse IgG$_3$ |
| | Campylobacter jejuni (7701) Antibody | mouse IgM |
| | Campylobacter jejuni (7711) Antibody | mouse IgG$_1$ |
| | Campylobacter jejuni (7721) Antibody | mouse IgG1 |
| | Campylobacter jejuni (7731) Antibody | mouse IgG$_1$ |
| | Campylobacter jejuni (BDI727) Antibody | mouse IgG1 |
| | Campylobacter jejuni (E10) Antibody | mouse IgG$_{2b}$ |
| | Campylobacter jejuni (H2) Antibody | mouse IgG$_1$ |
| | Campylobacter jejuni (H3) Antibody | mouse IgG$_{2b}$ |
| Staphylococcus aureus enterotoxin B | SEB (2B33) Antibody | mouse IgG$_1$ |
| | SEB (7931) Antibody | mouse IgG$_1$ |
| | SEB (B327) Antibody | mouse IgG$_{2b}$ |
| | SEB (B344) Antibody | mouse IgG1 |
| | SEB (B87) Antibody | mouse IgG$_1$ |
| | SEB (S222) Antibody | mouse IgG1 |
| | SEB (S643) Antibody | mouse IgG$_1$ |
| | SEB (SEB) Antibody | mouse IgG1 |
| Staphylococcus aureus enterotoxin C | SEC (C165) Antibody | mouse IgG2 |
| Staphylococcus aureus enterotoxin G | SEG (SEG-16) Antibody | mouse IgG$_{2a}$ |
| | SEG (SEG-59) Antibody | mouse IgG$_1$ |
| Staphylococcus aureus enterotoxin I | SEI (SEI-17A) Antibody | mouse IgG$_{2a}$ |
| | SEI (SEI-68) Antibody | mouse IgG$_1$ |
| against enterotoxin A of Staphylococcus aureus origin | SEA (1.B.496) Antibody | mouse IgG$_{2a}$ |
| | SEA (7935) Antibody | mouse IgG$_1$ |
| | SEA (A108) Antibody | mouse IgG$_{2b}$ |
| | SEA (A163) Antibody | mouse IgG$_1$ |
| | SEA (A228) Antibody | mouse IgG$_1$ |
| | SEA (A111) Antibody | mouse IgG$_{2a}$ |
| | SEA (C4) Antibody | mouse IgG$_1$ |
| | SEA (E8) Antibody | mouse IgG$_1$ |
| | SEA (H10) Antibody | mouse IgG$_{2b}$ |
| | SEA (S2) Antibody | mouse IgG$_{2a}$ |

Autoimmune disorders under study for autoantibodies as predictors.

| Disease | Clinical features | Status of autoantibody research |
|---|---|---|
| Addison's disease | Adrenal gland insufficiency: hypotension, weakness, and weight loss | Autoantibodies to adrenal tissues and enzyme 21-hydroxylase are highly predictive in children |
| Antiphospholipid syndrome | Recurrent clots in blood vessels | Autoantibodies signal the risk of various complications |
| Celiac disease | Gastrointestinal disorder triggered by gluten in food | Predictive autoantibodies that target the enzyme tissues translutaminase have been identified |
| Diabetes type 1: insulin dependent | Autoimmune destruction of insulin-producing pancreatic islet β cells | Autoantibodies appear years before the disease manifestations and elevated glucose in blood |
| Multiple sclerosis | Demyelination and multiple neurological deficits | Autoantibodies to proteins in the myelin sheaths of the nerve fibers predict the risk of disease |
| Myasthenia gravis | Muscle weakness: loss of Ach receptor density at the neuromuscular junction | Autoantibodies are detected in disease but not in presymptomatic phase by available tests |
| Rheumatoid arthritis | Chronic pain and inflammation of the joints | Autoantibodies to citrulline have been found years before the onset of symptoms |
| Systemic lupus erythematosus | Affecting several organs: joints, kidneys, and skin | Antibodies appear in 80% of the patients before onset of symptoms |

Adapted from Table 1.4 of K.K. Jain, *The Handbook of Biomarkers*, ISBN 160761684X, Springer 2010.

Figure 18

Examples of biosensors for cancer biomarkers analysis.

| Cancer marker detected | Biosensor principle | Assay principle | Limit of detection |
|---|---|---|---|
| AFP | Electrochemical | Protein array with 36 platinum electrodes Prussian blue with screen-printed amperometric sensors. | – |
| AFP and CEA | Electrochemical | Dual-electrode with amperometric detection. | (range 5-500 ng ml⁻¹) 1 ng ml⁻¹ |
| CA15-3 | Electrochemical | Antibody functionalized sol-gel film with potentiometric detection. | 5 U ml⁻¹ |
| CA125 | Electrochemical | Capillary electrophoretic. | – |
| CA19-9 | Electrochemical | Titania sol-gel on glassy carbon electrode with direct electrochemical detection of HRP. | 1.29 U ml⁻¹ (range 2-14 U ml⁻¹) |
| CEA | Electrochemical | Titania sol-gel on carbon electrode as an amperometric immunosensor. | – |
|  | Electrochemical | Faradic impedance spectroscopy using gold nanoparticle modified glassy carbon electrode. | – |
|  | Electrochemical | Immobilised thionine as a mediator between the electrode and HRP-labelled antibody. | (range 0.6-17 ng ml⁻¹, 17-200 ng ml⁻¹) |
|  | Electrochemical | Direct electrochemical detection of HRP in an immunosensor. | 0.4 ng ml⁻¹ (range 0.5-3.0 ng ml⁻¹, 3.0-120 ng ml⁻¹) |
| Ferritin |  | Chemiluminescence immunosensors. | – |
|  | Optical | Antibody immobilized on gold chip of a quartz crystal microbalance. | (range 0.1-100 ng ml⁻¹) |
| hCG | Mass sensitive | SPR based immunosensor. | – |
|  | Optical | A multi-channel piezoelectric quartz micro-array immunosensor. | – |
| PSA | Mass-sensitive | Fluorescence immunosensor. | (range 25-1500 U ml⁻¹) |
|  | Optical | Gold coated microporous membrane. | – |
|  | Electrochemical | Amperometric disposable electrode. | (range 25-1500 U ml⁻¹) |
|  | Mass sensitive | Capacitive immunosensor using lateral flow and impedance detection. | – |
|  | Optical | Antibody immobilized on gold chip of a quartz crystal microbalance. | – |
|  |  | Microcantilever immunosensors. | – |
|  |  | Microcantilever immunosensor. | (range 0.2-60 µg ml⁻¹) |
|  |  | SPR with colloidal gold nanoparticles. | 0.15 ng ml⁻¹ |

Adapted from Table 3 of I. Tothill, "Biosensors for Cancer Markers Diagnosis," *Seminars in Cell & Developmental Biology* 20 (2009), pp. 55–62.

Figure 19

Known biomarkers associated with cancer diagnosis and prognosis.

| Cancer type disease | Biomarker |
|---|---|
| Prostate | PSA, PAP |
| Breast | CA15-3, CA125, CA27.29, CEABRCA1, BRCA2, MUC-1, CEA, NY-BR-1, ING-1 |
| Leukaemia | Chromosomal abnormalities |
| Testicular | A-Fetoprotein (AFP), β-human chorionic gonadatropin, CAGE-1, EDO-1 |
| Ovarian | CA125, AFP, hCG, p53, CEA |
| Any solid tumor | Circulating tumour cells in biological gluids, expression of targeted growth factor receptors |
| Colon and pancreatic | CEA, CA19-9, CA24-2, p53 |
| Lung | NY-ESO-1, CEA, CA19-9, SCC, CYFRA21-1, NSE |
| Melanoma | Tyrosinase, NY-ESO-1 |
| Liver | AFP, CEA |
| Gastric carcinoma | CA72-4, CEA, CA19-9 |
| Esophagus carcinoma | SCC |
| Trophoblastic | SCC, hCG |
| Bladder | BAT, FDP, NMP22, HA-Hase, BLCA-4, CYFRA 21-1 |

Adapted from Table 1 of I. Tothill, "Biosensors for Cancer Markers Diagnosis," *Seminars in Cell & Developmental Biology* 20 (2009), pp. 55–62.

Figure 20

| | Antibody available | | | |
|---|---|---|---|---|
| Target Class | Specific Target | Analyte/Biomarker | Antibody | Method |
| Human conditions | Cardiac disease | Cardiac troponin<br>C-reactive protein | anti-human troponin I polyclonal antibody | immunohistochemistry |
| | Hormone | Thyroid stimulating Hormone | The monoclonal anti-hTSH (scFab and scFv fragments) | TSH immunoassay: streptavidin surface and recombinant site-specifically tagged biotinylated antibody fragments. Eu-labeled TSH |
| Environmental contamination | | Atrazine | scab | Amperometric. Competitive with recombinant scAb fragments (HRP label) |
| | Lead-induced neurobehavioral deficits | NCAM PSA | Anti-NCAM PSA Ab | immunofluorescence: fluorescein-conjugated goat anti-mouse IgM |
| Illicit drugs | | Morphine – 3- glucuronide | scFv (anti-M3G recombinant scFv antibodies) | SPR |
| Infectious Disease | | Non-structural protein 3ABC (Foot – and mouth) | scFVs: Recombinant Antibody Foot-and-Mouth disease (CRAb-FM) 26, -FM27 and -FM29 | a mouse monoclonal anti-E Tag/HRP conjugate (Pharmacia). TMB One solution (Promega) was used to develop the color reaction |
| | | HIV-1 virion infectivity factor | scFv (VH and VHD): anti-HIV-I VIF (virion infectivity factor) single fragment antibodies (4BL scFV) | Piezoelectric: HP/anti-HA monoclonal antibody conjugates were autoradiographed with the chemiluminescent ECL-Plus kit (GE healthcare) a |
| | | SARS virus | scFv (antibody against SARS-CoV) | Imaging ellipsometry: HRP-conjugated anti-M13 antibody followed by incubation with ortho-phenylene-diamine (OPD) |
| | | L. monocytogenes | scFv (phage bound) | Amperometric: Anti M13 rabbit IgG, HRP conjugated anti M13 rabbit IgG<br>SPR |
| Food Contamination | Foodstuffs | Aflatoxin B1 | scFv | SPR: antibodies (HRP-anti-AFB1) |
| | | Parathion | scFv | Piezoelectric. Enzyme immunoassay – grade horseradish peroxidase (HRP). |
| Biological warfare pathogens | | Brucella melitensis | single chain antibody variable region fragment (scFv) | Anti-mouse-HRP |
| | | Venezuelan equine encephalitis virus | scFv | Potentiometric |
| | | B. anthracis S-layer protein | scFv | Resonant mirror |

Figure 21

| | | Antibody available | | |
|---|---|---|---|---|
| Target Class | Specific Target | Analyte/Biomarker | Antibody | Method |
| Cancer and Cancer like Diseases | Lung | BPDE-dG PAH-DNA 8-oxodG | Anti BPDE-dG-mAb, Anti PAH-DNA-Ab, 8-oxodG monoclonal antibody | Immunohistochemistry A biotinylated 2nd Ab (Avidin-biotin-peroxidase complex), 3,3',5,5'-Tetramethylbenzidine |
| | | NY-ESO-1, CEA, CA19-9, SCC, CYFRA21-1, NSE | antibodies against NY-ESO-1, CEA, CA19-9, CYFRA21-1, NSE are commercially available | CA19-9: Titania sol-gel on carbon electrode as an amperometric immunosensor. CEA: Faradic impedance spectroscopy using gold nanoparticle modified glassy carbon electrode, immobilised thionine as a mediator between the electrode and HRP-labelled antibody. Direct electrochemical detection of HRP in an immunosensor. Chemiluminescence immunosensor. |
| | Prostate | PSA, PAP | anti-PSA and anti-PAP antibodies are commercially available | PSA: Gold coated microporous membrane. Amperometric disposable electrode. Capacitive immunosensor using lateral flow and impedance detection. Antibody immobilised on gold chip of a quartz crystal microbalance. Microcantilever immunosensor. Microcantilever immunosensor. SPR with colloidal gold nanoparticles. |
| | Breast | CA15-3, CA125, CA27.29, CEABRCA1, BRCA2, MUC-1, CEA, NY-BR-1, ING- | antibodies against CA15-3, CA125, CA27.29, CEABRCA1, BRCA2, MUC-1, CEA, NY-BR-1, ING-1 are commercially available | CA15-3: Antibody functionalised sol-gel film with potentiometric detection. CA125: Titania sol-gel on glassy carbon electrode with direct electrochemical detection of HRP. Capillary electrophoretic |
| | Testicular | α-Fetoprotein (AFP), human chorionic gonadotropin, CAGE-1, ESO-1 | antibodies against α-Fetoprotein (AFP), human chorionic gonadotropin, CAGE-1, ESO-1 are commercially available | AFP: Protein array with 36 platinum electrodes. Prussian blue with screen-printed amperometric sensor. Dual-electrode with amperometric |

Figure 21 (continued)

| | | Antibody available | | |
|---|---|---|---|---|
| Target Class | Specific Target | Analyte/Biomarker | Antibody | Method |
| Cancer and Cancer-like Diseases | Breast | CA15-3, CA125, CA27.29, CEA BRCA1, BRCA2, MUC-1, CEA, NY-BR-1, ING-1 | antibodies against CA15-3, CA125, CA27.29, CEA BRCA1, BRCA2, MUC-1, CEA, NY-BR-1, ING-1 are commercially available | CA15-3: Antibody functionalised sol-gel film with potentiometric detection. CA125: Titania sol-gel on glassy carbon electrode with direct electrochemical detection of HRP. Capillary electrophoretic |
| | Testicular | α-Fetoprotein (AFP), β-human chorionic gonadotropin, CAGE-1, ESO-1 | antibodies against α-Fetoprotein (AFP), β-human chorionic gonadotropin, CAGE-1, ESO-1 are commercially available | AFP: Protein array with 36 platinum electrodes. Prussian Blue with screen-printed amperometric sensor. Dual-electrode with amperometric |
| | Ovarian | CA125, AFP, hCG, p53, CEA | HRP-labeled CA 125 monoclonal antibody | CEA: Dual-electrode with amperometric detection. hCG: A multi-channel piezoelectric quartz micro-array immunosensor. Fluorescence immunosensor |
| | Gastric carcinoma | CA72-4, CEA, CA19-9 | horseradish peroxidase (HRP)-labeled CA 19-9 monoclonal antibody | |
| Drug discovery | | Phospho-EGFR/phospho-MAPK | EGFR inhibition by cetuximab | |
| | | COX-2 inhibition | prostaglandin E2 (PGE2) levels | |
| | | RNA transcripts | T-cell receptor signaling | |
| Immune Disorders | Failure of Transplanted Organs | The human leukocyte antigens (HLA) | HLA antibody | DynaChip HLA Antibody Analysis System (Life Technologies) |
| | Graft Versus Host Disease | human CD28 receptor | anti-CD28 antibodies are commercially available | TeLandscape R_ technology (TcLand SA) |
| | Systemic Lupus Erythematosus (SLE) | Adiponectin | anti-adiponectin antibodies are commercially available | |
| | Renal Allograft Failure | cytokines, chemokines, and receptor levels in urine | Luminex ®_ xMAP ® | PlexMark™ 3 Renal Biomarker Panel Assay (Life Technologies Corporation) |

Figure 21 (continued)

| | | Antibody available | | |
|---|---|---|---|---|
| Target Class | Specific Target | Analyte/Biomarker | Antibody | Method |
| Viral Infections | Viral Hepatitis | Hepatitis A virus (HAV) | HAV-specific monoclonal Antibody | PCR |
| | | Hepatitis C virus (HCV) | HCV antibody | immunoassay EIA, an immunoblot assay (RIBA-2) |
| | HIV | CSF neural markers (NFL, Tau, and GFAP) levels and a decline in CSF and serum neopterin and CSF and plasma HIV-1 RNA levels<br><br>APOBEC3G (apolipoprotein B mRNA-editing enzyme, catalytic polypeptide-like 3G, also known as CEM15 or hA3G) | antibodies against NFL, Tau, APOBEC3G, and GFAP are commercially available | • EIA tests for the detection and quantification of HIV-1 p24 antigen<br>• Western blot<br>• Latex agglutination<br>• Radioimmunoprecipitation<br>• Immunofluorescence for the detection of antibodies to HIV-1<br>• Viral cultures for the isolation and semiquantification of HIV-1 |
| Parasitic Infections | Malaria | (*Plasmodium falciparum* and *Plasmodium vivax*) Serum angiopoietin-1 and the angiopoietin-2/1 ratio | antimalarial antibodies | |
| | Schistosomiasis Infections | Schistosoma mansoni oligosaccharides | a specific antiglycan Mab | |
| Miscellaneous Disorders | Inflammatory bowel disease (IBD) | Calprotectin and lactoferrin | (atypical perinuclear anti-neutrophil cytoplasmic antibodies), anti-Saccharomyces Biomarkers of cerevisiae antibodies (ASCA) | |
| | Erectile Dysfunction | endothelin-1, cyclic guanosine monophosphate | anti-endothelin-1 antibodies are commercially available | |
| | Heat Stroke | Heat-shock protein (Hsp) 72 | anti-HSP 72 antibodies are commercially available | |
| | Neuropathic Pain | IL-1β and IL-6 | anti-IL-1β and anti-IL-6 antibodies are commercially available | |
| Toxicology | Cardiotoxicity | B-type natriuretic peptide (BNP), N-terminal proBNP (NT-proBNP), cardiac troponin T (cTnT), and cardiac troponin I (cTnI) | anti-human troponin I polyclonal antibody antibodies against BNP are commercially available | |
| Neurological disease | Inflammation | serum C3 and C4 | antibodies against C3 and C4 are commercially available | |

Figure 21 (continued)

| | Antibody available | | | |
|---|---|---|---|---|
| Target Class | Specific Target | Analyte/Biomarker | Antibody | Method |
| Oxidative Stress | Oxidative DNA Damage | 8-Oxoguanine | antibodies against 8-Oxoguanine are commercially available | OxyDNA Test (Biotrin); fluorescence method |
| Metabolic Disorders | Acute intermittent porphyria (AIP) | porphobilinogen (PBG) and 5-aminolevulinic acid (ALA), Observing liver function as well. IGF-1 and transthyretin | anti-PBG, anti-ALA, and IGF-, and transthyretin antibodies are commercially available | |
| | Diabetes-Associated Oxidative Stress | urinary 8-hydroxy-2'-deoxyguanosine | antibodies against 8-hydroxy-2'-deoxyguanosine are commercially available | |
| | Inflammation | C-reactive protein | anti-CRP antibodies are commercially available | |
| | Renal complications in type 2 diabetes mellitus | apolipoprotein B | anti-apolipoprotein B antibodies are commercially available | |
| | Endothelial dysfunction in type 2 diabetes mellitus | E-selectin | anti-E-selectin antibodies are commercially available | |
| | | Intercellular adhesion molecule 1 | anti-ICAM antibodies are commercially available | |
| | | Vascular cell adhesion molecule 1 | anti-VCAM antibodies are commercially available | |
| | Insulin resistance | Serum retinol binding protein-4 | anti-SRBP-4 antibodies are commercially available | |
| | Diabetes with cardiovascular complications | Adiponectin | anti-adiponectin antibodies are commercially available | |
| | | Glycosylated hemoglobin | fructose value | |
| Musculoskeletal Disorders | Rheumatoid Arthritis | TNF-α serum VEGF | anti-TNFalpha and anti-VEGF antibodies are commercially available | |
| | Osteoarthritis (OA) | heat-shock 90 kDa protein 1, alpha; inhibitor of kappa light polypeptide gene enhancer in B cells, kinase complex-associated protein; IL-13 receptor, alpha 1; laminin, gamma 1; platelet factor 4 (also known as chemokine (C-X-C motif) ligand 4); and tumor necrosis factor, alpha-induced protein 6; iNOS | antibodies against hsp 90-1, alpha; IkB, laminin, gamma 1; platelet factor 4 (also known as chemokine (C-X-C motif) ligand 4); and tumor necrosis factor, and iNOS are commercially available | real-time RT-PCR |

Figure 21 (continued)

| | | Antibody available | | |
|---|---|---|---|---|
| Target Class | Specific Target | Analyte/Biomarker | Antibody | Method |
| Liver Disease | Viral Hepatitis B and C | hyaluronic acid, amino-terminal propeptide of type III collagen (PIIINP), and tissue inhibitor of matrix metalloproteinase 1 (TIMP-1) Collagen IV AST-to-platelet ratio index | antibodies against hyaluronic acid, amino-terminal propeptide of type III collagen (PIIINP), and tissue inhibitor of matrix metalloproteinase 1 (TIMP-1), and Collagen IV are commercially available | FibroTest (BioPredictive) ActiTest (BioPredictive) (HCV-FibroSURE, LabCorp) |
| | Liver Injury | Alpha glutathione S-transferase (alpha GST) | alpha GST antibodies are commercially available | |
| | Liver Cirrhosis | tropomyosin and MFAP-4 | tropomyosin and MFAP-4 antibodies are commercially available | FibroMaxTM (Lab21 Limited) |
| Renal Disease | | C-reactive protein (CRP) homocysteine and asymmetric dimethylarginin | anti-CRP antibodies are commercially available | |
| | Glomerular Filtration Rate | Cystatin C | Cystatin C antibodies are commercially available | The DetectXTM Cystatin C Immunoassay Kit (Luminos LLC, Ann Arbor, MI) |
| | Acute Kidney Injury | in the plasma (NGAL and cystatin C) and urine (NGAL, KIM-1, IL-18, cystatin C, alpha 1-microglobulin, fetuin-A, Gro-alpha, and meprin) | NGAL, KIM-1, IL-18, cystatin C, alpha-1 microglobulin, fetuin A, gro-alpha, and meprin antibodies are commercially available | |
| | Diabetic Nephropathy | Albumin immunoglobulin G, transferrin, ceruloplasmin, and serum cystatin C | Albumin immunoglobulin G, transferrin, ceruloplasmin, and cystatin C antibodies are commercially available | |
| Pulmonary Diseases | Detection of AAT deficiency predisposing to emphysema | Blood finger prick: Alpha1 antitrypsin/AAT gene polymorphism | Alpha1-antitrypsin antibodies are commercially available | |
| | Detection of pulmonary hypertension in patients with chronic lung disease | Plasma: Brain natriuretic peptide (BNP) | anti-BNP antibodies are commercially available | |
| | Track changes in lung inflammation during an exacerbation of cystic fibrosis | Sputum and serum: Calprotectin | anti-Calprotectin antibodies are commercially available | |

Figure 21 (continued)

| Target Class | Specific Target | Analyte/Biomarker | Antibody available Antibody | Method |
|---|---|---|---|---|
| Pulmonary Diseases | Elevated in acute exacerbation of COPD | Serum: C-reactive protein (CRP) | anti-CRP antibodies are commercially available | |
| | The dose of omalizumab is that required is to reduce circulating free IgE levels to less than 10 IU/mL | Serum: IgE level | anti-IgE antibodies are commercially available | |
| | Increased specifically in COPD | Serum: Osteoprotegerin (OPG) | anti-OPG antibodies are commercially available | |
| | Exacerbation of COPD by respiratory tract infections | Serum: Serum amyloid A (SAA) | anti-SAA antibodies are commercially available | |
| | Interstitial lung disease Acute respiratory distress syndrome Radiation pneumonitis | Tracheal aspirates, Bronchoalveolar lavage, Pleural effusions. Surfactant proteins: A (SP-A) D (SP-D) | anti-SP-A and anti-SP-B antibodies are commercially available | |
| Obstetrics and Gynecology | Preeclampsia | vascular endothelial growth factor (VEGF), placental growth factor (PlGF), and their soluble VEGF receptor (sVEGFR1) or soluble fms-like tyrosine kinase (sFlt-1) albumin and serpina-1, placental Protein HtraA1 placenta-derived soluble TGF-β co-receptor, endoglin (sEng) RNA biomarkers | anti-VEGF, anti-serpina, anti-albumin, and anti HtraA1 antibodies are commercially available | |
| | Endometriosis | IL2RG and LOXL1, Interleukin-6 | anti-IL2RG and anti-LOXL1 antibodies are commercially available | |

Figure 21 (continued)

| | | Antibody available | | |
|---|---|---|---|---|
| Target Class | Specific Target | Analyte/Biomarker | Antibody | Method |
| Genetic Disorders | Down's Syndrome | β-human chorionic gonadotrophin (hCG), alpha fetoprotein (AFP), unconjugated oestriol (uE3), serum pregnancy associated plasma protein-A (PAPP-A), and dimeric inhibin A, ADAM12 | anti-hCG, anti-AFP, anti-uE3, and anti-PAPP-A antibodies are commercially available | |
| | Duchenne and Becker muscular dystrophy (DMD and BMD) | neuronal form of nitric oxide synthase (nNOS) | anti-nNOS antibodies are commercially available | |
| | Lysosomal Storage Disorders | LAMP-1 and saposin C | anti-LAMP-1 and anti-saposin C antibodies are commercially available | by ELISA |
| | Gaucher's disease | Chitotriosidase and chemokine CCL18 | anti-Chitotriosidase antibodies are commercially available | |
| | The mucopolysaccharidoses (MPS) | heparin cofactor II-thrombin (HCII-T) | anti-HCII-T antibodies are commercially available | |
| | Fucosidosis | FUCA1 gene, fuco-oligosaccharides and sphingolipids | anti-FUCA1 antibodies are commercially available | |
| Biomarkers Common to Multiple Diseases | Neuroendocrine tumors, cardiovascular disease, sepsis | Chromogranin A | anti-Chromogranin A antibodies are commercially available | |
| | Diabetes mellitus, sepsis, pulmonary diseases, acute myocardial infarction, renal dysfunction | C-reactive protein (CRP) | anti-CRP antibodies are commercially available | |
| | Myocardial infarction, renal failure, cancer, Alzheimer disease, amyotrophic lateral sclerosis, multiple sclerosis | Cystatin C | anti-Cystatin C antibodies are commercially available | |

Figure 21 (continued)

| Target Class | Specific Target | Analyte/Biomarker | Antibody available | Method |
|---|---|---|---|---|
| | | | Antibody | |
| Biomarkers Common to Multiple Diseases | Ischemic heart disease, infections | Natriuretic peptide | anti-Natriuretic peptide antibodies are commercially available | |
| | Alzheimer disease, Parkinson disease, Creutzfeldt-Jakob disease, AIDS encephalopathy, alcohol-induced organic brain disorders | Tau protein | anti-Tau antibodies are commercially available | |
| | Rheumatoid arthritis (serum and synovial fluid), neuroinflammations, ischemic heart disease | TNF-α | anti-TNF-α are commercially available | |
| Malnutrition | | HDL, and LDL plasma transthyretin and alpha 1-acid glycoprotein | transthyretin and alpha 1-acid glycoprotein antibodies are commercially available | |

Figure 21 (continued)

Antibody not available

| Target Class | Specific Target | Analyte/Biomarker | Antibody | Method |
|---|---|---|---|---|
| Cancer and Cancer-like Diseases | Leukaemia | Chromosomal abnormalities | | |
| | Any solid tumour | Circulating tumour cells in biological fluids, expression of targeted growth factor receptors | | |
| | Melanoma | Tyrosinase, NY-ESO-1 | | |
| | Liver | AFP, CEA | | |
| | Colon and pancreatic | CEA, CA19-9, CA24-2, p53 | | |
| | Esophagus carcinoma | SCC | | |
| | Trophoblastic | SCC, hCG | | |
| | Bladder | BAT, FDP, NMP22, HA-Hase, BLCA-4, CYFRA 21-1 | | |
| Toxicology | Hepatotoxicity | LDH release specific circulating miRNAs specific circulating miRNAs | | |
| | Nephrotoxicity | KIM-1, osteopontin, and vimentin transporters (Slc21a2, Slc15, Slc34a2), Kim 1, IGFbp-1, osteopontin, alpha-fibrinogen, and Ostalpha. | | |
| | Neurotoxicity | A human embryonic stem cell (hESC)-based | | two-hybrid systems, antibody arrays, protein chips, isotope-coded affinity tags, ICAT |
| Neurological disease | Alzheimer disease (AD) | AN-1792, a synthetic version of the protein fragment Aβ42 | | |
| Oxidative Stress | Oxidative Stress in Diseases | 1,4-Dihydroxynonane Mercapturic Acid (DHN- | | LC/MS An enzyme immunoassay (EIA) |

Figure 22

Antibody not available

| Target Class | Specific Target | Analyte/Biomarker | Antibody | Method |
|---|---|---|---|---|
| Metabolic Disorders | Liver disorders | Liver X Receptors | | |
| | Diabetes Mellitus | | | |
| | Hyperglycemia | Exhaled methyl nitrate | | Gas analysis |
| | | serum-free fatty acids and ketones | | |
| | Diabetes-Associated Oxidative Stress | serum malondialdehyde, lipid hydroperoxides, and lipoperoxides. | | |
| | | plasma thioredoxin | | |
| | | superoxide dismutase in RBCs | | |
| | | plasma protein carbonyl | | |
| | Inflammation | Plasma-soluble cell adhesion molecules | | |
| | | Monocyte IL-6 | | |
| | | Nitrotyrosine | | |
| | Renal complications in type 2 diabetes mellitus | Triglycerides | | |
| | | low-density lipoprotein | | |
| | | soluble tumor necrosis factor receptor | | |
| Immune Disorders | Renal Allograft Failure | miRNA expression patterns (miR-10a-3p, -10b, and let-7c) | | |
| | Systemic Lupus Erythematosus (ESL) | Fc receptor genes (disease susceptibility), complement C4d-bound erythrocytes (diagnosis or disease activity), CD27 plasma cells (disease activity), "interferon signature" (disease activity), and anti-C1q antibodies | | |
| | | C4d-Bearing Reticulocytes | | |
| | | CB-CAPS | | |
| | | levels of methylation of certain genes | | EpiSenseTM Lupus, based on its ArioSense technology (PCR-MS) |

Figure 22 (continued)

Antibody not available

| Target Class | Specific Target | Analyte/Biomarker | Antibody | Method |
|---|---|---|---|---|
| Musculoskeletal Disorders | Osteoporosis | Bone mineral density (BMD) | | Dual X-Ray Absorptiometry, (QCT) and MRI immunoassays |
| | | molecular biomarkers of bone turnover (pyridinoline (PYD) and deoxypyridinoline (DPD)) | | |
| Tuberculosis | M. tuberculosis | tuberculous meningitis (TBM) - Heat shock protein (hsp) antigen | | |
| | | volatile organic compounds (VOCs) | | GC/MS |
| Viral Infections | Viral Hepatitis | Hepatitis B virus (HBV): HBV surface antigen (HBsAg) HBV DNA, Cu/Zn ratios (hepatocellular carcinoma) | | Hepanostika HBsAg Ultra assay Bayer's HBV DNA assay and Abbott's HBV DNA assay |
| | SARS (severe acute respiratory syndrome)-associated coronavirus (SARS-CoV) | Cytokine profiles: IFN-g, IL-1b, IL-6, IL-12, and MCP-1 | | Biochip array technology (Randox Laboratories) |
| Liver Disease | non-alcoholic fatty liver disease | breath ethanol, ethane, and acetone | | |
| Pancreatitis | | Trypsinogen, trypsinogen activation peptide (TAP) | | TAP assay (Biotrin) |
| Pulmonary Diseases | Overexpression of VEGF and PlGF expression is a biomarker of COPD | Bronchoalveolar lavage fluid: Angiogenic growth factor overexpression | | |
| | Cystic fibrosis (CF) | Plasma: CF-specific serum proteomic signature | | |
| | A neuroendocrine activity biomarker that is increased in male smokers with impaired lung function | Serum: Chromogranin A (CgA) | | |

Figure 22 (continued)

Antibody not available

| Target Class | Specific Target | Analyte/Biomarker | Antibody | Method |
|---|---|---|---|---|
| Pulmonary Diseases | A prognostic biomarker for poor prognosis in exacerbation of COPD requiring hospitalization | Serum Copeptin, the precursor of vasopressin | | |
| | Measurement of oxidative stress in pulmonary diseases | Exhaled breath Condensate: $H_2O_2$, F2-isoprostanes, Malondialdehyde, 4-hydroxy-2-nonenal antioxidants | | |
| | Inflammatory lung disorders, e.g., asthma, Rhinosinusitis | Exhaled breath: Nitric oxide (NO) | | |
| | Higher levels of urinary NO are strongly associated with improved survival in acute respiratory distress syndrome | Urine, NO | | |
| Genetic Disorders | Phenylketonuria (PKU) | phenylalanine and tyrosine in neonatal blood samples | | spectrophotometry, fluorometry, immunoassay, and tandem mass spectrometry NeoLynx Screening Application-Manager (Micromass Inc.) |

Figure 22 (continued)

Antibody not available

| Target Class | Specific Target | Analyte/Biomarker | Antibody | Method |
|---|---|---|---|---|
| Biomarkers Common to Multiple Diseases | Most diseases with inflammation | Inflammation biomarkers | | |
| | Asthma (in breath), acute respiratory distress syndrome (in urine), cardiovascular disease (in plasma) | Nitric oxide | | |
| | Most diseases with oxidative stress | Oxidative stress biomarkers | | |
| | Traumatic brain injury, stroke, epilepsy (in CSF) | Serum 100B protein | | |
| | Rheumatoid arthritis (serum and synovial fluid), neuroinflammation, ischemic heart disease | TNF-α | anti-TNF-α are commercially available. | |

Figure 22 (continued)

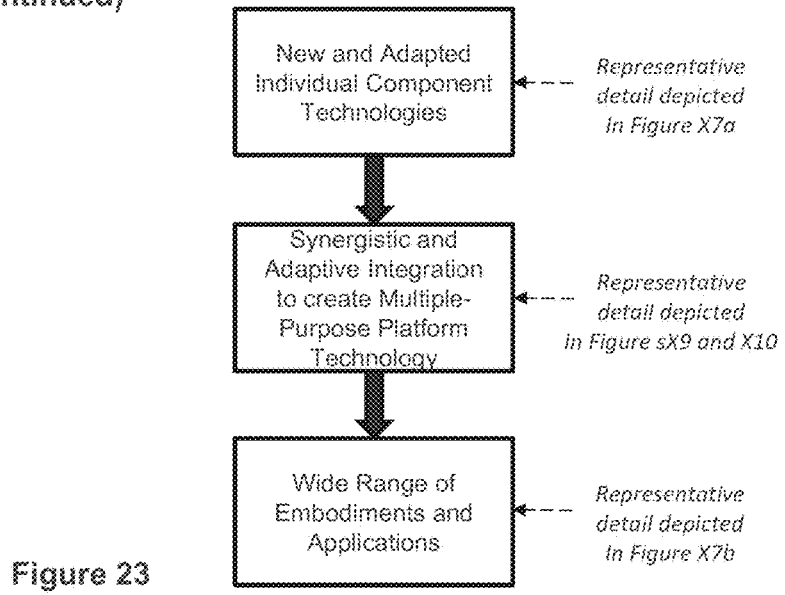

Figure 23

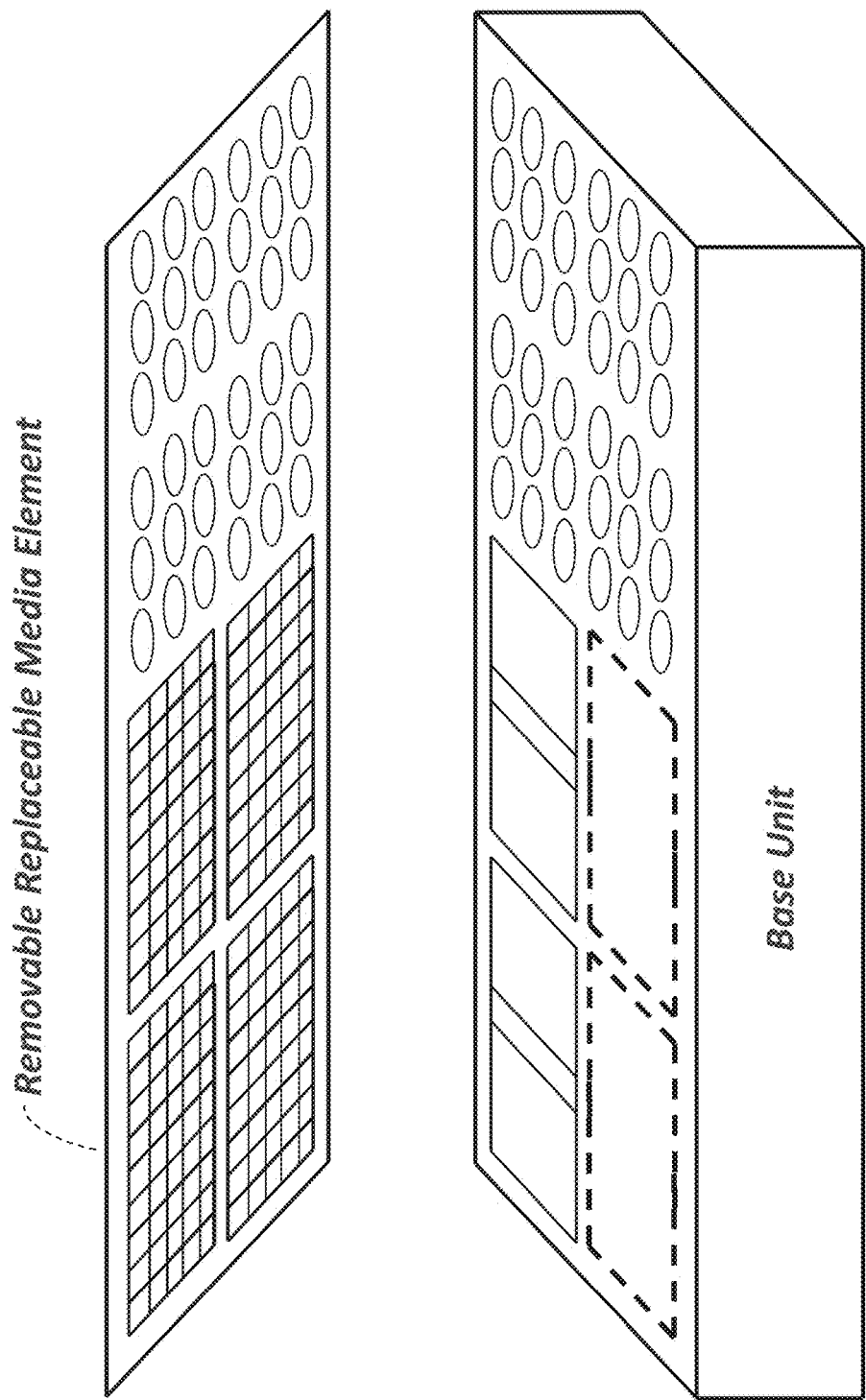

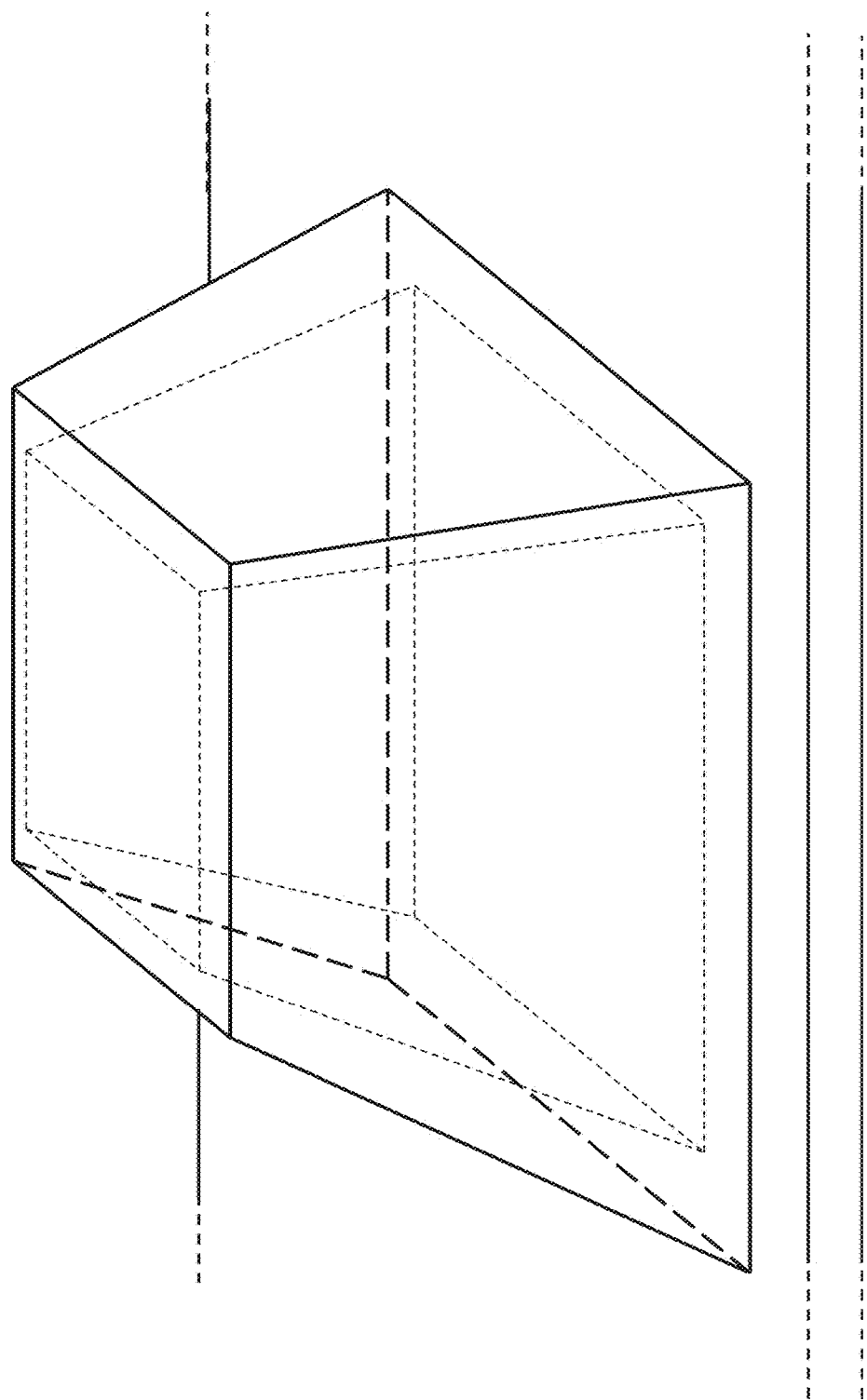

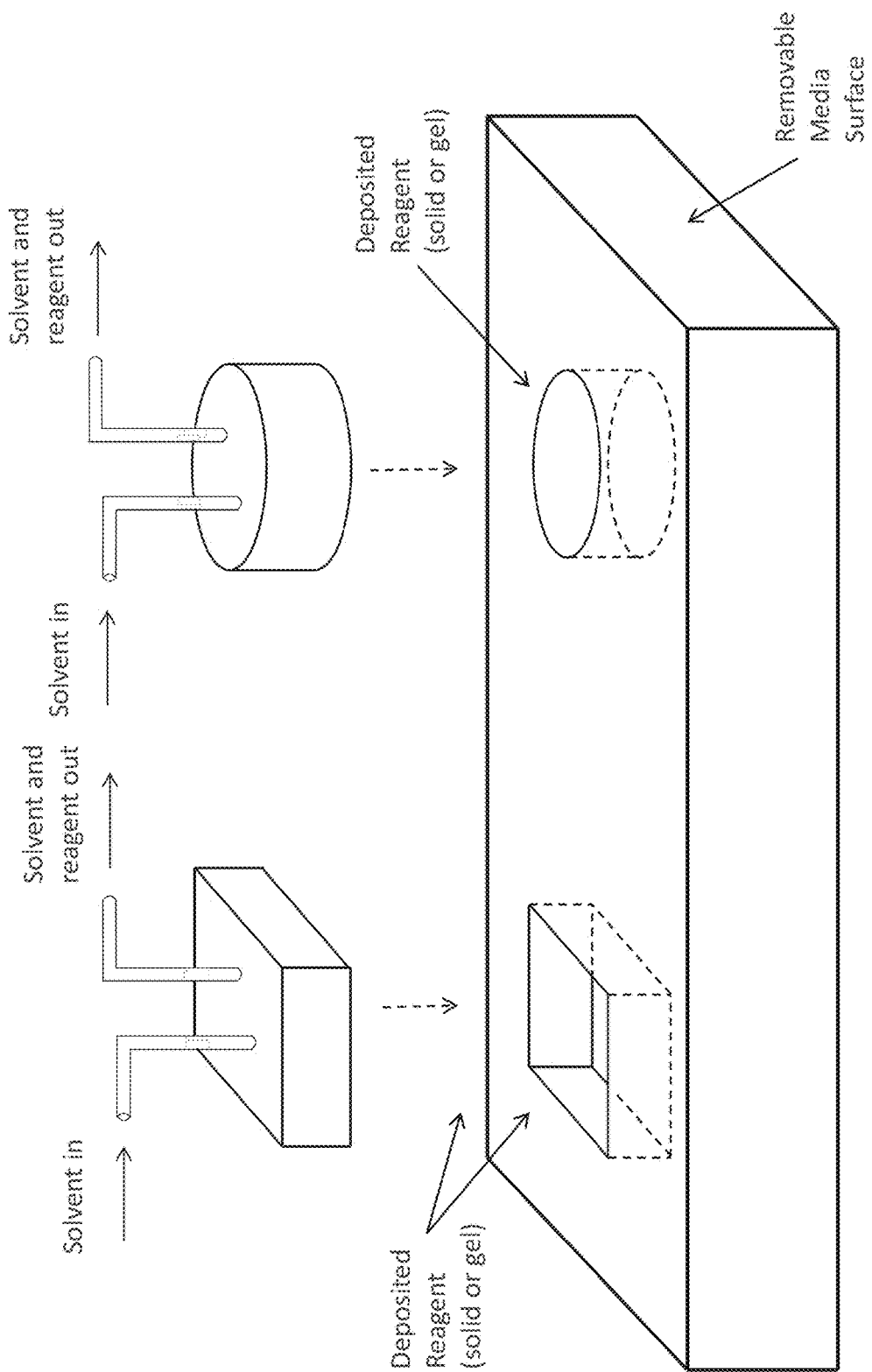

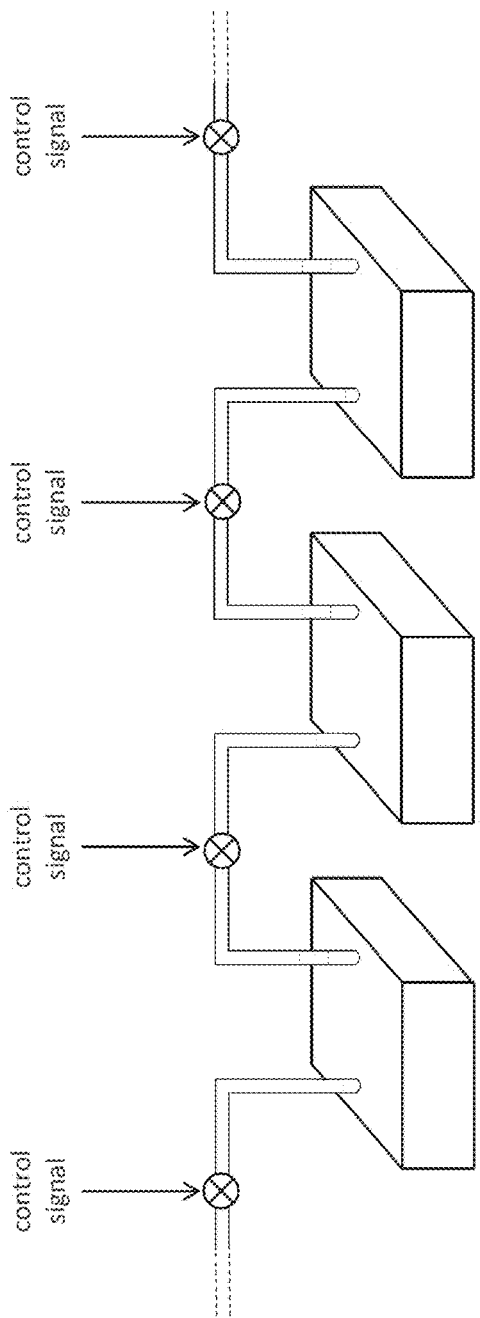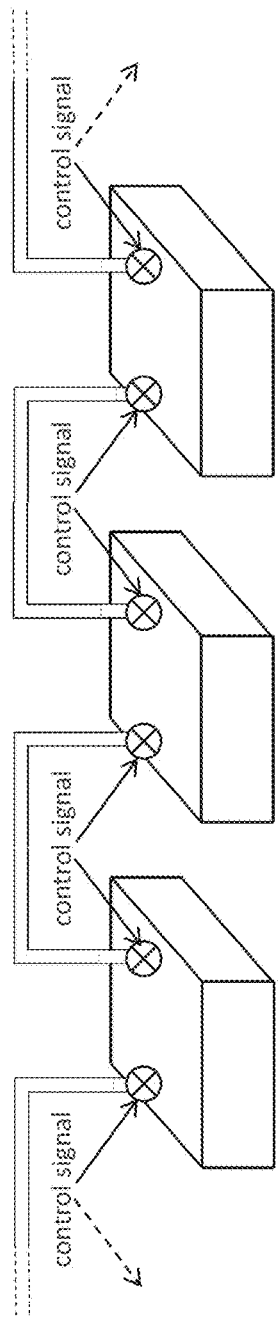
Figure 41a
Figure 41b

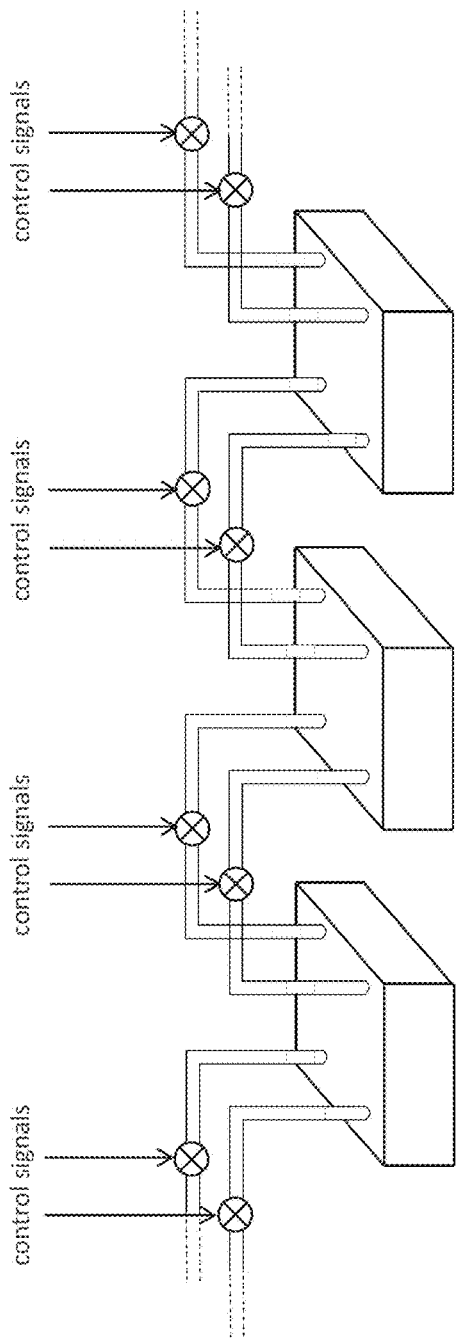
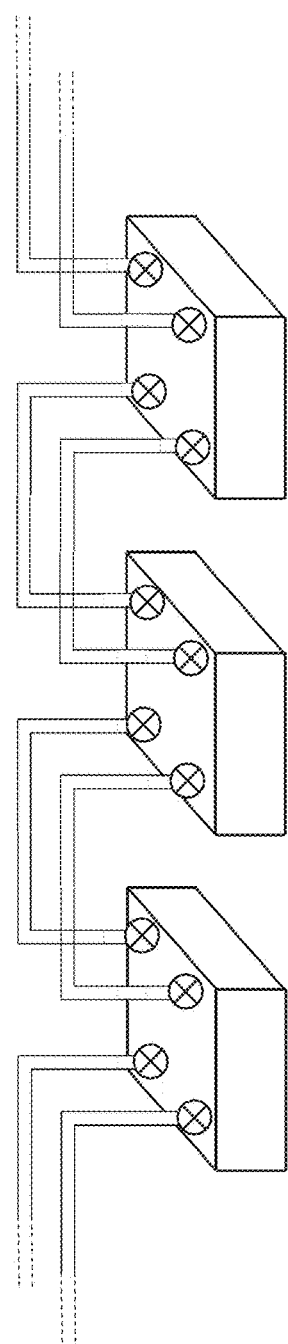
Figure 43a
Figure 43b

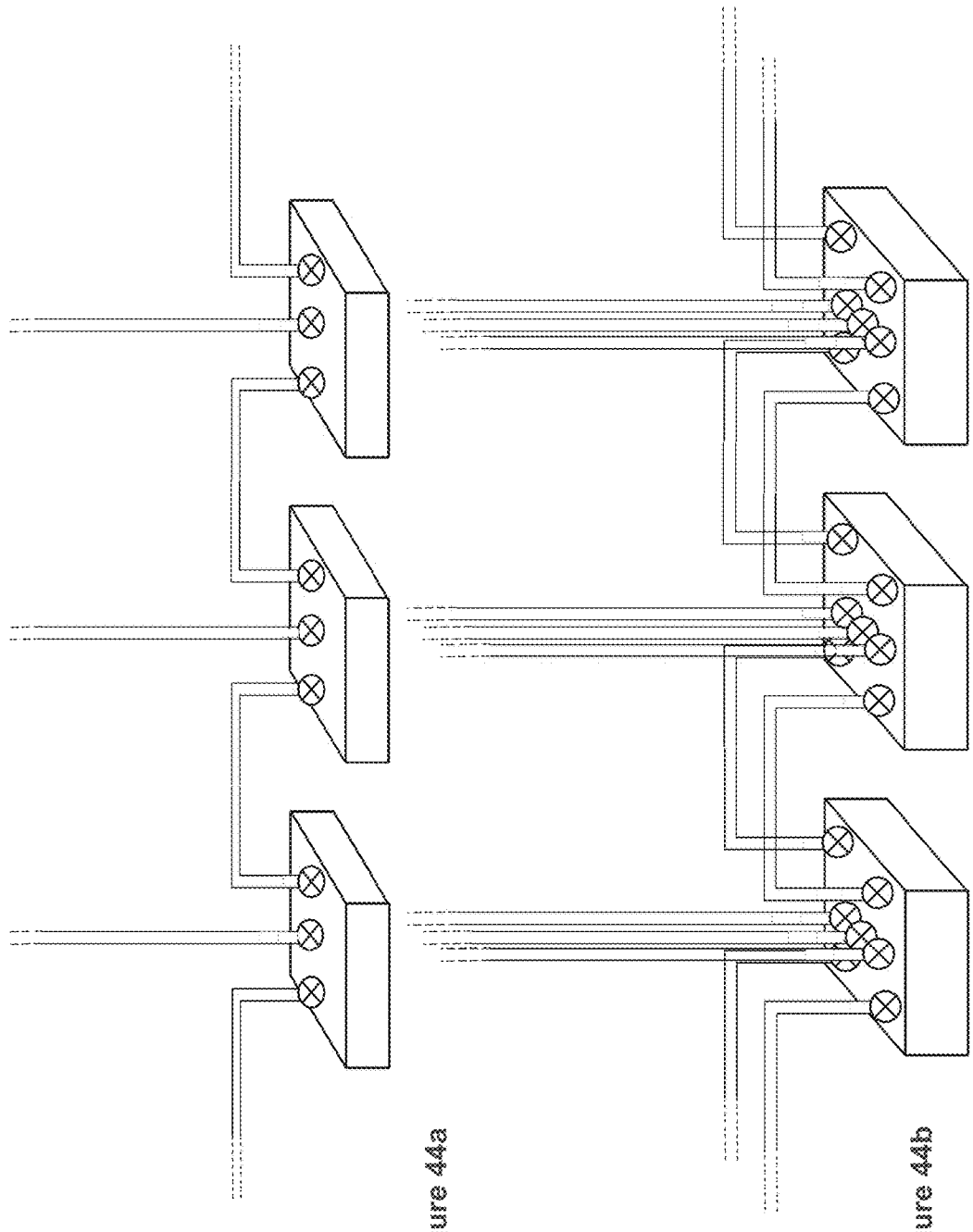

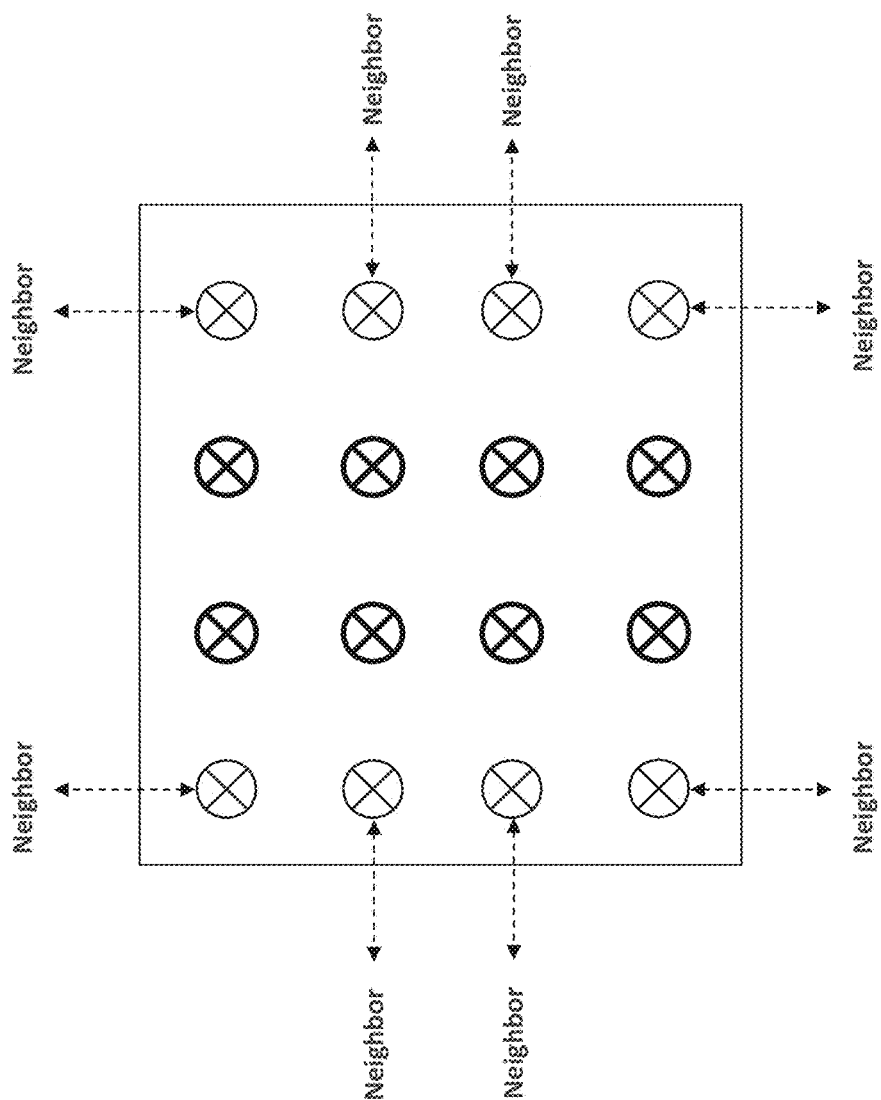

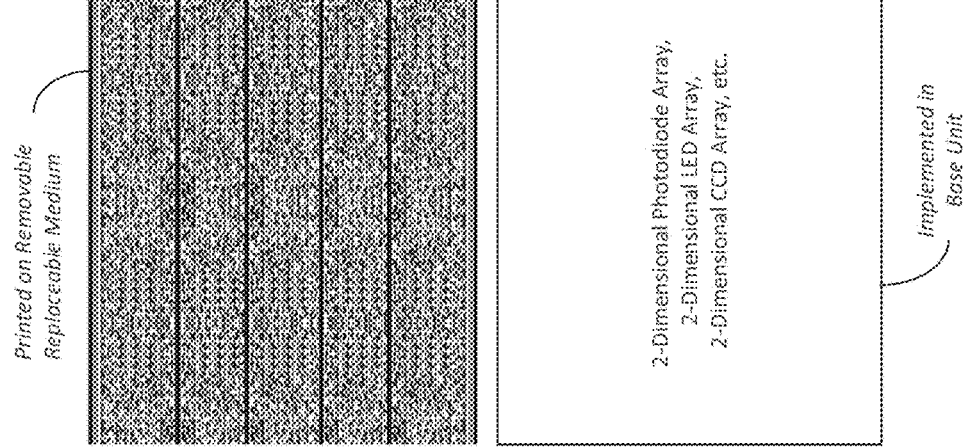
Figure 47c
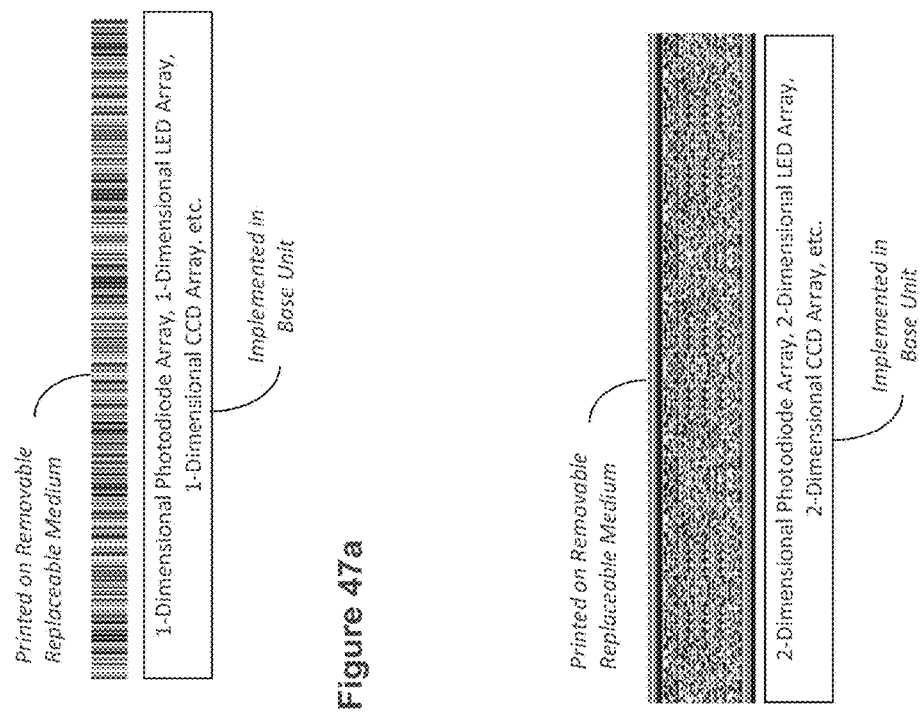
Figure 47a
Figure 47b

| Column | Row | Solid Reagent | Mixing Volume | Pass-Through/ Storage | Light Absorb Sensor/ Photo-stimulus | Fluorescence Sensor/ Photo-stimulus | Electrochemical Sensor | Selective Ion Sensor | BioFET Sensor |
|---|---|---|---|---|---|---|---|---|---|
| 1 | 1 | ✓ | | ✓ | | | | | |
| 1 | 2 | ✓ | | ✓ | | | | | |
| 1 | 3 | ✓ | | ✓ | | | | | |
| 1 | 4 | ✓ | | ✓ | | | | | |
| 1 | 5 | ✓ | | ✓ | | | | | |
| 1 | 6 | ✓ | | ✓ | | | | | |
| 1 | 7 | ✓ | | ✓ | | | | | |
| 2 | 1 | ✓ | ✓ | ✓ | | | | | |
| 2 | 2 | ✓ | ✓ | ✓ | | | | | |
| 2 | 3 | ✓ | ✓ | ✓ | | | | | |
| 2 | 4 | ✓ | ✓ | ✓ | | | | | |
| 2 | 5 | ✓ | ✓ | ✓ | | | | | |
| 2 | 6 | ✓ | ✓ | ✓ | | | | | |
| 2 | 7 | ✓ | ✓ | ✓ | | | | | |
| 3 | 1 | | ✓ | ✓ | ✓ | ✓ | | | |
| 3 | 2 | | ✓ | ✓ | ✓ | ✓ | | | |
| 3 | 3 | | ✓ | ✓ | ✓ | ✓ | | | |
| 3 | 4 | | ✓ | ✓ | ✓ | ✓ | | | |
| 3 | 5 | | ✓ | ✓ | ✓ | ✓ | | | |
| 3 | 6 | | ✓ | ✓ | ✓ | ✓ | | | |
| 3 | 7 | | ✓ | ✓ | ✓ | ✓ | | | |
| 4 | 1 | | ✓ | ✓ | | | ✓ | ✓ | |
| 4 | 2 | | ✓ | ✓ | | | ✓ | ✓ | |
| 4 | 3 | | ✓ | ✓ | | | ✓ | ✓ | |
| 4 | 4 | | ✓ | ✓ | | | ✓ | ✓ | |
| 4 | 5 | | ✓ | ✓ | | | ✓ | ✓ | |
| 4 | 6 | | ✓ | ✓ | | | ✓ | ✓ | |
| 4 | 7 | | ✓ | ✓ | | | ✓ | ✓ | |
| 5 | 1 | | ✓ | ✓ | | | | | ✓ |
| 5 | 2 | | ✓ | ✓ | | | | | ✓ |
| 5 | 3 | | ✓ | ✓ | | | | | ✓ |
| 5 | 4 | | ✓ | ✓ | | | | | ✓ |
| 5 | 5 | | ✓ | ✓ | | | | | ✓ |
| 5 | 6 | | ✓ | ✓ | | | | | ✓ |
| 5 | 7 | | ✓ | ✓ | | | | | ✓ |

Figure 49

| | Reagent C | Sensor 1 | Sensor 2 | Sensor 3 |
|---|---|---|---|---|
| | Reagent C | | | |
| | | | | |
| | | Sensor 4 | | |
| | | Sensor 5 | | |
| | | | | |
| | | | | |

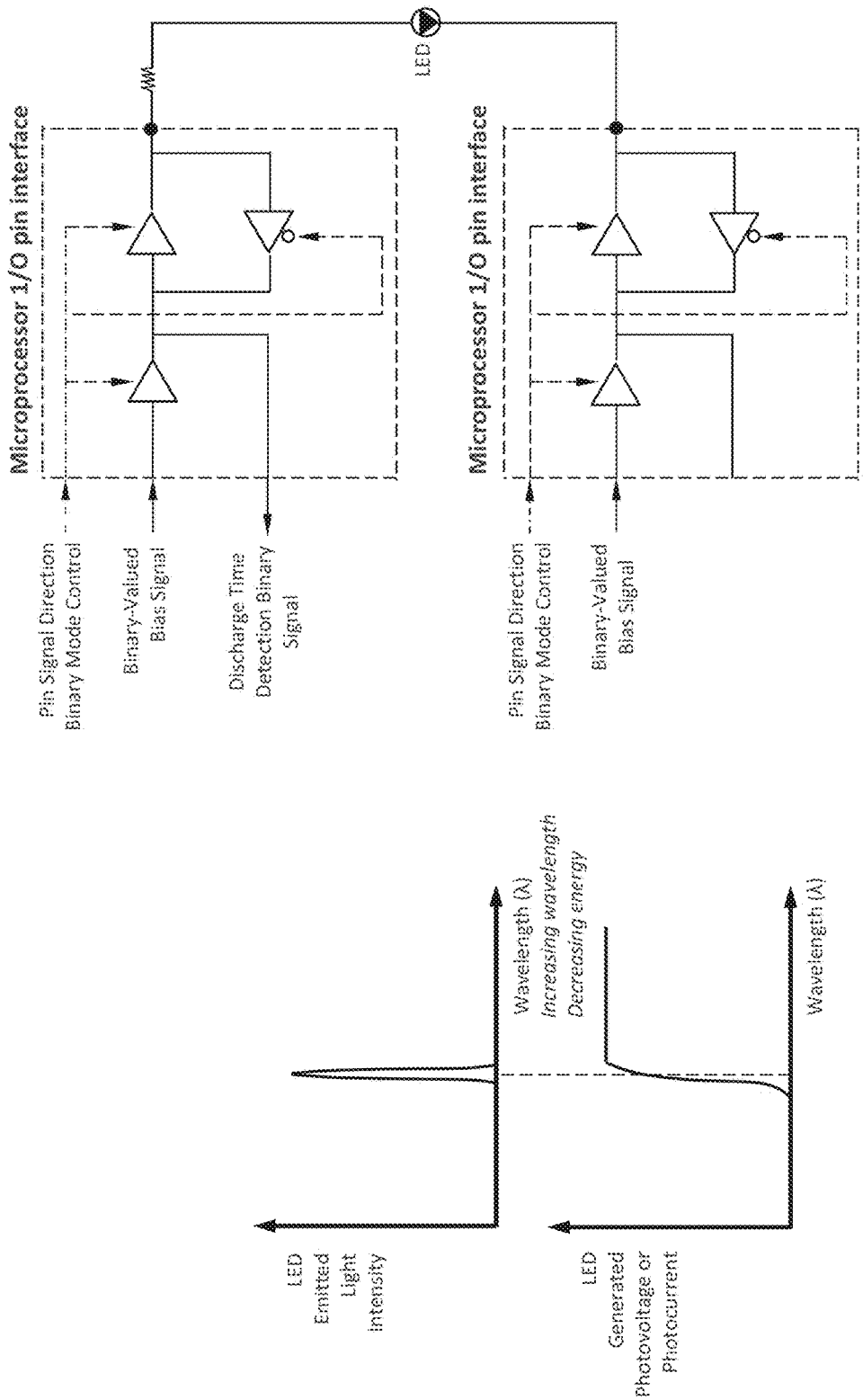

MICROPROCESSOR-CONTROLLED MICROFLUIDIC PLATFORM FOR PATHOGEN, TOXIN, BIOMARKER, AND CHEMICAL DETECTION WITH REMOVABLE UPDATABLE SENSOR ARRAY FOR FOOD AND WATER SAFETY, MEDICAL, AND LABORATORY APPLICATIONS

CROSS-REFERENCE TO RELATED CASES

This patent application claims priority from Provisional U.S. Patent Applications 61/595,651 and 61/595,681, both filed Feb. 6, 2012, as well as Provisional U.S. Patent Applications 61/595,692, 61/595,973, and 61/596,016, all filed Feb. 7, 2012, and Provisional U.S. Patent Applications 61/614,229 and 61/614,253, both filed Mar. 22, 2012, all seven of which are hereby incorporated by reference in their entirety.

COPYRIGHT & TRADEMARK NOTICES

A portion of the disclosure of this patent document may contain material, which is subject to copyright protection. Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

BACKGROUND OF THE INVENTION

Field of the Invention

The invention pertains to the area of miniature biochemical and chemical detectors for pathogens, biomarkers, toxins, and other materials, and more specifically to microprocessor-controlled microfluidic platform technologies comprising such miniature biochemical and chemical detectors. In various embodiments the invention provides a framework for and family of platform technologies for a next generation of pathogen, toxin, biomarker, and chemical sensor and analysis systems. The technology can be implemented in a small sized format and notably can be used for food and water safety testing in the field, distribution chain, laboratory, clinic, and home.

General Background

Humans, animals, crops, and the general environment are subject to many threats from pathogens, toxins, and disease. In the testing for these a vast diversity of diverse test frameworks, technologies, laboratory methods, and protocols have been devised, each incrementally building on existing and competing generations of test frameworks, technologies, laboratory methods, and protocols. Although competition among these can in principle reduce costs, in practice the diversity can increase costs and continually set the expenditure bar higher as one or another approach can do a superior job in some aspects but not other aspects. Large laboratories filled with large quantities of various expensive "required" technologies and materials become the entrenched solution. The volumes of manufacturing for the large diversity of evolving laboratory machines and materials are small, preventing meaningful economies of scale from being achieved or even envisioned, these high costs forces geographical and institutional centralization of testing with tremendous throughput, logistic, and economic barriers to the needed levels and most logical settings for monitoring, testing, and diagnosis.

In the approach put forth in the present invention, the immense diversity of aforedescribed evolving technologies and emerging alternative technologies can be mined for ranges of appropriate and adaptable component technologies that can, through careful systems design, be unified into a low cost platform capable of readily addressing many practical problems inherent in the needs for pathogen, toxin, and disease testing and monitoring and readily applicable to large manufacturing and distribution economies of scale. Further, the resulting technology base offers many additional applications to industry, R&D, the world's impoverished, and the economy.

Discussion begins first with a review of pathogens and toxins in food and water, followed by health and disease. This general background provides the setting for appreciating and understanding the value of the present invention.

Safety Improvement Opportunities in Food and Water Systems

There is vast need and concern for food and water safety domestically and worldwide. Outbreaks new of food-borne diseases in packaged, processed, and even locally produced food are ever-present in the developed world (costing lives, health, vast waste, and hundreds of millions of dollars) and of course viciously plague the undeveloped world (costing vast numbers of lives, health, and impeded economic development). Similarly, water quality has also been threatened by contamination, and as populations increase in areas involving farming, industry, mining, natural-gas/shale-oil "fracking," etc., the concerns are becoming more acute. Water quality is also involved in food safety as contaminated wash or process water can and has cause both biological and chemical food safety incidents. Further, both food and water are perpetual targets for terrorism, contamination by industrial dumping, mining, fossil-fuel drilling, waste-landfill leakage, waste-water handling failures, etc.

FIG. 1a depicts a simplified representation of large-scale commercial food distribution chains. At each point in the chain there is both the opportunity for food safety compromises and food safety testing. Because of the vast degree of (immensely multi-sourced) food aggregation and blending involved in processed foods (including ground meats, washed/packaged salad greens, basketed small tomatoes/fruits, as well as prepared meals, dairy products, and canned items), a small contamination incident or point source can widely propagate through massive amounts of products and geographic area. The ability to inexpensively and rapidly screen for a wide range of food pathogens and pollutants at every point in the chain would provide a tremendous step forward.

FIG. 1b depicts the smaller scale distribution arrangements associated with both "local food" trends in developed nations as well as the long-established systems and arrangements in rural areas and developing countries. Although the scales of individual food volumes are smaller in each instance of the depicted entities and steps than those associated with FIG. 1a, there far is less ability and framework to practically impose regulations, monitoring, and procedures than there are for the entities and steps in FIG. 1a. As a result, again there is considerable exposure to food contamination. Hereto, the ability to inexpensively and rapidly screen for a wide range of food pathogens and pollutants at every point in the chain would provide a tremendous step forward.

FIG. 2a depicts example large-scale water aggregation and distribution arrangements typically found at municipal, county, state, interstate, and in many cases (for example, shared rivers and lakes) international levels. As with the food network depicted in FIG. 1a, a small contamination incident or point source can widely propagate through massive amounts of products and geographic area, and the ability to inexpensively and rapidly screen for a wide range of water pathogens and pollutants at every point in the chain would provide a tremendous step forward.

Similarly, FIG. 2b depicts the smaller scale distribution arrangements associated with village, rural areas, individual farms, and homes found worldwide at all levels of economic development. There far is less ability and framework to practically impose regulations, monitoring, and procedures than there are for the entities and steps in FIG. 2a, and as a result, again there is considerable exposure to contamination. Once again, the ability to inexpensively and rapidly screen for a wide range of food pathogens and pollutants at every point in the chain would provide a tremendous step forward.

Creating a technology that can service such a vast range and scale of safety improvement opportunities in food and water systems must be small, inexpensive, fast, accurate, provide wide ranges of tests, include internal interpretation/analysis, and be easy to use, reliable, and constantly updated. Anything manufactured, be it a testing instrument or consumable items used by it, will be manufactured and distributed at a massive scale. The large manufacturing scale provides significantly many wide-ranging opportunities to reduce costs, create opportunities for a standard framework, and justify ongoing focused R&D to improve performance, capabilities, and ranges of applications. However, such a large manufacturing scale also increases the need for the technology to be realistically envisioned, thought-through, and carefully designed.

FIG. 3a depicts an example representation of how pathogens borne by food and/or water can be ingested by, absorbed by, and/or exposed to an organism (such as a human, animal, plant, etc.). In such a situation, a sample of the food or water can be presented to a pathogen detection process that is used to directly identify pathogens present in the food and/or water sample.

FIG. 3b depicts an example representation wherein pathogens borne by food and/or have already can be ingested by, absorbed by, and/or exposed to an organism and are now present in the organism. If a sample containing the pathogen can be obtained from the organism, that sample can be presented to a pathogen detection process that is used to directly identify pathogens present in that sample. In some cases the pathogen can be present in easily obtained bodily fluids or tissues of the organism, while in other cases biomarkers can be highly localized within tissues or confined fluids of the organism. (Biomarkers will be considered in extensive detail, but for the moment they can be regarded as indicators of a biological state.)

The above discussion motivates the need for testing of pathogens and toxins, at least in food and water. In many cases, however, the approach of FIG. 3b is not possible or not realistic. For example, the pathogen can have already been wiped out by the immune system, or can be in a part of the organism from which obtaining a sample is difficult, or the pathogen can be too rarefied within the organism to be adequately captured in the sample. In such cases, however, the pathogen could have induced a change in the biological state of the organism which can be identified by testing for biomarkers.

OVERVIEW OF THE INVENTION

The present patent application describes a platform technology for a next generation of pathogen, toxin, biomarker, and chemical sensor and analysis systems. The technology can be implemented in a small sized format and notably can be used for food and water safety testing in the field, distribution chain, laboratory, clinic, and home.

The invention provides a platform technology with rich ability to flexibly perform, create, deploy, maintain, and update a wide range of panels, assay, array, and/or sequence of tests for a wide range of substances and pathogens. The invention includes a unifying framework for widely-ranging miniature sensor implementation, fluidic/gas interfacing, electrical interfaces and optical interfaces, and further by collocating, allowing the integration a large number highly-selective sensors and chemical sensors—together as needed with appropriately selected supplemental sensors (for example temperature, pH, selective ions, etc.), into a common readily-manufacturable framework. The diverse sensor arrays give rise to statistical enhancing through novel statistical processing approaches.

The microprocessor-controlled microfluidic platform for pathogen, biomarker, toxin, and chemical detection with removable replaceable element comprising an updatable sensor media for field applications to food safety, water safety, clinical diagnosis, medical monitoring, and environmental monitoring. The invention is deployable and useable in a wide range of situations previously unavailable, and addresses many otherwise problematic aspects of field testing for food safety, water safety, epidemic outbreaks, routine diagnosis, and disease monitoring.

Additionally, various component methods, technologies, and approaches as well as additional natural extensions of the invention further provide for a wide range of other applications including:

Environmental monitors
Manufacturing monitors
Advanced cell incubators,
Infection process control and monitoring instruments,
Sequential or multipath biochemical reactors,
Cell signaling emulation environment instruments.

As the methods, technologies, and approaches comprised by the invention naturally provide a multiple-application platform technology framework, once employed for commercial manufacture and use in one or more initial application areas, the same underlying technology can be directly used or readily adapted as a platform to a serve wide range of entirely different medical and industrial applications. This will result in even greater broader use as a basic underlying platform technology as perfected higher-performance lower-cost manufacturing can then be further accelerated by the economies of scale resulting from the large resulting markets and institutionalized acceptance of the value of the invention's paradigms,

BRIEF DESCRIPTION OF THE DRAWINGS

The above and other aspects, features and advantages of the present invention will become more apparent upon consideration of the following description of preferred embodiments taken in conjunction with the accompanying drawing figures, wherein:

FIG. 1a depicts a simplified representation of large-scale commercial food distribution chains.

FIG. 1b depicts the smaller scale distribution arrangements associated with both "local food" trends in developed nations as well as the long-established systems and arrangements in rural areas and developing countries.

FIG. 4b depicts some examples of how the arrangement represented in FIG. 4a can influenced throughout by one or more other competitive or incidental materials or processes that can corrupt the four measurement scenarios represented in FIG. 4a.

FIG. 4c depicts some examples of how the arrangement represented in FIG. 4a can be influenced throughout by one or more noise sources or processes that can corrupt the four example measurement scenarios represented in FIG. 4a.

FIG. 14, adapted from world wide web at—flowcyt.salk.edu/fluo.html (visited Jan. 26, 2013), provides a table of some example fluorophores, their typical probe function, excitation wavelength, emission wavelength, and molecular weight.

FIG. 15, adapted from Table 1 of Conroy, S. Hearty, P. Leonard, R. O'Kennedy, "Antibody Production, Design and Use for Sensor-Based Applications," *Seminars in Cell &*

*Developmental Biology* 20 (2009), pp. 10-26, provides a table of example polyclonal and monoclonal antibody-based sensors and their associated analytes and transducers.

FIGS. 16a-16b provide a table of example commercially-available antibodies (for example, as provided by Santa Cruz Biotechnologies) that can be used in the aforedescribed electrochemical bioFETs, and optical sensors to detect these pathogens with high selectivity.

FIG. 17 provides a table of example antibodies for the detection of various example strains of Influenza.

FIG. 18, adapted from Table 1.4 of K. Jain, *The Handbook of Biomarkers*, ISBN 160761684X, Springer, 2010, provides a table of example autoimmune disorders under study for autoantibodies as predictors for disease.

FIG. 19, adapted from Table 3 of I. Tothill, "Sensors for Cancer Markers Diagnosis," *Seminars in Cell & Developmental Biology* 20 (2009), pp. 55-62, provides a table of example sensors for cancer biomarkers analysis.

FIG. 20, adapted from Table 1 of I. Tothill, "Sensors for Cancer Markers Diagnosis," *Seminars in Cell & Developmental Biology* 20 (2009), pp. 55-62, provides a table of example known biomarker associated with cancer diagnosis and prognosis.

FIG. 21 provides a table of example conditions, example associated biomarkers, and example antibodies responsive to those biomarkers.

FIG. 22 provides a table of additional example conditions and example associated biomarkers.

FIG. 23 depicts a high-level representation of the technical hierarchy of the invention.

Figure 24:
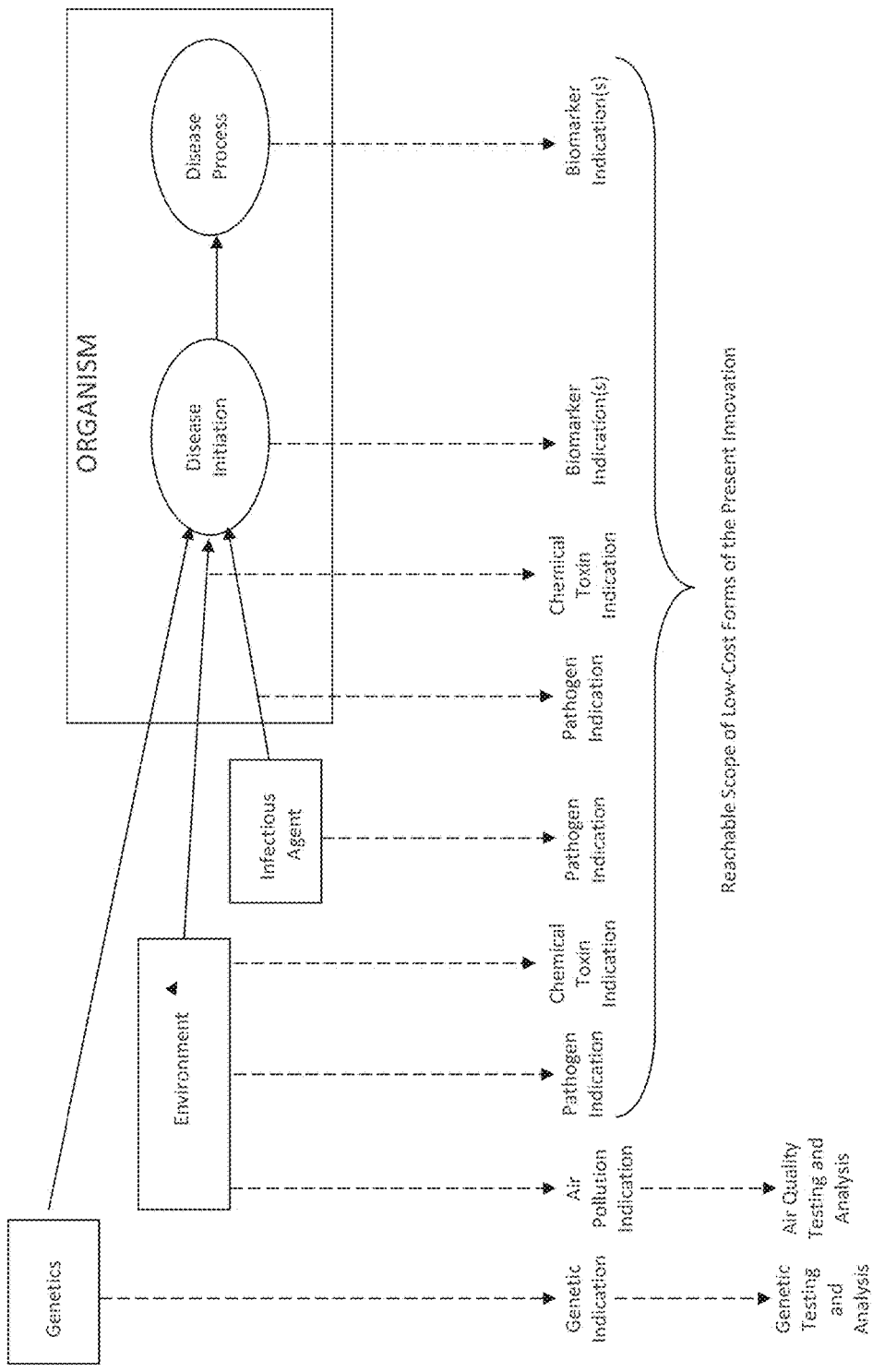

FIG. 24 depicts sensing opportunities, span by the bracket, that lie within the reachable scope of low-cost forms of the present invention.

Figure 25:
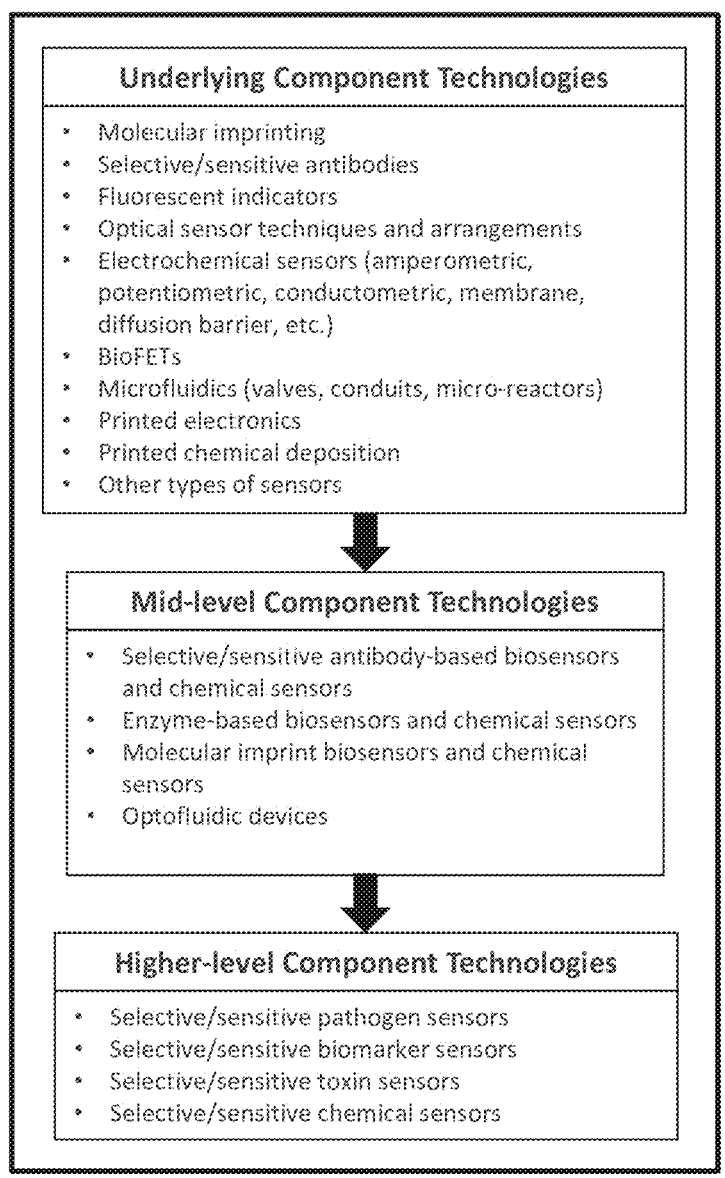

FIG. 25 depicts a representation of a starting point for understanding the invention based on new and adapted individual component technologies provided for by the invention.

Figure 26:
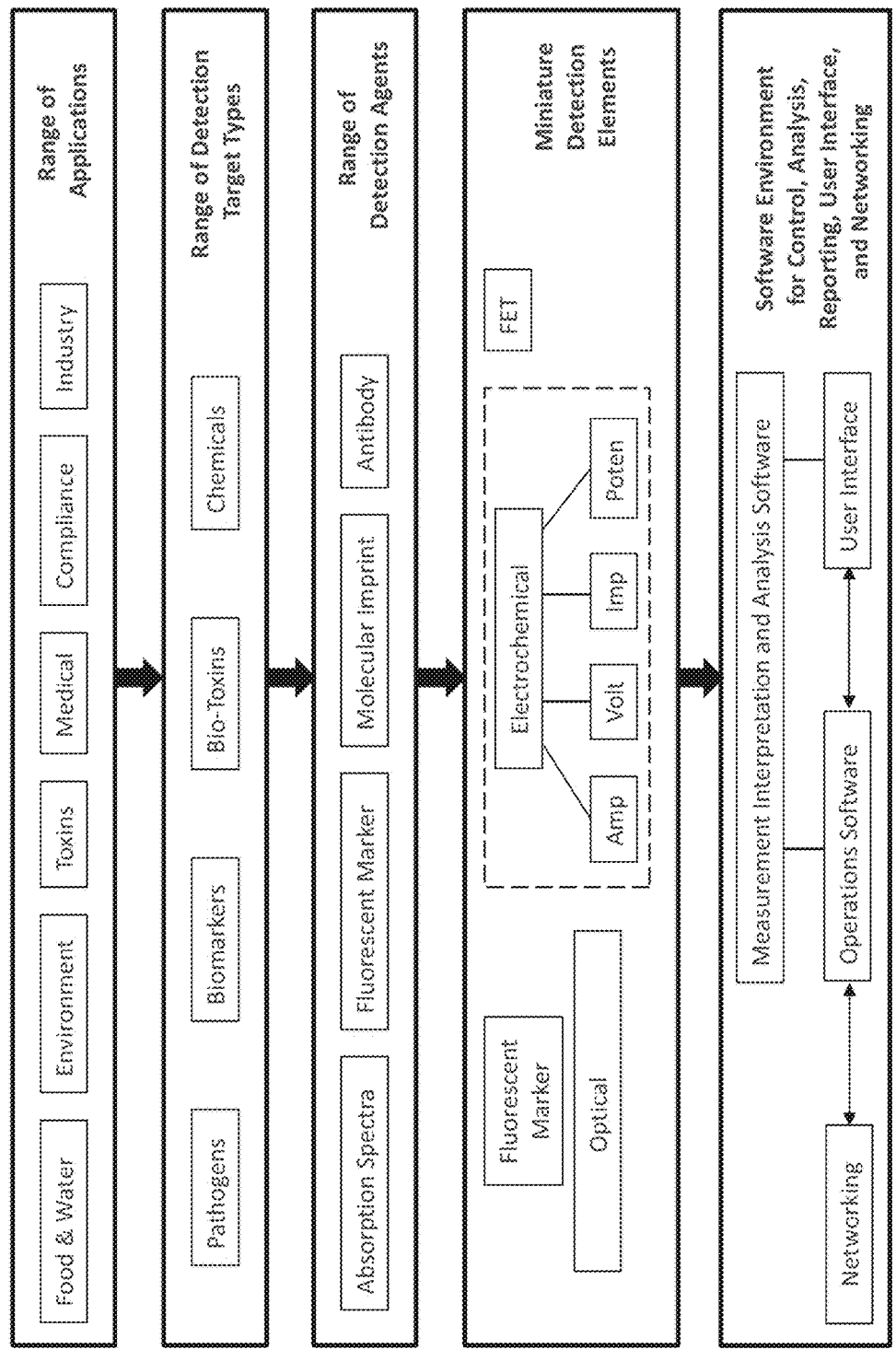

FIG. 26 depicts an example representation of the synergistic and adaptive framework provided and performed by the invention so as to create a flexible multiple-purpose platform technology.

Figure 27:
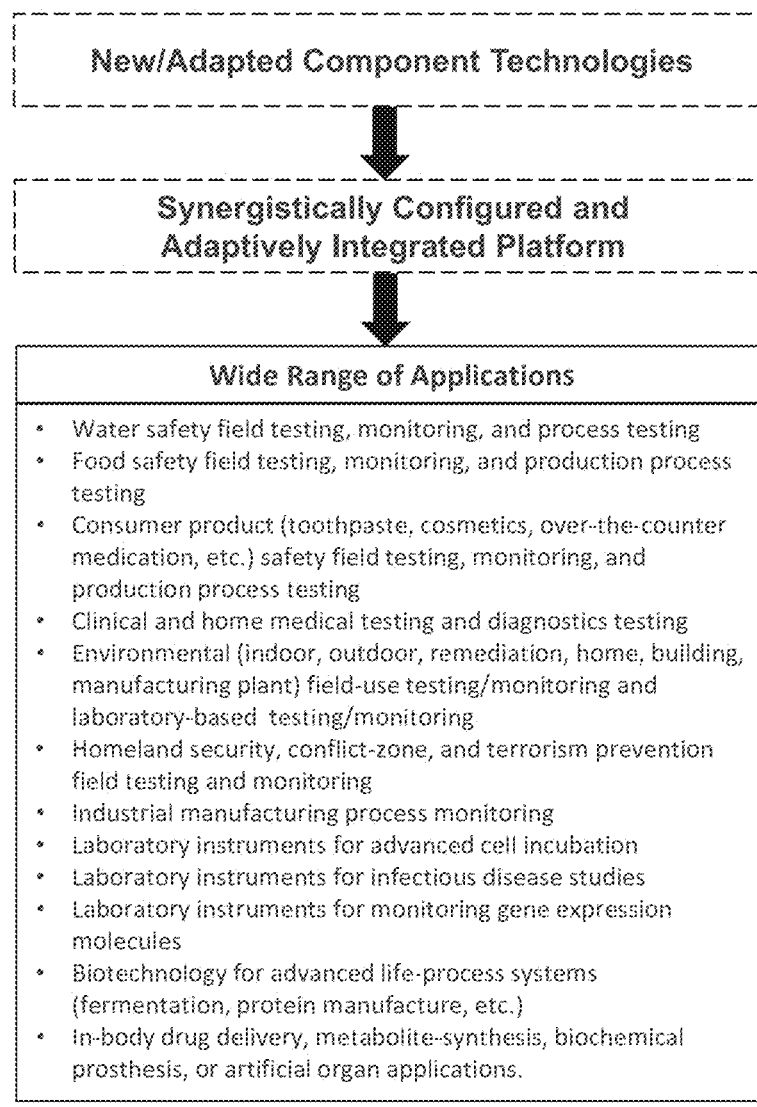

FIG. 27 depicts a representation of how the resulting flexible multiple-purpose platform technology can be leveraged to enable a wide range of embodiments and applications.

Figure 28:
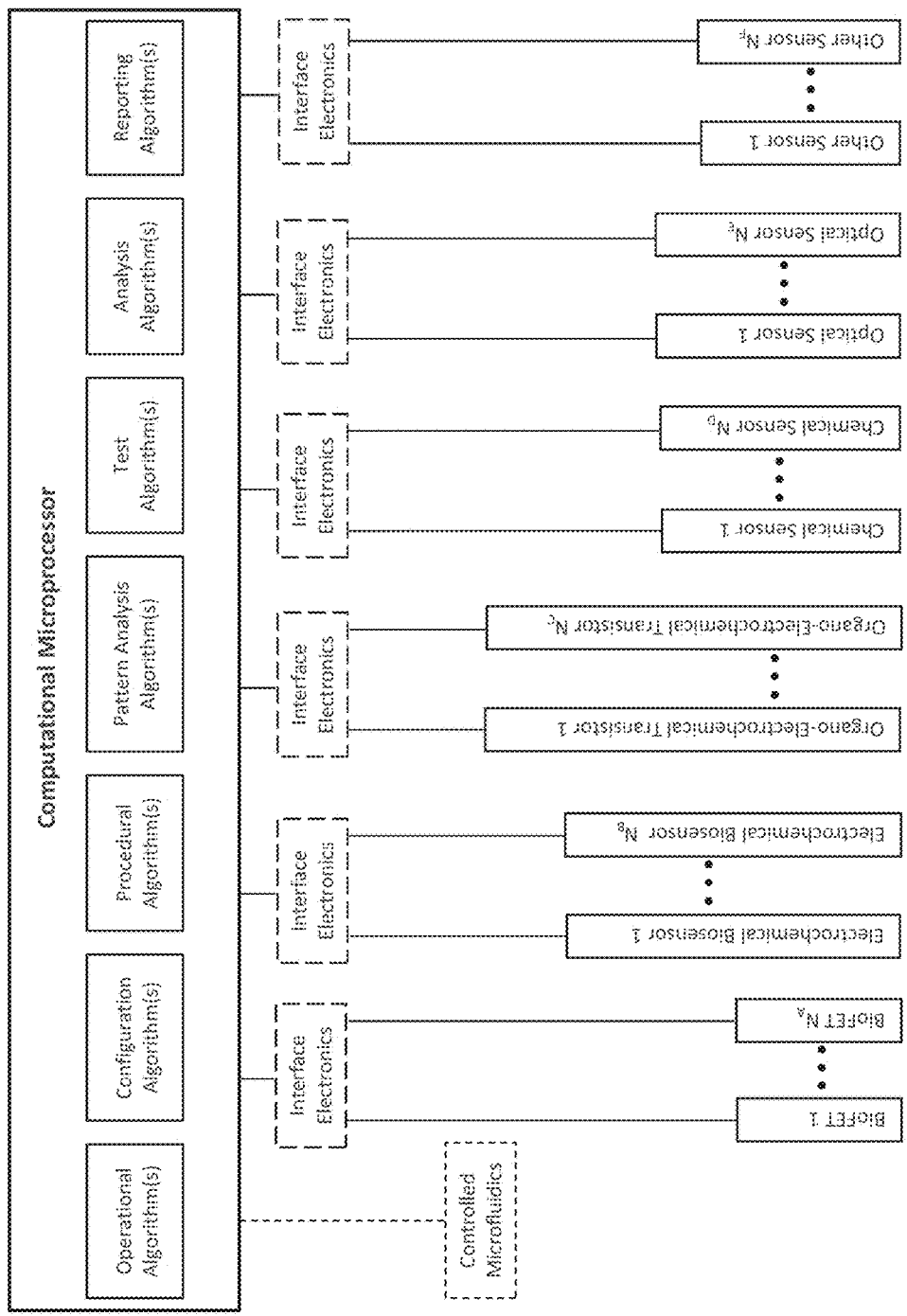

FIG. 28 depicts an overall overview of the software, signal input hardware, signal processing hardware, and software-control hardware provided for or implemented in various embodiments of the invention.

Figure 29:
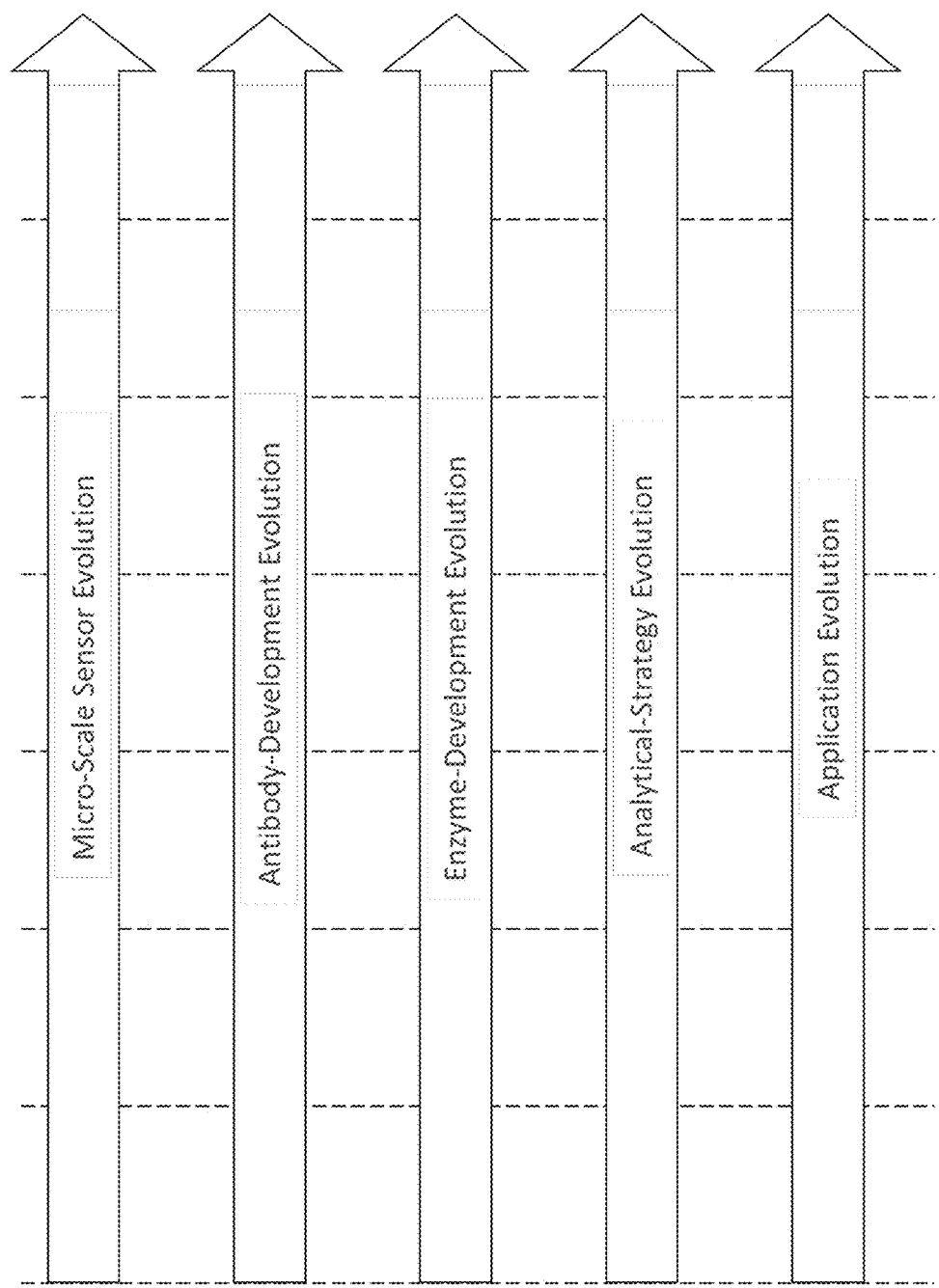

FIG. 29 depicts how technologies and materials applicable to the invention are anticipated to continue to evolve over time.

Figure 30:
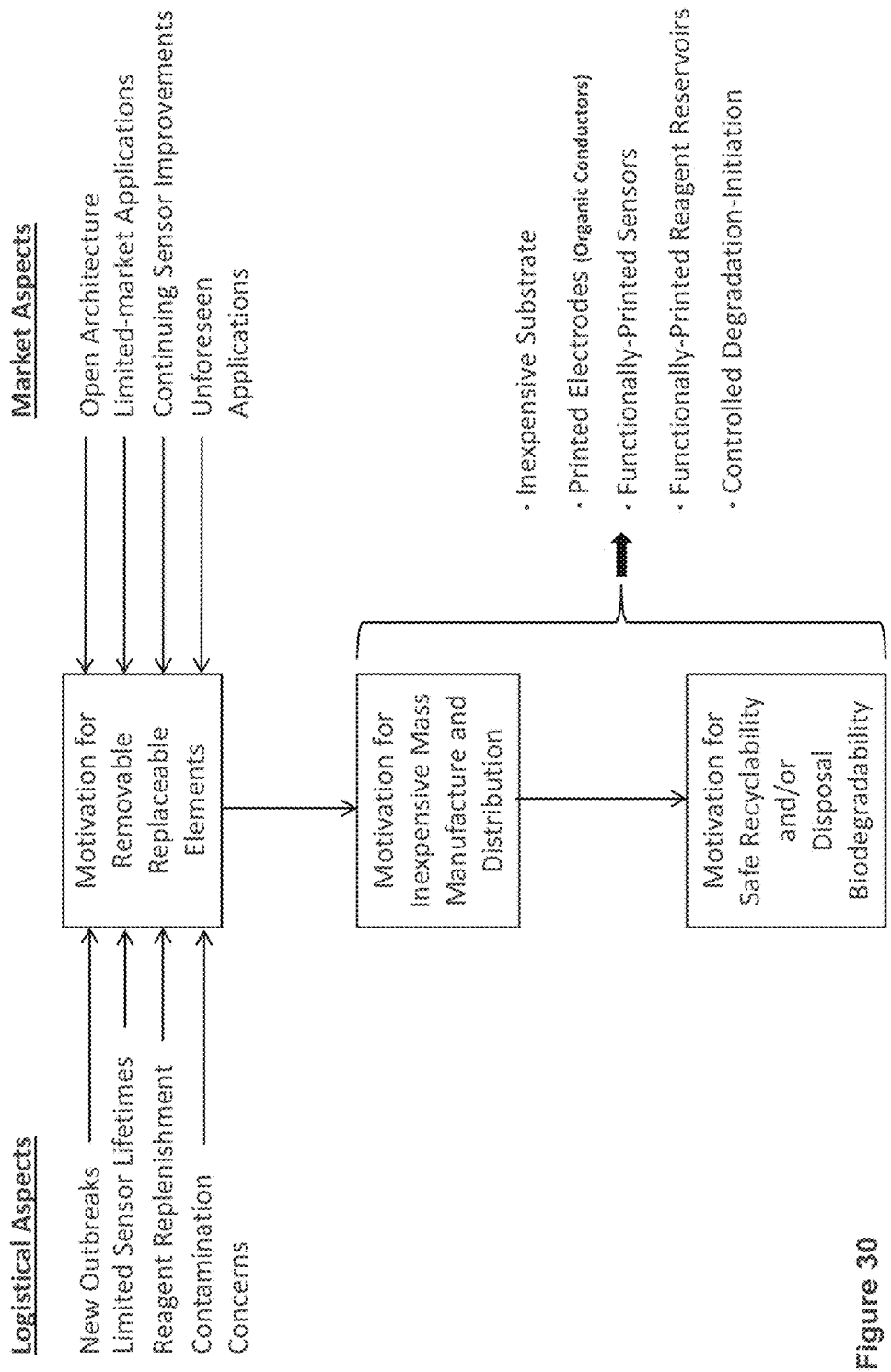

FIG. 30 depicts the broader market, logistics, economics, life-cycle, bio-hazard containment, materials recycling, and environmental considerations for the invention.

Figure 31A:
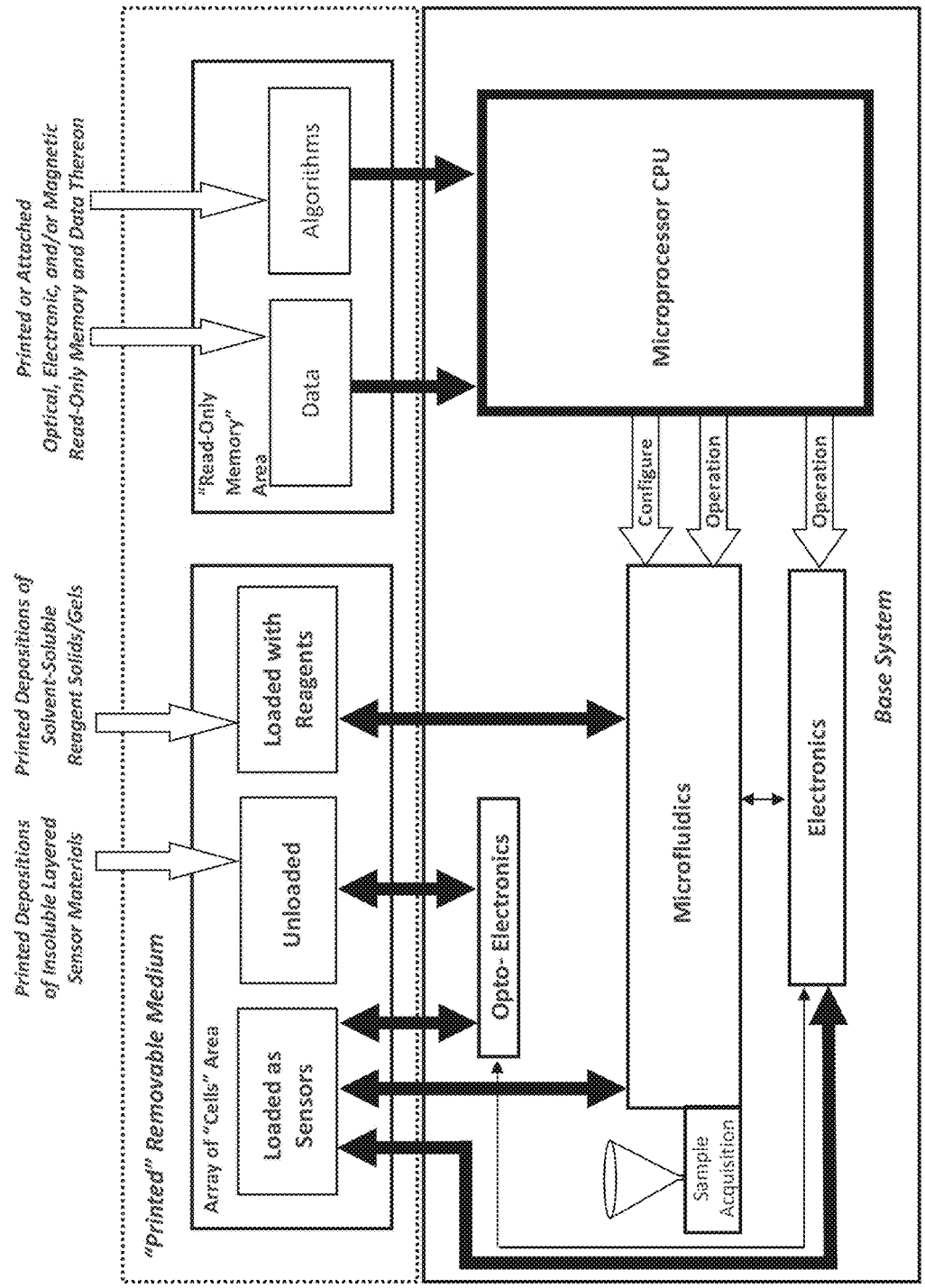

FIG. 31a depicts a representation of one example of many possible implementations of the invention.

Figure 31B:
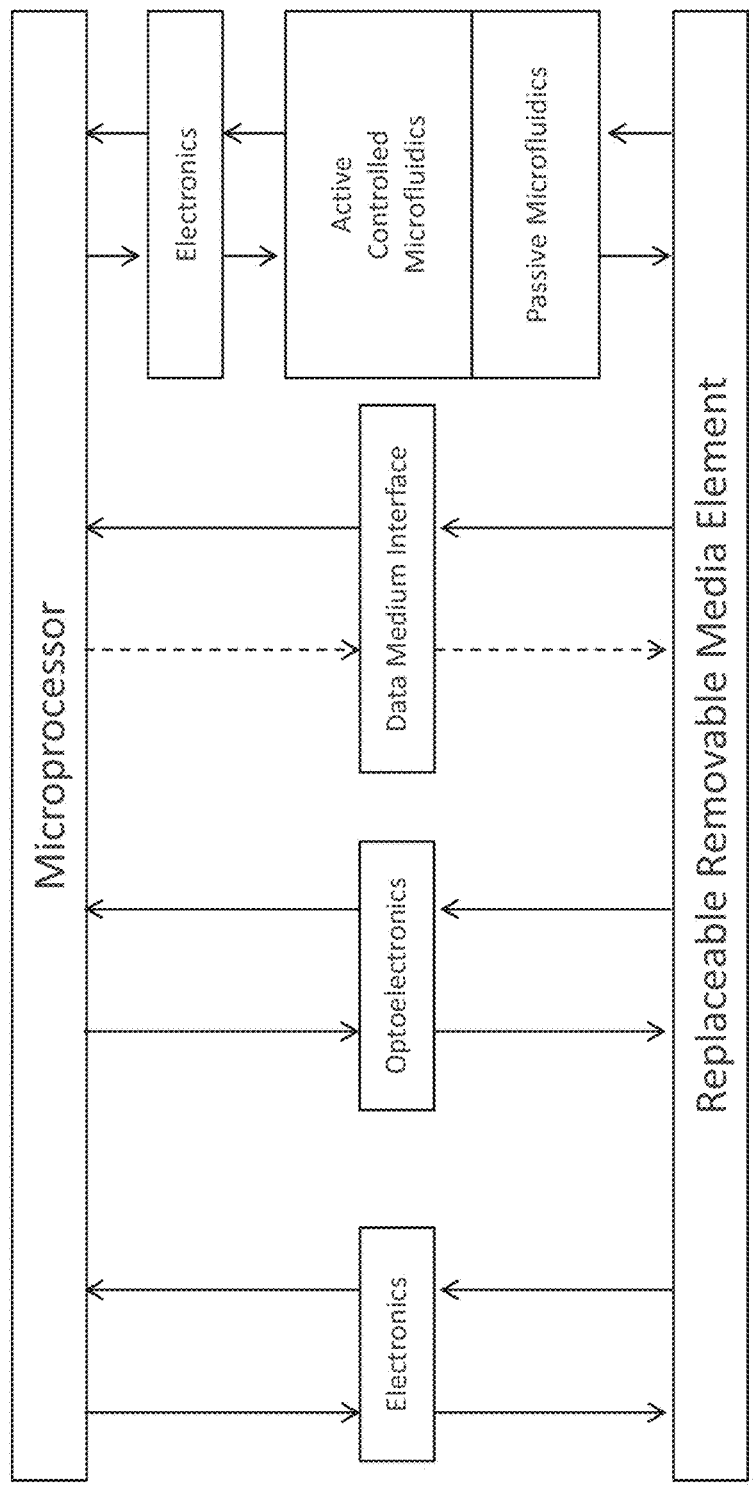
Figure 32A:
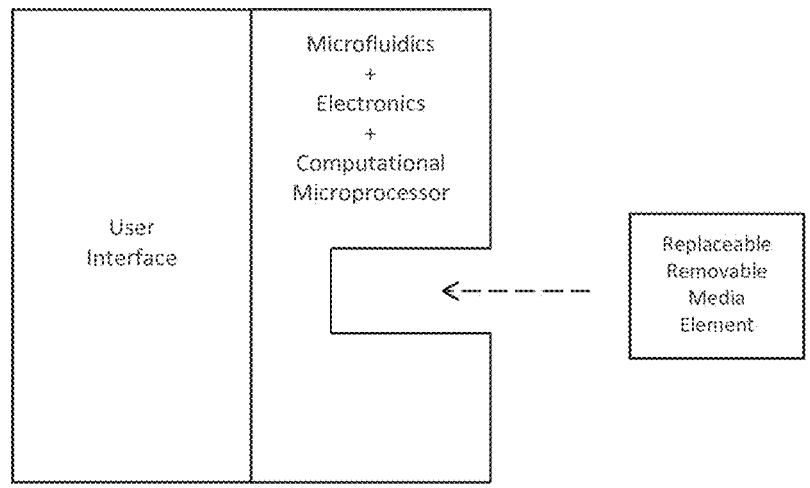
Figure 32B:
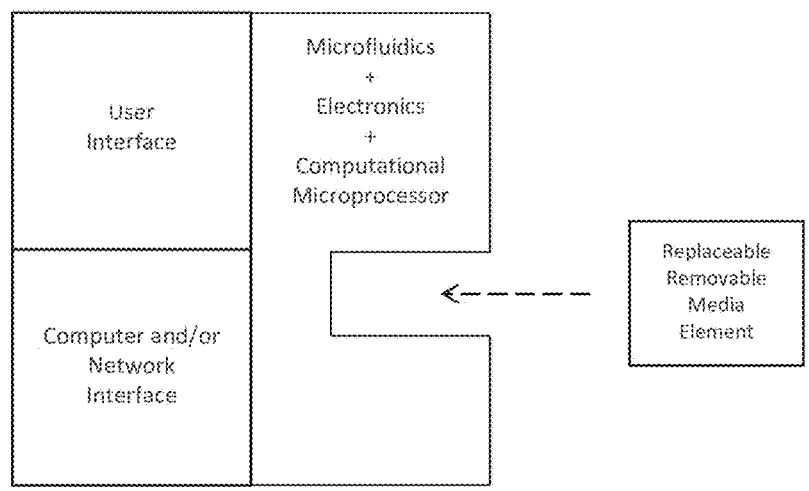
Figure 32C:
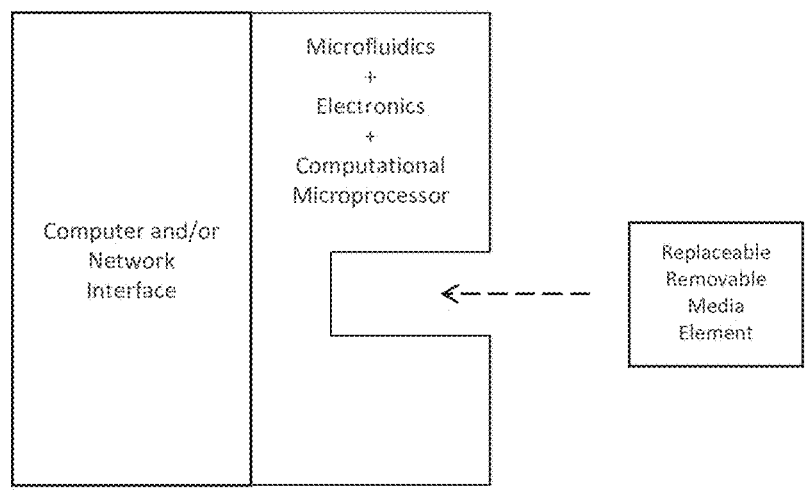

FIG. 31b depicts a simple high-level combined signal-flow and fluidic-flow representation of one example of many possible implementations of the invention FIG. 32 depicts simple high-level representations of examples of many possible user and interface implementations of the invention. FIG. 32a depicts an arrangement that comprises an internal user interface, which in turn can comprise for example software, user-operated controls, visual display elements, etc. FIG. 32b depicts a variation on the example arrangement of FIG. 32a wherein either or both of a computer interface (USB, Bluetooth, IR, etc.) and/or network interface (wireless LAN, wireless WAN, cellular, cabled-LAN, telephone land-line, etc.) is also provided. Similarly, FIG. 32c depicts a variation on the example arrangement of FIG. 32b wherein either or both of a computer interface (USB, Bluetooth, IR, etc.) and/or network interface (wireless LAN, wireless WAN, cellular, cabled-LAN, telephone land-line, etc.) is also provided, but in this example there is no internal user interface.

Figure 33:

FIG. 33 depicts an example representation of a timeline wherein after initial embodiments aimed at food and water safety are introduced, medical, health care, and industrial applications are then introduced, all supported with the hardware and systems framework described thus far and to follow.

Figure 34A:
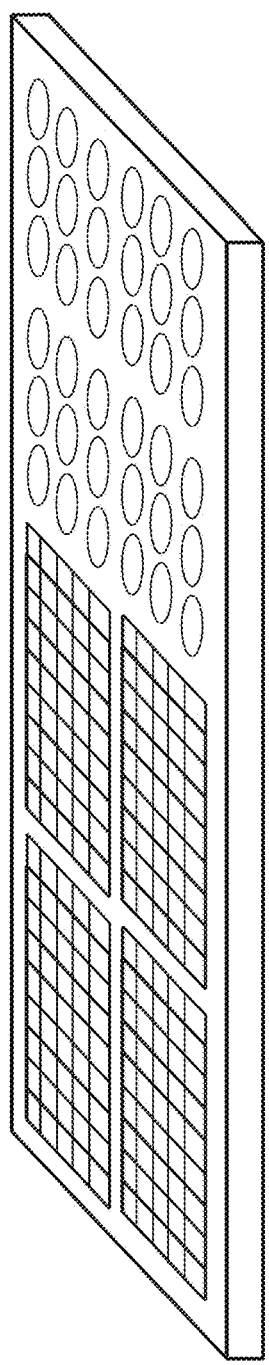
Figure 34B:
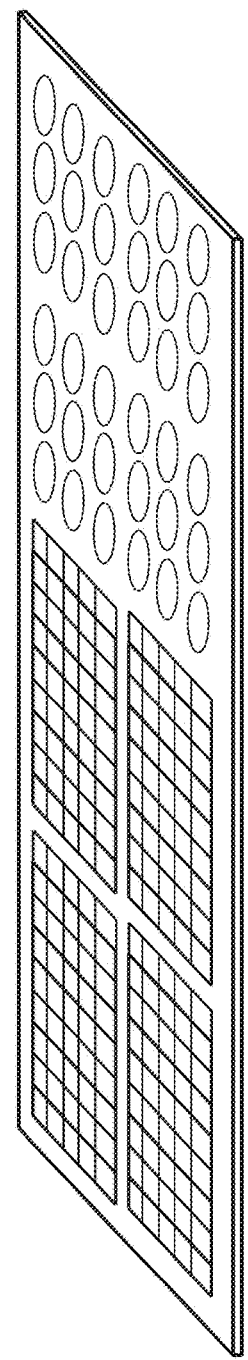
Figure 34C:
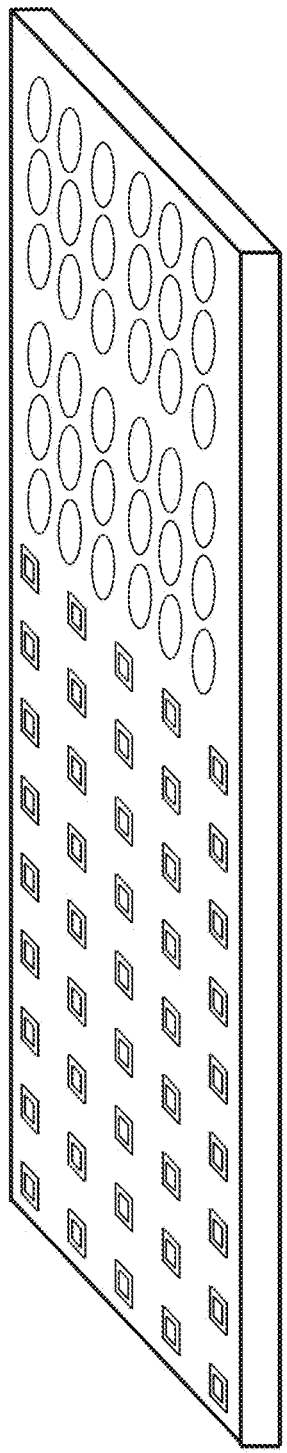

FIGS. 34a and 34b depict representations of example aspects of the removable replaceable media element. FIG. 34a depicts a thick removable replaceable media element, and FIG. 34b depicts a thin removable replaceable media element, FIG. 34c depicts an example variation on the arrangements depicted in FIG. 34a and FIG. 34b wherein printed deposits are separated by wider boundaries than those of the example arrangements depicted in FIG. 34a and FIG. 34b.

Figure 34D:
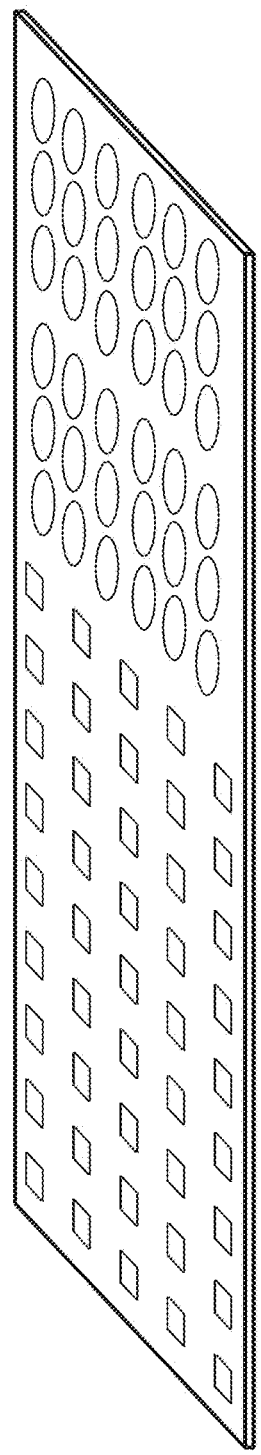

FIG. 34d depicts another example variation wherein indented wells are separated by wider boundaries than those of the example arrangements depicted in FIG. 34a and FIG. 34b.

Figure 34E:
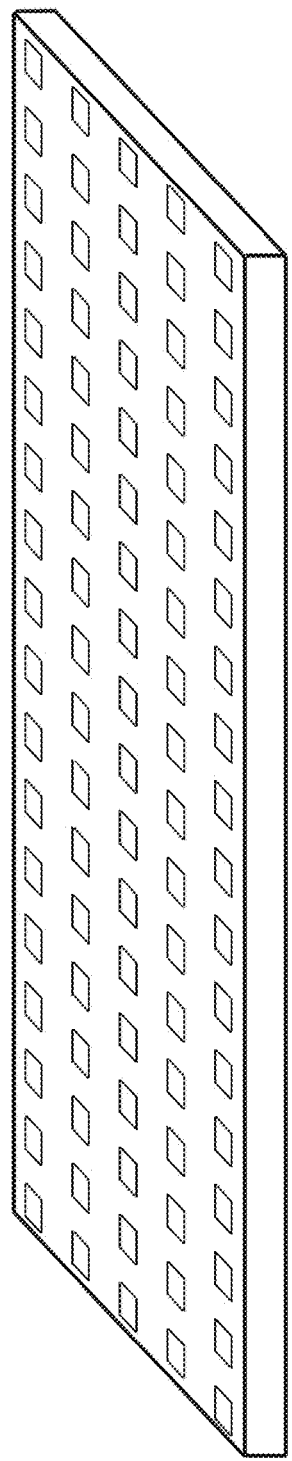

FIG. 34e an example variation on the arrangements depicted in FIG. 34a and FIG. 34b wherein printed deposits are only of one shape employed uniformly throughout.

Figure 34F:
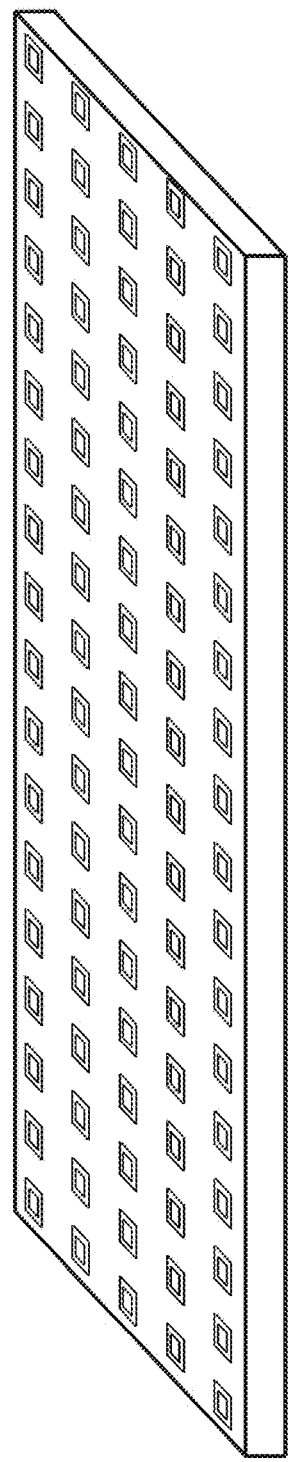
Figure 35A:
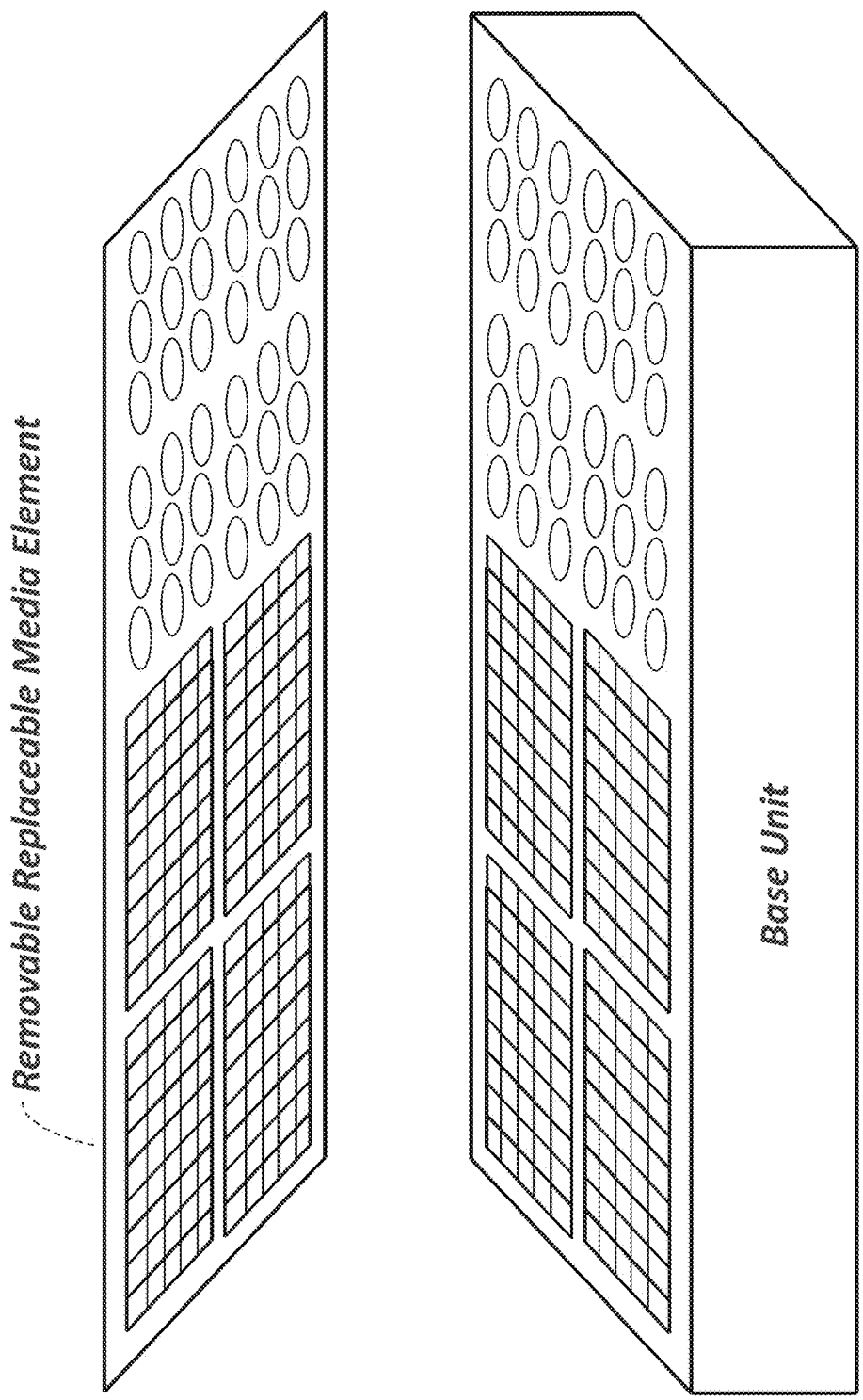

FIG. 34f depicts another example variation wherein indented wells are only of one shape employed uniformly throughout FIG. 35a depicts a representation of an abstract example illustrating how specific "sites" (comprising one or more sensors, reagent deposit, etc.) on a removable replaceable media element match up with associated site interface areas provided by a base unit, here where each of the example square/rectangular sites depicted are provided with their own separate interfacing arrangement.

Figure 35B:
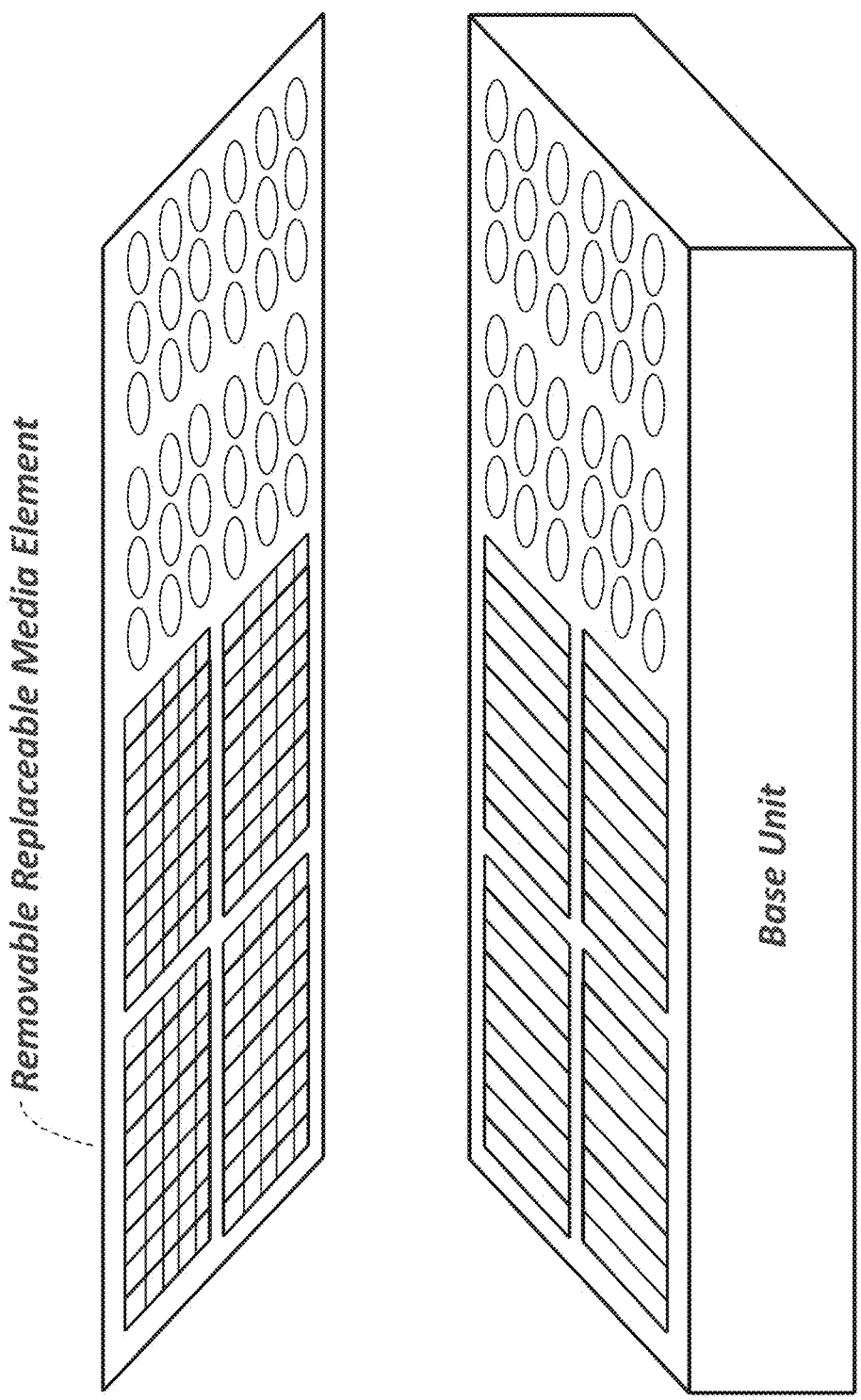

FIG. 35b depicts a variation on the example arrangement of FIG. 35a wherein small groups of multiple sites on the removable replaceable media element share a common interface arrangement—for example to provide multiple (non-interacting) sensors (comprised by the group of sites sharing that same interface arrangement instance) to be presented with the same analyte.

Figure 35C:
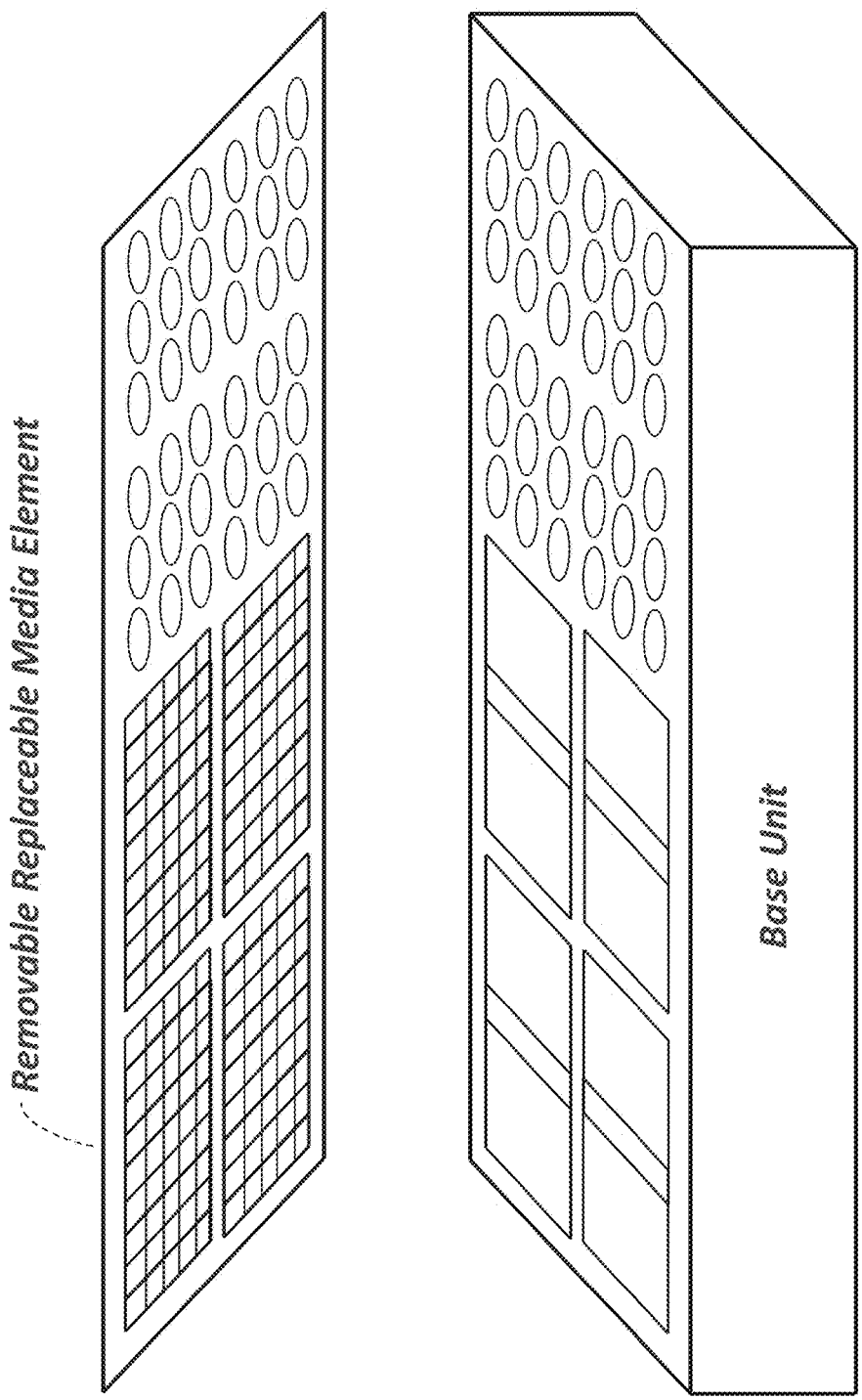

FIG. 35c depicts a variation on the example arrangement of FIG. 35a wherein larger groups of multiple sites on the removable replaceable media element share a common interface arrangement.

Figure 35E:
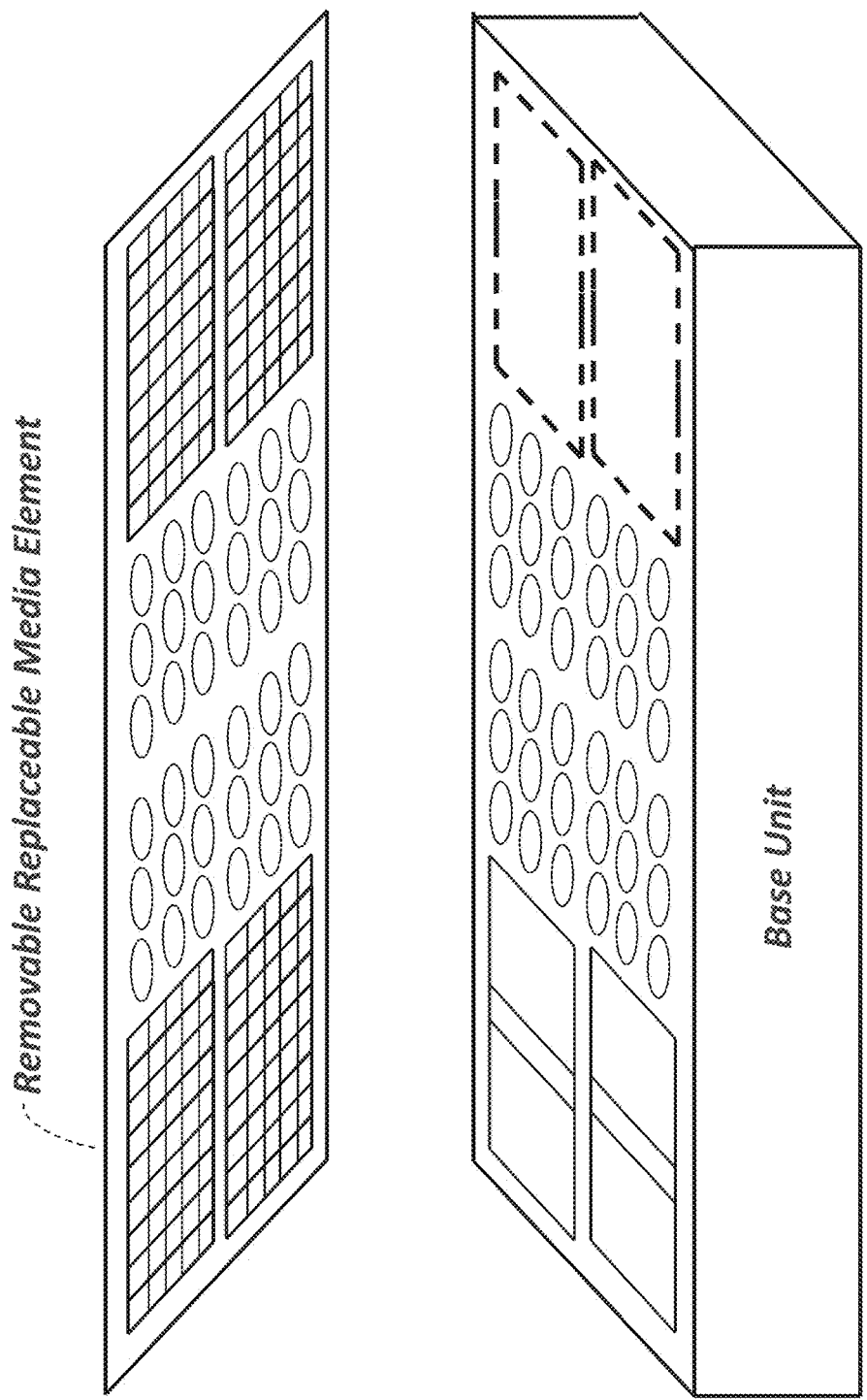

FIG. 35d depicts one exemplary arrangement with provisions for one or more removable replaceable interface modules associated with a particular subset of the base unit, as suggested by the dashed insert cavities. FIG. 35e depicts a second exemplary arrangement with provisions for one or more removable replaceable interface modules associated with a particular subset of the base unit, as suggested by the dashed insert cavities.

Figure 35F:
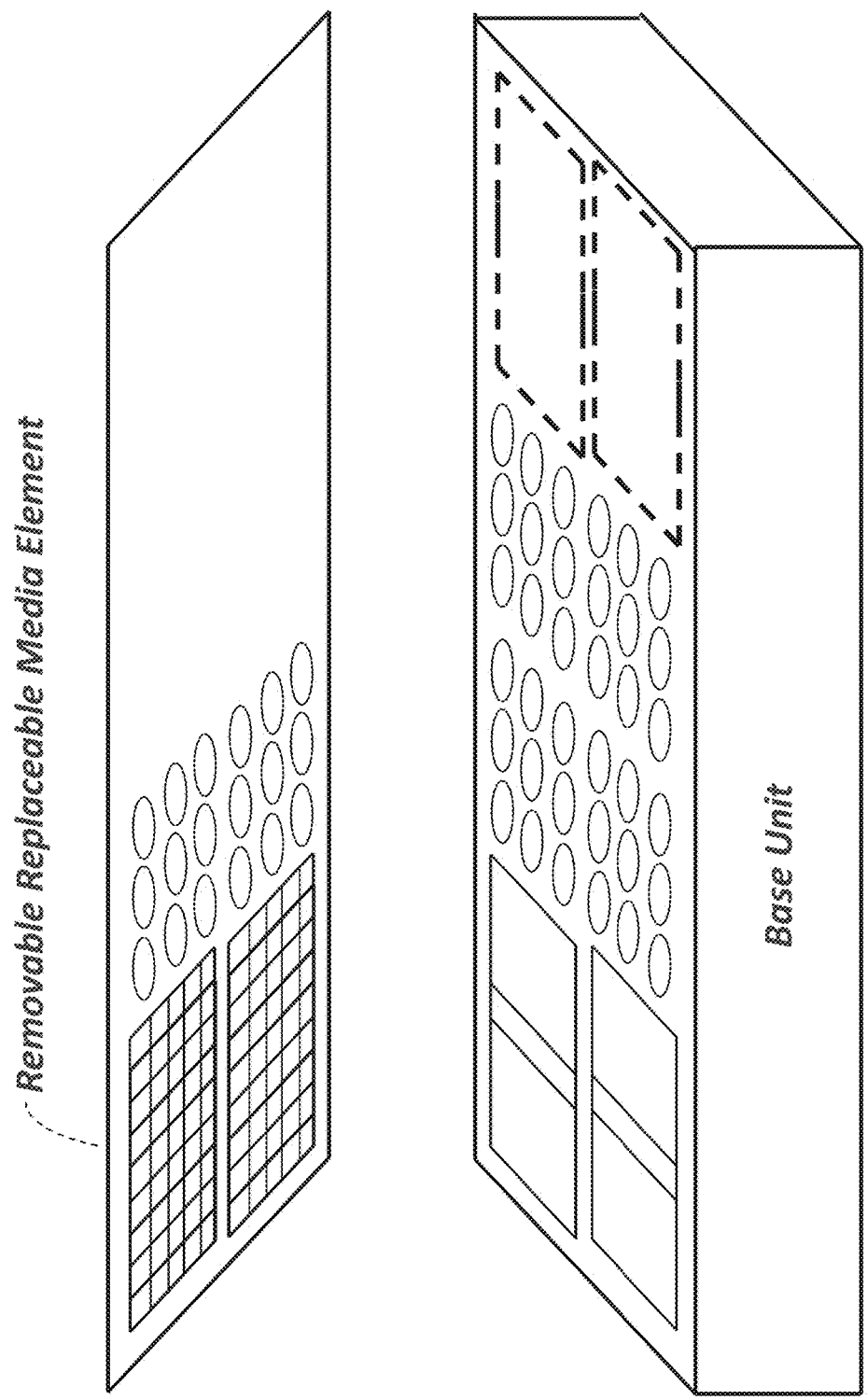

FIG. 35f depicts an example wherein the removable replaceable media element is selectively populated in only particular selected regions.

Figure 35G:
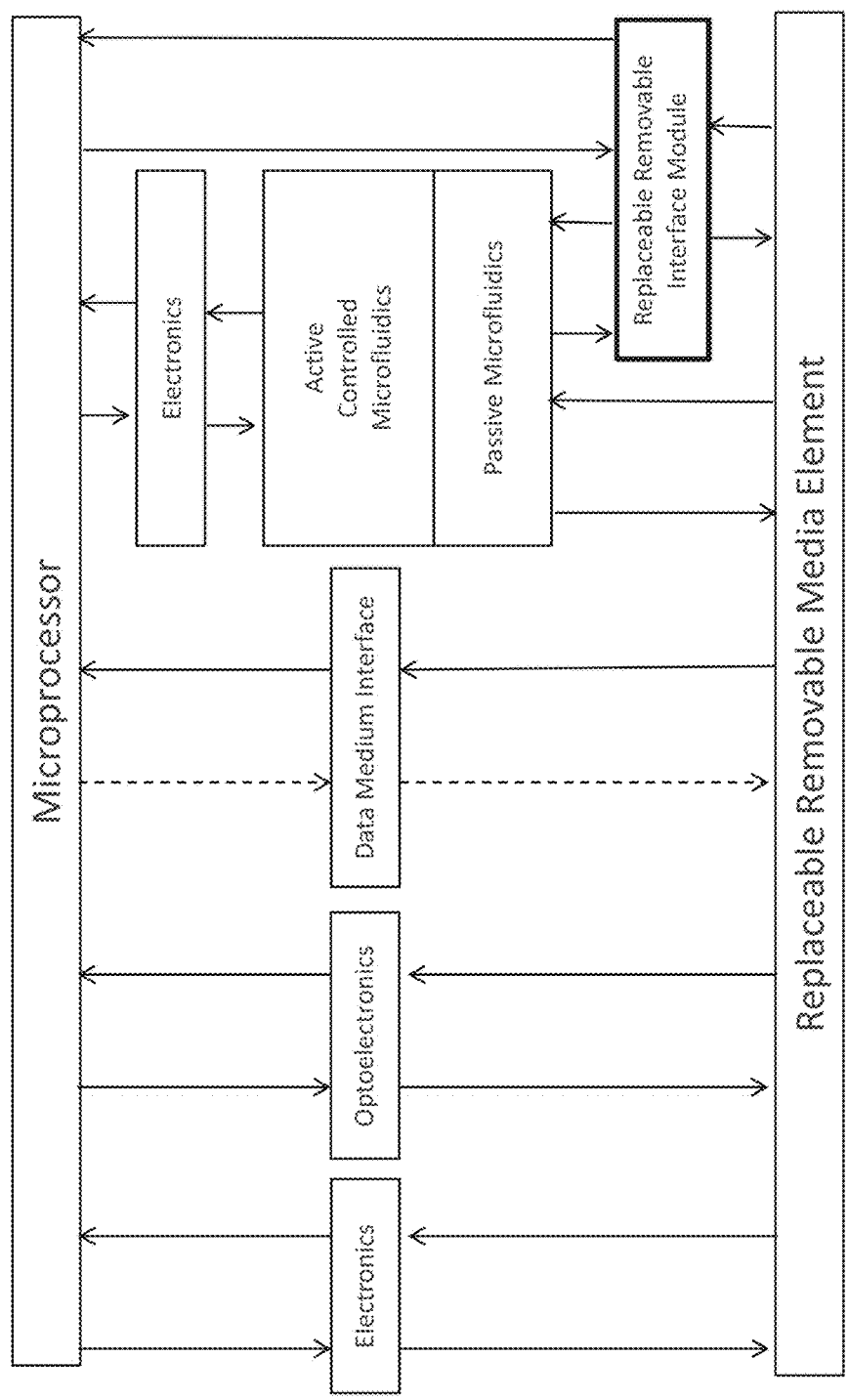

FIG. 35g depicts an example adaptation of the example architectural arrangement provided in FIG. 31b wherein a removable replaceable interface module is provided interfaces to the microfluidics and computing infrastructure.

Figure 36B:
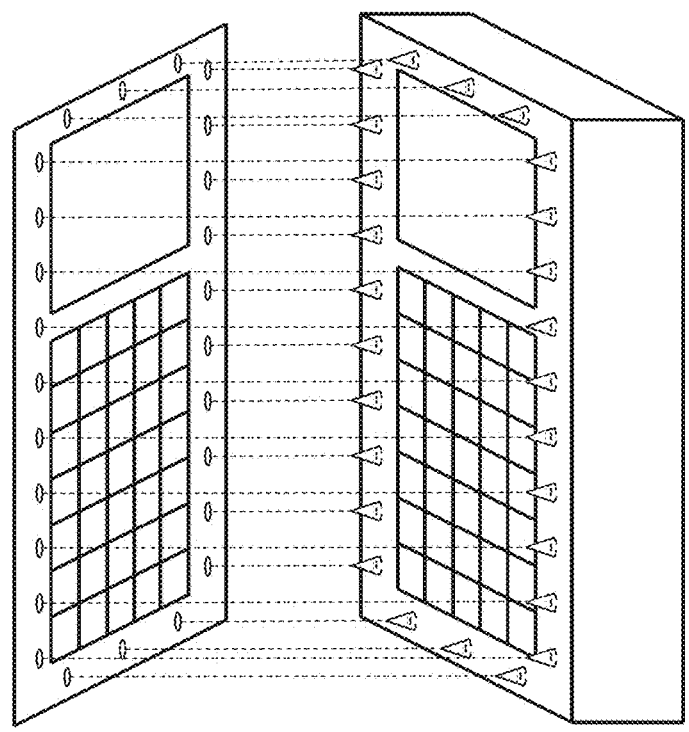
Figure 36A:
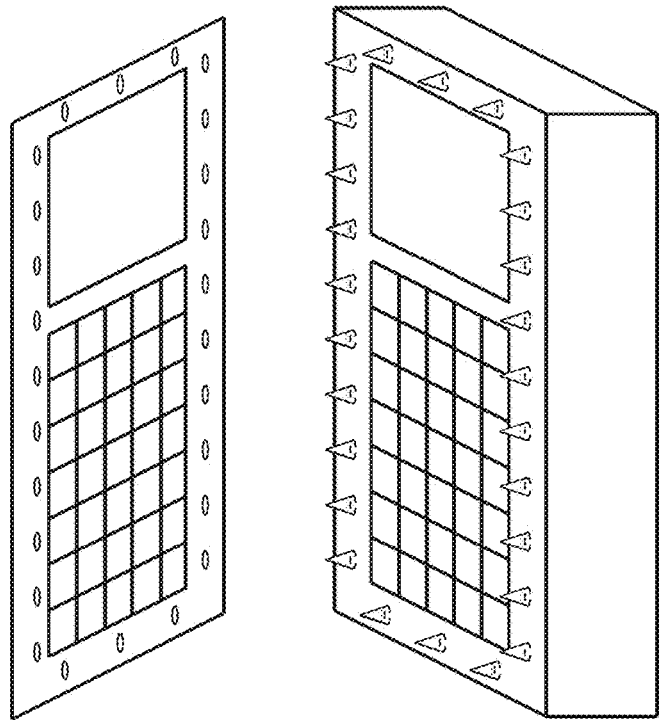

FIG. 36a depicts a representation of an abstract example removable replaceable media element and example precision alignment holes and the corresponding interface surface within the larger base unit.

FIG. 36b depicts a representation of an abstract example of how the alignment pins provided by the interface surface within the larger base unit align the removable replaceable media element by matching the hole locations in the removable replaceable media element.

Figure 36D:
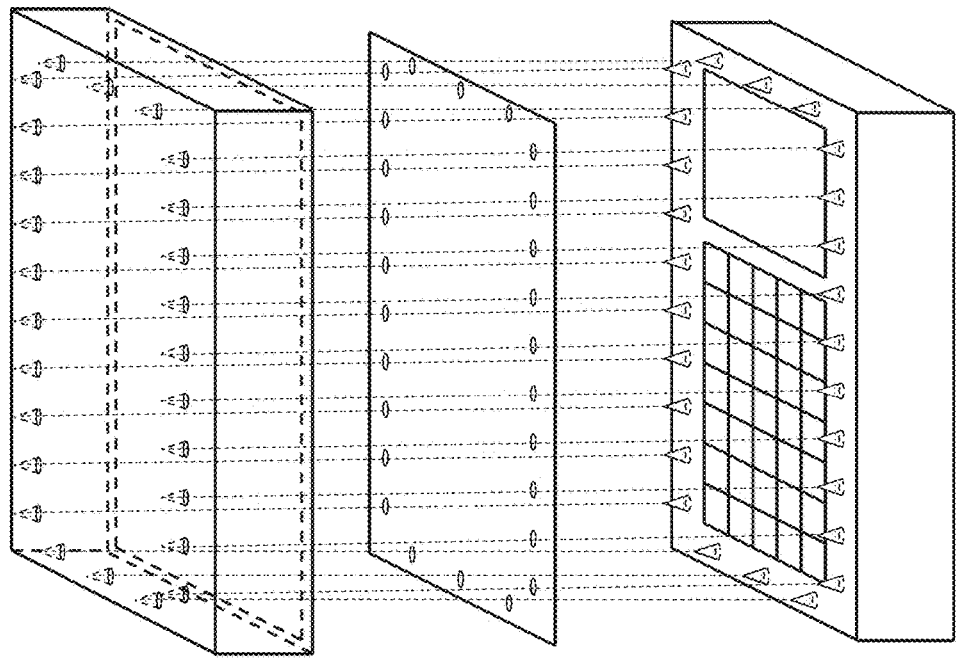
Figure 36C:
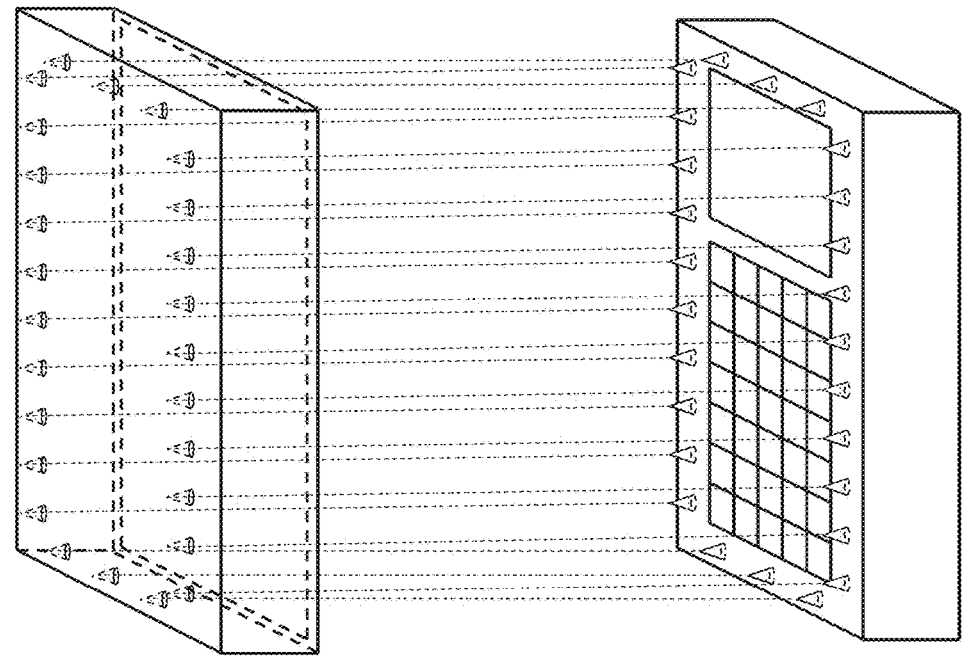

FIG. 36c depicts a representation of an abstract example of the interface surface within the larger base unit and a corresponding "lid" within the larger base unit having holes matching the alignment pins provided by the interface surface within the larger base unit.

FIG. 36d depicts a representation of an example of how the removable replaceable media element, interface surface within the larger base unit, and lid within the larger base unit align so as to provide precise alignment and fluid-tight contact between the removable replaceable media element and the interface surface within the larger base unit.

Figure 37:
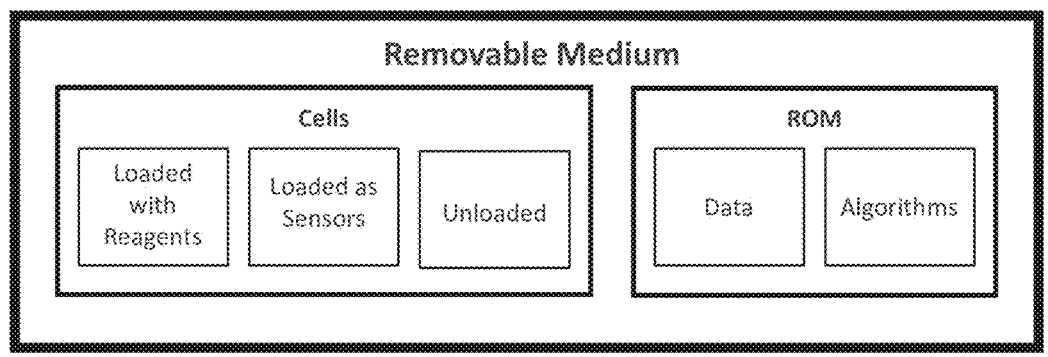

FIG. 37 depicts an example abstract representation of a removable replaceable media element used previously as part of FIG. 31a.

Figure 38:
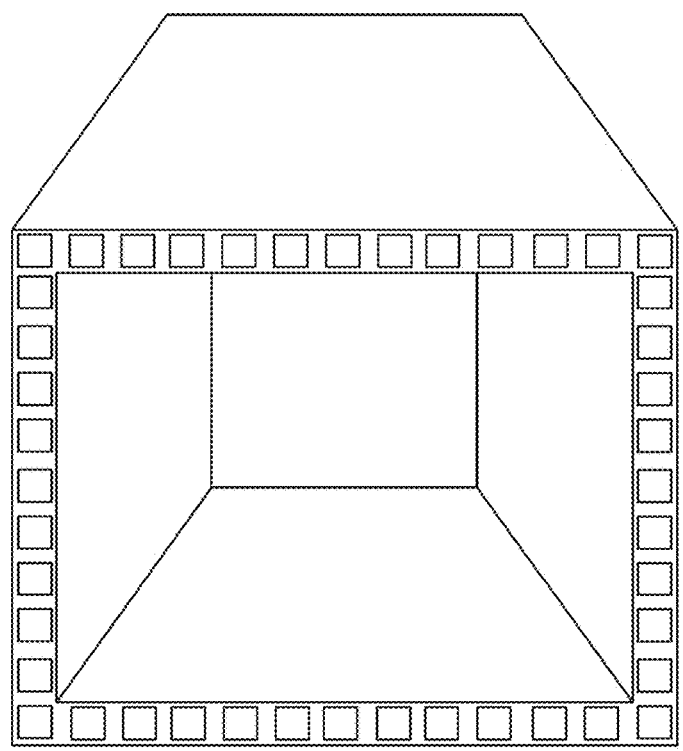

FIG. 38 depicts an example representation of the offset bottom view of a "cap" that meets and covers each site on the removable replaceable media element with a fluid-tight seal.

FIG. 39a depicts an example representation showing the "cap" described above (without attention to fluidic ports, electrical connections, mechanical support, etc.) interfacing with a site on the removable replaceable media element.

Figure 39B:
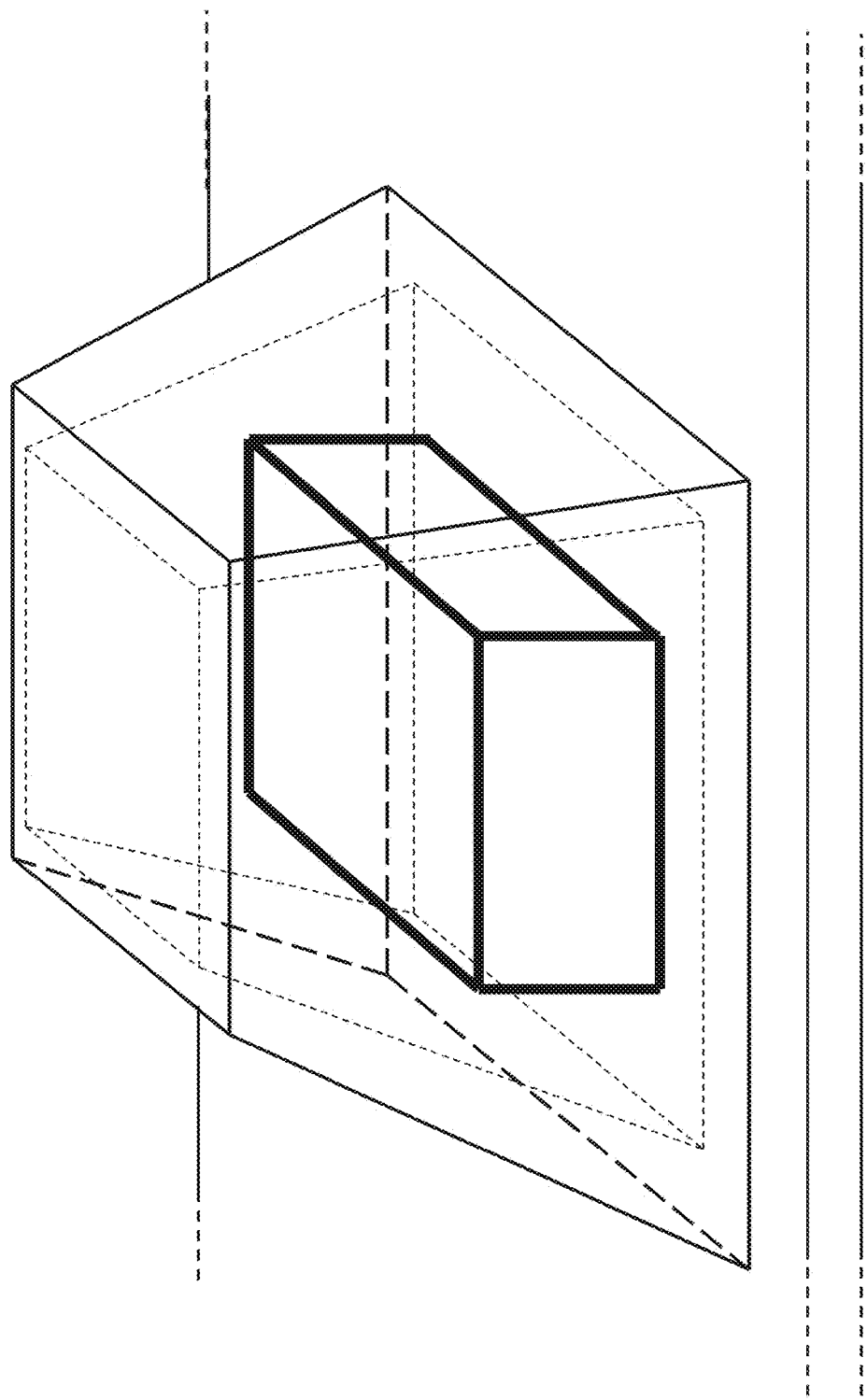

FIG. 39b depicts an example representation wherein the "cap" covers a site on the removable replaceable media element that comprises a printed sensor (here abstractly represented as a bold rectangular solid).

Figure 39C:
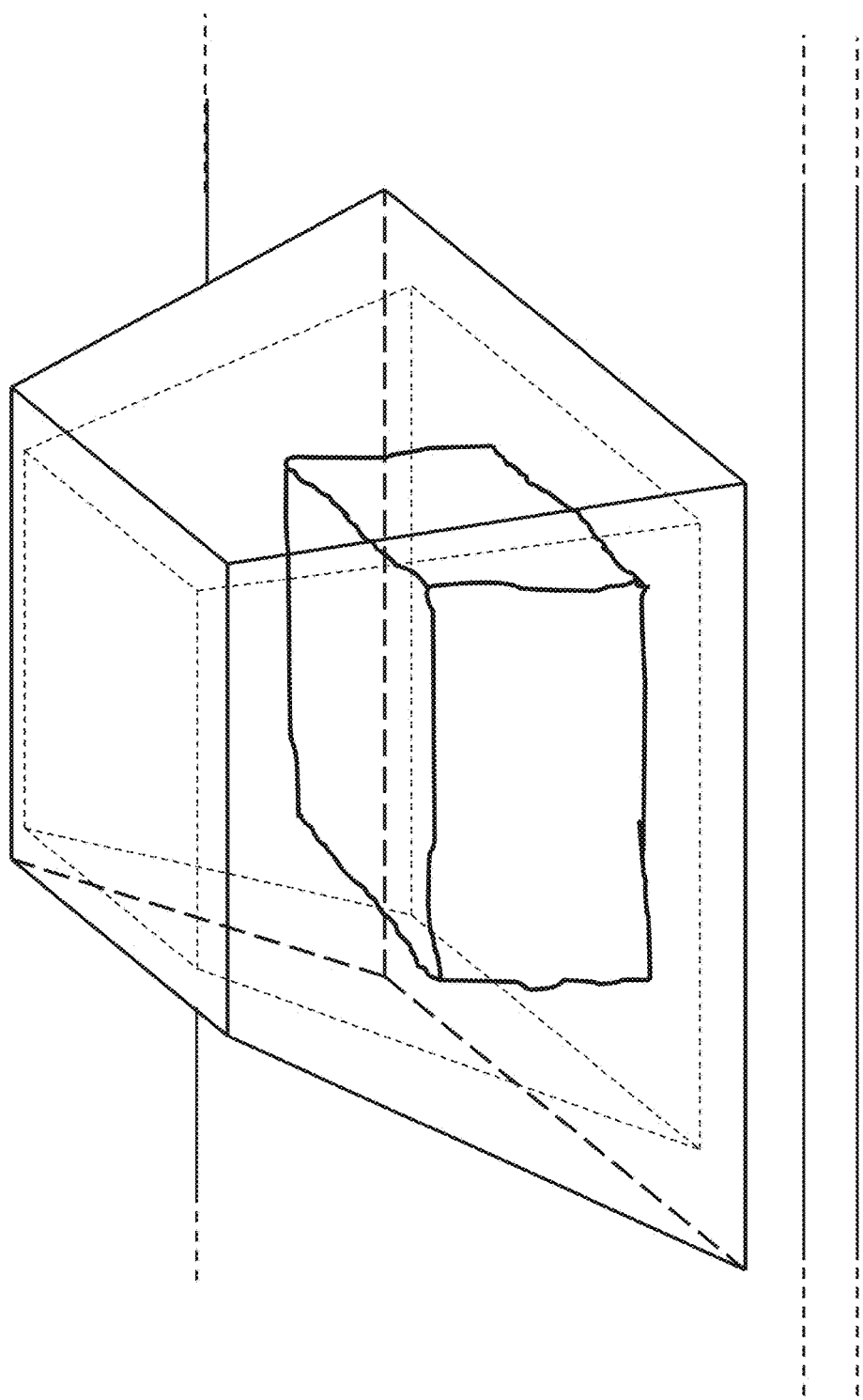

FIG. 39c depicts an example representation wherein a "cap" for covering an area within a removable replaceable media element that comprises a printed deposition comprising, for example, a solvent-soluble solid or gel in turn comprising a solvent-soluble reagent.

Figure 40A:
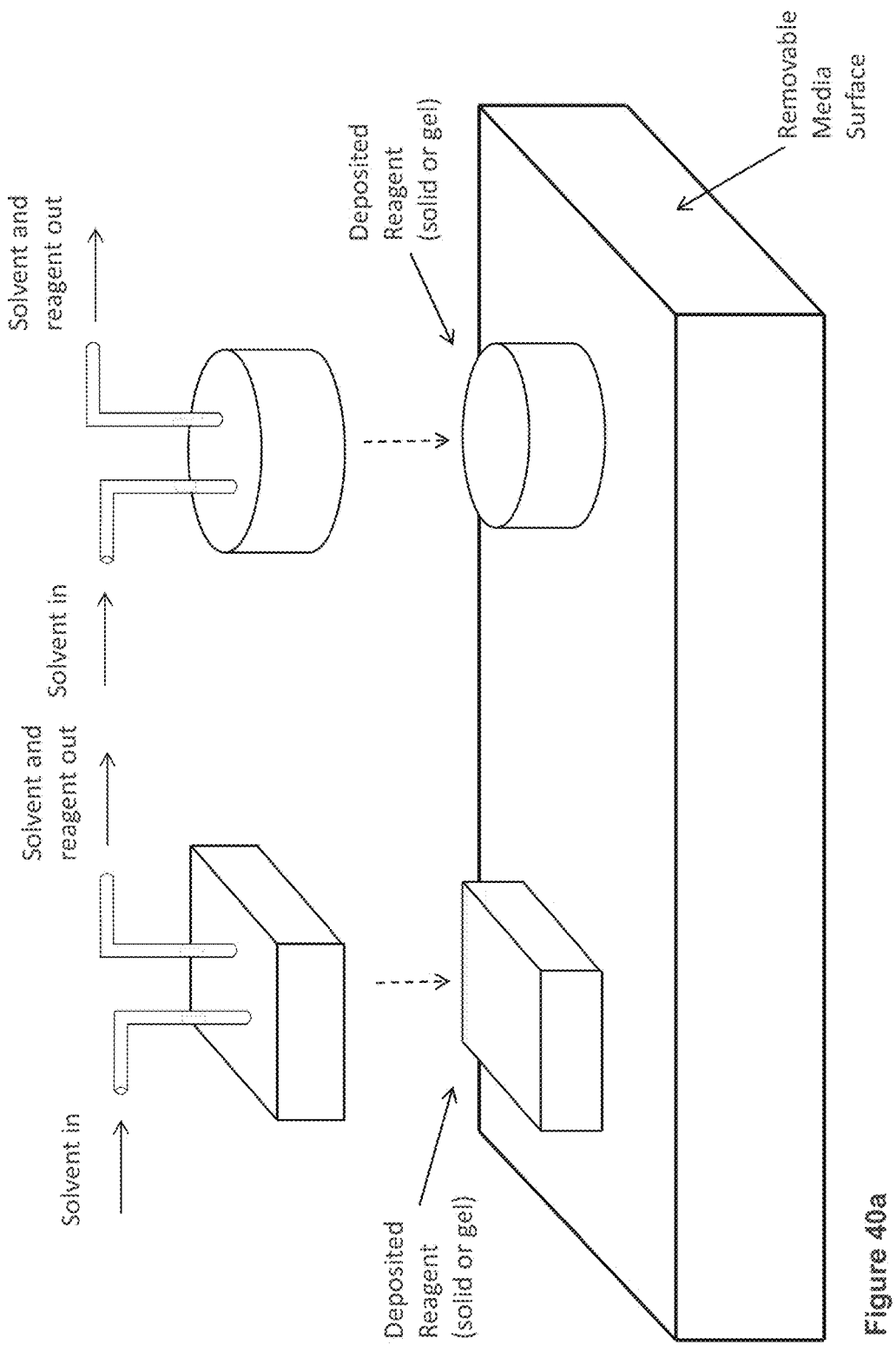

FIG. 40a depicts an example representation wherein the "cap" (for covering an area within a removable replaceable media element that comprises a printed reagent deposition) is provided with a fluidic port accepting solvent in and a fluidic port carrying solvent and reagent outward. Although untapered square-opening and round-opening caps are depicted, other cap shapes can be used.

FIG. 40b provides a variation on the arrangement depicted in FIG. 40a wherein the removable replaceable media element is of a form comprises wells.

FIG. 41a depicts an example representation wherein a row of neighboring "caps" are pair-wise connected by an "in-line"-valve-controlled fluidic link associated with that pair, resulting in a "daisy-chain" arrangement.

FIG. 41b depicts an example of use pairs of valves for each fluidic link.

Figure 42:
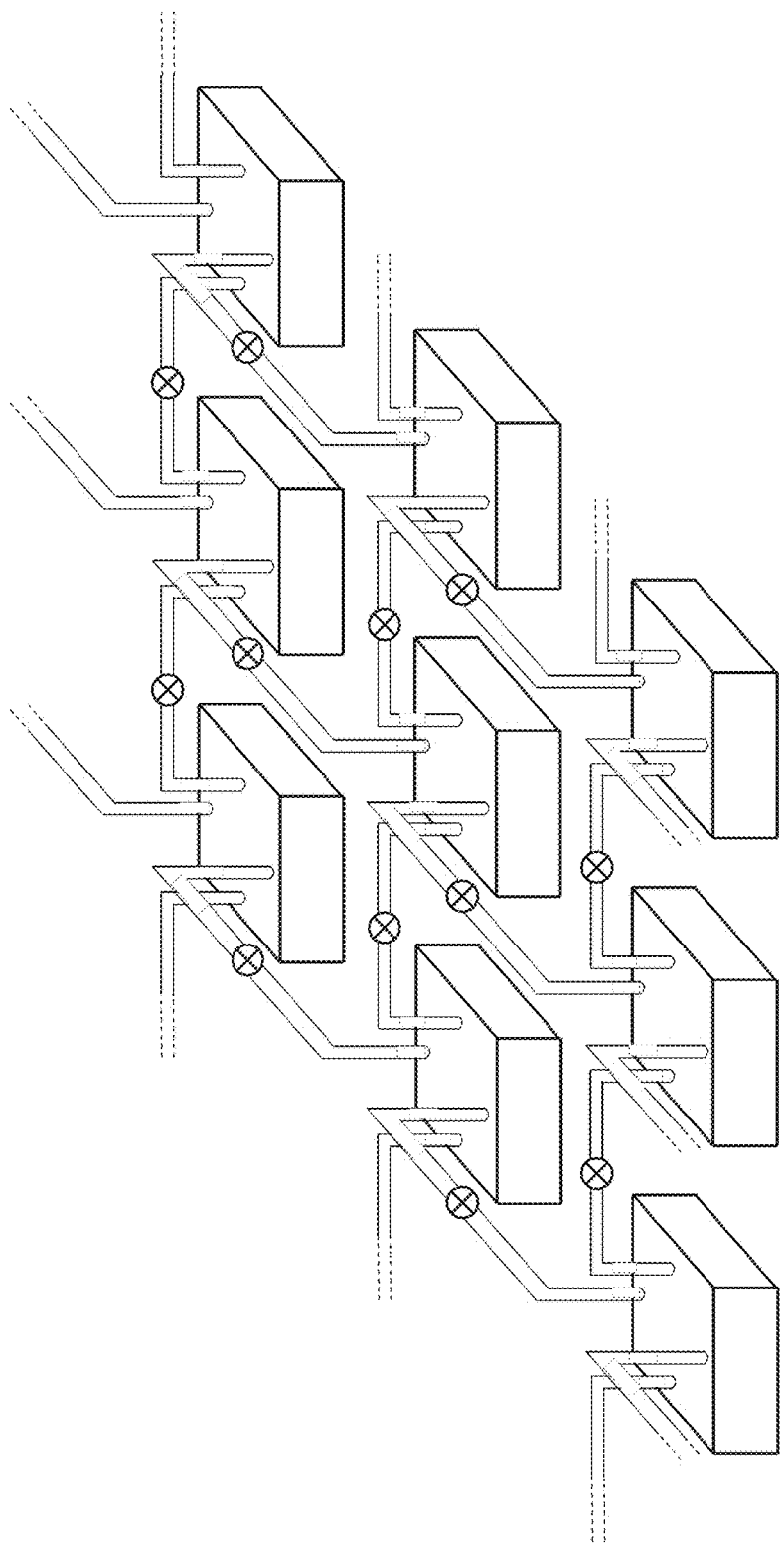

FIG. 42 depicts an example representation wherein a row of neighboring "caps" are pair-wise connected by a valve-controlled fluidic link associated with that pair, resulting in a two-dimensional "daisy-chain" arrangement.

FIGS. 43a-43b depict example representations wherein a row of neighboring "caps" are pair-wise connected by a valve-controlled fluidic link associated with that pair, resulting in a two-dimensional "daisy-chain" arrangement. In FIG. 43a, the "in-line" valve arrangement link depicted in FIG. 41a is used. In FIG. 43b, the "endpoint valve pair" arrangement depicted in FIG. 41b is used.

FIG. 44a depicts one example of fluidic interconnections among caps. FIG. 44b depicts another example of fluidic interconnections among caps supplemented with additional controllable fluidic paths.

Figure 45A:
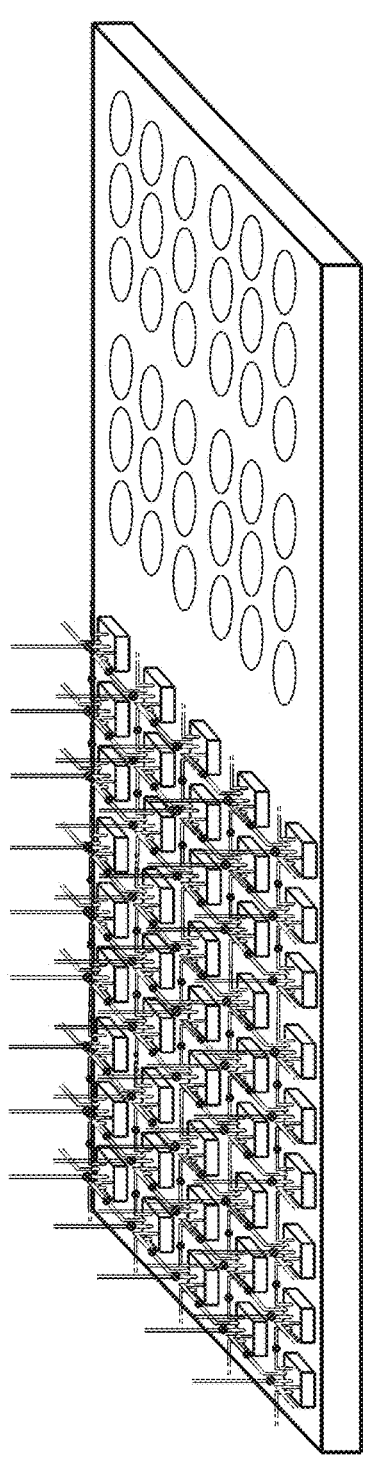

FIG. 45a depicts an example arrangement wherein caps interconnected with fluidics arrangements interface to associated sites on a portion of the removable replaceable media element.

Figure 45B:
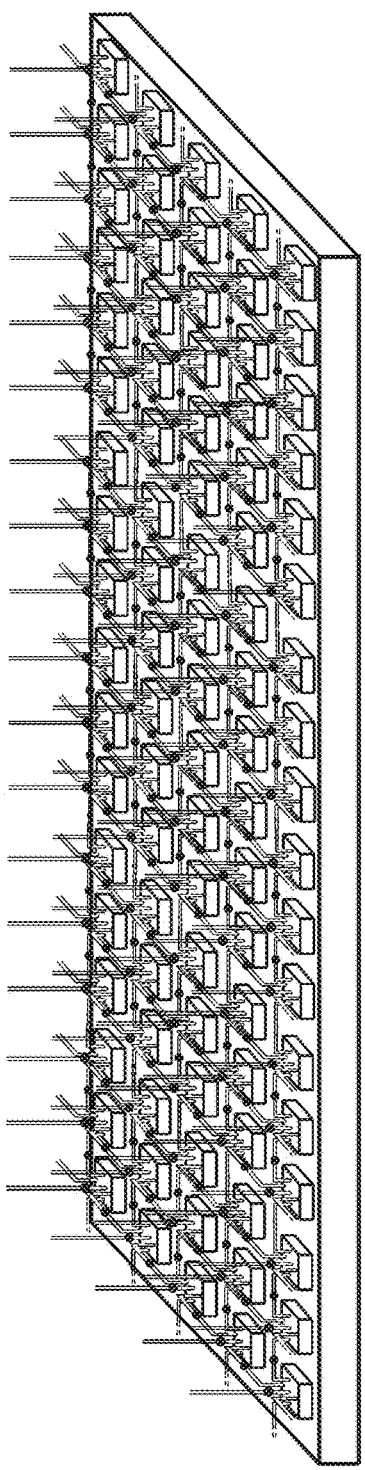

FIG. 45b depicts a variation on the example arrangement of FIG. 45a wherein the example arrangement is extended to encompass all possible sites of the removable replaceable media element.

Figure 45C:
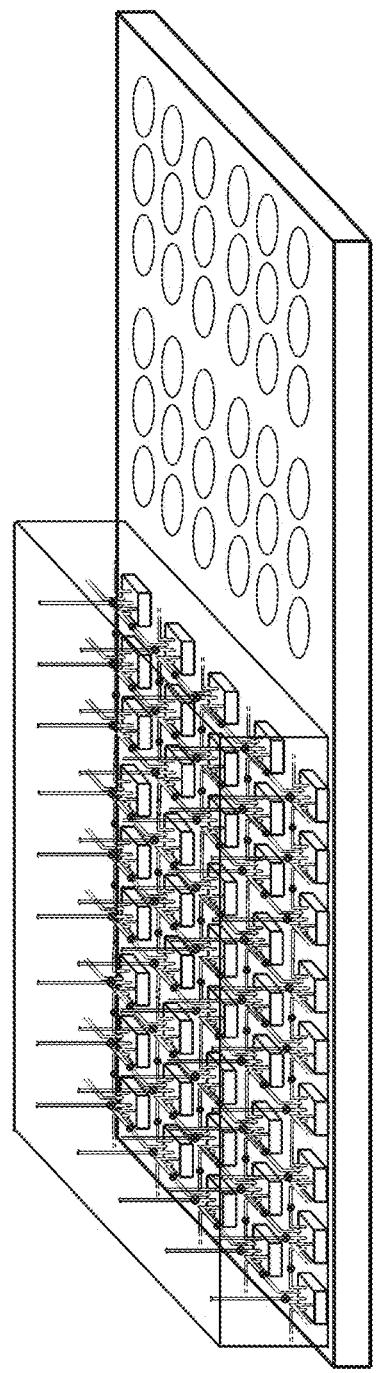
Figure 45D:
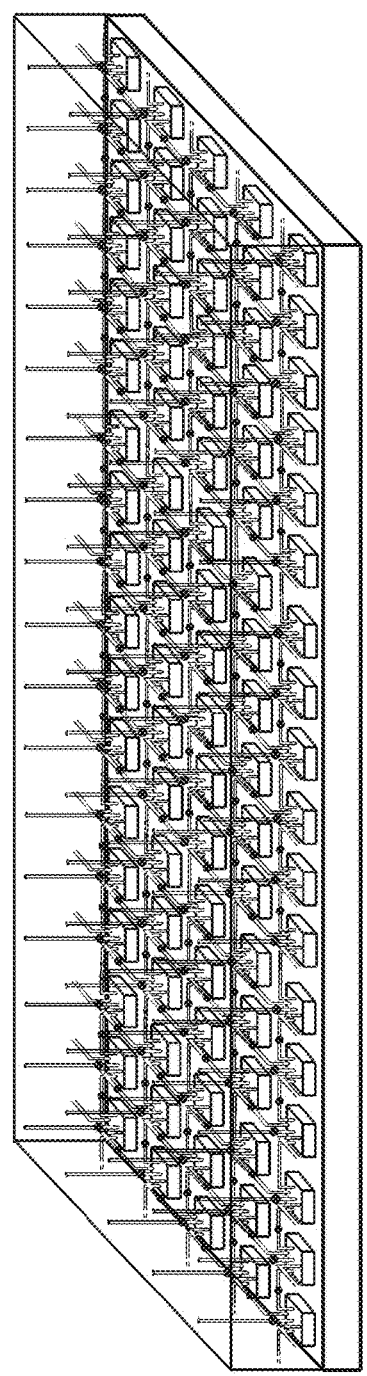

FIG. 45c depicts a variation on the example arrangement of FIG. 45a wherein at least the fluidics arrangements are comprised in an interfacing module, FIG. 45d depicts a variation on the example arrangement of FIG. 45c wherein the example arrangement is extended to encompass all possible sites of the removable replaceable media element.

Figure 45E:
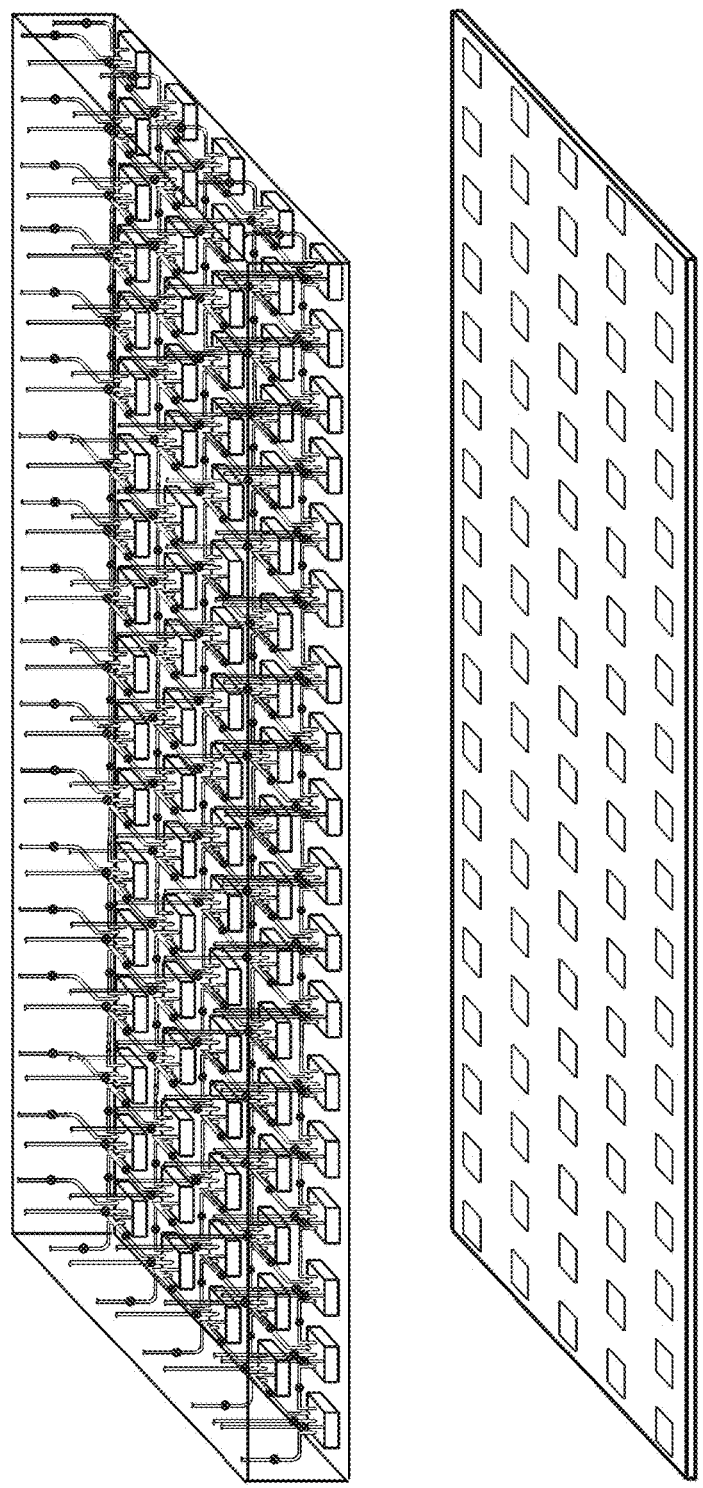
Figure 46B:
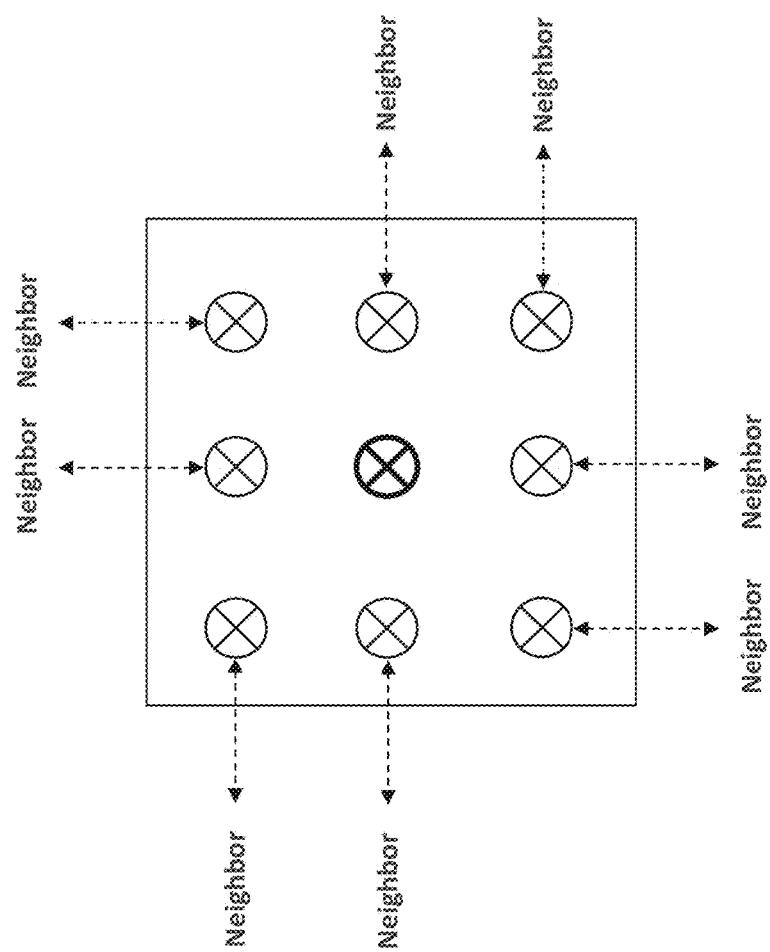
Figure 46C:
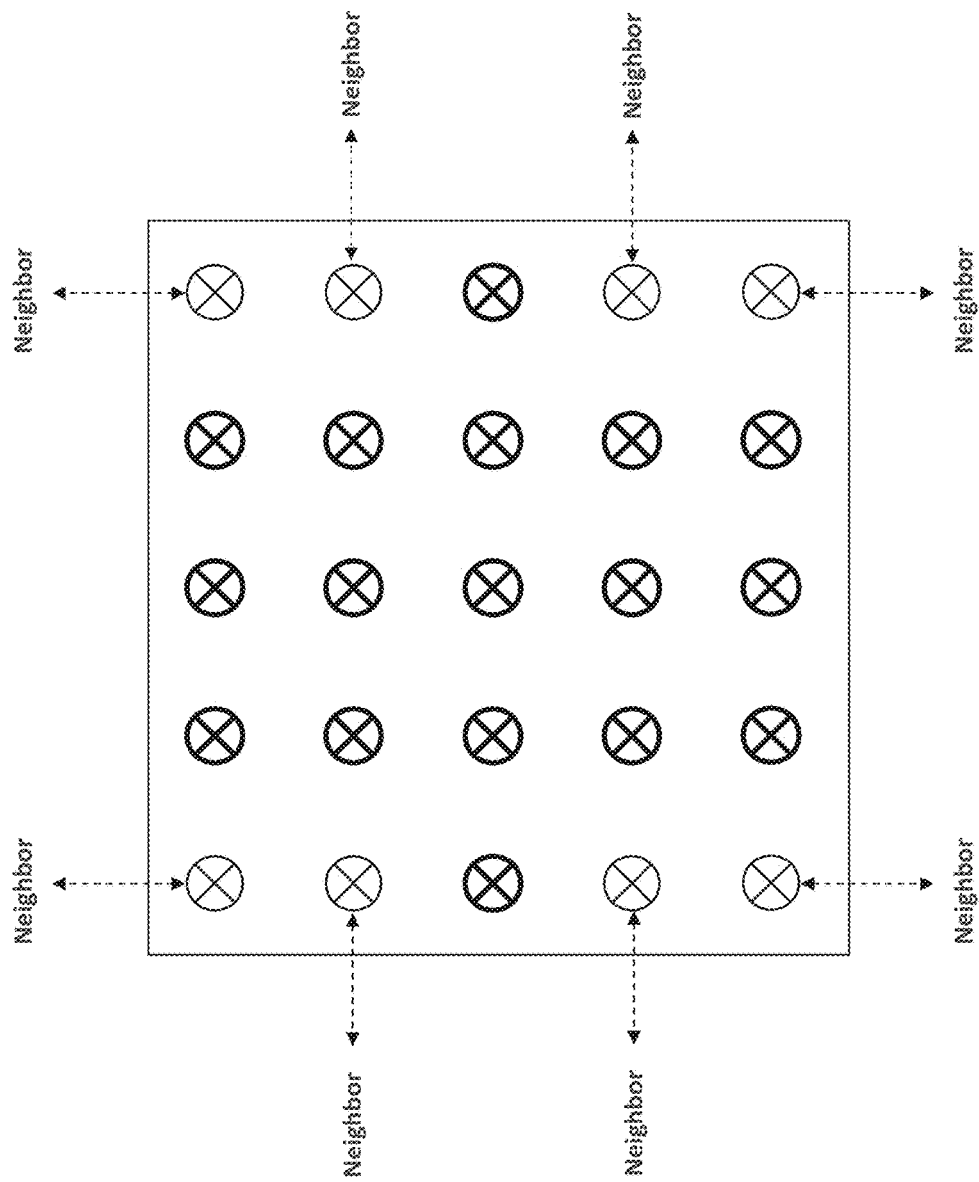

FIG. 45e depicts an example wherein the interfacing module can be configured to be inserted into either (at the choice of user or manufacturer product-design) the base unit or attached to the removable replaceable media element in either a fixed or replaceable arrangement, FIGS. 46a-46c depict representations of some examples wherein caps for fluidic interconnections can be arranged in various configurations depending on the complexity and architecture of the overall system including controlled valves at each fluidic port.

Figure 47C:
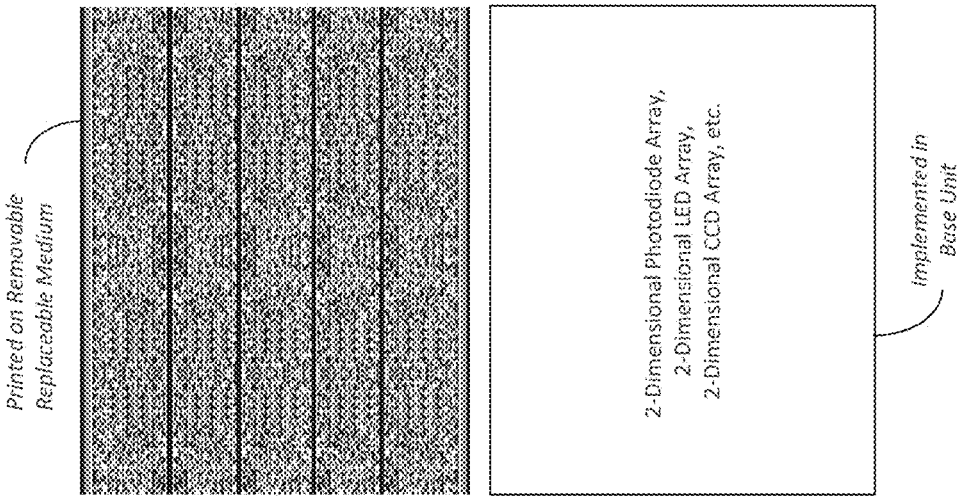
Figure 47A:
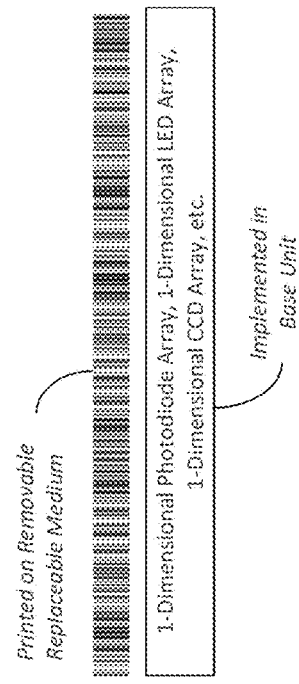
Figure 47B:
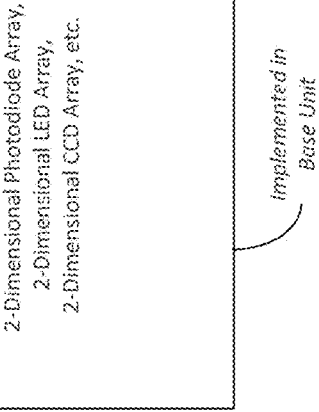

FIGS. 47a-47c depict representations of examples of how optical ROM printed on the removable replaceable media can be read by the base unit.

Figure 48:
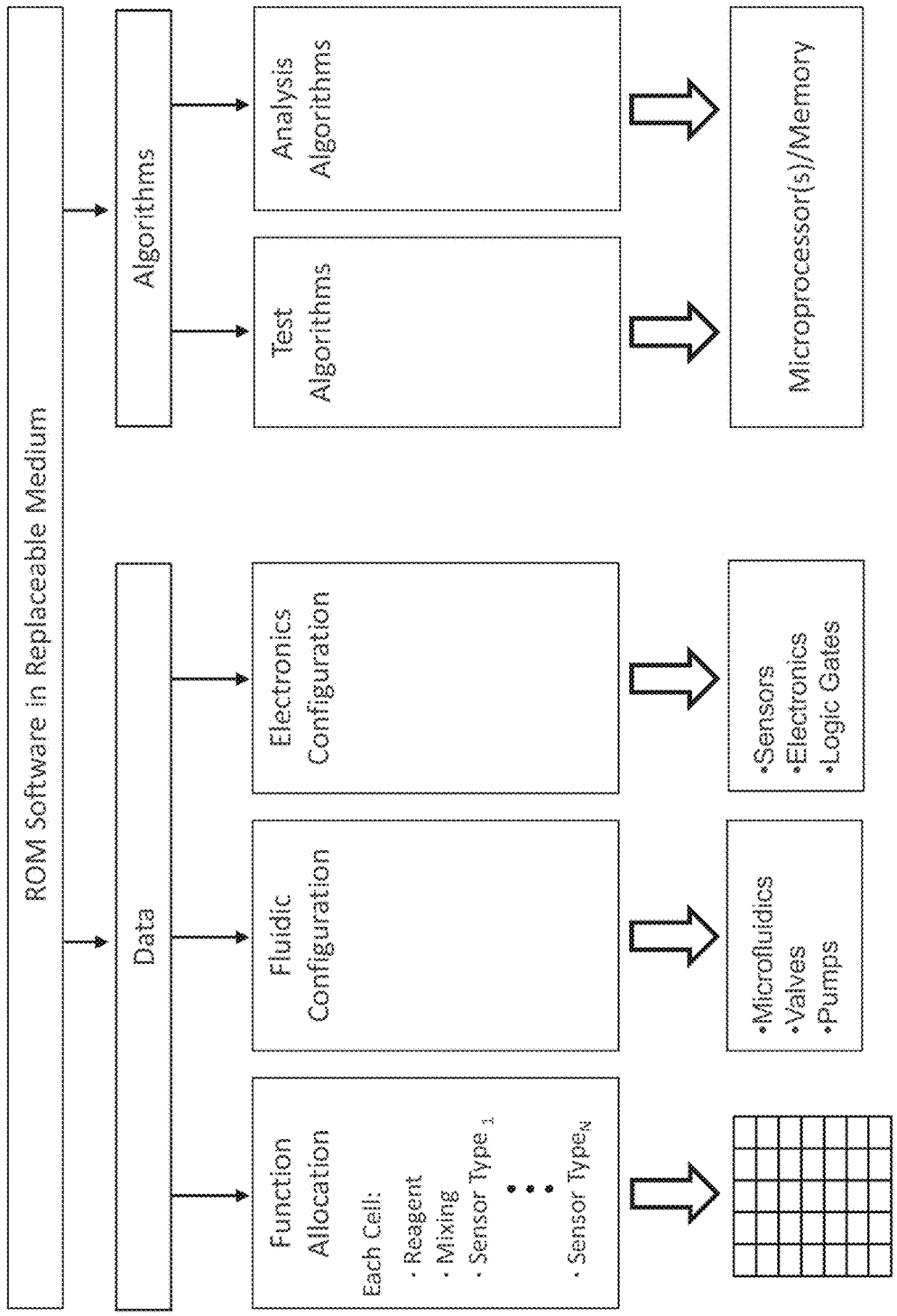

FIG. 48 depicts a representation of the information stored on the ROM (for example, configuration data, assignment data, data used by algorithms, test algorithms, analysis algorithms, etc.) comprised by the removable replaceable media.

FIG. 49 depicts a representation of example functional allocations that can be provided for each cap. In this case, a column organization is used, although clearly other approaches can clearly be employed instead.

Figures 50A, 50B:
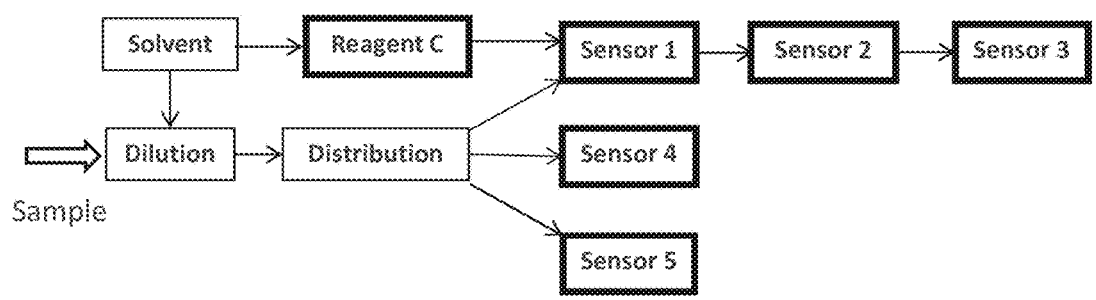

FIG. 50a depicts a representation of a fluidics-based test configuration.

FIG. 50b depicts a representation of the function allocation corresponding to the test configuration of FIG. 50a.

Figures 51A, 51B:
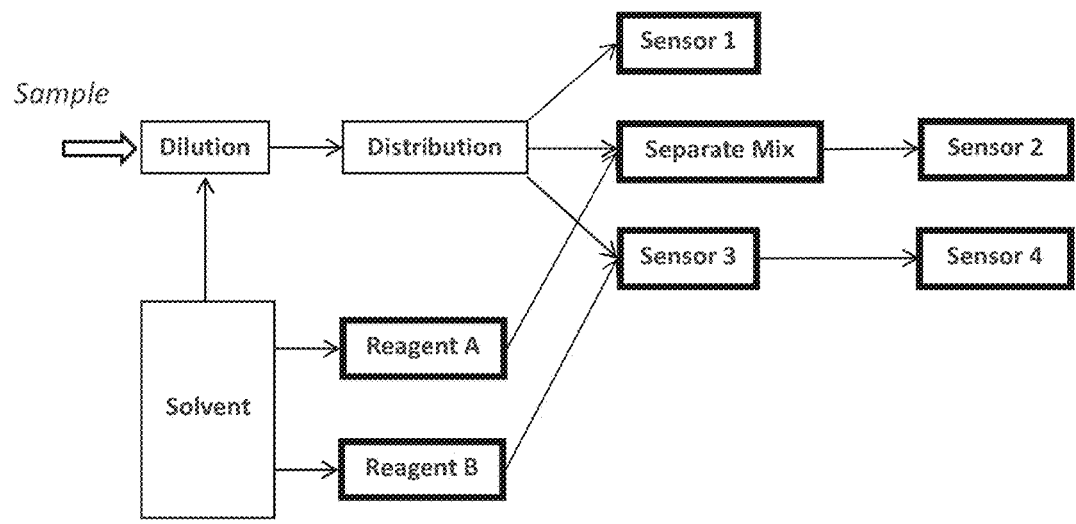

FIG. 51a depicts a representation of another fluidics-based test configuration.

FIG. 51b depicts a representation of the function allocation corresponding to the test configuration of FIG. 51a.

Figures 52A, 52B:
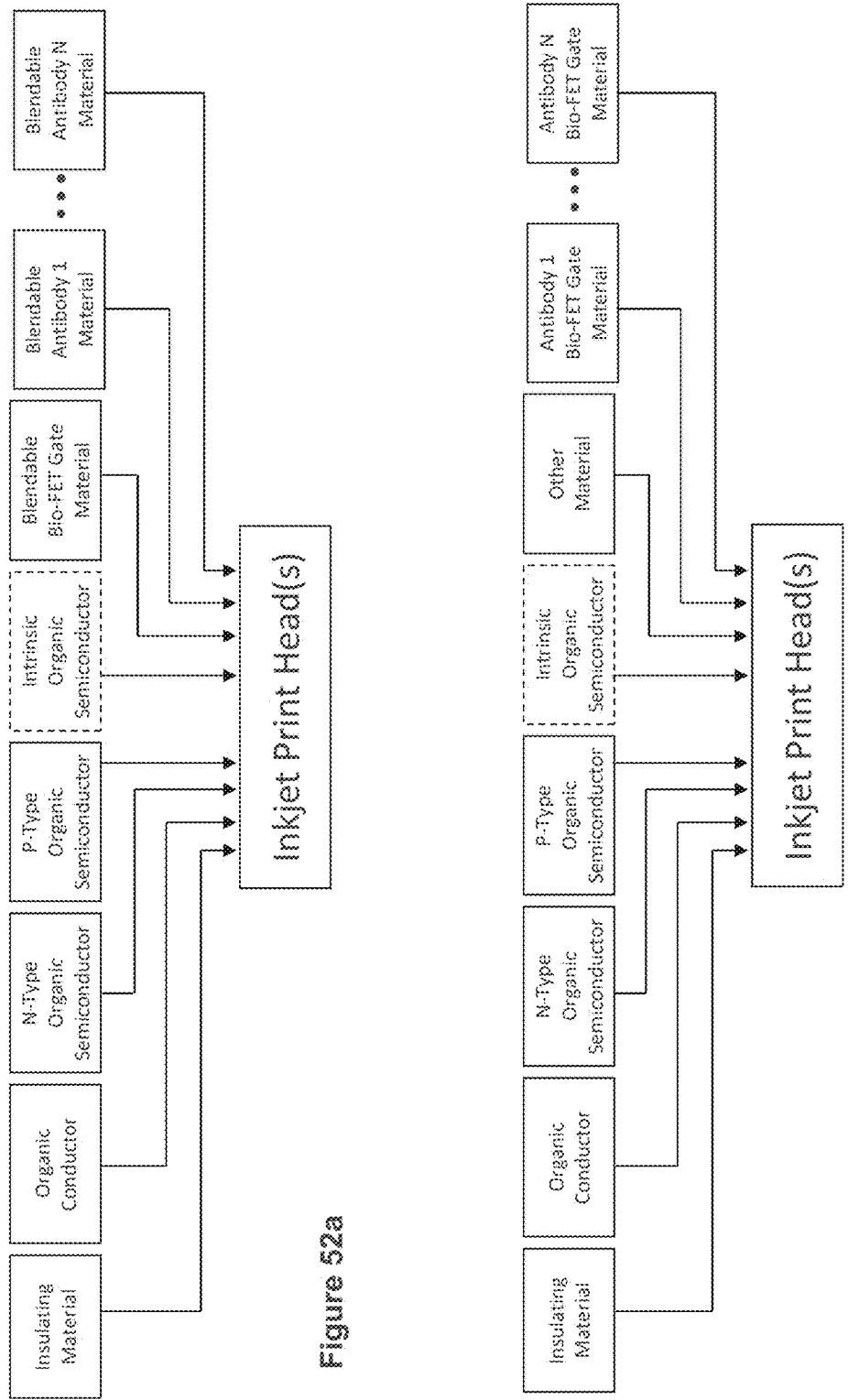

FIGS. 52a-52b depict representations of example functional printed methods that can be used, for example, to print the sensors on the removable replaceable medium. FIG. 52a depicts a representation of an example arrangement wherein a selection of antibodies can be selectively blended in the printing (or other deposition) action with a blendable bioFET gate material. FIG. 52b depicts a representation of an example arrangement wherein antibodies are blended with bioFET gate material in advance of the printing.

Figure 53B:
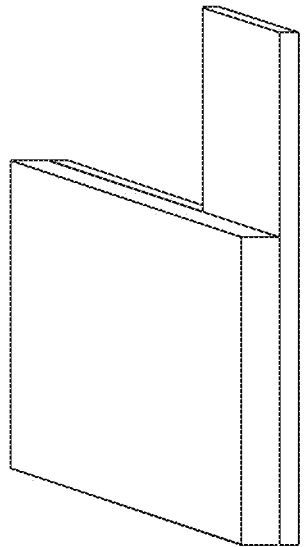
Figure 53D:
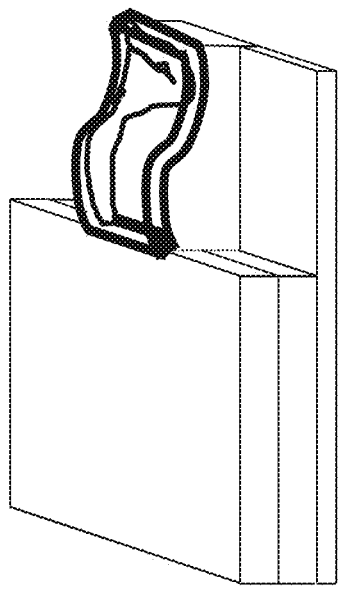
Figure 53A:
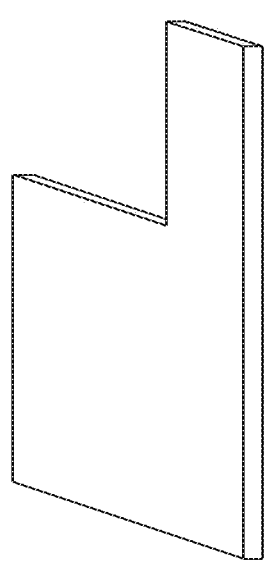
Figure 53C:
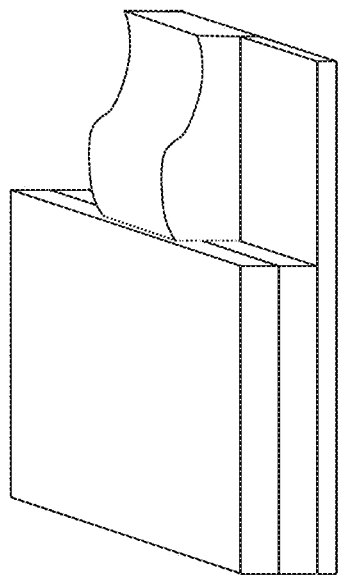
Figure 53F:
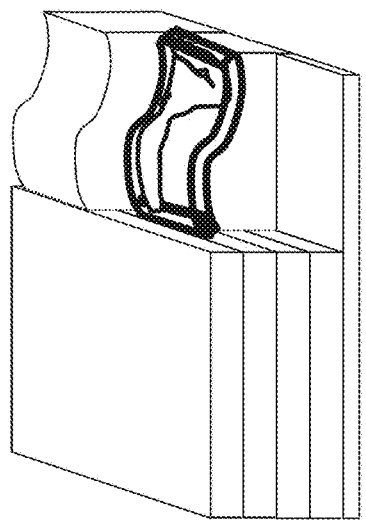
Figure 53H:
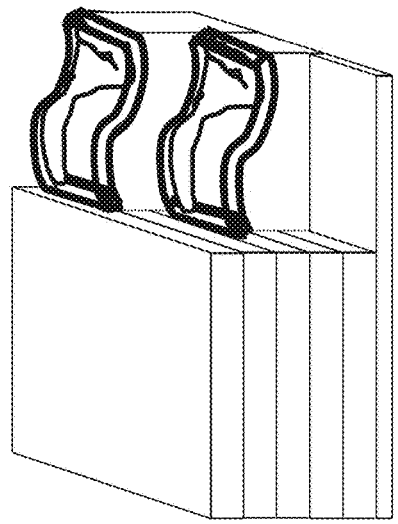
Figure 53E:
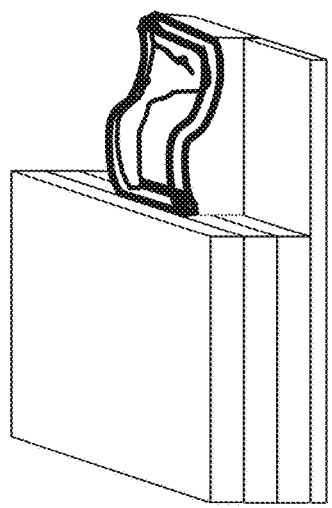
Figure 53G:
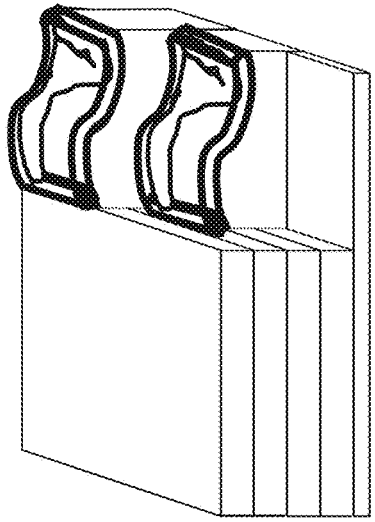

FIGS. 53a-53g depict representations of example layered deposition of a bioFET or electrochemical sensor. FIG. 53a depicts a representation of a first example conducting layer. FIG. 53b depicts a representation of a first example functional layer (semiconducting, insulating, dielectric, supporting, etc.), FIG. 53c depicts a representation of a first example side area electrical insulator—the shape and location is merely an example and many other arrangements are possible. FIG. 53d depicts a representation of a second example conducting layer. FIG. 53e depicts a representation of a second example functional layer (semiconducting, insulating, dielectric, supporting, etc.), FIG. 53f depicts a representation of a second example side area electrical insulator—the shape and location is merely an example and many other arrangements are possible. FIG. 53g depicts a representation of a third example conducting layer. FIG. 53h depicts a representation of a third example functional layer (selective detection material, semiconducting, insulating, dielectric, supporting, etc.).

Figure 54A:
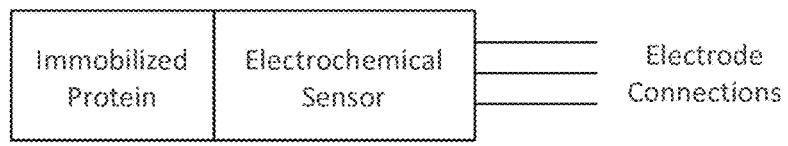

FIG. 54a depicts an example symbolic representation of an electrochemical sensor.

Figure 54B:
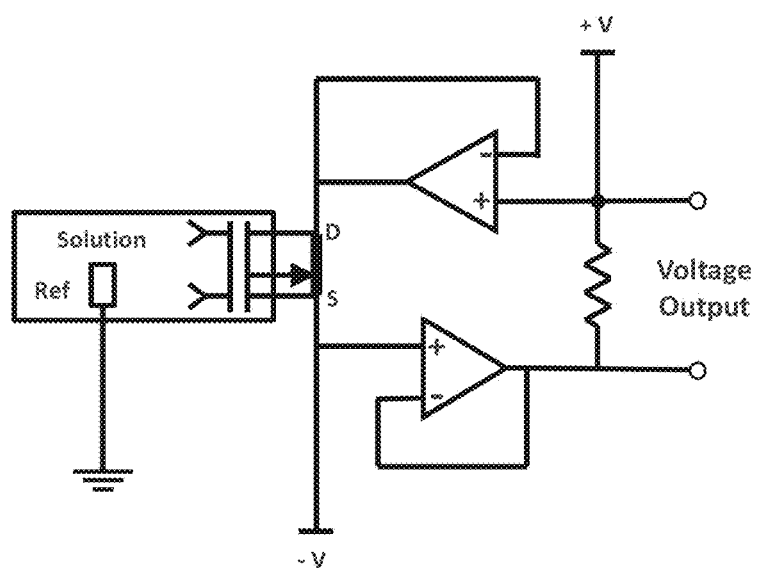

FIG. 54b depicts a representation of an example electrical interface to a bioFET sensor, the interface providing a voltage signal output.

Figure 55A:
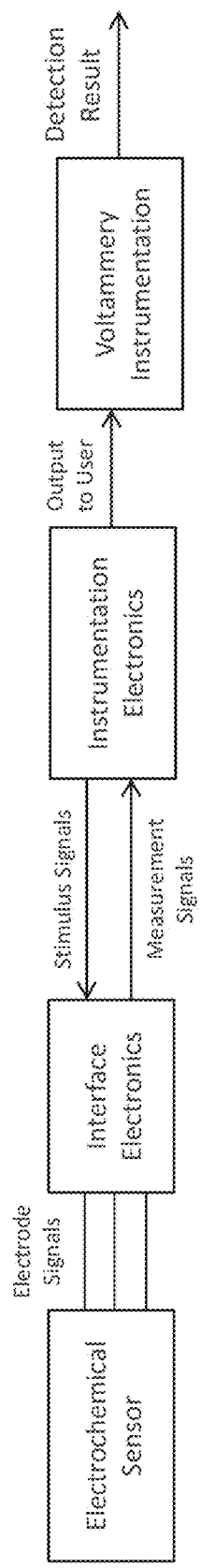
Figure 55B:
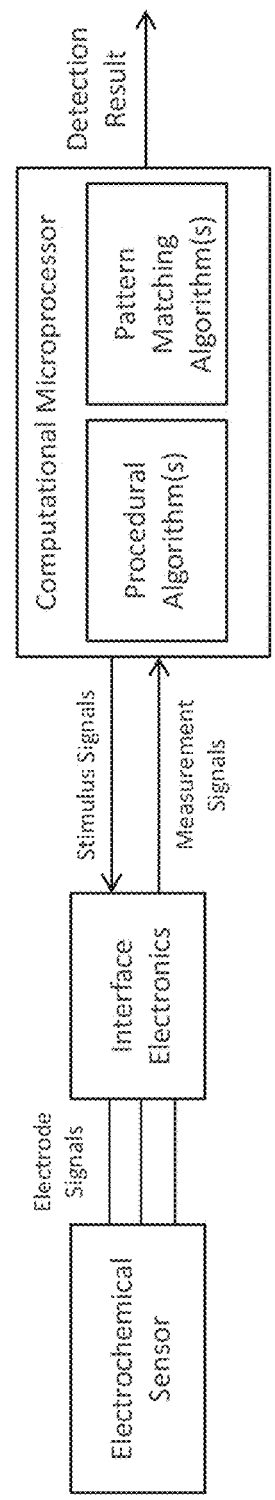

FIGS. 55a-55b depict representations of various types of example electronics interfacing and signal routing relating to an individual electrochemical sensor. FIG. 55a depicts representations of various types of example electronics interfacing and signal exchanges typically used to provide the conditions required to operate an individual electrochemical sensor. FIG. 55b depicts a simplified arrangement provided by the invention wherein the backend of the electrochemical sensor interface arrangement depicted in FIG. 55a is replaced, enhanced, and interpreted by algorithms executing on computational microprocessor or other computing platform (FPLA, embedded controller, remote computer, etc.).

Figures 55C, 55D:
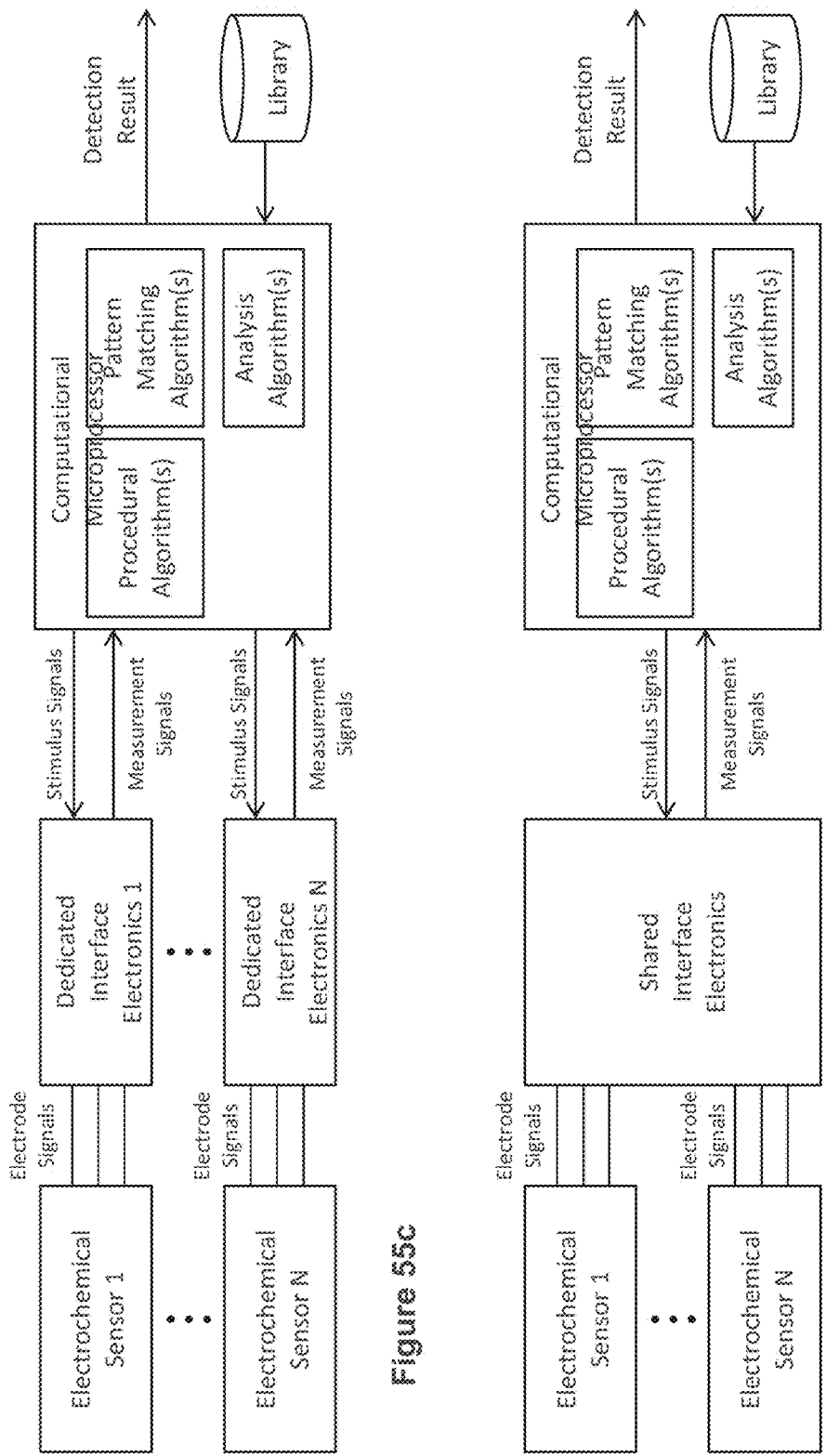

FIGS. 55c-55d depict representations of various types of example electronics sharing among a plurality of electrochemical sensors. FIG. 55c depicts a large number of electrochemical sensors, with a corresponding number of instances of dedicated electrochemical sensor interface electronics. FIG. 55d depicts an abstracted representation of various types of interface electronics sharing among a plurality of electrochemical sensors.

Figure 56A:
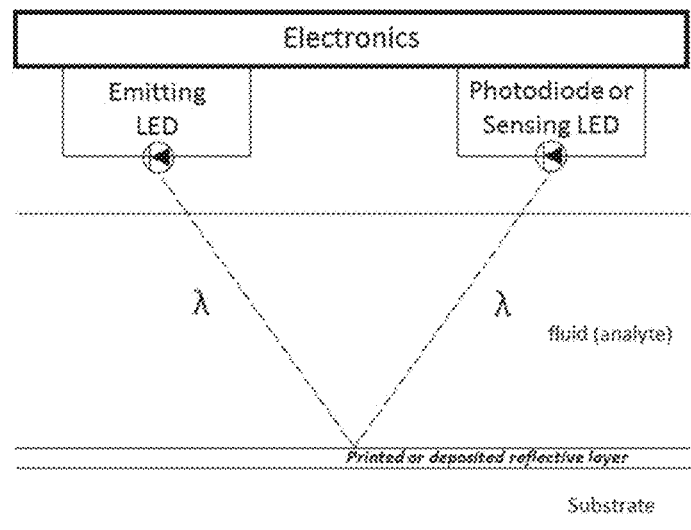

FIG. 56a depicts a representation of a miniature absorption optical sensor arrangement wherein both light emitted and light detecting elements are provided in the base unit. Here, an optical reflective coating is provided on the removable replaceable medium by functional printing.

Figure 56B:
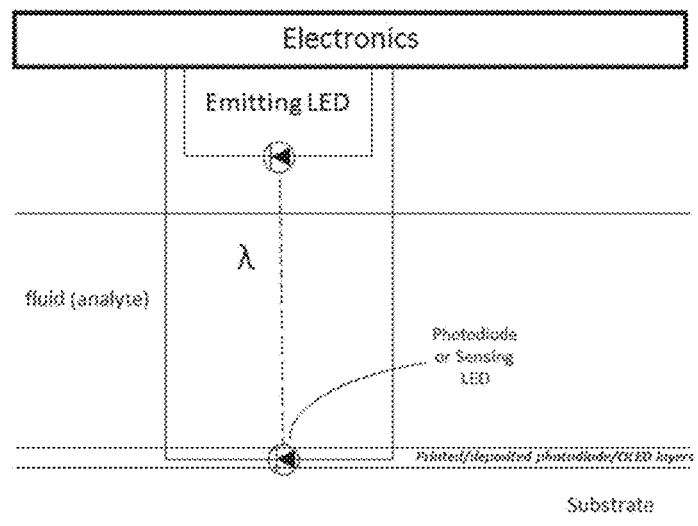

FIG. 56b depicts a representation of another miniature absorption optical sensor arrangement. Here, a photodiode or (wavelength selective) LED is provided on the removable replaceable medium by functional printing.

Figure 56C:
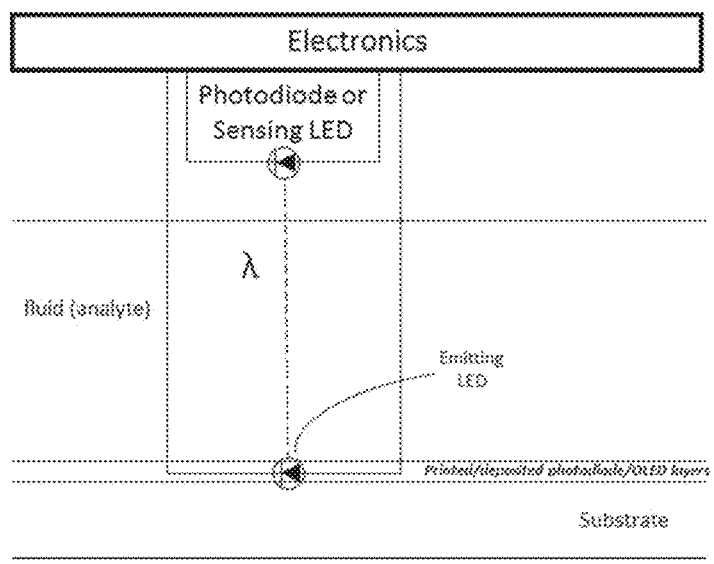

FIG. 56c depicts a representation of another miniature absorption optical sensor arrangement. Here, an emitted LED is provided on the removable replaceable medium by functional printing.

Figure 56D:
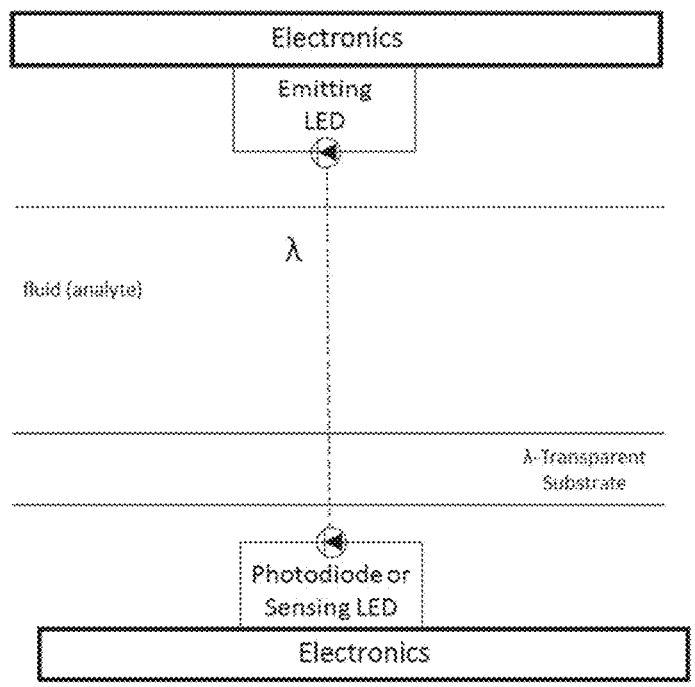

FIG. 56d depicts a representation of another miniature absorption optical sensor arrangement. Here, a photodiode or (wavelength selective) LED is provided in the lid of the base unit.

Figure 56E:
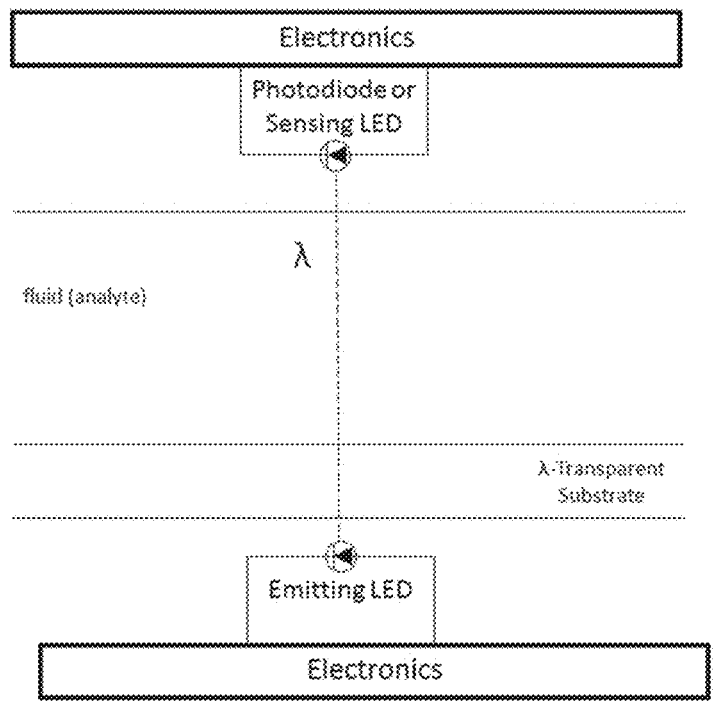

FIG. 56e depicts a representation of another miniature absorption optical sensor arrangement. Here, an emitted LED is provided in the lid of the base unit.

Figure 56F:
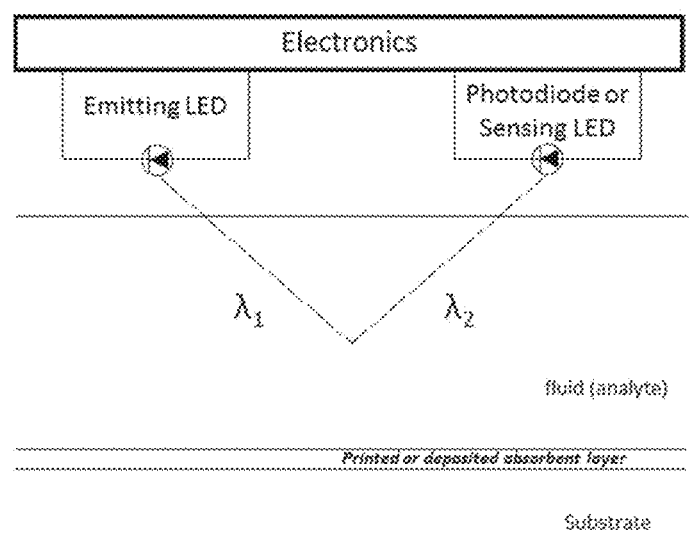

FIG. 56f depicts a representation of an example fluorescence optical sensor wherein both light emitted and light detecting elements are provided in the base unit and optical reflective coating is provided on the removable replaceable medium by functional printing.

Figure 56G:
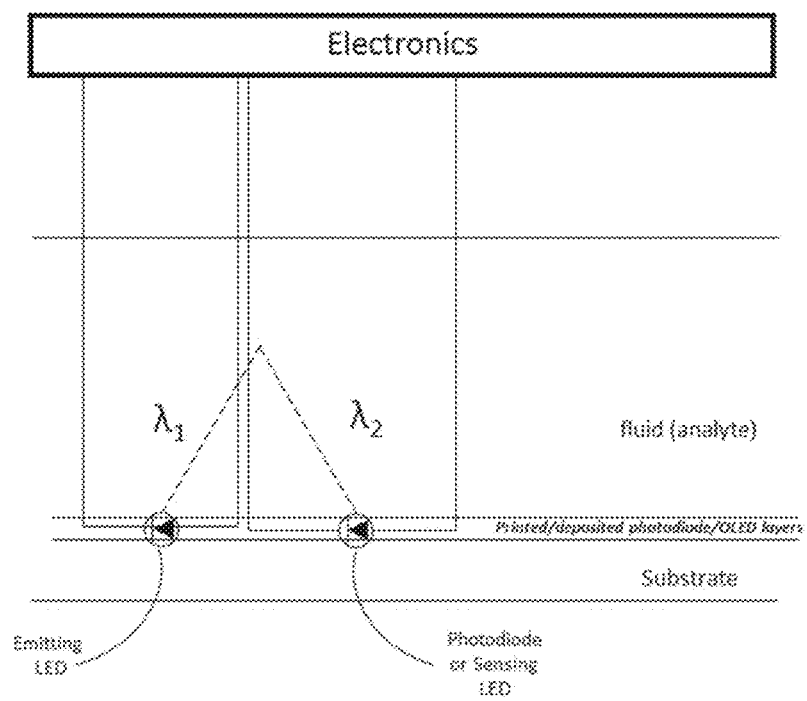

FIG. 56g depicts a representation of another miniature absorption optical sensor arrangement. Here, both an emitting LED and a photodiode or (wavelength selective) LED is provided on the removable replaceable medium by functional printing.

FIG. 57 depicts a representation of an example response of an LED used as a light source (top graph) and as a light sensor (bottom graph)

FIG. 58 depicts a representation of an example electrical interface allowing a given LED to be used as a light source, as a light sensor, or (using time-division multiplexing) both modalities.

Figure 59:
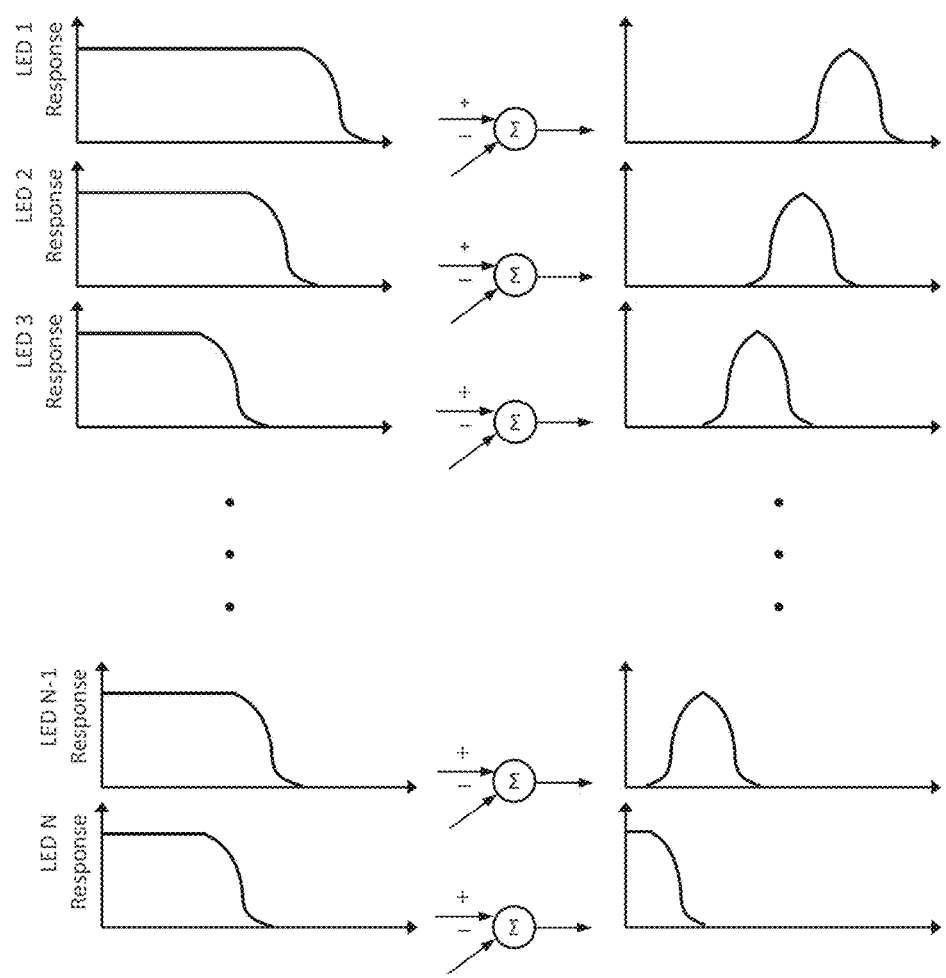

FIG. 59 depicts a representation of an example signal processing of received multiple-LED light sensor signals to produce wavelength-selective optical detectors without precision optical elements.

Figure 60:
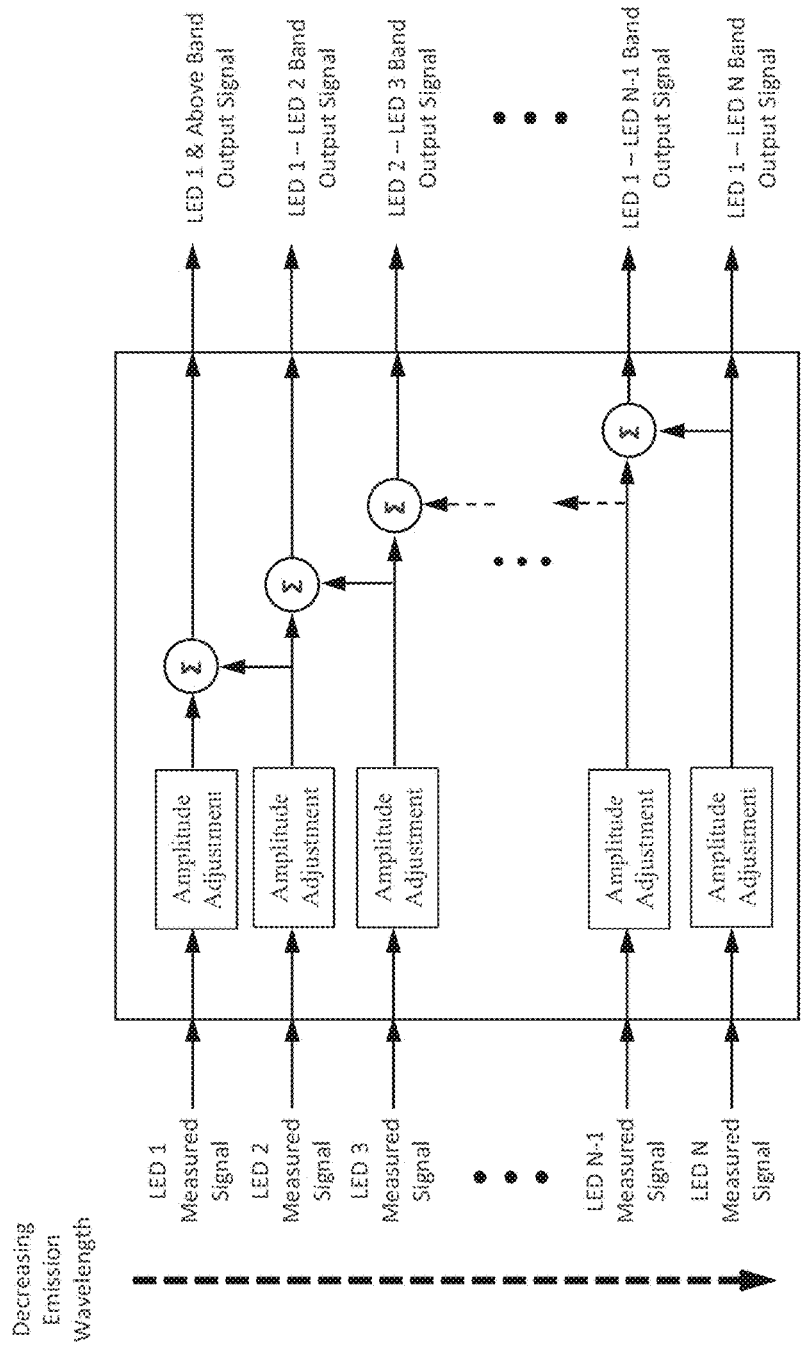

FIG. 60 depicts a refinement of the general principle depicted in FIG. 59 wherein calibrated (active. passive, preset, etc.) amplitude adjustments are used to normalize the individual wavelength-dependent photoelectric measurement signal amplitudes.

Figures 61A, 61B:
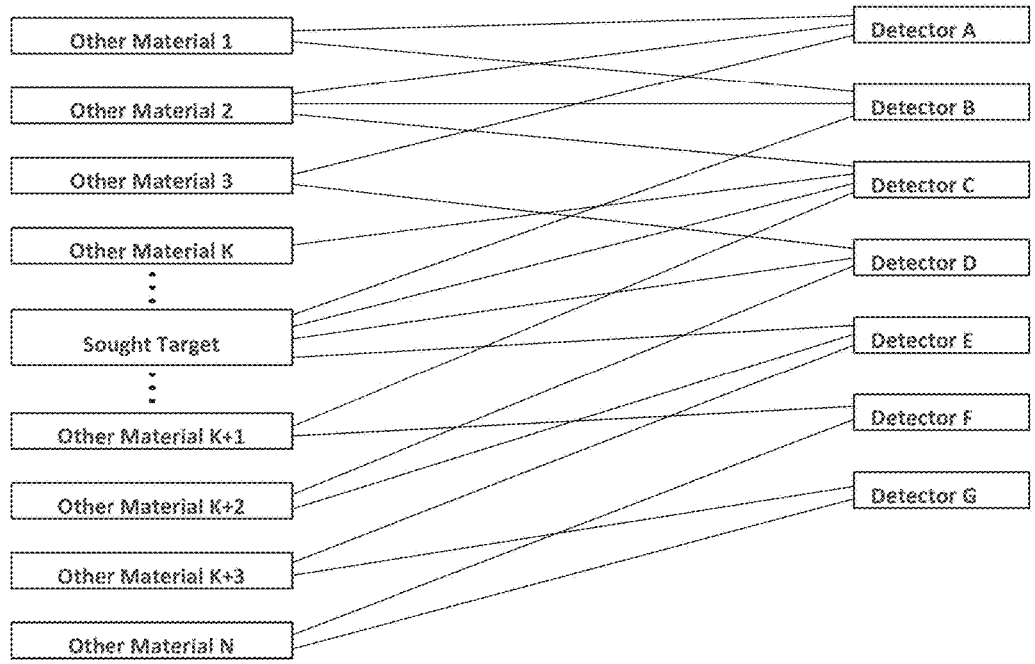

FIG. 61a depicts an example illustrative scenario wherein seven selective detector materials (designated A through G) are responsive or non-responsive to a sought target as well as various ones of N other non-target materials.

FIG. 61b presents a table summarizing each of the graphically represented response and non-response relationships represented in FIG. 61a.

Figure 62A:
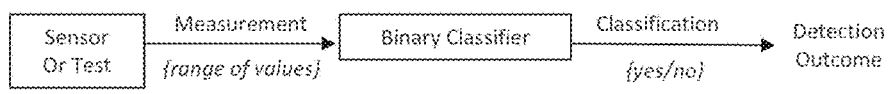

FIG. 62a depicts an example binary classifier" detector arrangement comprising a sensor or test providing a measurement quantity taking on a value from a range of values, the range comprising more than two values (that is the range have more than two possible values).

Figure 62B:
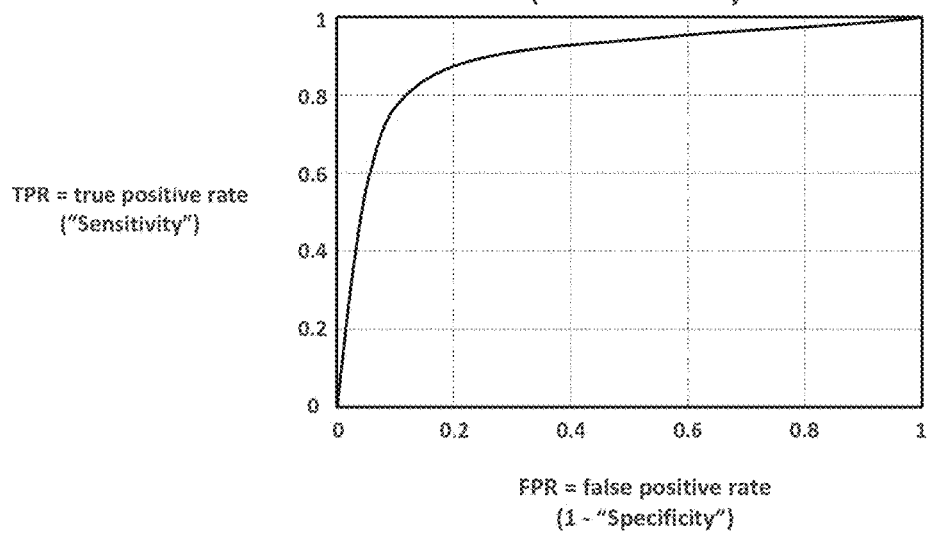

FIG. 62b depicts an example Receiver Operating Characteristic/Relative Operating Characteristic/ROC comprising an example ROC curve.

Figure 63:
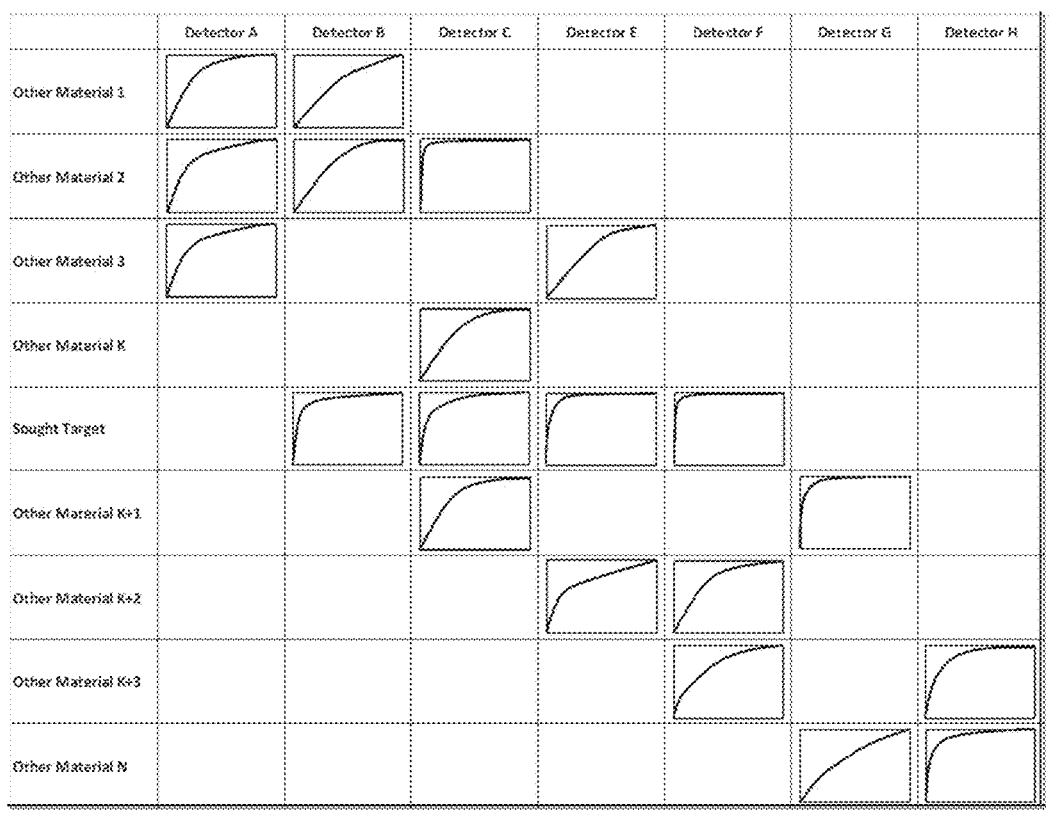

FIG. 63 depicts a representation taking the table provided in FIG. 61b and replacing the "X" entries signifying responsiveness with the associated underlying ROC curve reflecting the associated detection performance.

Figure 64A:
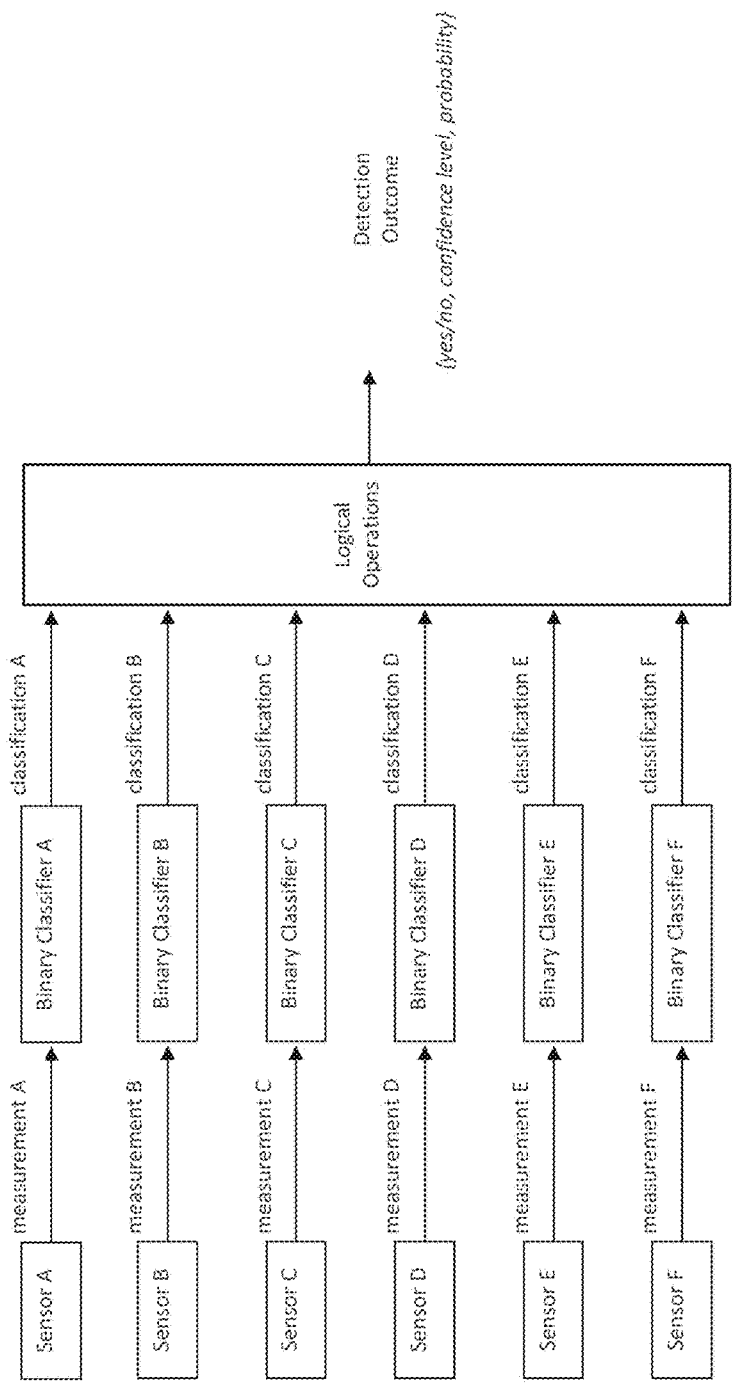

FIG. 64a depicts an example arrangement when in each of a collection of sensor/binary-classifiers present their yes/no outcomes, if any, to logic operations that in turn produce a superior "yes/no" outcome, additional information such as likelihood, confidence level, probabilities of "yes" being true, etc. for a single target material.

Figure 64B:
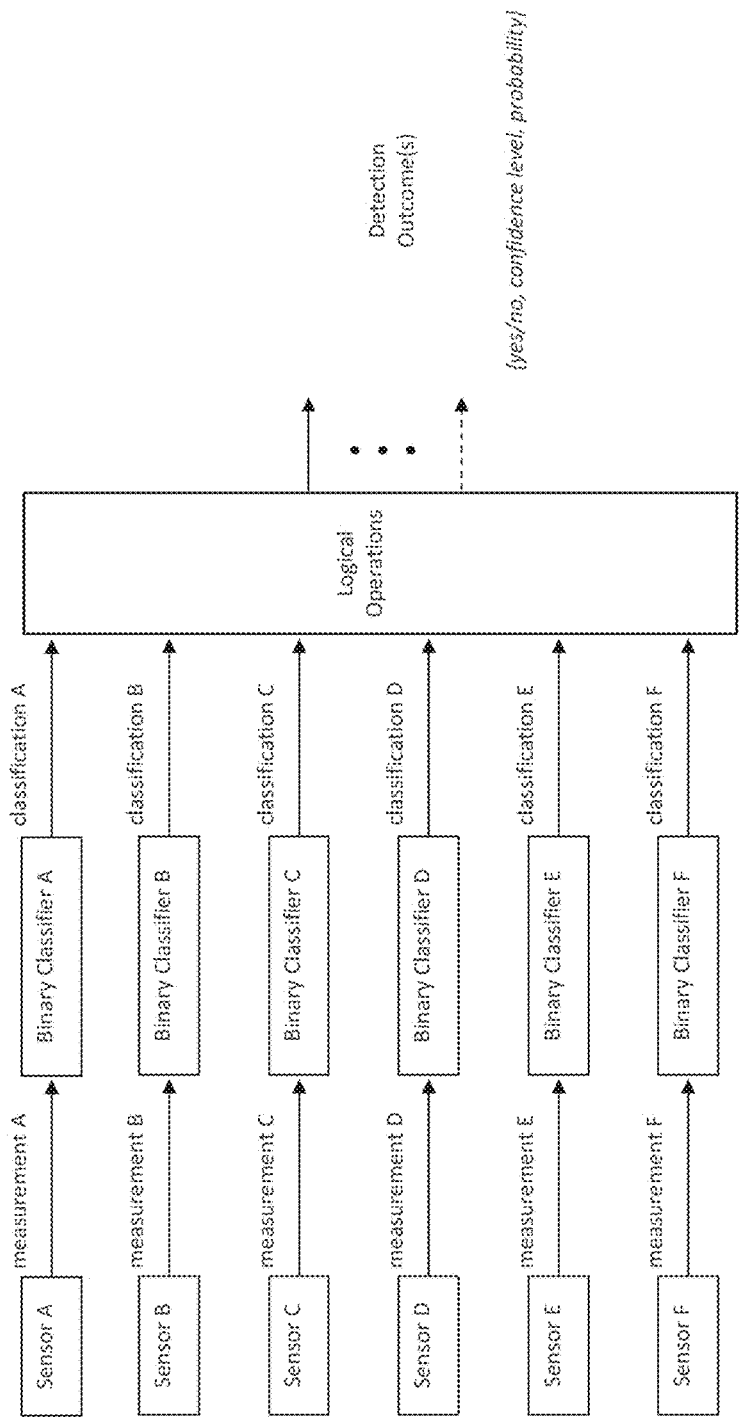

FIG. 64b depicts an example arrangement wherein various superior "yes/no" outcomes, additional information such as likelihood, confidence level, probabilities of "yes" being true, etc. can be produced for multiple materials and targets.

Figure 64C:
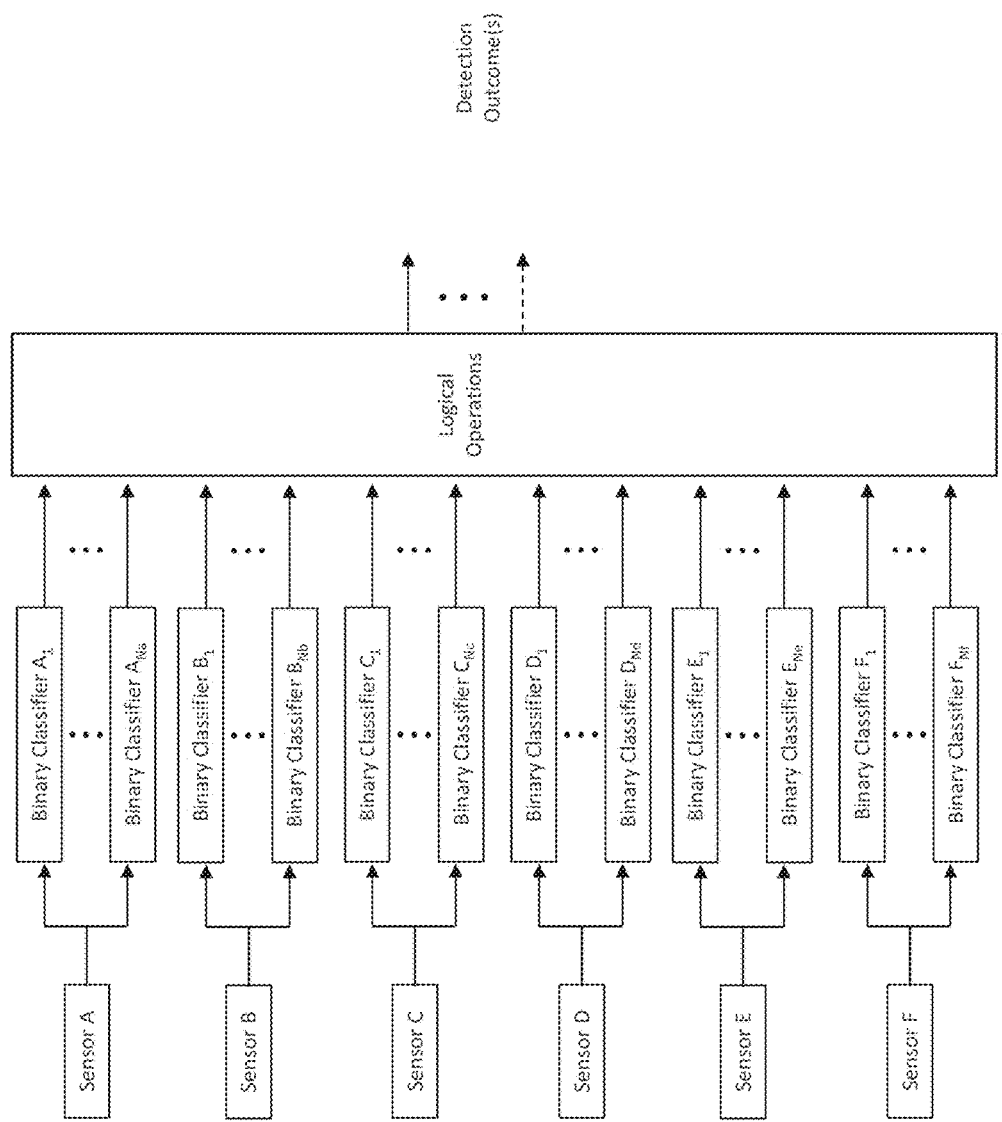

FIG. 64c depicts a variation on the arrangement depicted in FIG. 64b wherein different classifiers are provided for each pairing of target and selective detection material.

Figure 64D:
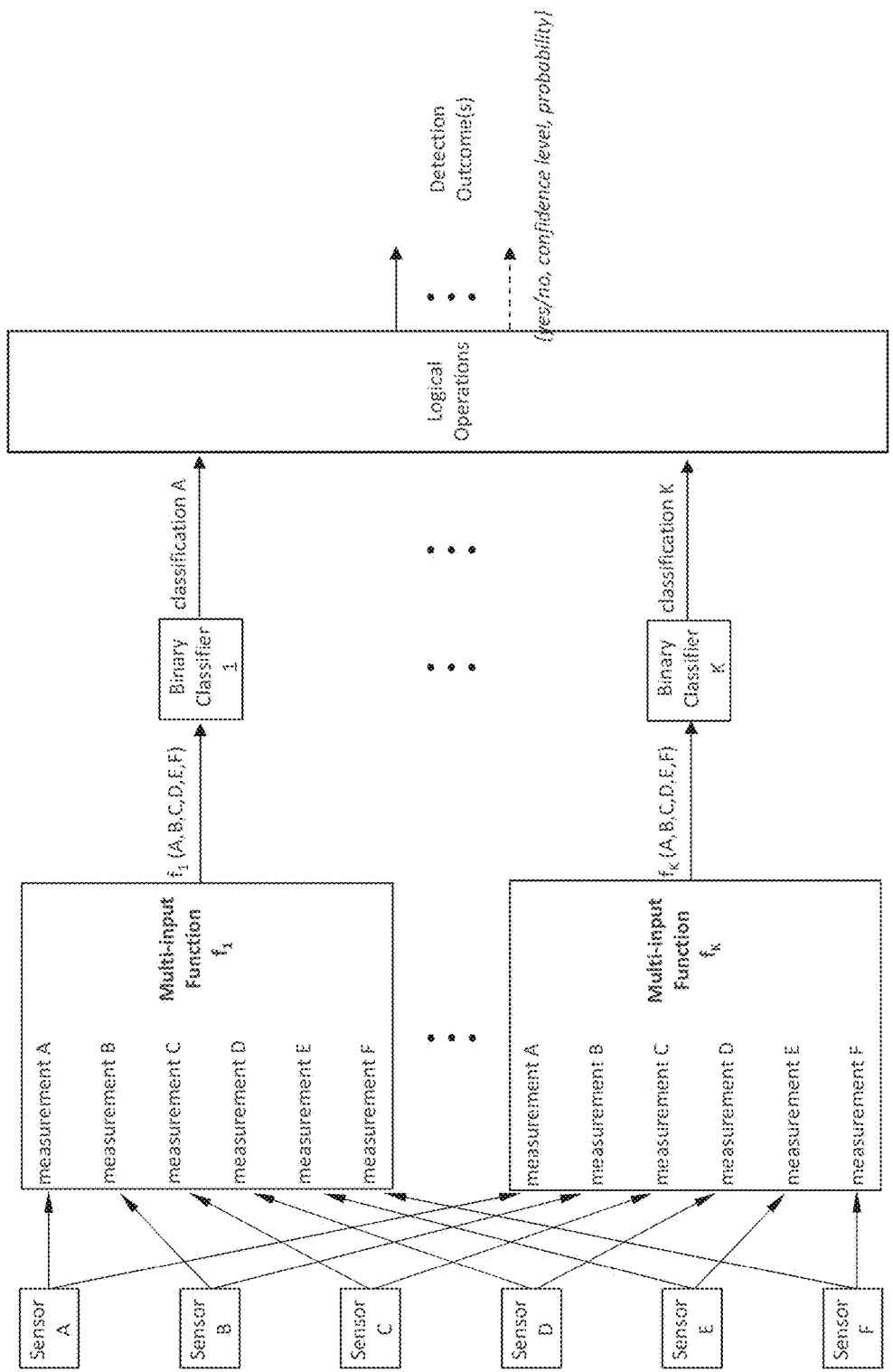

FIG. 64d depicts one approach to implementing vector quantizing useful to statistical processing for the invention although many other approaches are possible and anticipated.

Figure 64E:
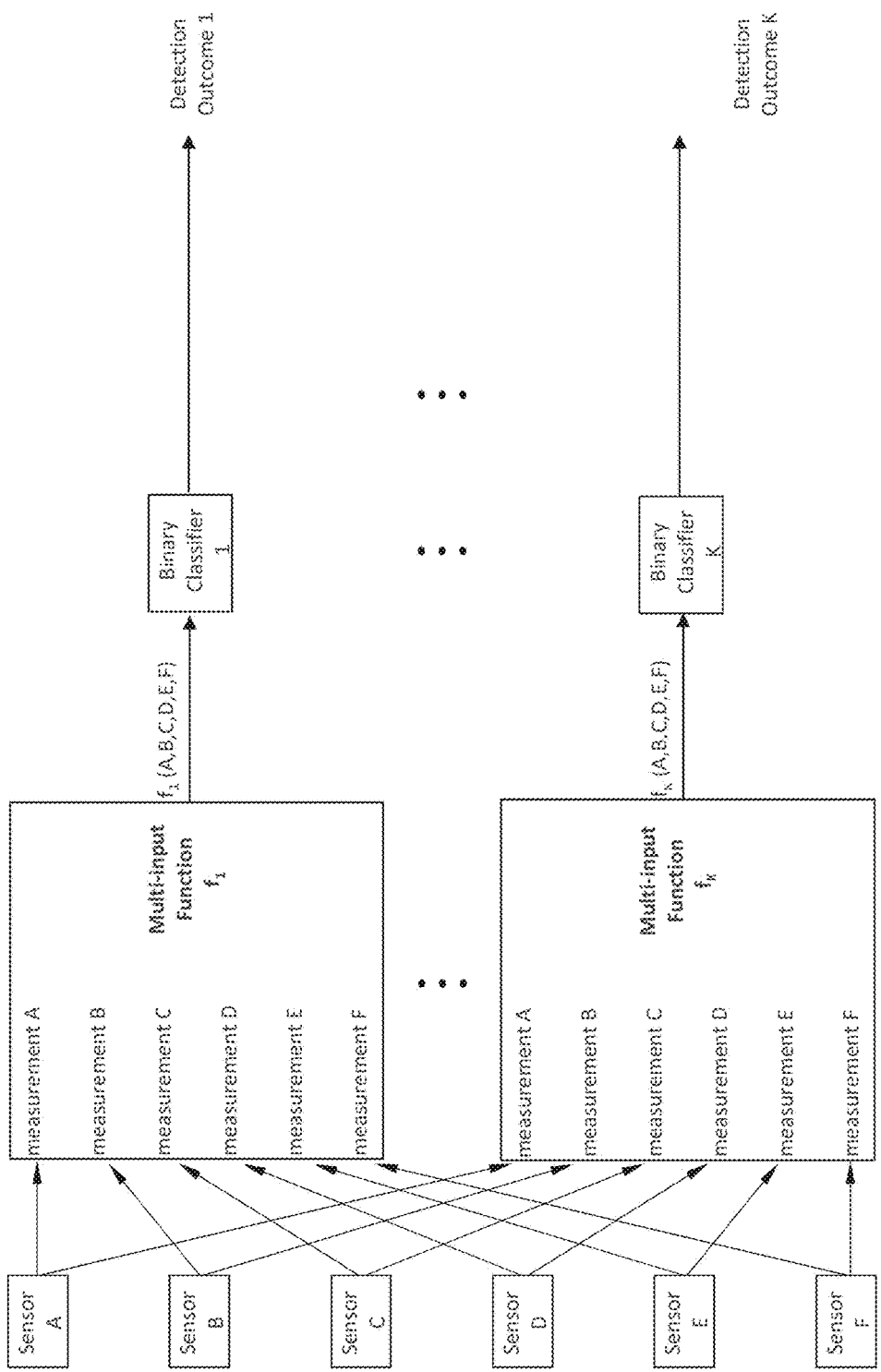

FIG. 64e depicts a simplified arrangement wherein the logical operations represented in FIG. 64d are omitted.

Figure 65:
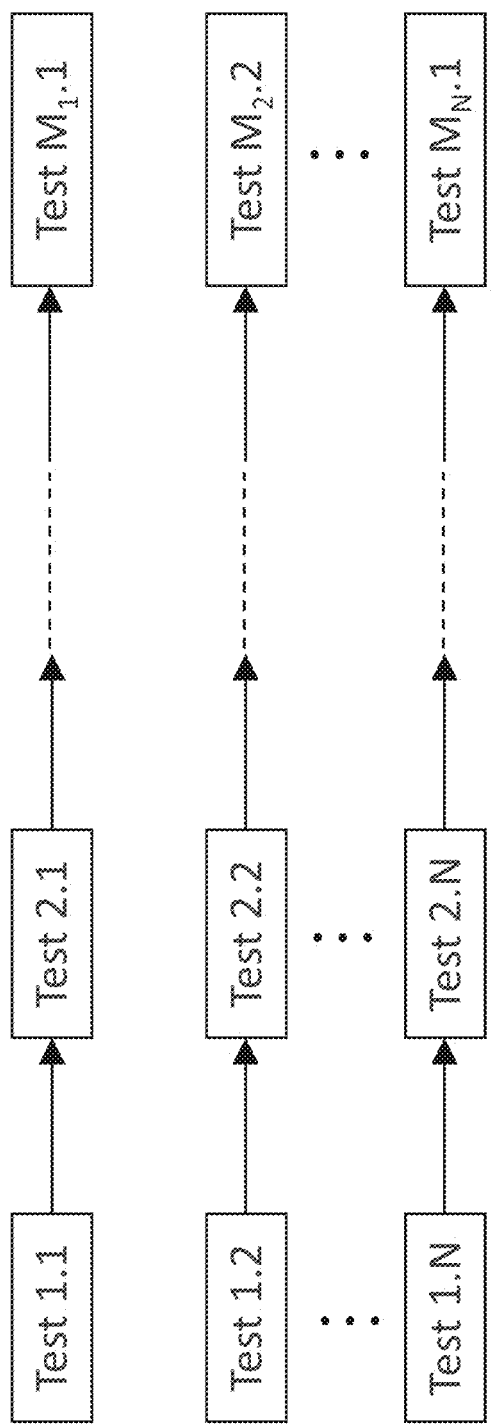
Figure 66:
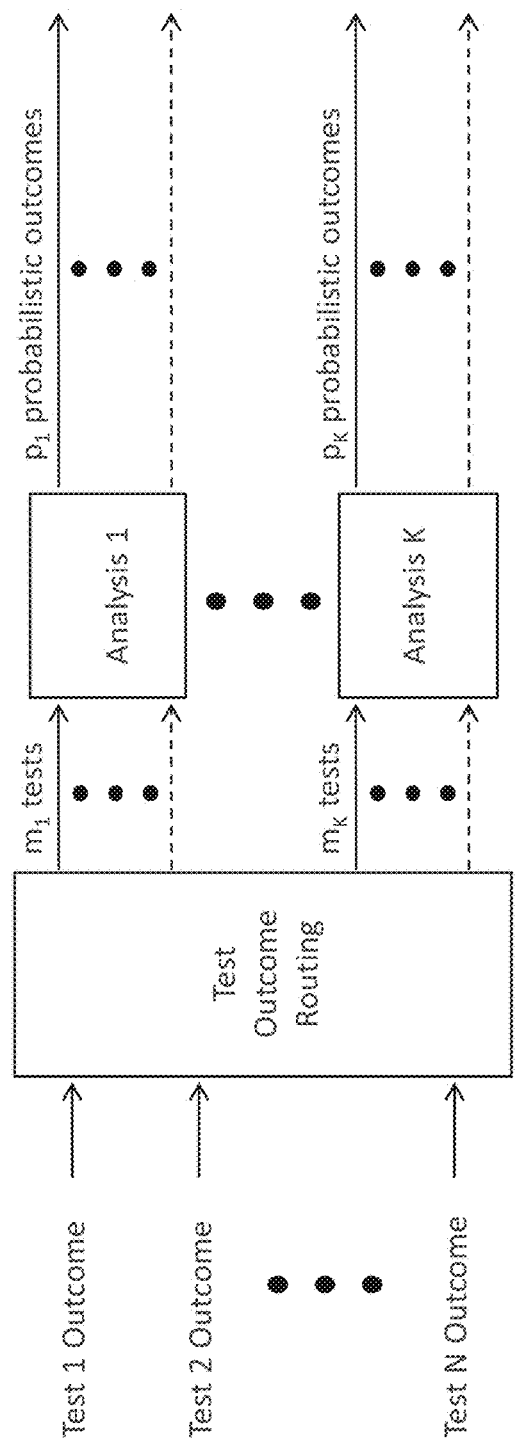

FIG. 65 depicts a representation of an example of parallel sequences of tests and/or test steps used to create measurement situations (via fluidic operations, sensor operations, and potentially other operations). Each measurement situation produces test outcomes FIG. 66 depicts a representation of an example approach wherein test outcomes are provided, via a test outcome routing arrangement, to a plurality of analysis actions implemented in software. Each analysis action uses at least one measurement and produces at least one probabilistic outcome conveying probabilities of various candidate determinations.

Figure 67:
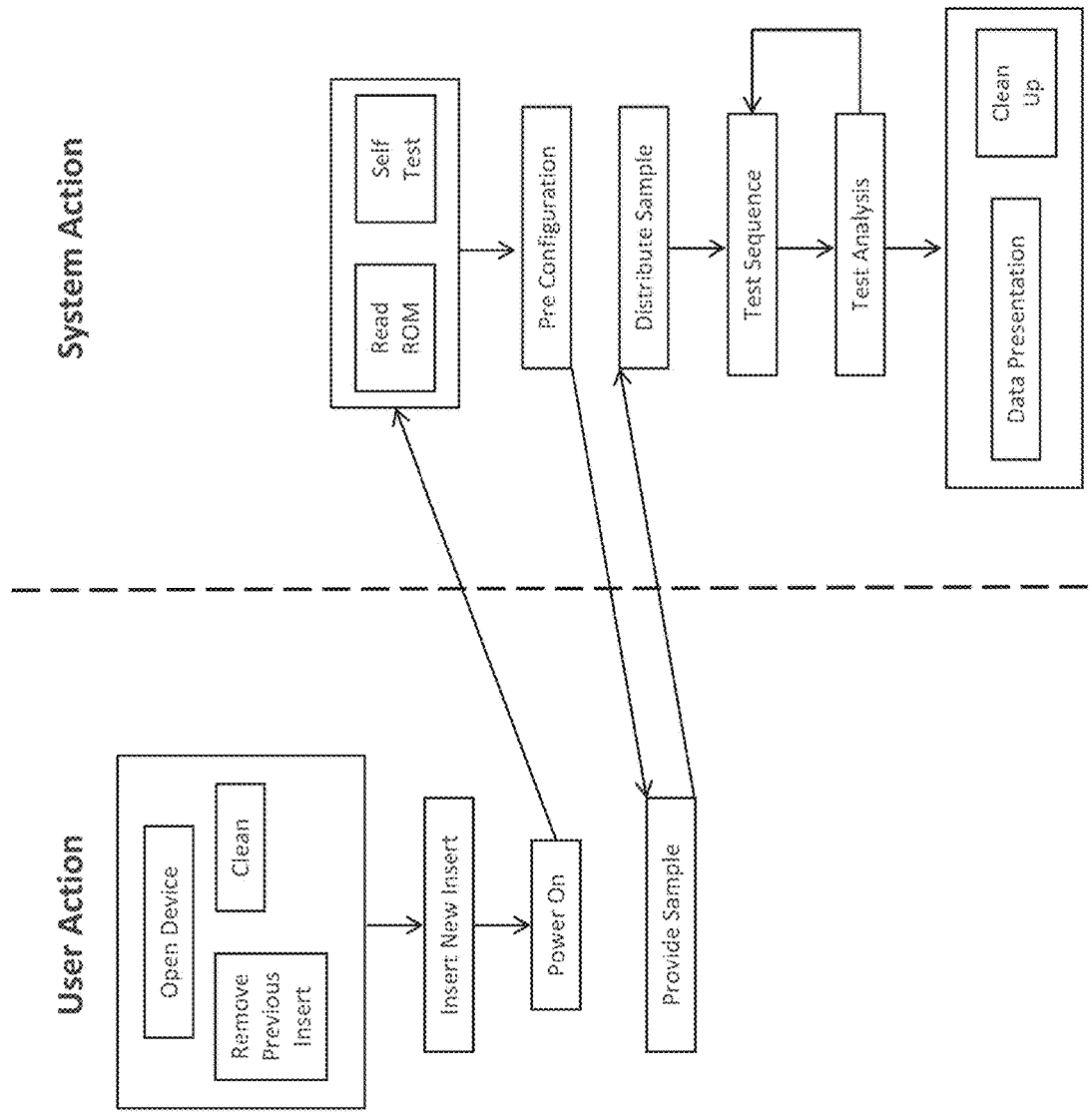

FIG. 67 depicts a representation of an example user experience scenario using an example implementation of the technology.

Figure 68B:
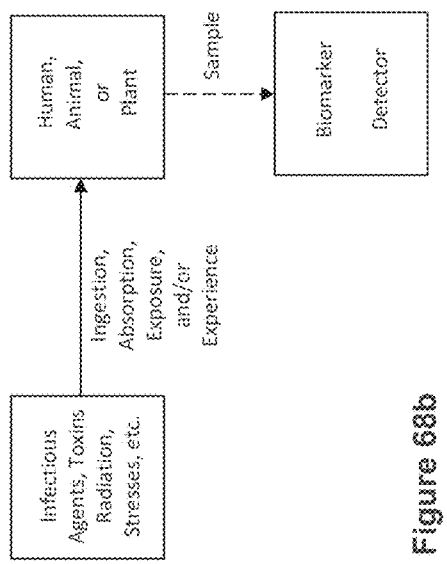
Figure 68A:
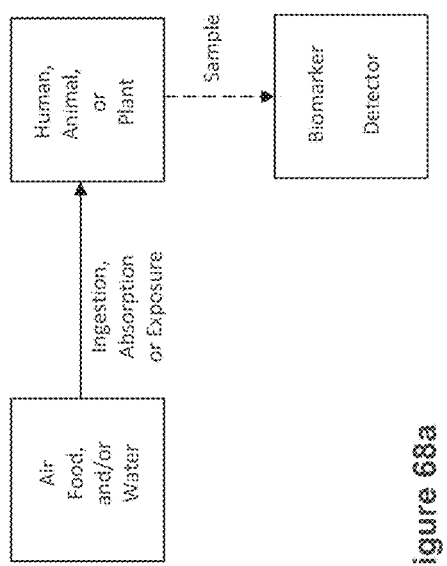

FIG. 68*a* depicts an example representation of a biomarker created by an organism in response to the ingestion, absorption, or exposure to a pathogen, wherein the biomarker present in a sample that can be obtained from the organism and provided to a corresponding biomarker sensor.

FIG. 68*b* depicts an example representation of a biomarker created by a disease invoked within an organism in response to the ingestion, absorption, or exposure to a pathogen, wherein the biomarker present in a sample that can be obtained from the organism and provided to a corresponding biomarker sensor.

Figure 68C:
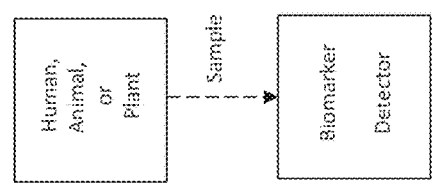

FIG. 68*c* depicts an example representation of a biomarker created more generally by a disease within an organism (for example kidney disease, cancer, Alzheimer's disease, etc., wherein the biomarker present in a sample that can be obtained from the organism and provided to a corresponding biomarker sensor.

Figure 69:
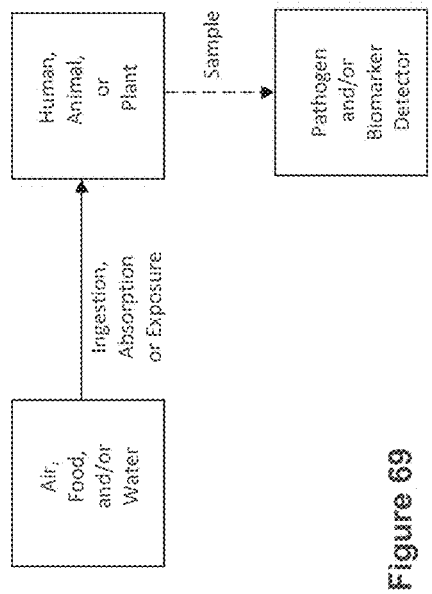

FIG. 69 depicts an example representation wherein an organism that has ingested, absorbed, and/or been exposed to a pathogen present in air, food, or water causes the organism to produce associated biomarkers that can be present in a sample provided to a biomarker detector.

Figure 70:
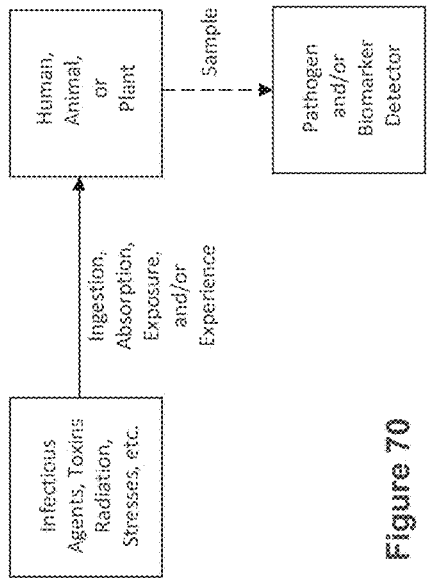

FIG. 70 depicts a more general example representation wherein an organism that has ingested, absorbed, been exposed, and/or experienced a pathogen, toxin, radiation, high temperature, or other harmful substance or harmful situation causes the organism to produce associated biomarkers that can be present in a sample provided to a biomarker detector.

Figure 71:
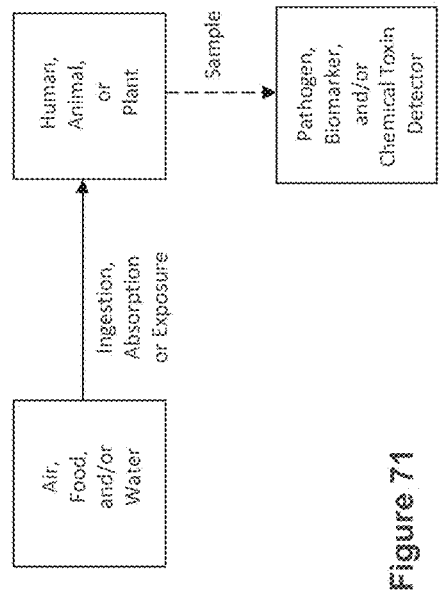

FIG. 71 depicts an example representation of an adaptation of the arrangement depicted in FIG. 69 wherein a sample is provided to an instance of the aforedescribed technology that is configured with pathogen sensors and/or biomarker sensors.

Figure 72:
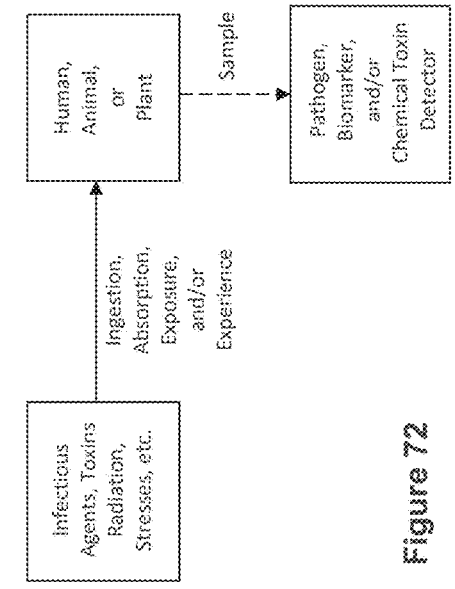

FIG. 72 depicts an example representation of an adaptation of the arrangement depicted in FIG. 70 wherein a sample is provided to an instance of the aforedescribed technology that is configured with pathogen sensors and/or biomarker sensors.

DETAILED DESCRIPTION

In the following description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention.

In the following description, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

The present patent application describes a platform technology for a next generation of pathogen, toxin, biomarker, and chemical sensor and analysis systems. The technology can be implemented in a small sized format and notably can be used for food and water safety testing in the field, distribution chain, laboratory, clinic, and home.

In one aspect, the invention provides sensor assay systems, as well as the removal medium apparatus and base unit comprised therein. These include, but are not limited to, biomarker sensor systems (including for example human biomarkers and environmental biomarkers), field analysis and diagnosis systems, laboratory analysis and diagnosis systems, disease diagnosis systems, food pathogen and toxin detection systems, water pathogen and toxin detection systems, array-based instrumented cell incubator systems, and cell signaling research systems.

In another aspect, the invention provides methods of using the sensor systems to detect chemicals or biochemical materials (such as biomarkers, pathogens, toxins, and the like) in an analyte (such as a fluid analyte).

In another aspect, the invention provides methods of manufacturing the sensor assay systems, as well as the removable medium apparatus and base unit comprised therein.

In another aspect, the invention provides statistical processing of multiple sensor outputs.

In another aspect, the invention provides for associated kits, supplies, and articles of manufacture that are suitable for any of the methods described herein.

Sensor Assay Systems

The present disclosure in some embodiments provides sensor assay systems (also referred to as "sensor devices" or "sensor systems") for analytes (such as fluid analytes) comprising a removable medium apparatus (also referred to herein as the "removable replaceable media element") and a base unit (also referred to herein as the "base unit"). Also provided are removable sensor medium apparatus and the base unit comprised therein. The removable sensor medium apparatus provides a replaceable sensing function for the sensor system. The base unit serves as a platform that, among other functions, 1) provides analytes (such as fluid analytes) or reagents to the removable sensor medium apparatus; and/or 2) receives and processes sensing signals from the removable sensor medium apparatus. This sensor assay system provided herein provides flexibility which allows different analytes to be analyzed using the replaceable medium apparatus. The system also makes it possible to 1) analyze multiple different analytes sequentially or simultaneously; 2) analyze multiple target agents in a single analyte simultaneously or sequentially; and/or 3) utilize different sensor methods for the analysis sequentially or simultaneously (for the same or different analytes or target agents). Depending on the purpose and use of the sensor assay system, the device can be portable or hand-held, or it can be of a larger scale. The device can be reconfigured to tailor the specific needs.

For example, in some embodiments, there is provided a removable medium apparatus for providing replaceable sensing function to an external base unit, the apparatus comprising a plurality (for example at least any of 5, 10, 20, 30, 40, 50, 100, 200, 300, 400, 500, or more) of isolated selective sensors (for example an array of selective sensors) on the surface of a substrate, the isolated selective sensors each comprising at least one layer of a selective detection material, and wherein each selective sensor is configured to provide a variation in a detectable signal responsive to a target agent in an analyte (such as a fluid analyte) provided to the selective sensor. In some embodiments, the removable medium apparatus further comprises a readable medium attached to the substrate comprising information associated with the at least one layer of a selective detection material on at least one of the isolated selective sensor. In some embodiments, the removable medium apparatus further comprises an alignment arrangement for aligning the substrate into a receiving arrangement within the base unit. In some embodiments, the removable medium apparatus further comprises a cap for at least one of the selective sensors. In some embodiments, the regions where selective sensors are located on the removable medium apparatus also serve as a reservoir for reagents and/or analytes. In some embodiments, the removable medium apparatus is fixed or replaceably attached to an interface module (for example an interface module comprising pumps, valves, caps, etc.). The interface module can be an integral part of the removable medium apparatus, an integral part of the base unit, or separately provided.

"Target agent" used herein broadly encompasses any materials contained in an analyte that can be detected by a sensor. These include, but are not limited to, cells, viruses, small molecules compounds, nucleic acids, proteins, peptides, polypeptides, and any other materials discussed herein. "Target agent" is also intended to encompass agents that lead to a change in the analyte, such as pH, oxidative state, and the like. Suitable target agents include, but are not limited to, biomarkers (such as human or environmental biomarkers), pathogens, toxins, cell signaling molecules, and any other target agents disclosed herein.

Suitable selective detection materials include, but are not limited to, antibodies, enzymes, oligonucleotides, DNA, RNA, PNA, or LNA, proteins, peptides, polypeptides, receptors, ligands, small molecules, aptmers, polysaccharides, or any selective detection materials disclosed herein.

The nature of the detectable signal depends on the nature of the sensor(s) used in the removable medium apparatus. These include, for example, electrical signals and optical signals.

In some embodiments, at least one of the selective sensors comprises at least one layer of a semiconductive material. For example, in some embodiments, there is provided a removable medium apparatus for providing replaceable sensing function to a base unit, the apparatus comprising a plurality of isolated selective sensors (for example an array of selective sensors) on the surface of a substrate, the isolated selective sensors each comprising at least one layer of a semiconducting material and at least one layer of a selective detection material, wherein the semiconducting material and the selective detection material form at least a portion of each selective sensor, and wherein each selective sensor is configured to provide a variation in an electrical signal responsive to a target agent in a fluid analyte provided to the selective sensor. In some embodiments, each of the isolated selective sensors is connected to an electrical connection. In some embodiments, the removable medium apparatus further comprises an electrical interface arrangement on the substrate, wherein the electrical interface arrangement is electrically linked to the electrical connections of each of the isolated electrical sensors, and wherein the electrical interface arrangement is further configured for electrically linking to an electrical interface within a base unit. In some embodiments, the removable medium apparatus further comprises a readable medium attached to the substrate comprising information associated with the at least one layer of a selective detection material on at least one of the isolated selective sensor. In some embodiments, the removable medium apparatus further comprises an alignment arrangement for aligning the substrate into a receiving arrangement within the base unit.

Suitable semiconductor materials include, but are not limited to, Si, ZnO, GaN, Ge, InAs, GaAs, C, any combinations thereof, or any other semiconductor materials disclosed herein.

In some embodiments, at least some of the selective sensors on the removable medium apparatus are electrochemical sensors, including, for example, potentiometric electrochemical sensors, amperometric electrochemical sensors, conductometric electrochemical sensors, and impedance electrochemical sensors. In some embodiments, at least some of the selective sensors on the removable medium apparatus are FET, ISFET, or Bio-FET sensors.

Because of the flexibility of the system configuration taught herein, the plurality of the selective sensors on the removable medium apparatus may detect a plurality of different target agents in an analyte (such as a fluid analyte). For example, in some embodiments, there is provided a removable medium apparatus for providing replaceable sensing function to an external base unit, the apparatus comprising a plurality of isolated selective sensors on the surface of a substrate, the isolated selective sensors each comprising at least one layer of a selective detection material, wherein at least two (such as at least any one of 3, 4, 5, 6, 7, 8, 9, 10, 15, 20, 25, 30, or more) of the selective sensors respond to a different target agent in an analyte (such as fluid analyte). This can be accomplished, for example, by including different selective detection materials in the different selective sensors. The sensor device provided herein therefore may allow simultaneous or sequential analyses of multiple target agents in a single analyte, and may fulfill the function which normally would require the use of large and complex assay systems. In some embodiments, at least one of the isolated selective sensors comprises at least one layer of a semiconducting material, wherein the semiconducting material and the selective detection material form at least a portion of the selective sensor.

Alternatively, a removable medium apparatus comprising different selective detection materials may be useful for detecting a single (or a few) target agent(s). For example, the different selective detection materials may be different antibodies recognizing the same or different epitopes on a single molecule. Simultaneously (or sequentially) analyzing/detecting the binding of the different antibodies to the same molecule reduces false positive detections, increases confidence in the reading results, and leads to an increase in detection sensitivity. For example, in some embodiments, there is provided a removable medium apparatus for providing replaceable sensing function to an external base unit, the apparatus comprising a plurality of isolated selective sensors on the surface of a substrate, the isolated selective sensors each comprising at least one layer of a selective detection material, wherein at least two (such as at least any one of 3, 4, 5, 6, 7, 8, 9, 10, 15, 20, 25, 30, or more) of the selective sensors comprises a different selective detection material from each other, and wherein the different selective detection materials respond to the same target agent in the analyte (such as fluid analyte).

The selective sensors on the removable medium apparatus can be of the same nature, i.e., all selective sensors on the removable medium apparatus are electrochemical sensors. In some embodiments, at least two of the selective sensors on the removable medium apparatus are different in nature. For example, one of the selective sensors can be an electrochemical sensor, while another selective sensor can be an organo-electrochemical transistor (OECT) sensor. In some embodiments, the removable medium apparatus can further comprise one or more optical sensor(s). Thus, for example, in some embodiments, there is provided a removable medium apparatus for providing replaceable sensing function to an external base unit, the apparatus comprising a plurality of isolated selective sensors on the surface of a substrate, the isolated selective sensors each comprising at least one layer of a selective detection material, wherein at least two (such as at least any one of 3, 4, 5, 6, or more) of the selective sensors are of different nature from each other. These difference selective sensors may cluster together by kind, for example, the apparatus may comprise one cluster of optical sensors and a different cluster of electrochemical sensors. Alternatively, the difference selective sensors are not clustered together by kind.

In some embodiments, there is provided a removable medium apparatus for providing replaceable sensing function to an external base unit, the apparatus comprising a plurality of isolated selective sensors on the surface of a substrate, the isolated selective sensors each comprising at least one layer of semiconducting material and at least one layer of a selective detection material, wherein the semiconducting material and the selective detection material form at least a portion of each selective sensor, and wherein each selective sensor is configured to provide a variation in an electrical signal responsive to target agent in a analyte (such as fluid analyte) provided to the selective sensor, wherein at least two (such as at least any one of 3, 4, 5, 6, or more) of the selective sensors are of different nature from each other.

In some embodiments, there is provided a removable medium apparatus for providing replaceable sensing function to an external base unit, the apparatus comprising a plurality of isolated selective sensors on the surface of a substrate, wherein at least one (such as at least any one of 2, 3, 4, 5, 6, 7, 8, 9, 10, 15, 20, 25, 30 or more) of the isolated selective sensors are optical sensors, and wherein at least one (such as at least any one of 2, 3, 4, 5, 6, 7, 8, 9, 10, 15, 20, 25, 30, or more) of the isolated selective sensors comprising at least one layer of semiconducting material and at least one layer of a selective detection material, wherein the semiconducting material and the selective detection material form at least a portion of the selective sensor, and wherein each selective sensor is configured to provide a variation in an optical or electrical signals responsive to target agent in an analyte (such as fluid analyte) provided to the selective sensor.

The removable medium apparatus provided herein can be useful for analyzing different analytes, such as fluid analytes. Suitable fluid analytes include, but are not limited to, aqueous solutions, slurries, suspensions, emulsions, micelles, gaseous solutions, and the like. The analyte can be a raw sample, e.g., a food sample, or it can be processed, e.g., a processed food sample. The processing step can be useful, for example, for reducing the background signal in the sample and/or enriching the chemical or biochemical to be detected by the sensor system. In some embodiments, both the raw sample and the processed sample are analyzed by using the same or different removable medium apparatus.

Various target agents can be detected using the removable medium apparatus provided herein. These include, but are not limited to, human biomarkers, environmental biomarkers, pathogens, and toxins. The materials can be small molecules, proteins, peptides, polypeptides, DNA, RNA, PNA, LNA, cells, microorganisms (such as bacteria and viruses), ionic molecules (e.g., iron, chromium, lead, copper, calcium, potassium, or combinations thereof), lipid, carbohydrates, and the like. Sensor configurations that are suitable for detecting such molecules are discussed in the sections below in more detail. Because of the flexible configurations of the systems described herein, a single sensor system and/or a single removable medium apparatus may be used to detect two or more different kinds of target agents. For example, the sensor system can be used to detect different pathogens and toxins in an environmental sample simultaneously.

In some embodiments, there is provided a removable medium apparatus for providing replaceable sensing function to an external base unit, the apparatus comprising a plurality of isolated selective sensors on the surface of a substrate, the isolated selective sensors each comprising at least one layer of a selective detection material, and wherein each selective sensor is configured to provide a variation in a detectable signal responsive to a target agent (such as any of the pathogens or toxins listed in Tables 1 and 2 below) in a food analyte (such as a food fluid analyte) provided to the selective sensor. In some embodiments, at least one layer of the selective detection material comprises an antibody recognizing the target agent (such as any of the materials listed in Tables 1 and 2 below). Pathogens or toxins that can be detected using the removable medium apparatus include, but are not limited to, acrylamide, aflatoxin, arsenic, bisphenol A, botulinum toxin, cadmium, a dioxin, a furan, a polychlorinated biphenyl (PCB), lead, melamine, an organophosphorus pesticide, a Staphylococcal enterotoxin B (SEB), and ricin. Exemplary selective detection materials that can be used for detecting the pathogens and/toxins are provided in Tables 1 and 2.

TABLE 1

Food Contaminants and Toxins

| Food Contaminant/Toxin | Antibody | Method |
| --- | --- | --- |
| acrylamide | | GC/MS, LC/MS, GC-nitrogen-phosphorus detector (NPD), or electron capture detector (ECD) |
| aflatoxin | | SPR using neutrophil porcine elastase as "bait" |
| arsenic | | Colorimetric pH indicator |
| bisphehol A | polyclonal antibody | SPR |
| Botulinum toxin | polyclonal antibody | SPR |
| cadmium | | localized surface plasmon resonance (LSPR) fiber-optic sensor comprising immobilized phytochelatins (PCs), ($\gamma$Glc-Cys)$_8$-Gly, on gold nanoparticle-modified optical fiber (NM$_{Au}$OF). |
| dioxins/furans/PCBs | polyclonal antibody | Antibody-coated piezoelectric |
| lead | | colorimetric assay based on DNAzyme-directed assembly of gold nanoparticles |
| melamine | polyclonal antibody | SPR/optical immunoassay |
| organophosphorus pesticides | | amperometric detection of thiocholine produced by hydrolysis of acetylcholine by immobilized acetylcholinesterase nanocomposites |
| Staphylococcal enterotoxin B (SEB) | polyclonal antibody | sandwich immunoassay |
| ricin | anti-ricin antibodies | sandwich immunoassay |

TABLE 2

Food-Borne Pathogens

| Food Pathogen | Exemplary Analyte/Biomarker | Antibody | Method |
|---|---|---|---|
| *Bacillus cereus* | *B. cereus* enterotoxin | | BCET-RPLA |
| *Campylobacter jejuni* | benzoylglycine amidohydrolase gene (hipO) | | RT-PCR |
| *Clostridium botulinum* | botulinum toxin serotype A or B | polyclonal antibodies | SPR |
| *Cryptosporidium parvum* | *Cryptosporidium* oocyst wall protein (COWP) | | RT-PCR |
| *Escherichia coli* O157:H7 | anti-O157 antibody | polyclonal | SPR |
| *Cyclospora cayetanensis* | whole oocytes | | Autofluorescence at 330 to 380 nm |
| *Giardia lamblia* | small subunit ribosomal RNA gene | | RT-PCR |
| Hepatitis A | | | RT-PCR |
| *Listeria monocytogenes* | | | RT-PCR |
| Norwalk, Norwalk-like, or norovirus | | | RT-PCR |
| *Salmonella* spp. | β-D-glucuronidase (GLUase) | | chromogenic/fluorogenic assay |
| *Staphylococcus aureus* | Staphylococcal enterotoxin B (SEB) | polyclonal antibody | sandwich immunoassay |
| *Shigella* sp. | β-D-glucuronidase (GLUase) | | chromogenic/fluorogenic assay |
| *Toxoplasma gondii* | B1 gene | | RT-PCR |
| *Vibrio* spp. | | | RT-PCR |
| *Yersinia enterocolitica* | | | RT-PCR |

In certain embodiments, the food toxin that can be detected is melamine. In certain embodiments, the melamine can be detected using any antibody shown in Table 3, below.

TABLE 3

Commercially Available Anti-Melamine Antibodies

| Company/Catalog No. | Host/Clonality | Conjugate/Tag/Label | Tested Applications | Immunogen |
|---|---|---|---|---|
| Antibodies-online.com/ABIN678398 | rabbit polyclonal | none | ELISA, immunofluorescence | OVA-conjugated melamine |
| Antibodies-online.com/ABIN723321 | mouse monoclonal | none | ELISA, immunofluorescence | OVA-conjugated melamine |
| Antibodies-online.com/ABIN678405 | rabbit polyclonal | FITC | immunofluorescence | OVA-conjugated melamine |
| Biorbyt/orb5636 | rabbit polyclonal | none | western blot, immunohistochemistry (paraffin), ELISA | KLH-conjugated melamine |
| Biorbyt/orb8484 | rabbit polyclonal | FITC | immunofluorescence, immunocytochemistry | KLH-conjugated melamine |
| Biorbyt/orb17013 | rabbit polyclonal | HRP | ELISA | Synthetic peptide |
| Biorbyt/orb13032 | rabbit polyclonal | gold | ELISA | Synthetic peptide |
| Biorbyt/orb13009 | rabbit polyclonal | biotin | ELISA | Synthetic peptide |
| Bioss/bs-0904R0HRP | rabbit polyclonal | HRP | ELISA | KLH-conjugated melamine |
| Bioss/bs-0939R-Cy3 | rabbit polyclonal | Cy3 | immunofluorescence | MAP Lys to Melamine |
| Bioss/bs-0939R-Cy7 | rabbit polyclonal | Cy7 | immunofluorescence | MAP Lys to Melamine |
| Bioss/bs-0939R-PE-Cy5 | rabbit polyclonal | PE-Cy5 | immunofluorescence | MAP Lys to Melamine |
| Bioss/bs-0904R-A555 | rabbit polyclonal | A555 | immunofluorescence | KLH-conjugated melamine |
| Bioss/bs-2182R-A647 | rabbit polyclonal | A647 | immunofluorescence | OVA-conjugated melamine |
| Bioss/bsm-2182M | mouse monoclonal | none | ELISA | OVA-conjugated melamine |
| Bioss/bsm-2182M-Cy5 | mouse monoclonal | Cy5 | immunofluorescence | OVA-conjugated melamine |
| Bioss/bsm-2182M-PE-Cy7 | mouse monoclonal | PE-Cy7 | immunofluorescence | OVA-conjugated melamine |
| Bioss/bsm-2182M-A350 | mouse monoclonal | A350 | immunofluorescence | OVA-conjugated melamine |

In some embodiments, there is provided a removable medium apparatus for providing replaceable sensing function to an external base unit, the apparatus comprising a plurality of isolated selective sensors on the surface of a substrate, the isolated selective sensors each comprising at least one layer of a selective detection material, wherein each selective sensor is configured to provide a variation in an detectable signal responsive to a target agent (such as an environmental biomarker, for example any one of the environmental biomarkers listed in Table 4) in an analyte (such as fluid analyte, for example a raw or processed fluid sample obtained from the environment, e.g., a water sample) provided to the selective sensor. In some embodiments, at least one layer of the selective detection material comprises an antibody recognizing the environmental biomarker. Environmental biomarkers that can be detected using the removable medium apparatus include, but are not limited to, lead, arsenic, cadmium, an organophosphate, parathion, benzene, a nitrate, a nitrite, a polycyclic aromatic hydrocarbon (PAH), cotinine, nicotine, bisphenol A, a polybrominated diphenyl ether, dioxin, a furan, a (PCB), Dichlorodiphenyltrichloroethane (DDT), a phthalate, formaldehyde, an aflatoxin, and toluene. Exemplary selective detection materials that can be used for detecting the environmental biomarkers are provided in Table 4.

TABLE 4

Environmental Biomarkers

| Environmental Pollutant | Antibody | Method |
|---|---|---|
| Lead (e.g., PSA NCAM expression) | Anti-NCAM PSA antibody | Immunofluorescence |
| Arsenic | | Colorimetric pH indicator |
| Cadmium | | localized surface plasmon resonance (LSPR) fiber-optic sensor comprising immobilized phytochelatins (PCs), |

TABLE 4-continued

Environmental Biomarkers

| Environmental Pollutant | Antibody | Method |
|---|---|---|
| Organophosphates (e.g., parathion) | ScFv | (Glc-Cys)$_8$-Gly, on gold nanoparticle-modified optical fiber (NM$_{Au}$OF). Piezoelectric enzyme immunoassay Amperometric detection of thiocholine produced by hydrolysis of acetylcholine by immobilized acetylcholinesterase nanocomposites |
| Benzene | | |
| Nitrate/nitrite | | Nitrate Reductase on screen printed electrodes Optical detection based on nitrite reductase immobilised in controlled pore glass |
| Polycyclic aromatic hydrocarbon | | Fluorescence-inhibitory, spectroscopic detection based on anti-PAH antibodies Immobilized recombinant bioluminescent *Escherichia coli* strain, harboring a lac::luxCDABE |
| Cotinine/Nicotine | | Metalloporphyrin based fluorescent chemosensor for selective detection of dinitrogen alkaloids |
| Bisphenol A | polyclonal antibody | SPR |
| Polybrominated diphenyl ethers | | SPR using T4 binding globulin (TBG) as "bait" |
| Dioxin/furan/PCBs | polyclonal antibody | Antibody-coated piezoelectric |
| Dichlorodiphenyl-trichloroethane (DDT) | | potentiometric detection based on immobilized dehydrohalogenase SPR |
| Phthalates | | Electrolytic detection with nanostructured titanium and iron oxides sensors |
| Formaldehyde | | pH detection based on alcohol oxidase (AOX) enzyme-conjugated acrylic microspheres |
| Alflatoxin | ScFv | SPR SPR using neutrophil porcine elastase as "bait" |
| Tolulene | | Phosphorescent detection based on immobilized Toluene ortho-monooxygenase |

In some embodiments, there is provided a removable medium apparatus for providing replaceable sensing function to an external base unit, the apparatus comprising a plurality of isolated selective sensors on the surface of a substrate, the isolated selective sensors each comprising at least one layer of a selective detection material, wherein the semiconducting material and the selective detection material form at least a portion of each selective sensor, and wherein each selective sensor is configured to provide a variation in a detectable signal responsive to a biomarker (such as a human biomarker) in an analyte (such as fluid analyte, for example a raw or processed human sample) provided to the selective sensor. In some embodiments, at least one layer of the selective detection material comprises an antibody recognizing the biomarker. Human biomarkers that can be detected by the removable medium apparatus include, but are not limited to, biomarkers provided in FIGS. 18-22.

Further provided are sensor assay systems (also referred to as "sensor devices") comprising any of the removable medium apparatus discussed herein. For example, in some embodiments, there is provided a sensor device comprising a removable medium apparatus and a base unit, wherein the removable medium apparatus comprising a plurality (for example at least any of 5, 10, 20, 30, 40, 50, 100, 200, 300, 400, 500, or more) of isolated selective sensors (for example an array of selective sensors) on the surface of a substrate, the isolated selective sensors each comprising at least one layer of a selective detection material, and wherein each selective sensor is configured to provide a variation in a detectable signal responsive to a target agent in an analyte (such as a fluid analyte) provided to the selective sensor. In some embodiments, the removable medium apparatus further comprises a readable medium attached to the substrate comprising information associated with the at least one layer of a selective detection material on at least one of the isolated selective sensor. In some embodiments, the removable medium apparatus further comprises an alignment arrangement for aligning the substrate into a receiving arrangement within the base unit. In some embodiments, the removable medium apparatus further comprises a cap for at least one of the selective sensors. In some embodiments, the regions where selective sensors are located on the removable medium apparatus also serve as a reservoir for reagents and/or analytes. In some embodiments, the removable medium apparatus is fixed or replaceably attached to an interface module (for example an interface module comprising pumps, valves, caps, etc.). The interface module can be an integral part of the removable medium apparatus, an integral part of the base unit, or separately provided.

In some embodiments, there is provided a sensor device comprising a removable medium apparatus and a base unit, wherein the removable medium apparatus provides a replaceable sensing function to the base unit, wherein the removable medium apparatus comprises a plurality of isolated selective sensors on the surface of a substrate, the isolated selective sensors each comprising at least one layer of semiconducting material and at least one layer of a selective detection material, wherein the semiconducting material and the selective detection material form at least a portion of each selective sensor, and wherein each selective sensor is configured to provide a variation in an electrical signal responsive to a target agent in an analyte (such as fluid analyte) provided to the selective sensor. In some embodiments, each of the isolated selective sensors is connected to an electrical connection. In some embodiments, the removable medium apparatus further comprises an electrical interface arrangement on the substrate, wherein the electrical interface arrangement is electrically linked to the electrical connections of each of the isolated electrical sensors, and wherein the electrical interface arrangement is further configured for electrically linking to an electrical interface within a base unit. In some embodiments, the removable medium apparatus further comprises a readable medium attached to the substrate comprising information associated with the at least one layer of a selective detection material on at least one of the isolated selective sensor. In some embodiments, the removable medium apparatus further comprises an alignment arrangement for aligning the substrate into a receiving arrangement within the base unit.

The base unit discussed herein in some embodiments comprises at least one computational processor for executing software and a receiving arrangement for receiving, aligning, and/or physically supporting the removable medium apparatus. In some embodiments, the base unit further comprises interface electronics for connecting to the electrical interface arrangement of a removable medium apparatus for producing of sensor measurement signals. In some embodiments, the base unit further comprises a medium reader for reading encoded data on a readable medium on the removable medium apparatus, which provides at least first information to the computational processor. In some embodiments, the base unit further comprises a user interface.

In some embodiments, the base unit further comprises a fluidic interface arrangement for providing a fluid analyte to the removable medium apparatus and/or providing/removing reagents to and from the removable medium apparatus. In some embodiments, the base unit comprises microfluidic channels for guiding fluid flow within the base unit and/or to the removable medium apparatus. In some embodiments, the isolated regions where the selective sensors are located may also serve as reservoirs for reagent solutions. In some embodiments, the base unit may further comprise reaction chambers or microfluidic channels for sample processing prior to feeding the processed sample to the removable medium apparatus. In some embodiments, the base unit further comprises pumps, valves, and/or other components for a microfluidic device.

Method of Using the Sensor Assay System

The sensor assay systems described herein can be used to analyze target agents within an analyte (such as fluid analyte) both qualitatively and quantitatively.

In some embodiments, there is provided a method of detecting a target agent in an analyte (such as fluid analyte) using a sensor device comprising a removable medium apparatus comprising a selective sensor comprising at least one layer of a selective detection material recognizing said target agent, the method comprising: 1) allowing the analyte (such as fluid analyte) to be in contact with the selective detection material, and 2) detecting a detectable signal (such as an electrical signal) from the selective sensors on the removable medium apparatus, wherein a variation (in some embodiments a characteristic variation) of the detectable signal (such as electrical signal) prior to and after the contact of the fluid analyte is indicative of the presence of the target agent. In some embodiments, the method further comprises replacing the removable medium apparatus with a second removable medium apparatus and repeating the steps 1) and 2). In some embodiments, the method further comprises providing an analyte. In some embodiments, the method further comprises processing the analyte (for example processing the analyte in the sensor device).

In some embodiments, there is provided a method of determining the amount (or concentration) of a target agent in an analyte (such as fluid analyte) using a sensor device comprising a removable medium apparatus comprising a selective sensor comprising at least one layer of a selective detection material recognizing said target agent, the method comprising: 1) allowing the fluid analyte to be in contact with the selective detection material, and 2) detecting a detectable signal from the selective sensors on the removable medium apparatus, wherein the change of the detectable signal after the contact of the fluid analyte correlates with (e.g., is directly proportional to) the amount (or concentration) of the target agent in the fluid analyte. In some embodiments, the method further comprises replacing the removable medium apparatus with a different removable medium apparatus and repeating the steps 1) and 2). In some embodiments, the method further comprises providing an analyte. In some embodiments, the method further comprises processing the analyte (for example processing the analyte in the sensor device).

In some embodiments, at least two different fluid analytes are provided to different selective sensors on the removable medium apparatus on the sensor device. This allows different fluid analytes be analyzed sequentially or simultaneously by using the same device (either by using the same removable medium apparatus or difference removable medium apparatus). For example, the method in some embodiments comprises providing a first fluid analyte to a first selective sensor on the removable medium apparatus, then, after a certain chemical or biochemical is detected in the first fluid analyte, providing a second fluid analyte to a second selective sensor on the same removable medium apparatus. The second fluid analyte can be, for example, a processed product of the first fluid analyte. In some embodiments, the second fluid analyte provided to the second selective sensor is transferred from the first selective sensor. Alternatively, the first and second fluid analytes are simultaneously analyzed.

The sensor assay systems described can be used for a broad spectrum of applications, which include, but are not limited to, detection of biomarkers (including for example human biomarkers and environmental biomarkers), detection of chemicals, contaminations, pathogens or toxins in a sample (such as a food sample or a sample from the environment), diagnosing disease, analyzing research samples, experimental assays, work-place compliance drug testing, and sports doping. The sensor devices described herein can also be useful for: 1) detecting and/or quantitating a specific kind of cells in a cell suspension sample, 2) detecting and/or quantitating a gas in a fluid sample; 3) cell signaling research system. The devices and their uses are further discussed below in more detail.

In some embodiments, there is provided a method of detecting a target agent (such as any of the chemicals listed in Tables 1 and 2 supra. in a food analyte (such as fluid food analyte, for example a raw or processed food sample) using a sensor device comprising a removable medium apparatus comprising a selective sensor comprising at least one layer of a selective detection material recognizing said target agent, the method comprising: 1) allowing the food analyte to be in contact with the selective detection material, and 2) detecting a detectable signal from the selective sensors on the removable medium apparatus, wherein a variation of the signal prior to and after the contact of the food analyte is indicative of the presence of the chemical (such as any of the chemicals listed in Tables 1 and 2 supra. In certain embodiments, the food toxin that can be detected is melamine. In certain embodiments, the melamine can be detected using any antibody shown in Table 3, supra. In some embodiments, the method further comprises replacing the removable medium apparatus with a different removable medium apparatus and repeating the steps 1) and 2). In some embodiments, there is provided a method of determining the amount of target agent (such as any of the chemicals listed in Tables 1 and 2 supra) in a food analyte (such as fluid food analyte, for example a raw or processed food sample) using a sensor device comprising a removable medium apparatus comprising a selective sensor comprising at least one layer of a selective detection material recognizing said target agent, the method comprising: 1) allowing the food analyte to be in contact with the selective detection material, and 2) detecting a detectable signal from the selective sensors on the removable medium apparatus, wherein the change of the signal after the contact of the food analyte correlates with the amount of the target agent (such as any of the chemicals listed in Tables 1 and 2 supra) in the food analyte. In certain embodiments, the food toxin that can be detected is melamine. In certain embodiments, the melamine can be detected using any antibody shown in Table 3, supra. In some embodiments, the method further comprises replacing the removable medium apparatus with a different removable medium apparatus and repeating the steps 1) and 2).

In some embodiments, there is provided a method of detecting an environmental biomarker in an analyte (such as fluid analyte, for example a raw or processed sample obtained from the environment, e.g., a water sample) using a sensor device comprising a removable medium apparatus comprising a selective sensor comprising at least one layer of a selective detection material recognizing said biomarker, the method comprising: 1) allowing the fluid analyte to be in contact with the selective detection material, and 2) detecting a detectable signal from the selective sensors on the removable medium apparatus, wherein a variation of the signal prior to and after the contact of the fluid analyte is indicative of the presence of the biomarker. In some embodiments, the method further comprises replacing the removable medium apparatus with a different removable medium apparatus and repeating the steps 1) and 2). In some embodiments, there is provided a method of determining the amount of an environmental biomarker in an analyte (such as fluid analyte, for example a raw or processed sample obtained from the environment, e.g., a water sample) using a sensor device comprising a removable medium apparatus comprising a selective sensor comprising at least one layer of a selective detection material recognizing said biomarker, the method comprising: 1) allowing the fluid analyte to be in contact with the selective detection material, and 2) detecting a detectable signal from the selective sensors on the removable medium apparatus, wherein the change of the signal after the contact of the fluid analyte correlates with the amount of the biomarker in the fluid analyte. In some embodiments, the method further comprises replacing the removable medium apparatus with a different removable medium apparatus and repeating the steps 1) and 2). Environmental biomarkers that can be detected and/or quantified include, but are not limited to, lead, arsenic, cadmium, an organophosphate, parathion, benzene, a nitrate, a nitrite, a polycyclic aromatic hydrocarbon (PAH), cotinine, nicotine, bisphenol A, a polybrominated diphenyl ether, dioxin, a furan, a (PCB), Dichlorodiphenyltrichloroethane (DDT), a phthalate, formaldehyde, an aflatoxin, and toluene.

In some embodiments, there is provided a method of detecting a biomarker (such as a human biomarker) in an analyte (such as fluid analyte, for example a raw or processed human sample) using a sensor device comprising a removable medium apparatus comprising a selective sensor comprising at least one layer of a selective detection material recognizing said biomarker, the method comprising: 1) allowing the fluid analyte to be in contact with the selective detection material, and 2) detecting a detectable signal from the selective sensors on the removable medium apparatus, wherein a variation of the signal prior to and after the contact of the fluid analyte is indicative of the presence of the biomarker. In some embodiments, the method further comprises replacing the removable medium apparatus with a different removable medium apparatus and repeating the steps 1) and 2). In some embodiments, there is provided a method of determining the amount of a biomarker (such as a human biomarker) in an analyte (such as fluid analyte, for example a raw or processed human fluid sample) using a sensor device comprising a removable medium apparatus comprising a selective sensor comprising at least one layer of a selective detection material recognizing said biomarker, the method comprising: 1) allowing the fluid analyte to be in contact with the selective detection material, and 2) detecting a detectable signal from the selective sensors on the removable medium apparatus, wherein the change of the signal after the contact of the fluid analyte correlates with the amount of the biomarker in the fluid analyte. In some embodiments, the method further comprises replacing the removable medium apparatus with a different removable medium apparatus and repeating the steps 1) and 2). Human biomarkers that can be detected and/or quantified include, but not limited to, those provided in FIGS. 18-22. Suitable human samples include, but not limited to, blood, blood-derived compositions such as plasma or serum, saliva, sweat, tears, urine, stool, earwax, secretions, sputum, phlegm, vomit, mucus, plasma, ductal fluid, exhaled breath, cerebrospinal fluid, milk, ductal fluid, and semen.

The methods can be useful for diagnosing various diseases in an individual, including, but not limited to, a bacterial infection, a viral infection, a parasitic infection, a neurological disease, a metabolic disorder, an immune disorder, a musculoskeletal disorder, a liver disease, a heart disease, a pancreatic disease, a renal disease, a pulmonary disease, a gynecological disease, a genetic disorder, toxicity, an autoimmune disease, a cancer, or a cancer-like disease. In some embodiments, the disease to be diagnosed is selected from the group consisting of: a *Listeria* infection, an *E. coli* 0157:H7 infection, a *Brucells melitensis* infection, an anthrax infection, a *Bacillus* infection, a *Campylobacter* infection, a *Clostridium* infection, a *Cryptosporidium* infection, a *Cyclospora* infection, a *Giardia* infection, a Norwalk or Norwalk-like viral infection, a norovirus infection, a *Salmonella* infection, a Staphylococcal infection, a *Shigella* infection, a *Toxoplasma* infection, a *Vibrio* infection, a *Yersinia* infection, a Venezuelan equine encephalitis viral infection, viral hepatitis A, viral hepatitis B, viral hepatitis C, HIV, SARS, malaria, schistosomiasis, lung cancer, ovarian cancer, gastric carcinoma, prostate cancer, breast cancer, leukemia, testicular cancer, a solid tumor cancer, a melanoma, liver cancer, pancreatic cancer, colon cancer, esophagus carcinoma, trophoblastic cancer, bladder cancer, organ transplant failure, renal allograft failure, graft-versus-host disease, inflammatory bowel disease, hepatotoxicity, cardiotoxicity, neurotoxicity, neuropathy, neuroinflammation, alcohol-induced organic brain disorder, Alzheimer's disease, inflammation, acute intermittent porphyria, diabetes mellitus, renal complications in type 2 diabetes mellitus, cardiovascular complications in type 2 diabetes mellitus, hyperglycemia, insulin resistance, rheumatoid arthritis, osteoarthritis, osteoporosis, tuberculosis, fatty liver disease, liver injury, cirrhosis, kidney injury, diabetic nephropathy, emphysema, cystic fibrosis, lung inflammation during and exacerbation of cystic fibrosis, impaired lung function due to smoking, COPD, asthma, rhinosinusitis, respiratory distress syndrome, interstitial lung disease, radiation pneumonitis, myocardial infarction, ischemic heart disease, preeclampsia, endometriosis, Duchene and Becker muscular dystrophy, phenylketonuria, lysosomal storage disorder, Gaucher's disease, mucopolysaccharidosis, fucosidosis, erectile dysfunction, heat stroke, neuropathic pain, fibromyalgia, traumatic brain injury, stroke, epilepsy, Parkinson's disease, and Creuzfeldt-Jakob disease.

Exemplary biomarkers and corresponding selective detection materials that can be useful for these diseases are provided in FIGS. 18-22. In some embodiments, the presence of a biomarker in a raw or processed sample from an individual may be indicative of 1) the presence or absence of a disease; 2) an increased or decreased likelihood of responsiveness to a treatment; 3) responsiveness or non-responsiveness to a treatment; 4) suitability for treatment; or 5) a need for continued treatment or termination of the treatment. In some embodiments, the sensor assay system, using a single or multiple removable medium apparatus, allows detection of a plurality of (such as any of 2, 5, 10, 20, 30, 40, 50, 60, 70, 80, 90, 100, 200, 300, 400, 500, or more) biomarkers. The presence/absence and/or levels of these biomarkers collectively provide a biomarker profile that is indicative of 1) the presence or absence of a disease; 2) an increased or decreased likelihood of responsiveness to a treatment; 3) responsiveness or non-responsiveness to a treatment; 4) suitability for treatment; or 5) a need for continued treatment or termination of the treatment. In some embodiments, the presence or absence of the biomarker (or a collective biomarker profile) is used as a basis for selecting an individual for a disease treatment.

Methods of Making the Sensor Assay Systems

Also provided herein are methods of making the sensor assay systems as well as the removable medium apparatus and base units comprised therein. The methods of manufacturing are discussed further below in more detail.

For example, in some embodiments, there is provided a method for making a removable medium apparatus for providing replaceable sensing function to an external base unit, the apparatus comprising a plurality of isolated selective sensors on the surface of a substrate, wherein each of the isolated regions the semiconducting material and selective detection material form at least portions of a selective sensor, the method comprising: depositing an array of isolated regions of semiconducting material on the surface of a substrate, the isolated regions comprising at least one layer of semiconducting material; depositing at least one layer of a selective detection material on each of the isolated regions in the array. In some embodiments, the method further comprises providing an electrical connection to each of the isolated regions of semiconducting material. In some embodiments, the method further comprises providing a digital file comprising at least information associated with the at least one layer of a selective detection material on at least one of the isolated region. In some embodiments, the digital file comprised by a readable medium attached to the substrate.

In some embodiments, the selective detection material deposited on at least one of the isolated regions comprises at least one antibody. In some embodiments, the selective detection material deposited on at least one of the isolated regions comprises at least one synthetic antibody. In some embodiments, the selective detection material deposited on at least one of the isolated regions comprises a molecularly imprinted material. In some embodiments, the selective detection material deposited on at least one of the isolated regions comprises a molecularly imprinted polymer.

In some embodiments, the deposition is accomplished by printing (such as inkjet-printing). In some embodiments, the deposition is accomplished by functional printing. In some embodiments, the selective detection material deposited on at least one of the isolated regions comprises an enzyme. In some embodiments the selective detection material deposited on at least one of the isolated regions comprises at least one membrane. In some embodiments, the isolated regions of semiconducting material are part of a field effect transistor. In some embodiments, at least one of the selective sensors in the selective sensor array is an electrochemical sensor. In some embodiments, the least one of the selective sensors in the selective sensor array is a photodiode.

In some embodiments, the substrate further comprises a deposit of a reagent material. In some embodiments, the substrate further comprises a deposit of a pH buffer material. In some embodiments, the digital file comprises information usable to operate a testing procedure. In some embodiments the digital file comprises information usable to perform a statistical analysis. In some embodiments, the digital file comprises date information. In some embodiments, the readable medium that is attached to the substrate by printing at least one material on the substrate. In some embodiments, the depositing of semiconducting material is performed by a printing process. In some embodiments, the depositing of selective detection material is performed by a printing process. In some embodiments, the electrical connections are deposited by a printing process. In some embodiments, the electrical connections are previously rendered on the substrate.

In some embodiments, the substrate further comprises an electrochemical sensor that does not employ a semiconducting material. In some embodiments, the substrate further comprises arrangements associated with at least one optical sensor. In some embodiments, the substrate further comprises an optical element. In some embodiments, the substrate further comprises an optical filter. In some embodiments, the substrate is attached to a second substrate so that the resulting arrangement is configured to comprise a fluidic channel.

In some embodiments, the at least one of the selective sensors in the selective sensor array is configured to detect a particular protein. In some embodiments, the at least one of the selective sensors in the selective sensor array is configured to detect a particular biomarker. In some embodiments, the at least one of the selective sensors in the selective sensor array is configured to detect a particular pathogen. In some embodiments, the at least one of the selective sensors in the selective sensor array is configured to detect a particular chemical species. In some embodiments, the at least one of the selective sensors in the selective sensor array is configured to detect a particular chemical toxin.

Methods of Implementing Statistical Processing of Sensor Measurement

Also provided herein are methods of implementing statistical processing of sensor measurements produced by the any one of the sensor assay systems described herein. For example, in some embodiments, there is provided a method for implementing statistical processing of sensor measurements produced by sensor assay system comprising a plurality of selective sensors, the method comprising: obtaining a collection of measurements, the collection comprising at least one measurement from a plurality of selective sensors, the measurements responsive to a target agent in an analyte, and the plurality of selective sensors comprising at least a collection of sensors, each responsive to a different attribute of the sample, and at least a collection of different types of sensors responsive to the same attribute of the sample; performing first mathematical operations on at least some of the measurements of the collection to produce a plurality of first mathematical outcomes, each first mathematical outcome comprising an associated value; performing a second mathematical operation on at least some of the first mathematical outcomes to produce at least one second mathematical outcome, each second mathematical outcome comprising an associated result value; wherein the result value is used to represent the outcome of a test to which the sample is interrogated, and wherein the first mathematical operations and second mathematical operation are chosen so that the statistical accuracy of the test is greater than the statistical accuracy of each individual sensor.

In some embodiments, the first mathematical operations produce a binary-valued mathematical outcome. In some embodiments, at least some of the first mathematical operations produce a mathematical outcome comprising more than two values. In some embodiments, the second mathematical operation produces a binary-valued mathematical outcome. In some embodiments, the second mathematical operation produces a mathematical outcome comprising more than two values. In some embodiments, the second mathematical operation produces a binary-valued mathematical outcome representing detection and an additional mathematical outcome comprising more than two values representing likelihood. In some embodiments, the second mathematical operation produces a binary-valued mathematical outcome representing detection and an additional mathematical outcome comprising more than two values representing a confidence level. In some embodiments, at least some of the first mathematical operations comprise at least a linear operation. In some embodiments, at least some of the first mathematical operations comprise at least a nonlinear operation. In some embodiments, the second mathematical operation comprises at least a linear transformation operation. In some embodiments, the second mathematical operation comprises at least a nonlinear operation. In some embodiments, at least some of the first mathematical operations are specified by at least one externally specified parameter. In some embodiments, the second mathematical operation is specified by at least one externally specified parameter. In some embodiments, at least one of the first mathematical operations are sequenced through a plurality of steps. In some embodiments, the second mathematical operation is sequenced through a plurality of steps. In some embodiments, at least one of the first mathematical operations and the second mathematical operation are sequenced together through a plurality of steps. In some embodiments, the at least one of the first mathematical operations and the second mathematical operation is sequenced through a plurality of steps, producing a series of at least second mathematical outcomes, wherein the series of at least second mathematical outcomes are stored as a file. In some embodiments, the at least one of the first mathematical operations is varied by a parameter, and the parameter is sequenced through a plurality of steps. In some embodiments, the second mathematical operation is varied by a parameter, and the parameter is sequenced through a plurality of steps. In some embodiments, the at least one of the first mathematical operations is varied by a first parameter, the second mathematical operation is varied by a second parameter, and the first and second parameters are sequenced through a plurality of steps.

Figure 3A:
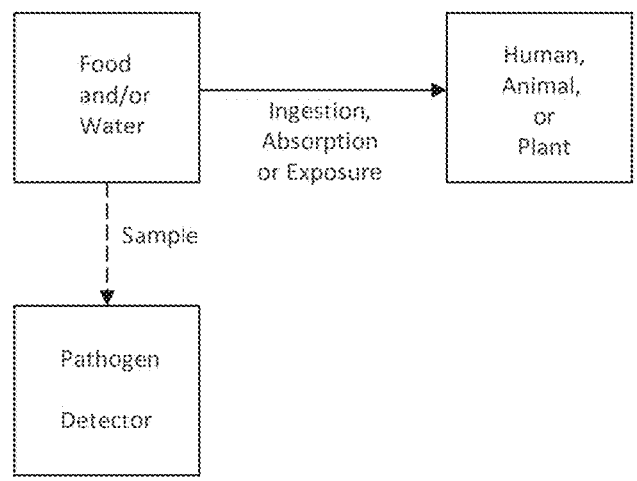
FIG. 3a depicts an example representation of how pathogens borne by food and/or water can be ingested by, absorbed by, and/or exposed to an organism (such as a human, animal, plant, etc.).
Figure 3B:
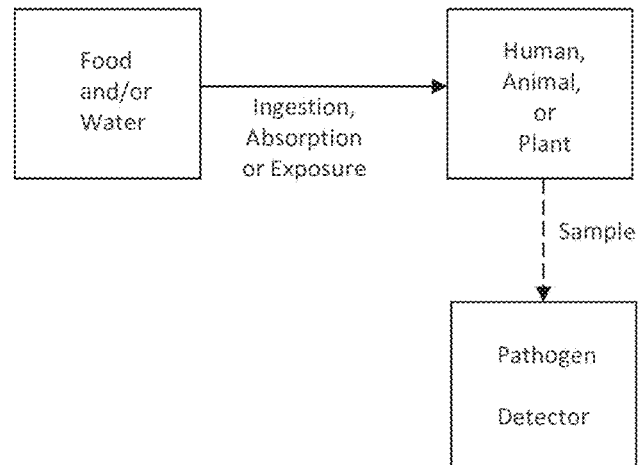
FIG. 3b depicts an example representation wherein pathogens borne by food and/or have already can be ingested by, absorbed by, and/or exposed to an organism and are now present in the organism.
Figure 4A:
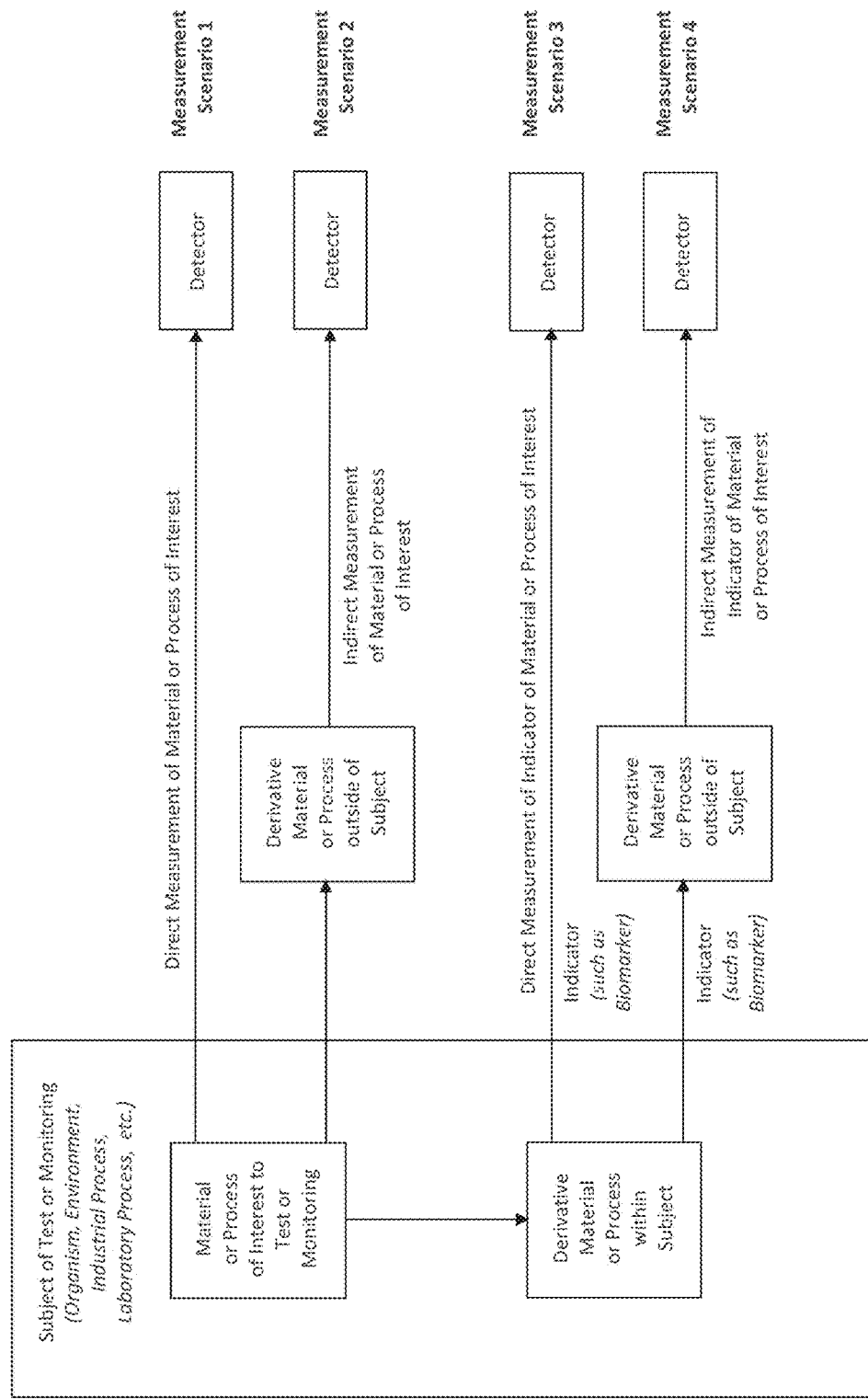
FIG. 4a depicts four example measurement scenarios for measuring (including detecting the presence of) a material or process of interest in the testing or monitoring of a subject.

Further as to the discussion associated with FIG. 3b, FIG. 4a depicts four example measurement scenarios for measuring (including detecting the presence of) a material or process of interest in the testing or monitoring of a subject.

In the first of these (Scenario 1) a material or process of interest is directly measured by a detector. For example, a specific protein can be recognized by a "highly-tuned" (high sensitivity and high selectivity) sensor (such as an immunosensor, to be described);

In the second example (Scenario 2) a material or process of interest is indirectly measured by a detector that actually measures a derivative material or process outside of the subject that is responsive to the material or process of interest;

In the third example (Scenario 3) a material or process of interest invokes a derivative material or process inside of the subject (an "indicator"), and that derivative material or process is directly measured by a detector;

In the fourth example (Scenario 4) a material or process of interest invokes a derivative material or process inside of the subject (indicator), and that derivative material or process (indicator) is indirectly measured by a detector that actually measures a subsequent derivative material or process outside of the subject that is responsive to the indicator, which itself is responsive to a material or process of interest.

For the moment it is notated that a biomarker (to be discussed) is an example of an indicator, and the derivative material or process outside of the subject can be part of a measurement protocol, the mechanism of a sensor, etc.

Figure 4B:
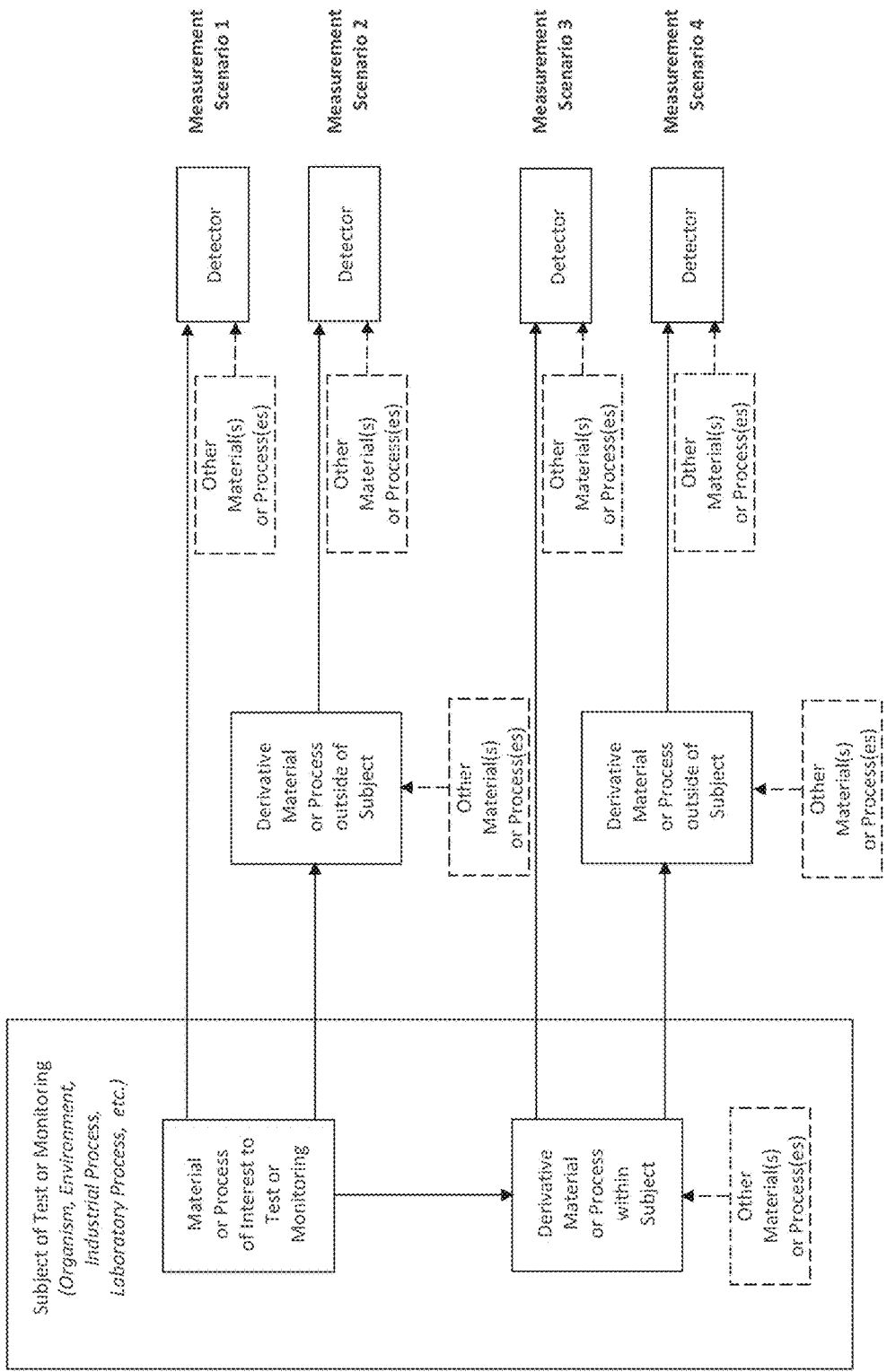

It is noted that essentially without exception all measurements, indicators, and underlying materials and processes are subject to disturbances, noise, and cases of mistaken identity. As an illustration of one aspect of this, FIG. 4b depicts some examples of how the arrangement represented in FIG. 4a can be influenced throughout by one or more other materials or processes that can corrupt the four example measurement scenarios represented in FIG. 4a. As suggested in FIG. 4b, these other materials or processes can influence the various derivative materials or processes inside and outside the subject, and can also influence the detection processes and detectors themselves in the four example measurement scenarios.

Figure 4D:
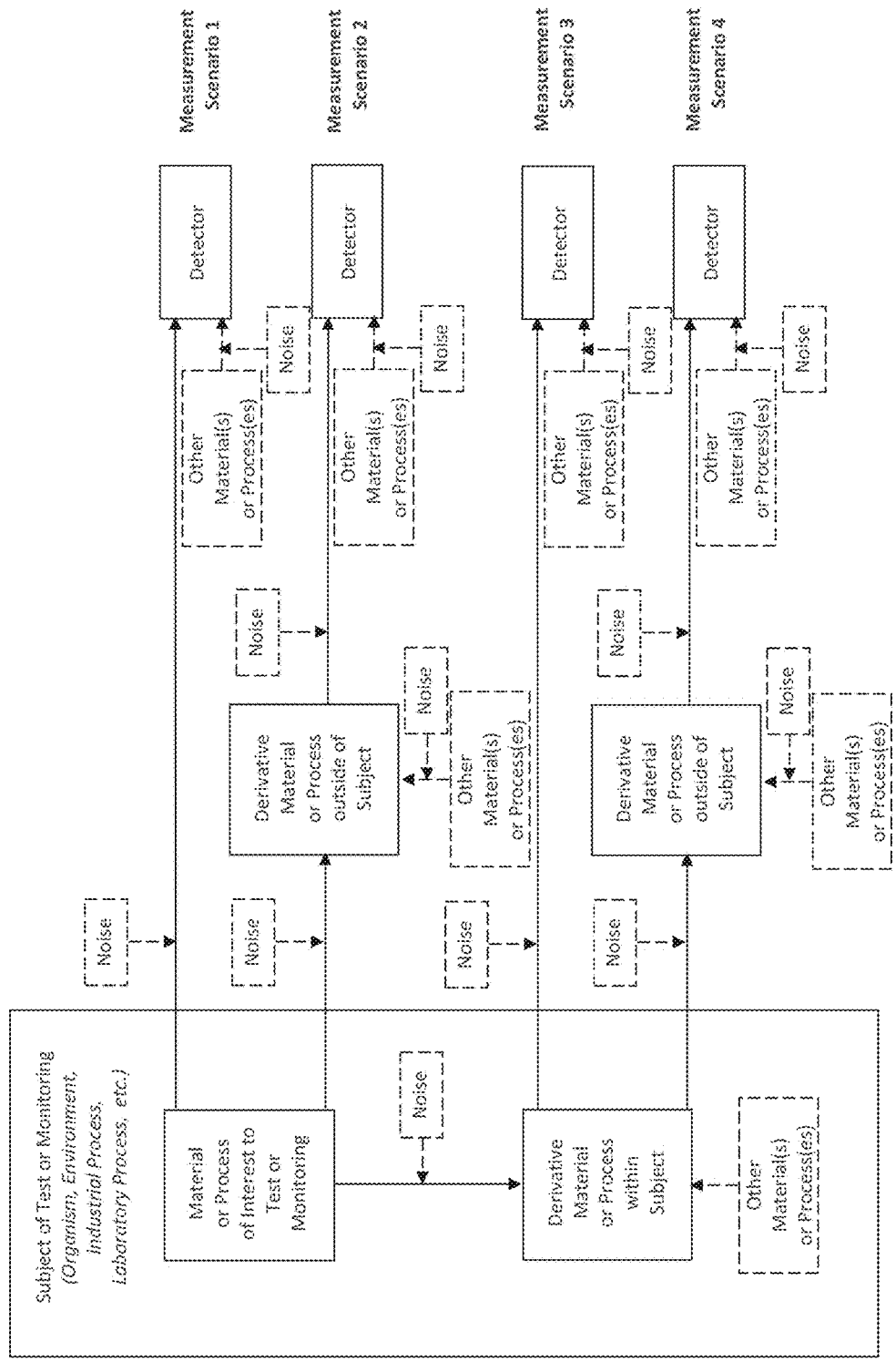
FIG. 4d depicts some examples of how the influences of competitive or incidental materials or processes both coexist with noise sources or processes and are also themselves subject to noise sources or processes

As another example of measurement challenges and issues, FIG. 4c depicts some examples of how the arrangement represented in FIG. 4a can be influenced throughout by one or more noise sources or processes that can corrupt the four example measurement scenarios represented in FIG. 4a. As suggested in FIG. 4c, these noise sources or processes can corrupt the integrity of the process and communication channels represented in FIG. 4a. Further, the influences of other competitive or incidental materials or processes suggested in FIG. 4b both coexist with noise sources or processes suggested in FIG. 4c, and additionally the influences of the competitive or incidental materials or processes themselves are also subject to noise sources or processes. FIG. 4d depicts some examples of how the influences of competitive or incidental materials or processes both coexist with noise sources or processes and are also themselves subject to noise sources or processes.

Figure 5A:
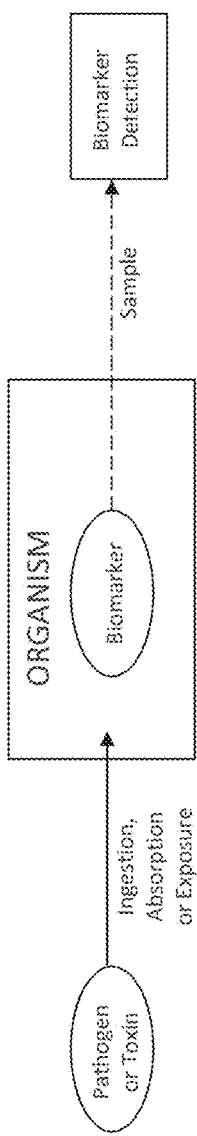
FIG. 5a depicts a representation of a situation where an organism (human, animal, cell, etc.) is subjected to a pathogen or toxin, resulting in the production, variation, or expression of a biomarker indicator that can be obtained through a sample obtained from the organism, the sample then provided to biomarker detection.
Figure 5B:
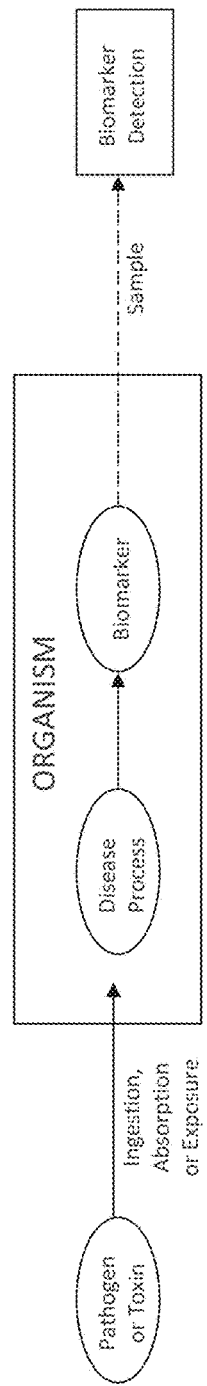
FIG. 5b depicts a representation of a situation where an organism (human, animal, cell, etc.) is subjected to a pathogen or toxin, resulting in a disease process that comprises the production, variation, or expression of a biomarker indicator that can be obtained through a sample obtained from the organism, the sample then provided to biomarker detection.
Figure 5C:
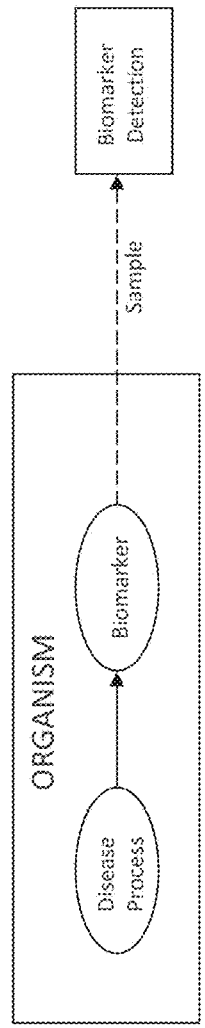
FIG. 5c depicts a representation of a situation where an organism (human, animal, cell, etc.) undergoes a disease process that comprises the production, variation, or expression of a biomarker indicator that can be obtained through a sample obtained from the organism, the sample then provided to biomarker detection.

With these aspects in mind, the detection framework can be expanded to include the benefits, limitations, and structure of direct and indirect measurement/detection of target materials or processes in a subject, including the use of indicators such as biomarkers. More specifically, since biomarkers are produced and associated with reactions to the existence of pathogens and toxins as well as disease processes, including genetic, degenerative and autoimmune diseases, including biomarkers in the pallet of detection targets greatly adds to the overall range of value of a detection laboratory, or in the case of the present invention, a detection system. As a simple illustration of various aspects of this point, FIG. 5a depicts a representation of a situation where an organism (human, animal, cell, etc.) is subjected to a pathogen or toxin, resulting in the production, variation, or expression of a biomarker indicator that can be obtained through a sample obtained from the organism, the sample then provided to biomarker detection. Similarly, FIG. 5b depicts a representation of a situation where an organism (human, animal, cell, etc.) is subjected to a pathogen or toxin, resulting in a disease process that comprises the production, variation, or expression of a biomarker indicator that can be obtained through a sample obtained from the organism, the sample then provided to biomarker detection. Alternatively, FIG. 5c depicts a representation of a situation where an organism (human, animal, cell, etc.) undergoes a disease process that comprises the production, variation, or expression of a biomarker indicator that can be obtained through a sample obtained from the organism, the sample then provided to biomarker detection.

Figure 6:
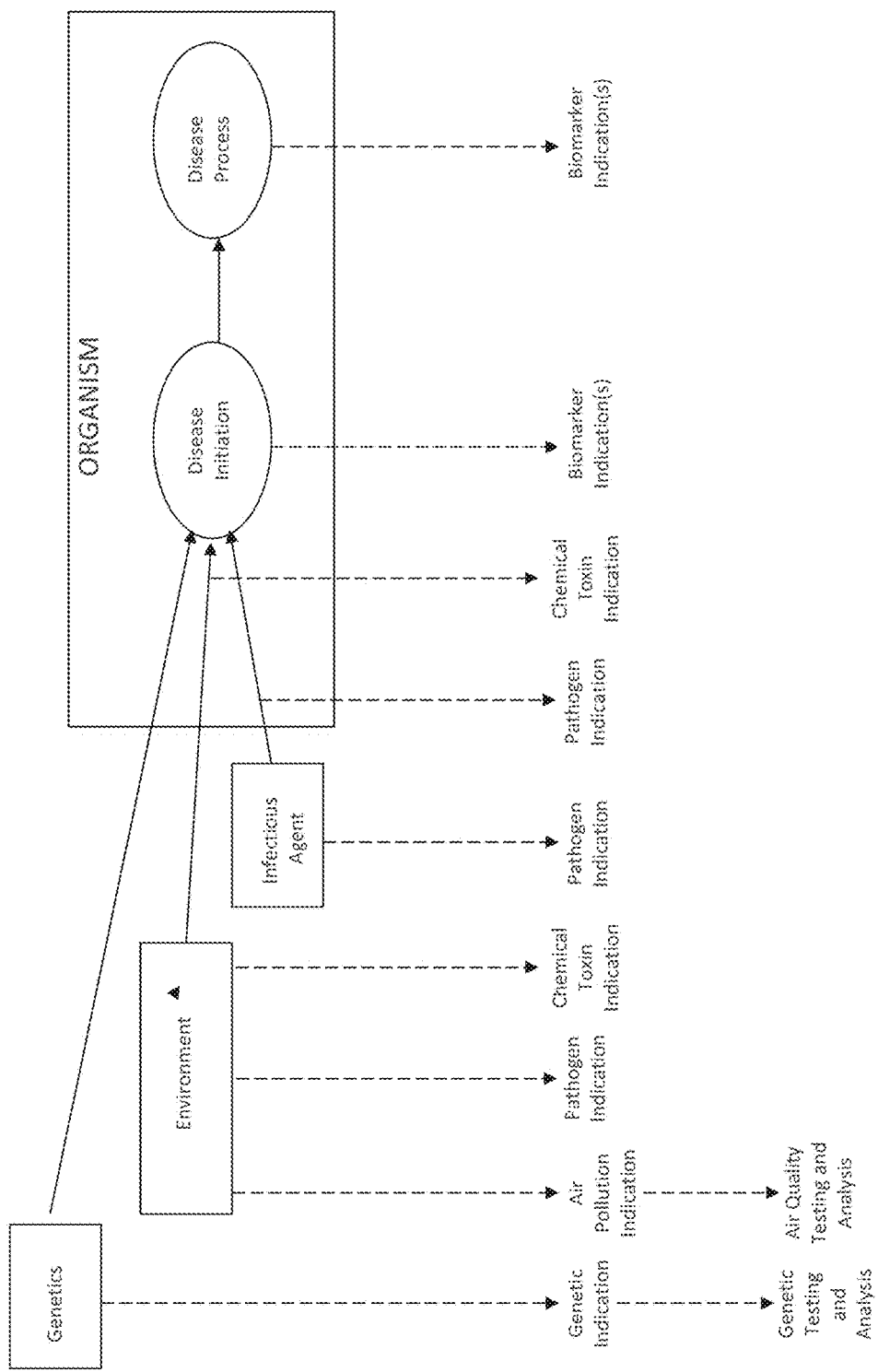
FIG. 6 depicts an example representation of various tests settings used to monitor health, disease, food, water, and the environment, and inherently provides an example representation of the role or one or more of genetic conditions, environmental conditions, and infectious agents in disease initiation.
Figure 7:
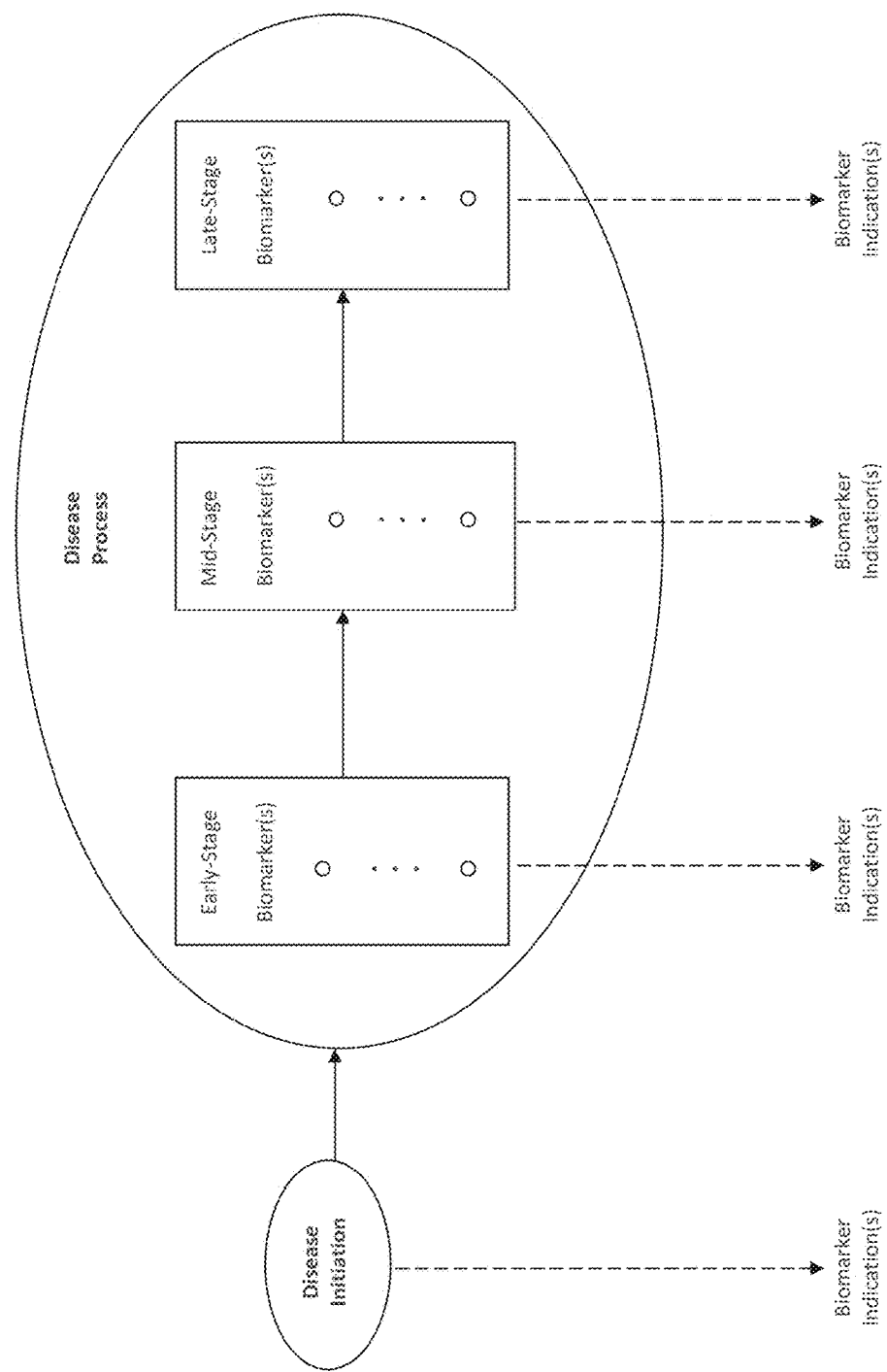
FIG. 7 depicts an example representation of the sequenced appearance of early-stage, mid-stage, and late-stage biomarkers.

Building on these, FIG. 6 depicts an expanded example representation of various tests settings used to monitor health, disease, food, water, and the environment. FIG. 6 also inherently provides an example representation of the role or one or more of genetic conditions, environmental conditions, and infectious agents in disease initiation. FIG. 6 further brings biomarkers into the context of the broader considerations for testing and monitoring to be addressed by the invention. For example, biomarkers associated disease initiation can provide alternative or corroborating evidence for specific pathogens or toxins. Additionally, biomarker sensing can be used for study of pharmaceutical processes in the body and drug testing. Yet further in the case of disease, as a disease within an organism progresses through various stages the organism can produce a variety of biomarkers responsive to the specific stage of the disease. This is suggested in FIG. 7 which depicts an example representation of the sequenced appearance of biomarkers specifically associated with disease initiation, early-stage disease, mid-stage disease, and late-stage disease.

Figure 8:
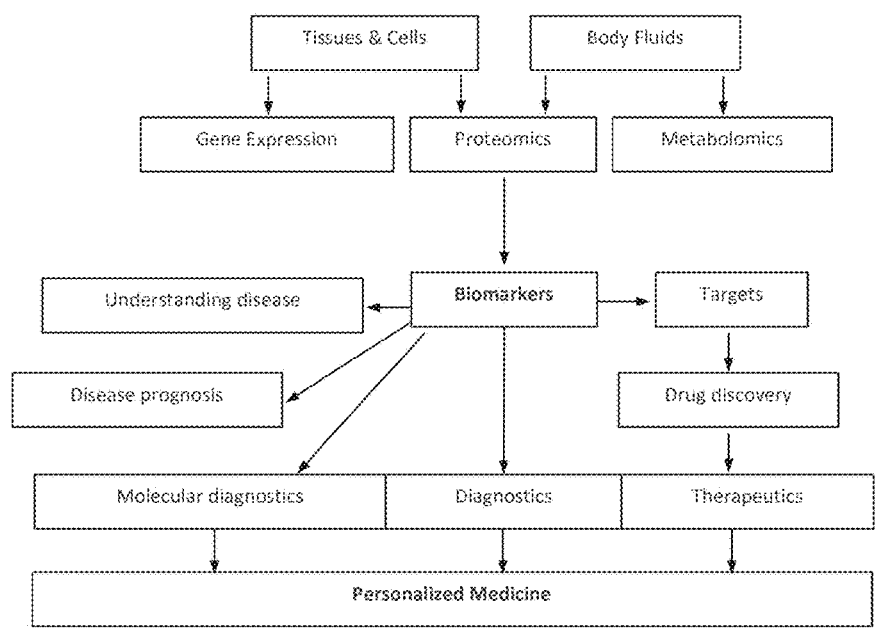
FIG. 8, adapted from K. K. Jain, *The Handbook of Biomarkers*, ISBN 160761684X, Springer, 2010, depicts a representative view of some example relationships of biomarkers with other technologies and aspects relating to health care.

Biomarkers can be used as signatures of chemical toxicity and have led to the discovery of improved descriptors of toxicity, toxicant classification, and exposure monitoring. More broadly, FIG. 8, adapted from K. K. Jain, *The Handbook of Biomarkers*, ISBN 160761684X, Springer, 2010, depicts a representative view of some example relationships of biomarkers with other technologies and aspects relating to health care. As will be seen, these open many additional application opportunities for the invention.

Existing and Emerging Sensor Technologies and Approaches Suitable or Adaptable for Full Microsystem Implementation This section briefly describes a number of existing and emerging sensor and chemical sensor technologies and approaches suitable or adaptable for full microsystem implementation. The synergistic use of existing sensor and chemical sensor technologies and approaches, a number of adaptations others and addition sensor innovations, plus yet other adaptations and innovations, as employed in the invention will provided in later discussion.

Figure 9A:
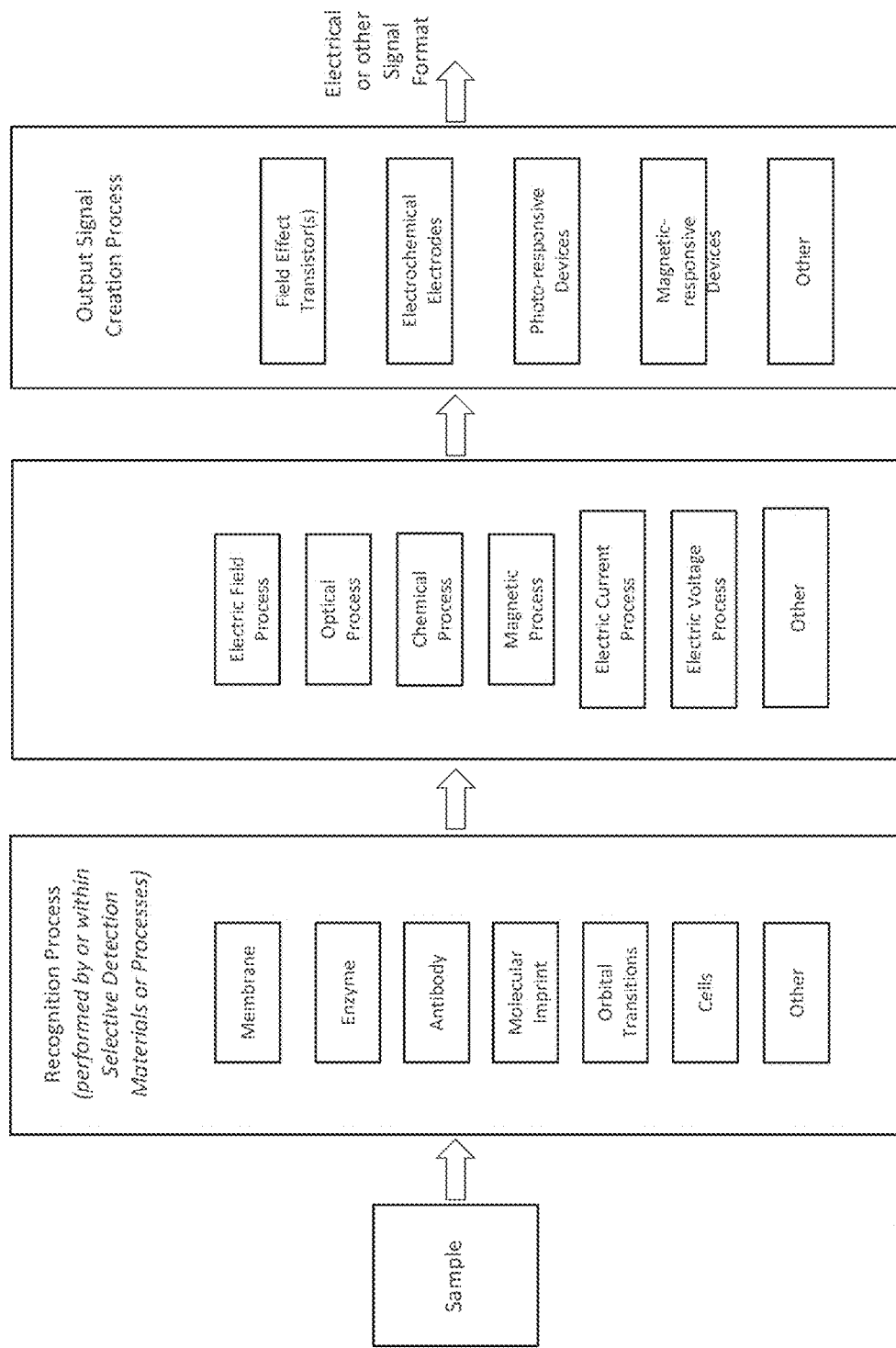
FIG. 9a depicts simplified unified view of the basis of biosensing technologies.

One simplified representation of a unified view of the basis of biosensing of relevance to the invention is provided in FIG. 9a. A sample is brought into interaction, communication, and/or physical contact, with a recognition process. In general, the recognition process internally employs a selective detection material or process such membranes, enzymes, antibodies, cells, molecular imprint materials, electron orbital transitions, magnetic resonances, etc. The recognition process results in an observable or measurable effect that is coupled by a transduction process (comprising for example one or more of an electric field, optical, chemical, magnetic, electric current, electric voltage, etc.) to an output signal process (which may comprise one or more field effect transistors, electrochemical electrode arrangements, photo-responsive electric devices, magnetic-responsive electric devices, etc.), typically advantageously producing an electrical signal. The many components of each class (distinguished as columns in the Figure) can be arranged in various combinations to form an extensive plethora of sensing approaches, systems, methods, and devices. Some sensing approaches can include more than one choice from each class—for example, an enzyme cascade could be used, and in one example embodiment of the invention to be discussed, living cells may be used to provide front-line recognition processes, and materials secreted through the membranes of the living cells can be subjected to at least a second-line recognition process (employing for example one or more enzymes, antibodies, molecular imprinted materials, etc.).

Figure 9B:
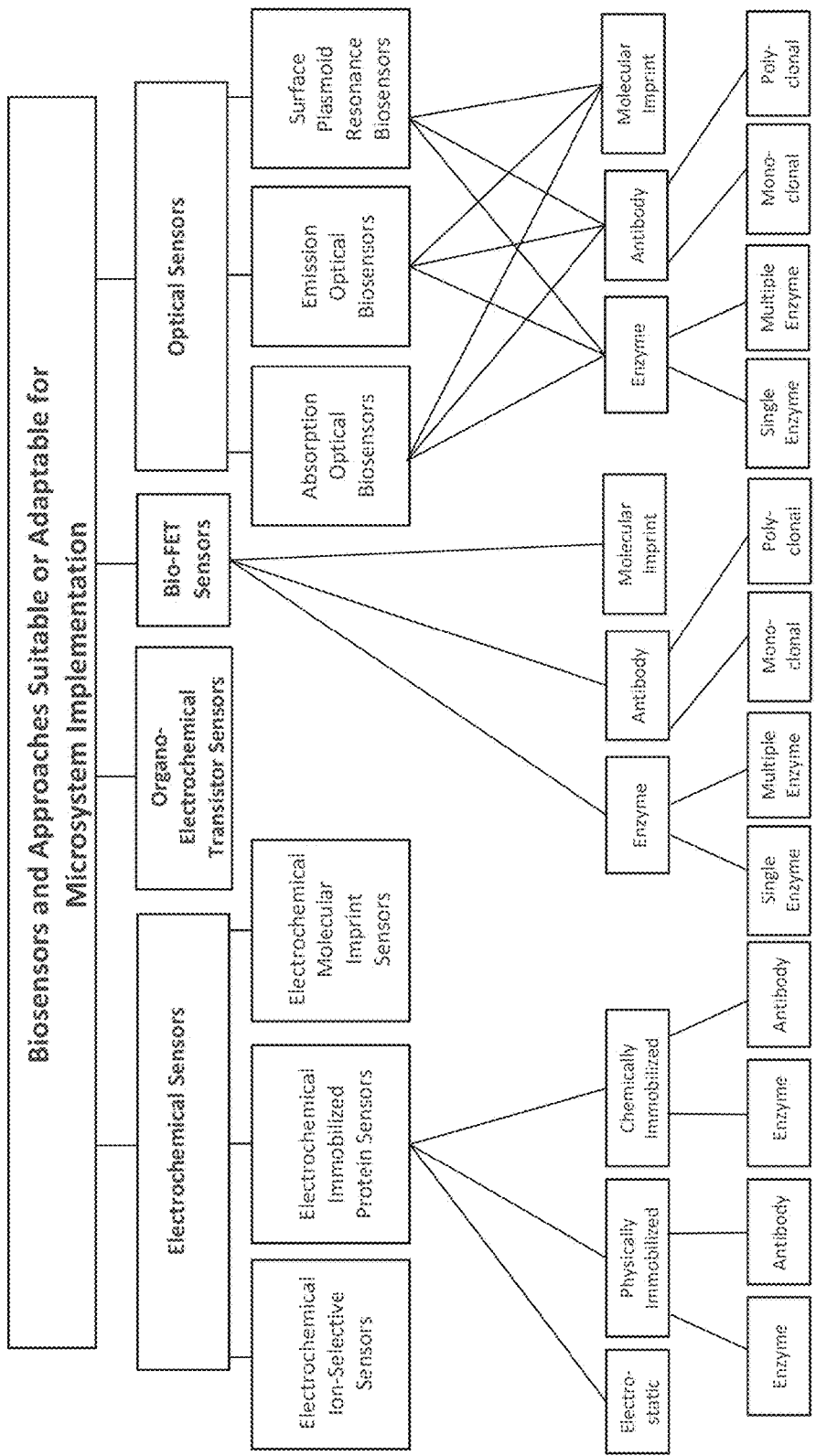
FIG. 9b provides a view of rapidly increasing number and diversity of sensor technologies and approaches suitable or adaptable for full microsystem implementation, many of which however are still either being prototyped in relatively large physical sizes, mostly for the convenience of inexpensive and flexible construction in a traditional laboratory.

In particular there are a rapidly increasing number and diversity of technologies and approaches for chemical sensor and sensor that are suitable or adaptable for microsystem implementation. Although not comprehensive nor exhaustively or precisely organized, FIG. 9b provides a relatively comprehensive view of these. Many of these sensor technologies and approaches are still either being prototyped in relatively large sizes, mostly for the convenience of inexpensive and flexible construction in a traditional laboratory. Many others are current implemented as small structures supplemented with large laboratory instruments and devices that can be simplified, focused, specialized, adapted, or otherwise miniaturized. Broadly these can be classified into at least the following electronic device and operation categories:

Electrochemical sensors;
Organo-Electrochemical Transistor (OECT) sensors;
Bio-FET sensors;
Optical sensors (these to be adapted to comprise opto-electrical devices), and these can include at least the following active sensing agents and sensing components:

Molecular imprint materials ("MIMs");
Antibodies (as well as synthetic antibodies);
Enzymes (as well as other proteins, synzymes, etc.);
Photo-responsive, photo-absorption, and photo emission materials.

Various configurations and arrangements of these in turn can function as "sensors," "immunosensors," "chemical sensors," etc, as will be discussed.

Figure 10:
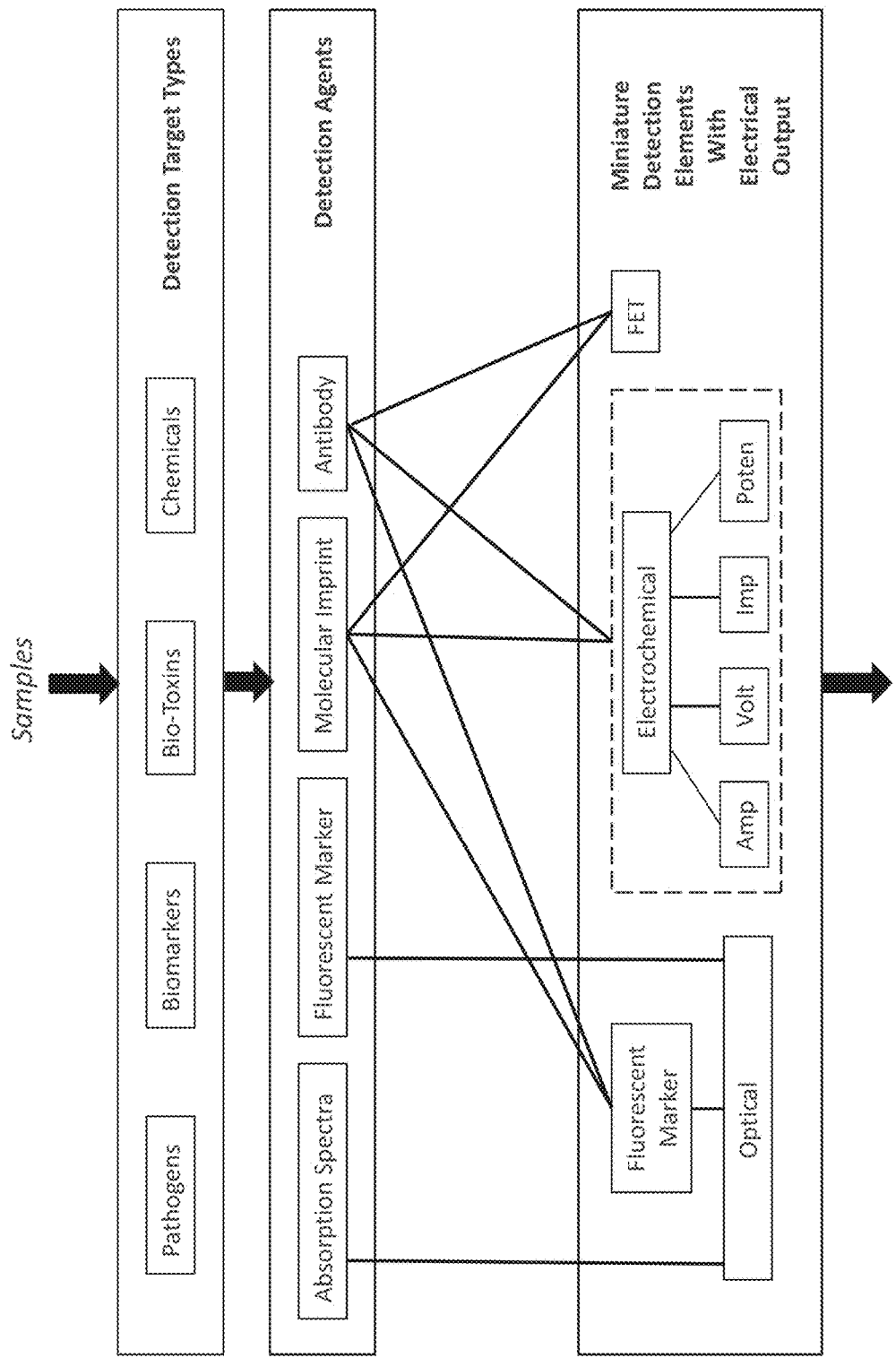
FIG. 10 depicts a representation of a recast of FIG. 9a in terms of the sensing method and technology components depicted in FIG. 9b in keeping with the unifying sensor strategies of the invention.

As will be seen, an important aspect of the invention is a unified framework for implementing, integrating, replacing, updating, and co-utilizing a wide variety of sensor types and technologies. By unifying the sensor implementation, fluidic/gas interfacing, miniaturizing approaches, electrical interfaces and optical interfaces, and further by collocating, and integrating a large number highly-selective sensors and chemical sensors—together with appropriately selected supplemental sensors (for example temperature, pH, selective ions, etc.)—the invention provides a rich ability to flexibly perform, create, deploy, maintain, and update a wide range of panels, assay, array, and/or sequence of tests for a wide range of substances and pathogens can be created. As to this, FIG. 10 depicts an example representation recasting of FIG. 9a in terms of the sensing method and technology components depicted in FIG. 9b in keeping with the unifying sensor strategies of the invention.

To begin consideration of these and their adaptation into the present invention, we first consider a fundamental variety of sensor types suitable or adaptable for microsystem implementation as used, adapted, and created for the present invention. After that treatment, recognition materials and related process for recognition processes (and where appropriate, associated transduction processes) are considered, Although many evolving and adapted details are provided in the recognition material and process discussion regarding antibodies and molecular imprinting, the invention also provides for the use of membranes and enzymes as recognition materials and/or in recognition processes. Next, although the use of antibodies, molecular imprinting, membranes, and antibodies provide an extensive range of sensing capabilities, these can be considerably expanded by further incorporating indicators as implicators, signatures, evidence, or surrogates for target biological processes. Accordingly, additional discussion of biomarkers and their advantageous use in the invention, in resonance with intended applications, is provided.

Electrochemical Sensing Methods and Devices

Classical, contemporary, and advancements in electrochemical sensors are known. A few remarks regarding aspects of current and emerging electrochemical sensors relevant to various aspect of the invention are made in this section.

There are various major types of electrical sensing process responsive to chemical conditions and processes that are employed in electrochemical sensors, for example:

"potentiometric electrochemical sensors" involve measuring the difference between two potentials (in units of volts) associated with the electrodes of an electrochemical sensor, "amperometric electrochemical sensors" involve measuring the current (in units of amperes) through an electrochemical sensor, "conductometric electrochemical sensors" (also referred to as "chemiresistors") involve measuring the "direct-current" (DC) resistance (in units of ohms) or conductance (in units of mhos) across an electrochemical sensor (resistance being the ratio of voltage to current and conductance being the ratio of current to voltage), "impedence electrochemical sensors" involve measuring the sinusoidal alternating current (AC) reactance, either as impedence (in units of ohms) or admittance (in units of mhos) across an electrochemical sensor over an adequate range of AC frequencies.

Also of importance is a means, process, material, or other arrangement providing adequate (or useable) selectivity of the sensors response to chemical or biochemical substances of interest with respect to expected range of chemical constituents in a sample. In some cases, sensors can be made very selective (for example, an antibody-based electrochemical sensor employing an antibody that responds only to a specific protein) or selective to a family of materials and thus in some applications requiring strict limitations on what can be in an applied sample. Examples of such means, processes, materials, and other arrangements include uses of membranes, specialized crystals, enzymes, and antibodies among many other approaches, and can include combinations of multiple means, processes, materials, and other arrangements. For a extensive examples of what types of quality chemical and biochemical detections that can be accomplished with simple means, processes, materials, and other arrangements for the family of simple 3-electrode electrochemical sensors comprising simple carbon paste electrodes, the reader may consult the extensive tables in the book by I. Svancara, K. Kalcher, A. Walcarius, K. Vytras, *Electroanalysis with Carbon Paste Electrodes*, CRC Press, 2012, ISBN 987-1-4398-3019-2 and the techniques and applications discussed in the book by Raluca-Ioana Stefan, Jacobus Frederick van Staden, Hassan Y. Aboul-Enein, *Electrochemical Sensors in Bioanalysis*, Marcel Dekker, 2001, ISBN 0-8247-0662-5.

The means, process, material, or other arrangement providing adequate (or useable) selectivity further typically employs an associated limitation on the sample applied to the sensor. For example, some sensors approaches are relevant only to dry gases, others relevant only to liquid samples, while others relevant to more complex samples such as suspensions (for example comprising cells), gases dissolved liquids, materials at thermodynamic critical points (such as vapors and gases including vapors), slurries, gases comprising particulates or colloids, emulsions in various stages (flocculation, creaming, coalescence, Ostwald ripening, etc.), micelles, etc. as well as combinations of these.

Figure 11A:
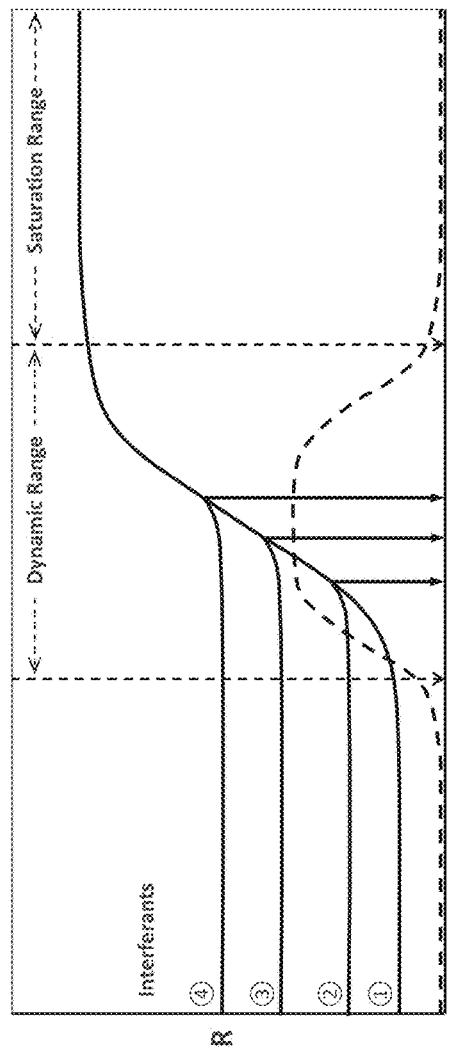
FIG. 11a, adapted from J. Janata, *ELECTROCHEMICAL SENSORS*, as disclosed at world wide web at electrochem.cwru.edu/encycl/art-s02-sensor.htm (visited Jan. 20, 2013), depicts an example representation of the dynamic range of a general electrochemical sensor.

FIG. 11a, adapted from J. Janata, *Electrochemical Sensors*, as disclosed at world wide web at—electrochem.cwr-u.edu/encycl/art-s02-sensor.htm (visited Jan. 20, 2013), depicts an example representation of the dynamic range of a general electrochemical sensor. The dynamic range of the electrochemical sensor is the range of chemical species concentration over which the signal produced by the sensor is accurately correlated to the concentration of the associated chemical material being sensed by the electrochemical sensor. At concentrations below and above this dynamic range, the sensor is at least inaccurate and in some cases does not even respond. Therefore, the anticipated concentration of the chemical species in a sample provided to the sensor defines whether a particular electrochemical sensor can realistically be used.

Figure 11B:
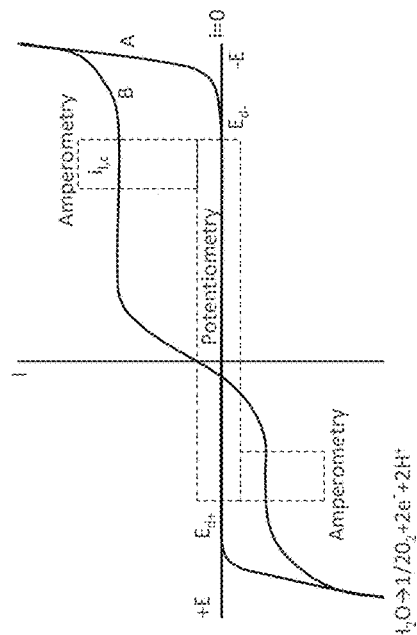
FIG. 11b, adapted from J. Janata, *Principles of Chemical Sensors* $2^{nd}$ edition, Springer, New York, 2009, depicts domains of potentiometric (horizontally-spanning region) and amperometric (vertically-spanning region) operation in the electrical I-V (current-voltage) curve of an example general electrochemical sensor.

FIG. 11b, adapted from J. Janata, *Principles of Chemical Sensors* $2^{nd}$ edition, Springer, New York, 2009, depicts domains of potentiometric (horizontally-spanning region) and amperometric (vertically-spanning region) operation in the electrical I-V (current-voltage) curve of an general electrochemical sensor. The overall I-V (current-voltage) curve represents the "equivalent charge transfer resistance" of the sensor. The highly non-linear shape of the depicted current-voltage curve is inherent and characteristic of virtually every electrochemical process, resulting from component charge transfer processes and mass transport processes.

Regarding miniaturization, it is noted that electrodes whose diameter is smaller than 20 μm ("microelectrodes") provide best performance as amperometric chemical sensors. Additionally, in the miniaturization potentiometric ion sensors, a chemical species-selective membrane is placed directly on (or used as) the insulator of a Field Effect Transistor (FET) input gate terminal, resulting in a miniaturized chemically selective field-effect transistor (CHEM-FET) or ion-sensitive field-effect transistors (ISFET) It is noted that the miniaturization of the reference electrode compartment within a potentiometric ion sensor limits its operational lifetime. However, aspects of the present invention prevent the need for long operational lifetimes and this long standing limitation and concern can be de-emphasized.

Figure 12A:
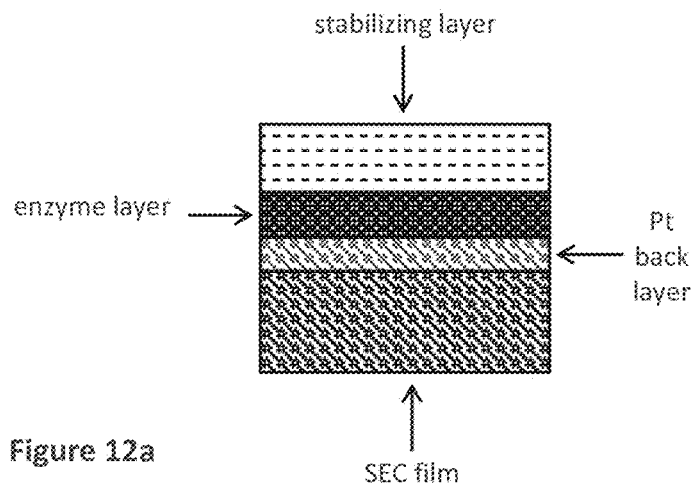
FIG. 12a, composited from aspects of FIG. 1.7 from Raluca-Ioana Stefan, Jacobus Frederick van Staden, Hassan Y. Aboul-Enein, *Electrochemical Sensors in Bioanalysis*, Marcel Dekker, 2001, ISBN 0-8247-0662-5, depicts a representation of an electrochemical sensor that can be used in conjunction with enzymes, antibodies, for rapid biomarker detection.

An aspect relevant to the invention is the fact that many of the electrochemical (and, as well be seen shortly, Bio-FET) sensors can be created from layered stacks of materials. As a first example of this, FIG. 12a, composited from aspects of FIG. 1.7 from Raluca-Ioana Stefan, Jacobus Frederick van Staden, Hassan Y. Aboul-Enein, *Electrochemical Sensors in Bioanalysis*, Marcel Dekker, 2001, ISBN 0-8247-0662-5, depicts a representation of an electrochemical sensor that can be used in conjunction with enzymes, antibodies, for rapid biomarker detection. This type of sensor technology can be used, for example, to create an experimental laboratory-scale microsensor and support system capable of detecting and distinguishing among four types of cancer from a single blood sample in less than 6 minutes (see Romanian Patent No. 506/Jan. 7, 2009, Raluca-Ioana van Staden and Jacobus Frederick van Staden, "STOC-MICROSENS-CMD") that lead to the prestigious 2010 WIPO Award for Best Women Inventor.

Figure 12B:
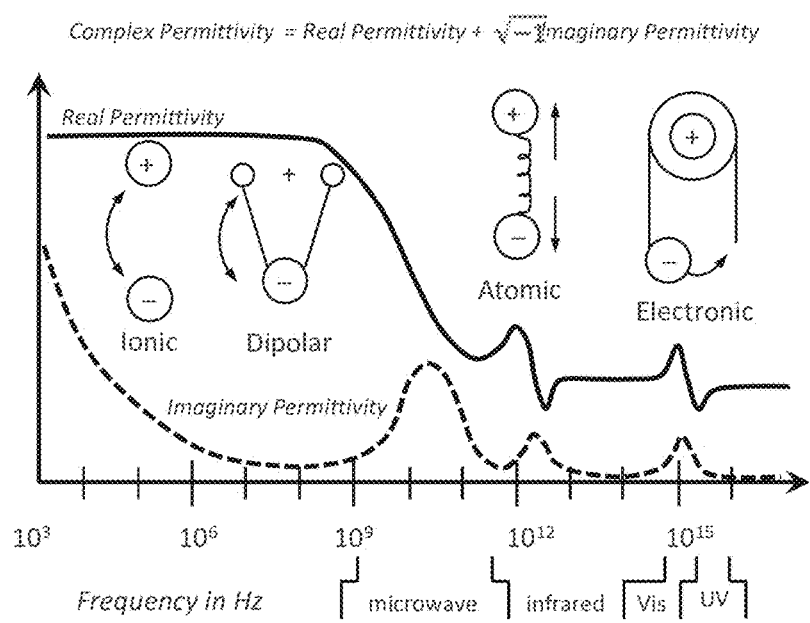
FIG. 12b (adapted from a figure on the "*Dielectric spectroscopy*" page of the Dr. Kenneth A. Mauritz's University of Southern Mississippi research group (as disclosed at world wide web at—wikipedia.org/wiki/Dielectric_spectroscopy visited Jan. 22, 2013), depicts variations in the real and imaginary components of dielectric permittivity of an example material over an extensive frequency range.

Electrochemical impedance spectroscopy (EIS), also referred to or associated with Dielectric Spectroscopy (DS) and Impedance Spectroscopy (IS), measures the electrical impedance of an analyte over a range of frequencies. The electrical impedance is responsive to the dielectric permittivity properties of the analyte which due to the electric dipole moment interaction with time-varying imposed (usually electrical) fields. In contrast to the voltammetry and amperometry electrochemical sensors described above (which involve measurement of DC or pulsed-DC electrode current as a function of applied electrode-solution voltage and rely on changing in electrode conditions), impedance sensors measure the electrical impedance by imposing a small AC voltage between sensor electrodes over a series or swept range of frequency and measuring the resulting AC current. FIG. 12b (adapted from a figure on the "*Dielectric spectroscopy*" page of the Dr. Kenneth A. Mauritz's University of Southern Mississippi research group (as disclosed at world wide web at—wikipedia.org/wiki/Dielectric_spectroscopy, visited Jan. 22, 2013), depicts variations in the real and imaginary components of dielectric permittivity of an example material over an extensive frequency range. As suggested in the figure, as frequency increases the dominating electrochemical processes evolve through regimes of ionic relaxation, dipolar relaxation, atomic resonances, and electronic resonances at higher energies.

An emergent subclass of electrochemical transducers, one that approaches the category of Biological Field Effect Transistors (Bio-FETS) to be discussed shortly, are Organo-Electrochemical Transistor (OECT) sensors. FIG. 5e depicts an example Organo-Electrochemical Transistor (OECT) sensor. Gold (Au) nanoparticles are shown as these typically increase charge density at channel surface and amplify the dedoping effect, often improving sensitivity by factors such as 100. FIG. 12c depicts a representation of an example Organo-Electrochemical Transistor (OECT) sensor including gold nanoparticles. OECT devices employing immunorecognition materials have been constructed that claim 1 ppm sensitivity, and can operate in at least two different mechanisms:

- Doping/Dedoping effects, for example where an antibody immobilized on the surface of a Field Effect Transistor gate channel surface binding to a charged ligand, the resulting fixed local charge that attenuates ion diffusion into the channel, thus altering the channel conductivity. As an example, an ElectroConductive Polymer (ECP) can be employed in the channel (such as P-type poly (3,4-ethylenedioxythiophene) ("PEDOT") doped with poly(styrenesulfonate "PSS" or blended with PSS to form the poly(3,4-ethylenedioxythiophene) poly(styrenesulfonate ("PEDOT:PSS") ionomer (i.e., a polymer comprising repeating sequences of electrically neutral and ionized moieties). Such a configuration can be used for example to detect negatively charged PSA when it binds to an antibody, behaves as a local charge sink, and hence attenuates cation transport to channel surface: in such an arrangement higher PSA concentrations induce higher channel conductivity.
- Antibody conformational changes, for example where an antibody is incorporated into a channel whose conductivity is affected by conformational changes in antibody that are induced by ligand binding Importantly to the invention, as will be seen, all of the electrochemical sensors and OCETs discussed can be fabricated as layered structures.

BioFET Sensing Methods and Devices

Classical, contemporary, and advancements in "bioFET" sensors are known. A few remarks regarding aspects of current and emerging bioFET sensors relevant to various aspect of the invention are made in this section.

Figure 12D:
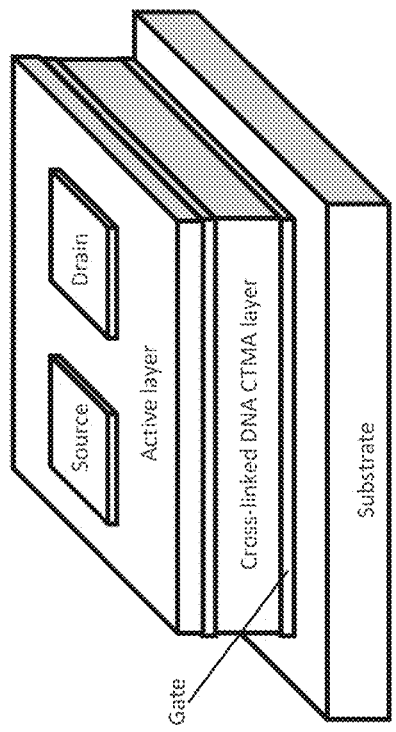
FIG. 12d depicts a representation of an ion-selective field-effect transistor.

FIG. 12d depicts a representation of an ion-selective field-effect transistor ("ISFET"). As suggested in the figure, most ISFET arrangements employ the analyte solution as the gate electrode of the Field-Effect Transistor (FET), while the source and drain of the ISFET are as those of a typical Metal-Oxide Semiconductor Field-Effect Transistor (MOSFET). The gate insulator, typically made employing $SiO_2$, $Si_3N_4$, $Al_2O_3$ and $Ta_2O_5$), can be affixed or otherwise modified to include or attach ion-selective substances. The selective activation by associated ions affects the electric fields presented to the gate insulator, in turn varying the current through the FET channel. Such a sensor can be used to sense pH and concentrations of various chemical compounds that affect the operation of sensors in a larger system examining the same sample. Further, additional materials and layer structures can be attached which comprise bio-selective materials that, when selectively activated by associated biomolecules, create ions that are measured by the ion-selective sensor. In order to miniaturize some ISFET arrangements, the depicted reference electrode becomes impractical and/or a limitation—for example due to issues of relative physical size and active-use aging—and Reference Field Effect Transistors (REFET) are employed instead. However these, too suffer from various limitations, including thermodynamic equilibrium, recalibration needs over the sensor lifetime, and other active-use aging issues. As will be seen, the classical concerns for reference electrodes and REFETs are evaded by the usage and operational modalities employed in the invention to be disclosed.

Figure 12F:
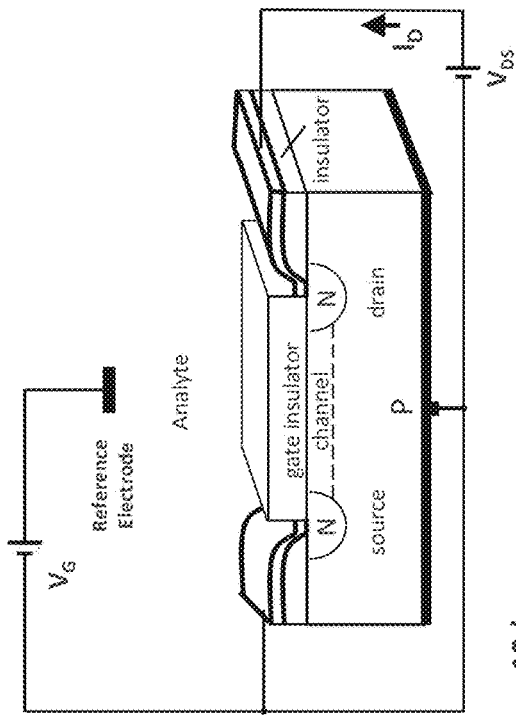
FIG. 12f, adapted from a variety of figures such as those in Philipp Stadler, et al., "Organic field-effect transistors and memory elements using deoxyribonucleic acid (DNA) gate dielectric," *Organic Electronics*, Vol. 8, No. 6, December 2007, pp. 648-654, depicts a representation of an organic field-effect transistor configured to operate as a biomolecule-selective field-effect transistor.
Figure 12C:
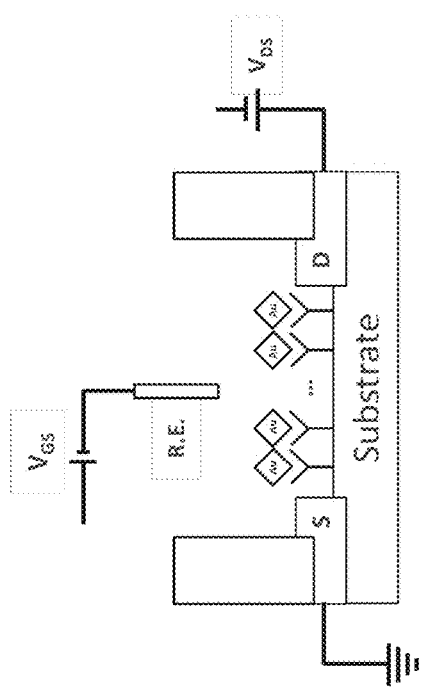
FIG. 12c depicts a representation of an example Organo-Electrochemical Transistor (OECT) sensor.
Figure 12E:
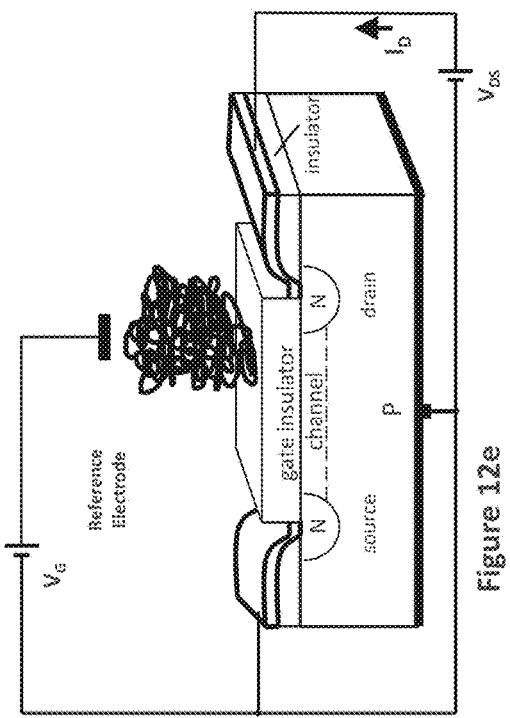
FIG. 12e depicts a representation of an enzyme-based or antibody-based biomolecule-selective field-effect transistor.

FIG. 12e, depicts a representational variation on the arrangement of FIG. 12d for an enzyme-based or antibody-based biomolecule-selective field-effect transistor. Such a sensor directly incorporates highly-selective materials or other layer structures that comprise bio-selective substances that are selectively activated by associated biomolecules in a manner that affects the conductivity or induced electric fields presented to the gate insulator, in turn varying the current through the FET channel.

As mentioned earlier, an aspect relevant to the invention is the fact that many of the Bio-FET sensors (and as discussed earlier, electrochemical sensors) can be created from layered stacks of materials. Further, the materials employed in sensors such as those depicted in Figures X5a-X5c can be functionally replaced with entirely other types materials (for example, organic semiconducting and conducting polymers) that can be inexpensively "printed" via so-called "Printed Electronics" and "Functional Printing" manufacturing technologies using fancier industrial-scale forms of ink-jet printers. The present invention exploits such "Printed Electronics" and "Functional Printing" manufacturing technologies (as will be discussed later). As independent confirmation of the validity of employing organic semiconducting and conducting polymers instead of the traditional materials used in such sensors (such as silicon and metals), FIG. 12f, adapted from a variety of figures such as those in Philipp Stadler, et al., "Organic field-effect transistors and memory elements using deoxyribonucleic acid (DNA) gate dielectric," *Organic Electronics*, Vol. 8, No. 6, December 2007, pp. 648-654, depicts a representation of an organic field-effect transistor configured to operate as a biomolecule-selective field-effect transistor.

Optical Sensing Methods

Classical, contemporary, and advancements in optical markers, optical labels, and optical sensors relevant to biological analysis are known. A few remarks regarding aspects of current and emerging optically-based detection technologies relevant to various aspect of the invention are made in this section.

Figure 13B:
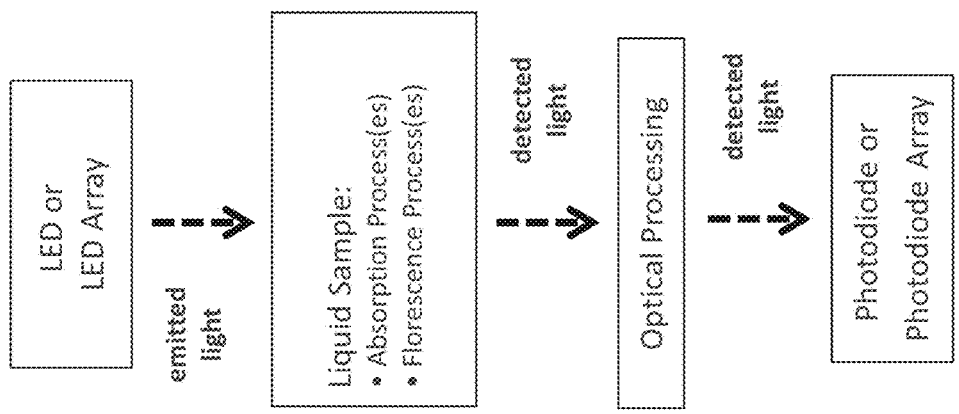
FIG. 13b depicts an alternative unified representation of an exemplary light absorption and fluorescence optical sensor.
Figure 13A:
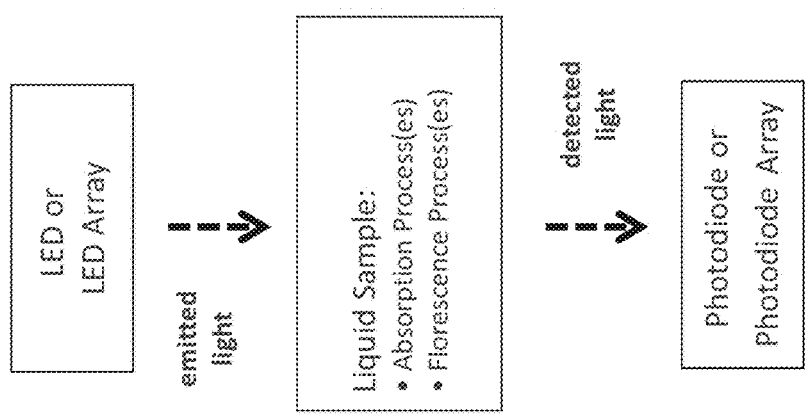
FIG. 13a depicts a unified representation of an exemplary light absorption and fluorescence optical sensor.
Figures 13C, 13D:
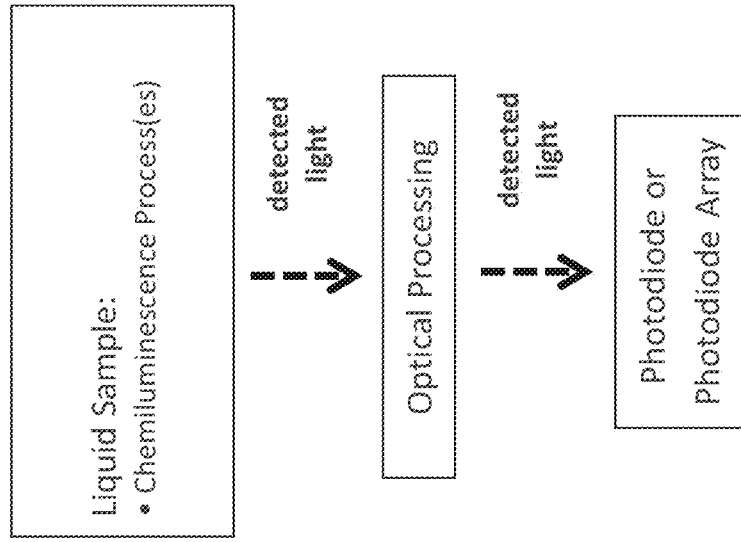
FIG. 13c depicts a simplified representation of an example chemiluminescence optical sensing arrangement.
FIG. 13d depicts an alternative simplified representation of an example chemiluminescence optical sensing arrangement.

FIG. 13a and FIG. 13b depict simplified representations of some example light absorption and florescence optical sensing arrangements, while FIG. 13c and FIG. 13d depict simplified representations of example chemiluminescence optical sensing arrangements. In most contemporary laboratory instruments, space-consuming expensive precision optical elements, such as diffraction gratings with precise alignments to photodiode arrays, are employed.

In particular, as will be shown, an aspect relevant to the invention is that many types of optically-based detection technologies such as those employed in microplate/microarray technologies and techniques can be modified or adapted for useful miniaturized implementation. Most optical techniques employing optically-based technology for biochemical applications have been developed in the product and technology context of large laboratory instruments, and thus the comprehensive miniaturized implementations taught later in the specification differ from current trends in industry and academic research. For example, some of the modifications and adaptations to be presented leverage small ultraviolet LEDs, while other modifications and adaptations leverage a family of wavelength-selective LED-based sensing technologies as taught later in this and associated patent applications that remove with the need for large and/or expensive precision optical components and precise alignment needs requiring expensive manufacturing processes.

As to optical detection involving the emission of light, an important example of optically-based technology for biochemical applications is the use of fluorophores (also called fluorochromes) which absorb excitation light of a first wavelength (usually ultraviolet or visible light), attain an electronic excited state, and as the excited state decays emit light at a second (lower-energy, longer) wavelength, typically arranged to be in the visible (or in some cases, infrared) light range. Fluorophores are used as staining dyes for tissues, cells, enzyme substrates, etc. and used as a probe or indicator (when its fluorescence is selectively affected by effects of species polarities, proximate ions, excitation light polarization, etc.) and can be arranged to covalently bond to a biological molecule (such as enzymes, antibodies, nucleic acids, and peptides) so as to optical mark the location and presence or activity of that biological molecule. Fluorophores can be used to mark cells, structures or materials within cells, and in conjunction with antibodies and other selective or modulating agents in microarrays. Although most fluorophores are organic small molecules, it is noted that fluorophores size can sterically affect the biological molecule it is used to tag, as well as other effects. It is also noted that solvent polarity can affect fluorescence intensity. The tables provided in FIGS. 14a-14b, adapted from world wide web at—flowcyt.salk.edu/fluo.html (visited Jan. 26, 2013), list a few example fluorophores, their typical probe function, excitation wavelength, emission wavelength, and molecular weight.

Although far less prevalent, another optical detection involving the emission of light are chemiluminescence tags and labels. The origin of emitted light from chemiluminescence processes is distinguished from the fluorescence processes of fluorophores in that the electronic excited state producing emitted photons result from a chemical reaction instead of excitation by incoming light. One example is luminal ($C_8H_7N_3O_2$) which is employed in microarray, assays, and other detection of copper, iron, cyanides, and specific proteins by Western Blot.

Further, in measuring at least fluorophore light emission, there are at least two measurement techniques that can be made and used in marking strategy design. The first of these is measuring of the formal light amplitude or formal light intensity of the fluorophore emissions, usually spatially normalized (for example per observational unit volume of sample, per unit area of an observational field, etc.), and normalized with respect to background levels or other factors. The second of these is the measurement of fluorescent lifetime which typically are effectively unaffected by probe concentration, excitation instability, photobleaching, washout, and other phenomena complicating amplitude and intensity measurements. Since fluorescent decay times are in the range of 1-20 ns, short excitation pulses, high-speed optical sensors, and radio-frequency electronics can be required. Alternatively, phase modulation techniques, such as those described by H. Szmacinski and J. Lakowicz in the article "Fluorescence Lifetime-based Sensing and Imaging," Sensors and Actuators B: Chemical (Proceedings of the 2nd European Conference on Optical Chemical Sensors and Sensors), Volume 29, Issues 1-3, October 1995, pp. 16-24 and earlier book chapter "Lifetime-based Sensing Using Phase-Modulated Fluorometry" in *Fluorescent Chemosensors for Ion and Molecule Recognition*, American Chemical Society, 1993, ISBN 0-8412-2728-4, Chapter 13, pp. 197-226. Additional fluorescence sensing technologies and methods of value in incorporating into the invention include time-resolved fluorescence detection and measurement techniques responsive to fluorescent polarization and anisotropy phenomena, Each of the two above optical detection arrangements involve emission of light, but optical-based detection can also leverage absorption of light, for example employing colorimetry and photospectroscopy. One important example of this is Enzyme-Linked Immunosorbent Assay (ELISA) technologies that employ enzymes (as well as antibodies or other selectively-responsive agents) to invoke visual color changes responsive to the presence of a target material. An example specialized product area employing these is the ArrayTube™ technology comprising a vertically-oriented reaction vessel arranged with a (non-fluorescent) colorimetric array at the vessel bottom. An example 'selection-guide' treatment comparing fluorescent, chemiluminescent, and colorimetric detection schemes and agents can be found in Selecting the Detection System—J. Gibbs, Life Sciences "Colorimetric, Fluorescent, Luminescent Methods," ELISA Technical Bulletin—No. 5, Corning Incorporated, 2001 (as disclosed at world wide web at—catalog2.corning.com/Lifesciences/media/pdf/elisa5.pdf, visited Jan. 27, 2013). Analogous to the fluorophore, the moiety responsible for the color of a molecule is called a chromophore.

A great many fluorophores and chromophores are permanently active (albeit modulated by solvent polarity, pH, temperature, etc.) and do not change their emission or absorption properties as a result of any binding event. Such markers simply tag molecules such as enzymes and antibodies and variations in emission or absorption properties of the sample or parts of the sample result from changes in spatial concentration of enzymes, antibodies, etc. as they cluster in their binding within localized regions of antigen. Other fluorophores and chromophores are or can be configured to change their light emission/absorption properties in direct response to binding events—for example as with calcium markers. Addition performance considerations can be considered, for example whether the fluorophores and chromophores are intrinsic or extrinsic as considered in T. Bell et al., "Intrinsic Chromophores and Fluorophores in Synthetic Molecular Receptors," in *Fluorescent Chemosensors for Ion and Molecule Recognition*, American Chemical Society, 1993, ISBN 0-8412-2728-4, Chapter 7, pp. 85-103. Related techniques of value to the invention include fluorescent probes that indirectly sense analytes via chemical reactions, for example but not limited to "turn-on" fluorescent probes discussed for example in M. Jun, B. Roy, K. Ahn, "Turn-on fluorescent sensing with reactive probes," *Chem. Commun.*, 2011, Issue 47, pp. 7583-7601.

DNA-oriented microarrays (also called "DNA chips" and "biochips") comprise small DNA regions arranged in an array on a plate material, and are used to simultaneously measure gene expression levels of many samples or tests in parallel, genotyping of genome regions, etc. employing fluorophores, chemiluminescent, or other types of labels or tags.

Protein-oriented microarrays employing fluorophores are widely used for identification, characterization, and study of disease biomarkers, protein-protein interactions, specificity of DNA-binding and protein variants, immune response, etc. These methodologies provide an important contemporary tool for next-generation understanding of cell biology, disease, and drug development as explained, for example, in C. Wu, (ed.), *Protein Microarray for Disease Analysis: Methods and Protocols*, 2011, ISBN 1617790427, or in the handbook provided by Amersham Biosciences entitled *Fluorescence Imaging: Principles and methods*, 2002 (document 63-0035-28 Rev. AB, 2002-10, as disclosed at world wide web at—cancer.duke.edu/DNA/docs/Phosphorimaging%20_%20Fluorescent_Scanning/Fluorescence/02OImaging %20Handbook.pdf, visited Jan. 26, 2013). In addition to their use in biochemical samples, they can also be used in living cells to monitor cell metabolism and cell signaling, for example as with "Fluo-Calcium" indicators and in the techniques described in R. Wombacher, V. Cornish, "Chemical tags: applications in live cell fluorescence imaging" *J. Biophotonics* 4, No. 6, pp. 391-402 (2011).

Accordingly, the invention can leverage adaptations of this technology base so as to provide support for applications involving measure gene expression levels of many samples or tests in parallel, genotyping, next-generation understanding of cell biology, disease, and drug development. Of relevance to the adaptations made in the invention to be described is that the ranges of light wavelengths for excitation emission are those of commercially manufactured Light Emitting Diodes (LEDs), and, as explained, that LEDs of differing emission wavelengths can be used as wavelength-selective detectors.

Recognition by Antibody Materials

As described earlier, antibodies are an important tool in creating highly selective sensors, and in particular an important (although not necessarily unique) enabler for creating sensors responsive to biomarkers.

Antibodies are large Y-shaped glycoproteins created within B-cells, secreted though or bound to the B-cell membrane, and used by the immune system of a higher organism to identify and neutralize foreign materials such as bacteria and viruses. A particular antibody recognizes a unique part of a particular associated foreign material (called the antigen) at a molecular level, typically with astonishing selectivity. The antigen can be a protein, virus, cell, or even small molecule chemical. According, this span of chemical to biochemical further provides the ability of antibodies to recognize with high specificity materials that function as toxins and biomarkers.

Although other production techniques can be employed, most antibodies are commercially manufactured by injecting a provided antigen into an animal with a suitable immune system (typically a mammal such as a mouse, rat, rabbit, goat, sheep, horse, or chickens), and blood (or eggs in the case of chickens) from these animals is harvested, producing large quantities of polyclonal antibody comprising a plurality of different types of antibodies that will bind to that antigen. Additional steps are employed to refine these, purify, and in many cases further sort by type of antibody to produce separated monoclonal antibodies.

A large and rapidly expanding collection of well-tailored quality highly-selective antibodies are commercially available. For example, Santa Cruz Biotechnologies currently affordably offers more than 54,000 high-quality highly-selective antibodies. Commercial services for creating custom antibodies are readily available.

Importantly, efforts to transcend the costs, limitations, and use of animals in developing and in particular designing high-specificity antibodies solely by in vitro techniques have had increasing promise and early demonstrable successes, including synthetic antibody libraries that are capable of yielding selectivity functions and specificities that have not been previously possible. A recent review is provided in S. Miersch, S, Sidhu, "Synthetic Antibodies: Concepts, Potential and Practical Considerations," *Methods*, Elsevier, August 2012, 57(4), pp. 486-98. As described in "Recombinant Antibody Technology for the Production of Antibodies Without the Use of Animals," (as disclosed at world wide web at—alttox.org/ttrc/emerging-technologies/cell-based/way-forward/echko-dozier/, visited Jan. 28, 2013), synthetic ("recombinant") antibodies can be made from antibody genes synthesized in a laboratory or obtained from human cells, fully eliminating animals from the antibody-production process. Table 5 below, adapted from Conroy, S. Hearty, P. Leonard, R. O'Kennedy, "Antibody Production, Design and Use for Sensor-Based Applications," *Seminars in Cell & Developmental Biology* 20 (2009), pp. 10-26, presents examples of recombinant antibody-based sensors.

TABLE 5

| Disease and Analyte | Antibody Form | Transducer |
| --- | --- | --- |
| HIV-1 virion infectivity factor | scFv (VH and VHD) | Piezoelectric |
| L. monocytogenes | scFv | SPR |
| SARS virus | scFv | Imaging ellipsometry |
| L. monocytogenes Biowarfare | scFv (phage bound) | Amperometric |
| Venezuelan equine encephalitis virus | scFv | Potentiometric |
| B. anthracis S-layer protein Haptens | scFv | Resonant mirror |
| Morphine-2-glucuronide Contaminants | scFv | SPR |
| Aflatozin B1 | scFv (mono and dimeric) | SPR |
| Parathion (insecticide) | scFv | Piezoelectric |
| Atrazine | scFv | Amperometric |

Additional aspects of importance in this area include "catcher" and "carrier" fragments of recombinant antibodies, discussed for example in the published thesis of C. Steinhauer, *Protein Microarrays Based on Recombinant Antibody Fragments: Catcher and Carrier—a Crucial Combination*, LAP Lambert, 2010, ISBN 3843375690. Related biochemical materials and approaches that can be included as an alternative to animal-produced antibodies employed in sensors used in the invention include synbodies and unstructured peptides. Further approaches to synthetic antibodies can be found in N. Hopkins, "Antibody Engineering for Sensor Applications" in M. Zourob, (ed.), *Recognition Receptors in Sensors*, Springer, 2010, ISBN 978-1-4419-0918-3, pp. 451-529.

FIG. 15, adapted from Table 1 of Conroy, S. Hearty, P. Leonard, R. O'Kennedy, "Antibody Production, Design and Use for Sensor-Based Applications," *Seminars in Cell & Developmental Biology* 20 (2009), pp. 10-26, provides a table of example polyclonal and monoclonal antibody-based sensors and their associated analytes and transducers. Antibody-based sensors, also called immunosensors, can be made in a variety of underlying technologies, as shown in FIG. 9b, and that can be made selectively responsive to any of a wide range of materials including, for example, specific proteins (including enzymes), specific pathogens, specific cells, specific chemicals, specific toxins, and specific biomarkers.

The polyclonal aspects of contemporary antibody production as well as the expanding and potential design capabilities for synthetic antibodies, more than one antibody can be responsive to the same pathogen. As will be described, the invention provides for leveraged use of multiple antibodies responsive to the same pathogen so as to obtain parallel redundant results than can be used to improve reliability and/or handle nuances of pathogen variants.

Example Antibodies Useful in Pathogen Sensing

The range of pathogens that can be detected with antibodies, and thus potentially with antibody-based sensors, is vast and can include both toxin-producing and disease-producing types. As described earlier, by using antibodies responsive to specific pathogens, sensor technologies can be made that could be useful for diagnosis of the existence of pathogens, infections by pathogens, and the existence and stage of pathogen-invoked disease. By providing associated software for operating and analyzing the tests, the invention to be described can be used for highly selective medical diagnosis of disease.

As a first example, attention is redirected to the opening discussion food and water safety. The most dominant food and water pathogens typically encountered include *S.* spp., *Clostridium Perfirngens, Pseudomonas* spp., *Bacillus Cereus, Campylobacter Jejuni, L. Monocytogenes, Salmonella* spp., *E. coli* 0157:H7, *Shigella*, Norovirus, Norwalk-like viruses, *Legionella, Clostidium Botulinum, Yesinia Enterocolitica*, and *Vibrio* spp. As an example, the table provided in FIGS. 16a-16b depicts example commercially-available antibodies (for example, as provided by Santa Cruz Biotechnologies) that can be used in the aforedescribed bioFETs and/or electrochemical sensors to detect these pathogens with high selectivity. As a second example, attention is redirected to the yearly world-wide concerns of influenza viruses. As is well known, influenza rapidly evolves in a constant arms race with vaccines, habits of civilization, and the evolving immune responses and transportation of human, domestic animal, and wild animal populations. FIG. 17 provides a table of example antibodies for the detection of various example strains of Influenza.

Example Antibodies Useful in Biomarker Sensing

As described earlier, by employing antibodies responsive to biomarkers of specific diseases, sensor technologies can be made that could be useful for medical diagnosis of disease. By providing associated software for operating and analyzing the tests, the invention to be described can be used for highly selective medical diagnosis of disease.

By way of example, FIG. 18, adapted from Table 1.4 of K. K. Jain, *The Handbook of Biomarkers*, ISBN 160761684X, Springer, 2010, provides a table of example autoimmune disorders under study for autoantibodies as predictors for disease. Similarly, FIG. 19, adapted from Table 3 of I. Tothill, *"Sensors for Cancer Markers Diagnosis," Seminars in Cell & Developmental Biology* 20 (2009), pp. 55-62, provides a table of example sensors for cancer biomarkers analysis, while FIG. 20, adapted from Table 1 of I. Tothill, *"Sensors for Cancer Markers Diagnosis." Seminars in Cell & Developmental Biology* 20 (2009), pp. 55-62, provides a table of example known biomarker associated with cancer diagnosis and prognosis.

Additionally, biomarkers have been identified that are useful for workplace-compliance drug testing. By employing antibodies responsive to biomarkers associated with illicit drug use, sensor technologies can be made that could be useful for workplace-compliance drug testing. By providing associated software for operating and analyzing the tests, the invention to be described can be used for highly selective workplace-compliance drug testing.

Further, biomarkers have been identified that are useful for sports doping testing. By employing antibodies responsive to biomarkers associated with banned sports doping substances, sensor technologies can be made that could be useful for sports doping testing. By providing associated software for operating and analyzing the tests, the invention to be described can be used for highly selective sports doping testing.

Yet further, and quite importantly, environmental and ecological researchers and policy makers have come to appreciate the role of biomarkers as important tools for monitoring many aspects of ecology, environment, national security, public health, agriculture, with new realizations of the opportunities and imperatives rapidly emerging. By sampling or monitoring appropriate environmental or ecological elements, components, and members, such air, ground water, surface water, soils, natural flora, crops, wildlife, domesticated animals, ocean regions, fish, other aquatic organisms, etc. early warnings of great consequence to humans, economies, urban areas, countryside, fisheries, etc. can be had. This emerging topic is immense, but a quick flavor of the importance, breadth, possibilities, governmental policy aspects, and practical matters can be had from a combination of the recent book *Ecological Biomarkers—Indicators of Ecotoxicological Effects* edited by C. Amiard-Triquet, J.-C. Amiard, P. Rainbow, CRC Press, 2012, ISBN 978-1-43-988017-3, the short paper "Integrated Biomarkers in Aquatic Organisms as a Tool for Biomonitoring Environmental Pollution and Improved Ecological Risk Assessment" by A. Valavanidis and T. Vlachogianni (as disclosed at world wide web at—chem-tox-ecotox.org/wp/wp-content/uploads/2010/01/01-January-20101.pdf visited Jan. 28, 2013), and the series of four papers commissioned by the European Science Foundation in the September 1994, Volume 3, Issue 3, issue of *Ecotoxicology*. By employing antibodies responsive to environmental and ecological biomarkers, sensor technologies can be made that could be useful for many aspects of ecology, environment, national security, public health, agriculture, and new rapidly emerging opportunities and imperatives. By providing associated software for operating and analyzing the tests, the invention to be described can be used for highly selective monitoring of these ecological, environmental, national security, public health, agriculture, and other rapidly emerging opportunities and imperatives.

Recognition by Molecular Imprinting Materials

As described above, biochemical materials and approaches that can be employed as alternatives to animal-produced antibodies for sensors used in the invention include synthetic and recombinant antibodies, recombinant antibody fragments, synbodies and unstructured peptides. In contrast to all of these, Molecularly Imprinted Material (MIM) technologies, such as Molecularly Imprinted Polymers (MIPs), leverage synthetic materials as an alternative to antibodies in highly selective sensors. MIMs can be used to recognize and bind to a target molecule with high affinities and specificities that can rival antibodies, receptors, and enzymes.

Molecularly imprinted polymers (MIPs) can be inexpensively and reproducibly manufactured by polymerizing commercially available monomers in the presence of a templating molecule structurally similar to a specified target molecule. Because MIPs are heavily cross-linked, and thus cannot experience conformational rearrangement, MIPs provide far superior stability to biological antibodies, offering considerably longer shelf-life, less stringent storage requirements, and can be used with extreme pH, temperature, ionic strength, and other operating conditions outside that of most antibodies. A representative review is provided in L. Ye, K. Mosbach, "Molecular Imprinting: Synthetic Materials As Substitutes for Biological Antibodies and Receptors," *Chemistry of Materials,* 2008, 20, pp. 859-868).

MIMs still fall short in matching or exceeding the specificity and cross reactivity rejection of biological antibodies, and this has been viewed as a problem in diagnostics because of higher probabilities of false positives. However, various aspects of the invention's methodology, architecture, and statistical processing approaches provided for by the present invention can inherently significant diminish this concern.

As sensors relevant to the invention, one of many representative reviews and summaries regarding the use of MIMs and MIPs as selectivity agents in sensors is provided in G. Guan, B. Liu, Z. Wang, Z. Zhang "Imprinting of Molecular Recognition Sites on Nanostructures and Its Applications in Chemosensors," *Sensors,* 2008, 8, pp. 8291-8320. Of additional utility to the invention is the fact that MIMs have demonstrated robust liquid and gas chemical sensors for more than a decade (see for example F. Dickert, O. Hayden, "Molecular Imprinting in Chemical Sensing," *Trends in Analytical Chemistry*, vol. 18, no. 3, 1999).

Other Recognition Materials

Many other types of selective detection materials can be used by the invention, including peptides, genetically engineered proteins, carbohydrates, nucleic acids, oligonucleotides, amtamers, phages, and even living cells and tissues cultured from plants and animals. A representative survey of such additional types of selective detection materials that can be employed by the invention can be found in the extensive book M. Zourob, (ed.), *Recognition Receptors in Sensors*, Springer, 2010, ISBN 978-1-4419-0918-3.

Recognition of Biomarker Indicators

This section provides additional information regarding biomarkers and their sensing by sensors. The material herein is drawn from the references listed below as well as other embedded references as cited.

Ibtisam E. Tothill, "Sensors for cancer markers diagnosis," *Seminars in Cell & Developmental Biology* 20, 2009, pp. 55-62.

Paul J. Conroy, Stephen Hearty, Paul Leonard, Richard J. O'Kennedy, "Antibody production, design and use for sensor-based applications," *Seminars in Cell & Developmental Biology* 20, 2009, pp. 10-26.

Alphonsus H. C. Ng, Uvaraj Uddayasankar, Aaron R. Wheeler, "Immunoassays in microfluidic systems," *Anal Bioanal Chem* 397, 2010, pp. 991-1007.

Eric Stern, Aleksandar Vacic, Nitin K. Rajan, Jason M. Criscione, Jason Park, Bojan R. Ilic, David J. Mooney, Mark A. Reed, Tarek M. Fahmy, "Label-free biomarker detection from whole blood," *Nature Nanotechnology (Letters)*, Vol. 5, February 2010.

Hsiao-Kang Chang, Fumiaki N. Ishikawa, Rui Zhang, Ram Datar, Richard J. Cote, Mark E. Thompson, Chongwu Zhou, "Rapid, Label-Free, Electrical Whole Blood Bioassay Based on Nanosensor Systems," *ACS Nano*, Vol. 5, No. 12, 2011, pp. 9883-9891.

A biomarker (also referred to as a "biological marker") is a chemical, ion, compound, (more commonly) protein, complex of proteins, antibody, etc. that provides a reliable indication, at least in part, of at least one (of at most a few) discernible biological state(s) of an organism (such as a human or animal, but also a cell, tissue, plant, symbiotic organism, etc.). The formal definition put forth by the NRC in 1987 indicated a biomarker "is a xenobiotically-induced variation in cellular or biochemical components or processes, structures, or functions that is measurable in a biological system or sample." Additional definitions, perspectives, and examples of biomarkers, along with relations to some specific associated diseases are provided in the discussion to follow.

Biomarkers can be detected and characterized by many different kinds of technologies over a wide spectrum of molecular levels, spanning for example the genome, epigenome, transcriptome, proteome, metabolome, lipidome, etc. A recent overview can be found in I. Riedmaier, M. Pfaffl, "Transcriptional biomarkers—High Throughput Screening, Quantitative Verification, and Bioinformatical Validation Methods," *Methods*, Elsevier, January 2013, 59(1), pp. 3-9.

Ideally a biomarker uniquely indicates a specific unique biological state of the organism, but more typically a given biomarker can be associated with a group of biological states, and similarly a given specific biological state can give rise to more than one biomarker. For example, a certain biomarker useful for drug testing can also appear under other circumstances, for example extreme exercise, intake of specific foods or vitamins, etc. Similarly, a disease like cancer can result in the production of more than one biomarker.

For the purposes of this discussion, biomarkers are typically produced by the organism the biomarker is found in. In some application settings, however, the term "biomarker" is also or alternatively used for traceable diagnostic materials externally provided to the organism (for example, barium, radioactive iodine, etc.) which localizes in one or more portions of the organism responsive to type of cell, type of tissue, metabolic condition, etc. The biomarker can in some cases be present in easily obtained bodily fluids or tissues, while in other cases biomarkers can be highly localized within tissues or confined fluids. The present invention can be arranged to be responsive to a wide range of instances of both of these cases, as well as other situations (for example when the organism generates a biomarker responsive to both an abnormal biological state after the introduction of diagnostic materials externally provided to the organism).

The present invention adapts a number of widely scattered and divergent biomarker assay materials, associated techniques, and miscellaneous sensor approaches into a unified framework that can be commonly and inexpensively manufactured on a removable replaceable medium and wherein the plurality of sensor output data. Biomarkers provide the invention with opportunities for measurements wherein interpretations of measured values signify, imply, or correlate to disease processes, pathogenic processes, pharmacologic responses, dietary responses, normal biological metabolism, etc. Some examples include:

Selected enzymes (transaminases, bilirubin, alkaline phosphatase, etc.) for various specific liver function normalcies and pathologies, Selected enzymes (serum creatinine, creatinine clearance, cystatin C, etc.) for various specific kidney function normalcies and pathologies, KRAS protein for certain types of cancer (CRC, EGFR-associated), CK-MB, troponin I, troponin T for cardiac muscle injury, STAT6 protein for certain types of kidney disease, ACPA (anti-citrullinated protein/peptide antibody) for rheumatoid arthritis, (Now controversially) PSA (prostate specific antigen) as a biomarker for prostate cancer, NNK for tobacco exposure.

Often numerous biomarkers can be associated with a particular disease state. An ideal biomarker, according to the FDA, must be specifically associated with a particular disease or disease state and be able to differentiate between similar physiological conditions. It is desirable if standard biological sources, such as serum and urine, could be used for identifying biomarkers. Desirable biomarkers have associated rapid, simple, accurate, and inexpensive detection means together with a standard reference baseline, for example with high specificity, high sensitively, reflect a disease state, and useful for diagnosis as well as for disease monitoring during and following therapy. Examples of biomarkers relevant to clinical test and biopharmaceutical R&D include:

simple molecules (metabolites, carbohydrates, steroids, lipids, etc.), peptides, proteins (insulin, hemoglobin A and C, PSA, C-reactive protein, etc.), RNA, mRNA, MicroRNA (miRNA),

DNA:

Autosomal (only within cell nucleus, two copies per cell),

Mitochondrial (throughout cytoplasm, numerous copies per cell),

Genes,

Cells such as platelets or T cells,

Autoantibodies.

Some example biomarkers suitable or potentially suitable for recognition by antibodies and accordingly of potential use in the invention can be found in the tables presented in FIG. 21a-21i and FIGS. 22a-22e.

However, there are many other types of biomarkers relevant to the invention. As described earlier, FIG. 8 depicts a representative view of some example relationships of biomarkers with other technologies and aspects relating to health care.

Example of Cancer Biomarkers and Use of Antibodies

Cancer biomarkers suitable or potentially suitable for recognition by antibodies can be found in the tables presented in FIG. 21a-21i and FIGS. 22a-22e. Experimental sensor systems for perform cancer biomarker detection directly from human whole blood, for example collected by a finger prick, in real time or within a few minutes, some with detection performance at least 2 orders of magnitude better than the clinically relevant level for diagnosis. [see H.-K. Chang, et al., "Rapid, Label-Free, Electrical Whole Blood Bioassay Based on Nanosensor Systems, 2011, G. Mor, et al. "Diagnostic Markers for Early Detection of Ovarian Cancer, *Cancer Biomarkers* 2008, 4, pp. 190-191, K. Steffiensen, et al., "Multiplex Serum Tumor Markers for the Prediction of Early Relapse in Ovarian Cancer Patients," *Reprod. Sci.,* 2008, 15, p. 856, I. Visintin, et al., "Diagnostic Markers for Early Detection of Ovarian Cancer," *Clin. Cancer Res.* 2008, 14, pp. 1065-1072, and Romanian Patent No. 506/Jan. 7, 2009, Raluca-Ioana van Staden and Jacobus Frederick van Staden, "STOC-MICROSENS-CMD").

Metabolomic and Glycomic Biomarkers

Metabolites can diagnostically serve as "canaries in the coal mine as indicators of human health and can be highly sensitive and responsive to food, lifestyle, environment, seasons, and even mood. Because there are only 2,500 metabolites that are biomarkers of metabolism as compared to 25,000 genes and approximately a million proteins, the limited number enables an easier, more quantitative method of analysis. Currently less than 1% of known metabolites are employed in routine clinical testing, but there is an R&D for the development of clinical tests based on metabolic biomarkers. Similarly, there is advancing understanding of the importance of post-translational modifications such as glycosylation in health and disease processes. Glycosylation is greatly affected by diseases such as cancer, and serum glycan biomarkers of various diseases have been identified; for example, glycan biomarkers for breast cancer.

Genes, Genetic Biomarkers, and Peptide Biomarkers Further Extending the Scope and Application of the Invention As is well known, genes are sequences of chromosomal DNA used to produce a protein or RNA molecule. A gene includes not only the actual coding sequences but also adjacent nucleotide sequences required for the proper expression of genes, i.e., for the production of a normal mRNA molecule. Only one kind of mRNA is made for each gene. Gene activity ("gene expression") employs a gene's DNA as a blueprint to produce a specific protein. Not all the genes are expressed in a typical human cell and the genes expressed vary from one cell to another. Human mRNAs present in saliva can be used as biomarkers of oral cancer. A protein cannot be synthesized without its mRNA being present. However, a protein can remain in a cell when its mRNA is no longer present, and mRNA can be present in abundance but the message is not translated into proteins. There is, thus, no general correlation between the availability mRNA and protein in a cell. Additionally, peptides play a central role in almost all biological processes. They function as biochemical messengers (for example, insulin, calcitonin, and angiotensin) or occur as metabolites of proteins.

The functions of cells, tissues, and organs are controlled by gene expression, and malfunctioning genes are involved in most diseases. There is a need to assess DNA damage because of the impact that different insults on genetic material can have on human health. Gene expression can in many circumstances create observable biomarkers, and some gene mutations can affect observable biomarkers. In some arrangements and applications, for example in the laboratory, genes themselves, DNA, various forms of RNA, and peptides themselves can be used as biomarkers recognizable by antibody-based or enzyme-based selective detection materials.

Autosomal DNA genes are confined to the cell nucleus and have two copies per cell, but mitochondrial DNA (mtDNA) genes are distributed throughout the cell cytoplasm and have numerous copies per cell. Each mitochondrion contains its own separate set of genes, and mtDNA encodes for many of these More than 100 mutations of mtDNA been associated with a wide range of human diseases and contribute to the aging process.

MicroRNAs (miRNAs), small mostly non-coding RNA gene products, are molecules derived from larger segments of "precursor" RNA that are found in all diverse multicellular organisms. Recent studies of miRNA expression implicate miRNAs in viral disease, neurodevelopment, and cancer. In higher eukaryotes, the role of miRNAs in regulating gene expression could be as important as that of transcription factors.

Cells as Biomarkers of Disease

Changes in cells themselves can be used as biomarkers of disease.

Biomarkers for Identification of Stem Cells

Antibodies have facilitated the identification of stem cells, and stem cells in solid organs also can be identified using cell surface markers.

Biomarker Sensors

In particular it is noted that by incorporating antibody or other types of pathogen sensors with sensors specifically responsive to biomarkers of pathogens or biomarkers of disease, the aforedescribed technologies can be used to create rapidly available data for medical analysis and diagnosis. By providing associated software for operating and analyzing the tests, the technology can be used for highly-selective medical diagnosis of not only infection but also of disease. Biomarkers for disease initiation can provide alternative or corroborating evidence for specific pathogens or toxins. Additionally, biomarker sensing can be used for study of pharmaceutical processes in the body and drug testing.

In some cases biomarkers of interest can react with antibodies. In such cases the associated biomarker sensor is employed as an immunosensor, for example realized via a printable field effect transistor with a gate element configured with an antibody. The resulting printed sensor can be printed on the removable replaceable medium element. Alternatively, an optical sensing technique can be used.

In some cases biomarkers of interest are themselves antibodies that can react to an organic or biological compound. In such cases the associated biomarker sensor can be realized via a printable field effect transistor with a gate element configured with the organic or biological compound. The resulting printed sensor can be printed on the removable replaceable medium element. Alternatively, an optical sensing technique can be used.

In some cases biomarkers of interest are enzymes that can react to a protein or other organic or biological compound. In such cases the associated biomarker sensor can be realized via a printable field effect transistor with a gate element configured with the protein or the organic or biological compound. The resulting printed sensor can be printed on the removable replaceable medium element. Alternatively, an optical sensing technique can be used.

In some cases biomarkers of interest are non-enzymic proteins that can react with an enzyme or other organic or biological compound. In such cases the associated biomarker sensor can be realized via a printable field effect transistor with a gate element configured with the enzyme or the organic or biological compound. The resulting printed sensor can be printed on the removable replaceable medium element. Alternatively, an optical sensing technique can be used.

In some cases biomarkers of interest can simply comprise simple chemicals or ions. In such cases the associated biomarker sensor is simply a chemical sensor, for example realized via a printable field effect transistor with an appropriate configured gate element. The resulting printed sensor can be printed on the removable replaceable medium element. Alternatively, an optical sensing technique can be used.

Thus, a wide range biomarker sensing capabilities can be implemented with sensors compatible with the aforementioned technology and in particular many of these sensors can be implemented with printable FET or printable electrochemical sensors.

As discussed earlier, FIG. 20 and FIG. 19, respectively, provide example known biomarker associated with cancer diagnosis and prognosis and example sensors for cancer biomarkers analysis. FIGS. 22a-22e provide a table of additional example conditions and example associated biomarkers, and FIGS. 21a-21i provide a table of example conditions, example associated biomarkers, and example antibodies responsive to those biomarkers.

Incorporation of Chemical Sensors for Sensing of Chemicals and Chemical Toxins

As described earlier, chemical sensors (for example ion, pH, etc.) can also be included among the sensors printed on the removable replaceable medium element, or realized with optical techniques. As just mentioned, chemical sensors can in some cases be used as biomarker sensors. Additionally, the invention also provides for chemical sensors to be used for the sensing of chemical toxins. For example, chemical sensors can be employed for sensing compounds such as ammonia, urea, heterocycles such as dioxins, metal ions, etc. The most universal approach is to use antibodies as these can provide a wide range of selective recognition of specific small molecule compounds. However. other chemical sensing technologies have become well established. By way of illustration, urea can be sensed in various ways, for example with amperometric electrochemical techniques.

Metal ions can be optically sensed, for example, with fluorescent techniques with sensitivities of parts per billion employing, for example spiropyrandinolines, DNAzymes, or other techniques. Metal ions can be electrochemically sensed, for example, with DNAzymes, amino acids, peptides, or other techniques. Many such methods employ complexification of the ion, and complexes can be chosen to select for metal ion size.

Dioxins can be sensed by molecularly-imprinted polymer sensors, antibody-based sensors, etc.

Leveraging Combined Sensor Framework for Mixed Target Sensing

Accordingly, in an example embodiment, the invention further provides for some of the sensors to be configured for pathogen sensing and other sensors to be configured for biomarker sensing, In another example embodiment, the invention further provides for some of the sensors to be configured for pathogen sensing, other sensors to be configured for biomarker sensing, and yet other sensors to be configured for chemical toxin sensing.

Various other combinations are anticipated and provided for by the invention.

Broader Aspects of the Invention

With example selections of relevant sensor and detection technologies and initial steps towards a unified sensor framework for a wide and in fact open range of detection capabilities established, attention is now directed to a wider view of encompassing additional and broader aspects of the invention.

As described earlier, FIG. 6 depicts an example representation of the role or one or more of genetic conditions, environmental conditions, and infectious agents in disease initiation. Genetic sequencing can provide genetic indications, for example presence of a cancer-implicated gene. Environmental conditions can include air pollutants. Provisions can be made to the present invention to accommodate the acquisition and processing of samples for these, but extra complexity and cost can typically be expected.

In contrast, the remaining seven indications depicted in FIG. 24 span by the bracket readily lie within the reachable scope of low-cost forms of the present invention as will described below. Four of these involve samples obtained from the organism, and two of these involve biomarkers. FIG. 24 motivates the opportunities for a combined platform combining pathogen sensors, biomarker sensors, and chemical sensors. Within FIG. 24, the sensing opportunities, span by the bracket, lie within the reachable scope of low-cost forms of the present invention. Additionally, the invention additionally provides for the inclusion of "electronic nose" and other selective gas-sensing technologies that can be used so as to include other aspects and opportunities depicted and not depicted in FIG. 24.

The invention employs several component core, design, and fabrication technologies including:
 Organic semiconducting and conducting polymers,
 Printed electronics and functional printing,
 Microfluidic systems and their fabrication,
 A range of currently experimental sensor technologies that have been or can be adapted for microfluidic use,
 Rapidly-advancing commercial production of a wide ranges of highly selective antibodies and enzymes,
 Laboratory methods and analysis, together with associated biochemistry, for pathogen detection,
 Reconfigurable microprocessor-controlled Lab-on-a-Chip (RLoC) technologies (U.S. patent application Ser. Nos. 11/946,678 and 13/314,170),
 Microfluidic chemical bus technologies (U.S. Pat. No. 8,032,258 and pending U.S. patent application Ser. Nos. 13/251,286 and 13/251,288),
 Microfluidic and Lab-on-a-Chip development technologies (U.S. patent application Ser. Nos. 12/328,726 and 12/328,713).

FIG. 23 depicts a high-level representation of the technical hierarchy of the invention. The starting point is based on new and adapted individual component technologies provided for by the invention; these are discussed immediately below and represented in more detail in FIG. 25. Next, a synergistic and adaptive integration of these is provided and performed so as to create a flexible multiple-purpose platform technology; this is represented in more detail in FIG. 26 with reference to the unified sensing framework depicted earlier in FIG. 10. Leveraging the resulting flexible multiple-purpose platform technology, a wide range of embodiments and applications are enabled; represented in more detail in FIG. 27.

To begin, as depicted in FIG. 25, example component technologies employed in the present invention include underlying component technologies such as:
 Molecular imprinting,
 Selective/sensitive antibodies,
 Fluorescent indicators,
 Optical sensor techniques and arrangements,
 Electrochemical sensors (amperometric, potentiometric, conductometric, membrane, diffusion barrier, etc.),
 BioFETs,
 Microfluidics (valves, conduits, microreactors),
 Printed electronics,
 Printed chemical deposition,
 Other types of sensors,
which are in turn configured in the present invention to provide mid-level component technologies such as:
 Selective/sensitive antibody-based sensors and chemical sensors,
 Enzyme-based sensors and chemical sensors,
 Molecular imprint sensors and chemical sensors,
 Optofluidic devices,
which in turn are configured to provide higher-level component technologies such as:
 Selective/sensitive pathogen sensors,
 Selective/sensitive biomarker sensors,
 Selective/sensitive toxin sensors,
 Selective/sensitive chemical sensors.

As provided for by the invention, and will be taught in the present patent application, these all are in turn synergistically configured and adaptively integrated along with other novel aspects of the invention to provide a powerful, flexible platform technology for supporting a wide range of diverse applications, including (depicted in part in FIG. 27):
 Water safety field testing, monitoring, and process testing,
 Food safety field testing, monitoring, and production process testing,
 Consumer product (toothpaste, cosmetics, over-the-counter medication, etc.) safety field testing, monitoring, and production process testing,
 Clinical and home medical testing and diagnostics testing,
 Environmental (indoor, outdoor, remediation, home, building, manufacturing plant) field-use testing/monitoring and laboratory-based testing/monitoring,
 Homeland security, conflict-zone, and terrorism prevention field testing and monitoring,
 Industrial manufacturing process monitoring,
 Laboratory instruments for advanced cell incubation,
 Laboratory instruments for infectious disease studies,
 Laboratory instruments for monitoring gene expression molecules,
 Biotechnology for advanced life-process systems (fermentation, protein manufacture, etc.),
 In-body drug delivery, metabolite-synthesis, biochemical prosthesis, or artificial organ applications.

As described earlier in conjunction with FIG. 10, by unifying the sensor implementation, fluidic/gas interfacing, miniaturizing approaches, electrical interfaces and optical interfaces, and further by collocating, and integrating a large number highly-selective sensors and chemical sensors—together with appropriately selected supplemental sensors (for example temperature, pH, selective ions, etc.)—the invention provides a rich ability to flexibly perform, create, deploy, maintain, and update a wide range of panels, assay, array, and/or sequence of tests for a wide range of substances and pathogens can be created. As to implementing the platform in a universal context to a wised range of applications, earlier-cited FIG. 26 depicts an example representation of the synergistic and adaptive framework provided and performed by the invention so as to create a flexible multiple-purpose platform technology. Further as to implementing the lower three functional blocks depicted in FIG. 26, namely the Range of Detection Agents, Range of Miniature Detection Elements, and Software Environment for Control, Analysis, Reporting, User Interface, and Networking, FIG. 28 depicts an overall overview of the software, signal input hardware, signal processing hardware, and software-control hardware provided for or implemented in various embodiments of the invention. In FIG. 28 the software is depicted at the top (signifying the software is oriented as being closer to the user), while the signal, sensor, and fluidic hardware is in the lower portion of the figure (signifying these are oriented as being closer to the sample(s) being analyzed.

Market, Logistic, Economic, Life-Cycle, Bio-Hazard, and Environmental Aspects of the Invention Technologies and materials applicable the invention will continue to evolve over time as depicted in FIG. 29. Thus the invention provides for an evolution ability in order to keep up with and incorporate such anticipated developments, as well as to a reasonable range of un anticipated developments.

Updatable software is one easily-met aspect of this goal that can be readily incorporated, but updating of sensors, reagents, and other aspects is far more challenging. However, the invention includes an innovative solution to this, leveraging a removable, practical, inexpensively-manufactured replaceable medium that actually includes a wide spectrum of low-cost sensors and reagents and memory for software. The format of the removable medium approach provides opportunities to address a number of other issues including life-cycle and disposal, and the broader system design readily facilitates extensions into a wide range of broader applications immediately spanning into health care and industrial applications.

FIG. 30 depicts the broader market, logistics, economics, life-cycle, bio-hazard containment, materials recycling, and environmental considerations associated with the invention. On the logistics side, there will always be new outbreaks, new concerns, new types of biological and chemical contamination exposures, and new types of testing methodologies and improvements that are difficult if not completely impossible to predict. Although software changes to address aspects of this degree of variability and uncertainty can be provided by various methods, the variability of the types of physical sensors and associated testing reagents necessary requires some way of physically updating at least some aspects of a testing device addressing the needs spelled on in conjunction with FIGS. 1a, 1b, 2a, and 2b. Further, at least some of the sensors employed will have limited lifetimes (for example, antibodies and enzymes could degrade) and be subject to contamination after one or more uses. Together these motivate the need for a removable replaceable media element that somehow includes at least reagents and sensors and perhaps software.

From the market viewpoint, a removable replaceable media element that somehow includes at least reagents and sensors and some associated means of providing associated "replaceable" software offers an immediate opportunity for providing an 'open architecture' for a next generation pathogen and biomarker sensor and analysis system. Such an 'open architecture' allows for third-party development that can address a wider range and greater number of markets (both large and small). This increases the overall market size for the technology, which in turn reduces its production, operational, and life-cycle costs. This also creates an easy entry point for rapid expansion into medical/health-care and industrial applications for the same device and removable replaceable-media technology (as well as many unforeseen applications that will ultimately arise). Further, the greater market facilitated by the open architecture also allows for easy incorporation of sensor technology improvements, and also increases the opportunity for improved and simplified operation by users of such devices.

These forces will result in price-points and operational-simplicity points low enough to allow the technology to reach individual consumers, developing nations, impoverished communities, and displaced populations. In the case of developing nations, impoverished communities, and displaced populations, the resulting device could provide tremendous good as these are the very environments where catastrophic outbreaks are possible.

The technical features, value proposition, and market considerations both give rise to and require inexpensive mass manufacturing and distribution. These in turn give rise to the need for the removable replaceable medium to comprise inexpensive materials that are straightforwardly and inexpensively assembled. An initial solution to this is to:

Use an inexpensive substrate for the removable replaceable medium such as some type of polymer or plastic. (In various implementations, the substrate can be rigid or can be flexible.)

Employ functional printing (such as inkjet-printed functional polymers deposited directly onto the inexpensive substrate) for manufacturing the sensors and electrical aspects:
  Printed electrodes (using organic polymer conductors)
  Printed sensors (comprising solvent-insoluble and/or protected layers of semiconducting polymers, materials comprising enzymes/antibodies, deposition layers of enzymes/antibodies, etc.)
  Printed transistors (comprising layers of semiconducting polymers and organic polymer conductors) for electronics.

Employ functional printing for manufacturing of reagent reservoirs (for example in the form of depositions solvent-soluble solids or gels)

Employ functional printing for manufacturing of Read-Only Memory ("ROM") (for example in the form of printed optical codes such as printed optical bar codes, printed optical matrix codes, printed holographic codes, printed magnetic code stripe, printed electronic data memory, etc.)

If optical sensing is used, the inexpensive substrate could be, for example:
  Engineered to transparent for light pass-through at the needed wavelengths, and/or
  Employ functional printing of a optically reflective layer (reflective at the needed wavelengths)

Further, the removable replaceable medium element and its contents can be designed and configured to facilitate recycling, bio-hazard neutralization and/or controllable degradation facilitated by a termination-solvent or degradation-initiation fluid, etc.

In one aspect of the invention, the removable replaceable medium element comprises an array of sensors on a substrate. In another aspect of the invention, the removable replaceable medium element additionally comprises electrical conductors. In another aspect of the invention, the removable replaceable medium element additionally comprises sensor interface electronics.

In another aspect of the invention, the removable replaceable medium element additionally comprises data storage ROM. In another aspect of the invention, the removable replaceable medium element additionally comprises read/write data storage.

In another aspect of the invention, the removable replaceable medium element additionally comprises deposits of at least one reagent.

In another aspect of the invention, the removable replaceable medium element comprises passive fluidics for transport of one or more liquids, gases, suspensions, slurries, etc. In another aspect of the invention, the removable replaceable medium element comprises fluidics elements forming at least part of a valve for controlling the flow of one or more of liquids, gases, suspensions, slurries, etc. In another aspect of the invention, the removable replaceable medium element comprises fluidics elements forming at least part of a pump inducing the flow of one or more of liquids, gases, suspensions, slurries, etc.

FIG. 31a depicts a representation of one example of many possible implementations of the invention. In this example, the removable element is configured to fit inside or attach to a base unit comprising at least microfluidics, a microprocessor, various electronics, opto-electronics for optical sensing, and sample acquisition arrangements (as well as power sources, housing, EMI shielding, fluid solvent reservoir(s), any user-operated controls, network interfaces, computer interfaces, visual display elements, etc.). Sample acquisition arrangements in various implementations of the technology can involve one or more elements such as a fluid port, entry funnel, entry vestibule, solvent introduction arrangement, solvent mixing arrangement, one or more valves, one or more fluid pumps, one or more gas/air pumps, etc. As another example representation. FIG. 31b depicts a simplified high-level combined signal-flow and fluidic-flow representation of one example of many possible implementations of the invention. This representation emphasizes abstracted hardware and transactions with the removable element.

As another example representation, FIGS. 32a-32c depicts simple high-level representations of examples of many possible user experience and interface implementations of the invention. For example, FIG. 32a depicts an arrangement that comprises an internal user interface, which in turn can comprise for example software, user-operated controls, visual display elements, etc. FIG. 32b depicts a variation on the example arrangement of FIG. 32a wherein either or both of a computer interface (USB, Bluetooth, IR, etc.) and/or network interface (wireless LAN, wireless WAN, cellular, cabled-LAN, telephone land-line, etc.) is also provided. Similarly, FIG. 32c depicts a variation on the example arrangement of FIG. 32b wherein either or both of a computer interface (USB, Bluetooth, IR, etc.) and/or network interface (wireless LAN, wireless WAN, cellular, cabled-LAN, telephone land-line, etc.) is also provided, but in this example there is no internal user interface. Many variations on these examples are of course possible. Additionally, in various embodiments the base unit can be implemented so as to accept and support more than one removable replaceable media element.

Although considerable more detail will be provided demonstrating how such a relatively simple device framework can offer a such an expansively wide range of flexible, software controlled capabilities, and effectively support an open architecture approach to sensor technologies and statistical processing, at this point it should be clear that the invention provides a general purpose framework wherein a wide variety of biochemical and/or chemical sensors (and potentially other sensors as well), together with associated reagents and associated configurational and operations software, all collectively targeted to a specific test or group of tests can be supported via a customized inexpensively manufactured removable replaceable media element.

For example, an initial market focus can be directed to food safety and water safety. By simply configuring the removable replaceable media element with various other types of collections of chemical inexpensively manufactured (biochemical, chemical and/or other) sensors, associated reagents, and (configurational and operations) software on a removable replaceable media element, the technology can immediately be applied to a wide range of additional applications. As a depiction of such a product and manufacturing, technology, and market-broadening development strategy, FIG. 33 depicts an example representation of a timeline wherein after initial embodiments aimed at food and water safety are introduced, medical, health care, and industrial applications are then introduced, all supported with the hardware and systems framework described thus far and to follow.

Additionally, the networking capabilities provide for a wide range of practical and expansion capabilities such as (a) reporting to central agencies or regional care facilities, (b) download of software upgrades, additional algorithms, and databases, (c) remote operation, (d) remote testing, (e) access to additional patient records, (f) accessing more powerful computing for more complex data analysis, (g) interconnecting the present invention with lab equipment, and (h) interconnecting at least the computing environments of two or more instances of the present invention so that they can collectively act as a single larger unit in various ways.

Base Unit and its Interfacing Removable Replaceable Media Element

FIGS. 34a and 34b depict representations of example aspects of the removable replaceable media element. The examples shown here comprise example arrays of closely-spaced square or rectangular sites and example arrays of more-separated circular sites. In the system, each site can be configured to provide or serve as one or more of a reagent reservoir, electrically-based sensor, optically-based sensor, mixing area, chemical/biochemical reaction area, etc. From the viewpoint of the removable replaceable media element, each site is fabricated (for example, using functional printing, depositions, etc.) as either open, comprising elements for a specific type of sensor, or comprising a lump of a specific type of reagent or material (for example, solvent-soluble, gas-generating, soap, emulsifier, disinfectant, etc.). The examples depicted here can be configured in other ways, i.e., various site shapes, counts, layouts, and spacing. In one approach, the removable replaceable media element can be thick as in FIG. 34a, thin as FIG. 34b, or other arrangement. The shape of the removable replaceable media element can be rectangular as depicted but can also be a (fixed-position or rotatable) circular disk, trapezoidal, etc. Further, the sites can simple be designated areas where one or more layers of functional printing depositions are printed, or can comprise additional structure (for example, comprising or using indented wells where one or more layers of deposition are laid into, etc.).

The arrangements depicted in FIG. 34a and FIG. 34b represent a high-density arrangement wherein printed deposits and/or indented wells associated with (or partially forming) an array of sites occupy most of the regional surface area and separating boundaries are relatively thin, FIG. 34c depicts an example variation on the arrangements depicted in FIG. 34a and FIG. 34b wherein printed deposits associated with (or partially forming) an array of sites are separated by wider boundaries, and FIG. 34d depicts another example variation wherein indented wells are separated by wider boundaries.

The arrangements depicted in FIGS. 34a-34b depict a variety of shapes for printed deposits and/or indented wells—in particular suggesting some sites having a rectangular or square cross-sectional shape and other sites having a circular, elliptical, rounded, or polygonal-like shape. These shape choices are merely examples and other cross-sectional shapes (for example hexagonal, rhomboidal, trapezoidal, etc.) can be used as found to be advantageous. FIG. 34e an example variation on the arrangements depicted in FIG. 34a and FIG. 34b wherein printed deposits are only of one shape employed uniformly throughout, while FIG. 34f depicts another example variation wherein indented wells are only of one shape employed uniformly throughout The invention involves interactions between the removable replaceable media element (for example as represented in the top portion of FIG. 31a, the bottom portion of FIG. 31b, and the right portions of FIGS. 32a-32c) and the base unit (for example as represented in the bottom portion of FIG. 31a, the top portion of FIG. 31b, and the left portions of FIGS. 32a-32c).

FIG. 35a depicts a first functional representation of an example of how the open faces of sites comprised by a removable replaceable media element are to match up with site interface areas on an interface surface within the base unit. It is noted that the number of sites, grouping of sites, number of groupings, shape of sites, shape of the groupings, border areas between sites, border areas between groupings, overall layout, etc. are merely intended to represent a single abstracted example and are by no means restrictive or limiting as to those and other aspects of the removable replaceable media element. In the example arrangement of FIG. 35a, all of the square/rectangular sites depicted are provided with their own separate interfacing arrangement. FIG. 35b depicts a variation on the example arrangement of FIG. 35a wherein small groups of multiple sites on the removable replaceable media element share a common interface arrangement—for example to provide multiple (non-interacting) sensors (comprised by the group of sites sharing that same interface arrangement instance) to be presented with the same analyte. FIG. 35c depicts a variation on the example arrangement of FIG. 35a wherein groups comprising larger of multiple sites on the removable replaceable media element share a common interface arrangement.

Note that each of the site groups can be of the same size, as suggested in FIG. 35b, or alternatively site groups can be of differing sizes, as suggested in FIG. 35c. Further, even though some sites may be grouped to share a common interface in the base unit as depicted in FIGS. 35b-35c, the base unit can provide individual interfaces to other sites. This is suggested by the rounded sites depicted in FIGS. 35b-35c, Such arrangements can be useful for many reasons, for example so as to provide dedicated interface architectures to certain types of specialized sensors, reagent deposits, etc.

Further as to the abstract examples provided in FIGS. 35a-35c, in each of these various regionalized groupings of sites are depicted. These, if implemented, can be used for various additional functional purposes, for example to provide added degrees of electric field, magnetic field, or optical isolation, to create well-defined duplication/redundant copies to recover from failure conditions, etc. An important additional potential use provided for by the invention is the support for a removable replaceable interface module associated with a particular subset of the base unit, for example as suggested by the dashed insert cavities depicted in FIG. 35d and in FIG. 35e. Such a removable replaceable interface module could be used to facilitate for example (a) field maintenance for parts of a base unit implementation that wear, age, clog, contaminate, etc. more often than others, (b) field upgrades where technology advancements are anticipated, and (c) "open architectures" to support a wide range of entirely different types of base unit sensing and analysis capabilities, be they available at higher cost, useful for only specialized applications, used for throughput expansion, used for test redundancy, anticipated future technologies, and entirely unexpected future technologies.

As specific examples for (c), efforts have been underway to miniaturize mass spectrometry (for example as taught in S. Le Gac, A. van den Berg, *Miniaturization and Mass Spectrometry*, RSC Publishing 2009, ISBN 978-0-85404-129-9), gas chromatography (for example the inexpensive Mini GC Plus Gas Chromatograph manufactured by Vernier Software & Technology, LLC, 13979 S.W. Millikan Way Beaverton, Oreg. 97005), "electronic nose" gas-sensing technologies, as well as other classically large lab instrument systems to a scale that is within applicability, packaging, and technology development reach of being realizable in the form of such a removable replaceable interface module compatible with the present invention. Accordingly, the "open architecture" provision provided for by the invention allows for considerable third-party innovation, second-sourcing, and cost competition. Additionally the "open architecture" provision provided by the invention allows for the incorporation of fundamentally new sensing technologies, for example in the area of optofluidics and optical resonance sensing technologies. Examples of promising optofluidics and optical resonance sensing technologies applicable to the invention are described, for example, in the following articles in *Advanced Photonic Structures for Biological and Chemical Detection*, X. Fan (ed.), Springer, ISBN 978-0-387-980607:

Chen, "Microresonantor Sensors Made in Polymers with Functional Chromophore Dopants," pp. 7-34.

C-Y Chao, T. Ling, L. Guo, "Label-Free Biochemical Sensors Based on Optical Microresonantors," pp. 177-227.

White, H Zhu, J. Suter, X. Fan, "Label-Free Biosensing with the Optofluidic Ring Resonator," pp. 377-393.

J. Goddard, S. Mandal, D. Erickson, "Optically Resonant Nanophotonics Devices for Label-Free Biomolecular Detection," pp. 445-470.

H. Schmidt, A. Hawkins, "Single Molecule Analysis with Planar Optofluidics," pp. 487-512.

In such open architecture arrangements, it can be advantageous for the removable replaceable media element to be selectively populated in smaller regions, for example as in the half-populated example depicted in FIG. 35f, and more fully populated for other applications. Further as to the "open architecture" provisions of the invention involving removable replaceable interface module, FIG. 35g depicts an example adaptation of the example architectural arrangement provided in FIG. 31b wherein a removable replaceable interface module is provided interfaces to the microfluidics and computing infrastructure. Other architectural arrangements are of course possible, anticipated, and provided for by the invention.

The invention provides for a wide range of possible arrangements for insuring adequate degrees of alignment of removable replaceable media elements (such as described and represented for example in the top portion of FIG. 31a, the bottom portion of FIG. 31b, and the right portions of FIGS. 32a-32c) with the base unit (such as described and represented for example in the bottom portion of FIG. 31a, the top portion of FIG. 31b, and the left portions of FIGS. 32a-32c). As a first example, FIG. 36a depicts an abstract primitive "caricature" representation of an example removable replaceable media element with a small number of sites, ROM area, and example precision alignment holes and the corresponding interface surface within the larger base unit. In this example the interface surface provides alignment pins; here the alignment pins are shown with a tapered shape although other alignment pin shapes are possible. Also, although the alignment pins are depicted here with round cross-sectional shapes, the alignment pins could have different cross-sectional shapes.

FIG. 36b depicts a representation of an abstract example of how the alignment pins provided by the interface surface within the larger base unit align the removable replaceable media element by matching the hole locations in the removable replaceable media element. FIG. 36c depicts a representation of an abstract example of the interface surface within the larger base unit depicted in FIG. 36a and a corresponding "lid" within the larger base unit having holes matching the alignment pins provided by the interface surface within the larger base unit. FIG. 36d depicts a representation of an abstract example of how the removable replaceable media element, interface surface within the larger base unit, and lid within the larger base unit align so as to provide precise alignment and fluid-tight contact between the removable replaceable media element and the interface surface within the larger base unit.

The invention provides for the removable replaceable media element to comprise a data storage element. FIG. 37 depicts an example abstract representation of a removable replaceable media element used previously as part of FIG. 31a. As indicated earlier, the Read-Only Memory ("ROM") can take the form of printed optical codes (such as printed optical bar codes, printed optical matrix codes, printed holographic codes, for example as taught in C. Harmon, Lines of Communications, Helmers Publishing, 1994, ISBN 0-911261-07-9), printed magnetic code stripe, printed electronic data memory (for example as described in Thin Film Electronics ASA, Xerox PARC, "Thinfilm Unveils First Scalable Printed CMOS Memory," press release, Jan. 9, 2012, (as disclosed at world wide web at—printelectronic-news.com/3178/thinfilm-unveils-first-scalable-printed-cmos-memory, visited 03/22/12). In some embodiments, it can be advantageous to additionally include an ability to write data onto the data storage element (date used, patient information, test outcomes, etc,) as suggested in the dashed path depicted in FIG. 31b.

In an embodiment, the readable medium is attached to the removable replaceable media element by printing of at least one material on the removable replaceable media element. In another embodiment, the readable medium is a separately manufactured label attached to the removable replaceable media element by a melding, adhering, or other attachment method or process.

In an embodiment, the readable medium is attached to the removable replaceable media element comprises date information associated with the materials on the removable replaceable media element. In an embodiment, the readable medium is attached to the removable replaceable media element comprises serial number information.

In an embodiment, the readable medium is attached to the removable replaceable media element comprises information usable to perform a test procedure. In an embodiment, the readable medium is attached to the removable replaceable media element comprises information usable to perform a statistical analysis.

In an embodiment, the readable medium is attached to the removable replaceable media element comprises information specifying parameters used by at least one algorithm. In an embodiment, the readable medium is attached to the removable replaceable media element comprises information specifying at least one algorithm.

The interface and reading of these by the base unit will be considered later.

Caps for Encapsulating Sites, their Associated Material Flow, Electrical, and Optical Interfacing, and Interconnection Examples of caps for encapsulating sites, their associated material flow, electrical, and optical interfacing, and the interconnection of the caps are now considered. In some implementations, such caps are comprised by the base unit and provide an interface to the removable replaceable media element. In other implementations, such caps are comprised within the removable replaceable media element. In yet other implementations, such caps are comprised by both the base unit and the removable replaceable media element. In still other implementations, at least some caps are implemented by the combination of features, elements or aspects of the base unit and features, elements or aspects of the removable replaceable media element.

To begin, material flow handling can be arranged transport fluids, gases, fluids comprising gas, and fluid analyte comprising suspensions, slurries, cells, emulsions, micelles, etc. In the below, the discussion will be made in terms of fluids and fluidics, but it is to be understood that throughout this is fully intended to extend to cover additional materials and situations such as suspensions (for example comprising cells), gases dissolved liquids, materials at thermodynamic critical points (such as vapors and gases including vapors), slurries, gases comprising particulates or colloids, emulsions in various stages (flocculation, creaming, coalescence, Ostwald ripening, etc.), micelles, etc. as well as combinations of these to the degree allowed by physics.

FIG. 38 depicts an example representation of the offset bottom view of a "cap" that meets and covers each site area of the removable replaceable media element with, for example a fluid-tight and/or gas-tight seal. The cap edge can comprise one or more electrical connection electrodes or arrays of such electrodes for interfacing with the (printed or other form of) electrical conductors affiliated with any sensor(s) implemented in the corresponding site of the removable replaceable media element. Multiple electrodes are provided for redundancy and thus reliable electrical connection, multiple electrical paths, etc. The cap could have one or more such electrodes. The "cap" depicted in FIG. 38 is merely representational—it can have a rectangular, circular, or other shape opening, can comprise sensor elements (such as UV or visible-range LEDs, UV or visible-range photodiodes, temperature sensors, pressure sensors, etc.), fluidic ports (as will be seen shortly), controlled valves, mixing elements, turbulence-inducing or suppression elements, fluidic-current routing elements, etc., and can vary with site location in accordance with a site-specialization plan (wherein, for example, some sites only support a first one or a few possible functions while other sites support a second one or a few possible functions).

Regarding sensors or sensor components on the removable replaceable media element that comprise electrical connections, each "cap" can be configured to cover an associated region of a removable replaceable media element that comprises one or more, the cap can comprise associated electrical connections for making electrical contact with corresponding electrical connection on the removable replaceable media element. The electrical connections for one or more sensors or sensor components at a particular site can be routed to an electrical connection region located at the associated site, surrounding the site, on at least one edge of the site, near at least one edge of the site, etc. on the removable replaceable media element, for electrical connection through electrical contacts comprised by an associated cap, a group of caps, or other arrangement.

In other implementations, electrical connections for one or more sensors or sensor components can in additional or instead be routed to an electrical connection region in another part of the removable replaceable media element. In some implementations, at least one electrical connection for one or more sensors or sensor components is made to an electrical shielding arrangement comprised by the removable replaceable media element. In some implementations, at least one electrical connection for one or more sensors or sensor components is made to an electrical circuit (for example, an amplifier, differential amplifier, current source, comparator, analog-to-digital converter, digital-to-analog converter, etc. the removable replaceable media element. In some implementations, at least one electrical connection to an electrical circuit (for example, an amplifier, differential amplifier, current source, comparator, analog-to-digital converter, digital-to-analog converter, etc. on the removable replaceable media element is made to electrical connections on the removable replaceable media element arranged to electrically connect with electrical connections at the associated site, surrounding the site, on at least one edge of the site, near at least one edge of the site, etc. on the removable replaceable media element.

In some electrical sensing arrangements (such as has been described earlier), the site or area can further comprise additional electrical elements including but not limited to electrical shielding, diodes, transistors, resistors, capacitors, inductors, ferrites, electronic circuitry, etc. as well as materials suitably conductive, insulating, etc. In some electrical sensing arrangements (as will be described later), the cap can further comprise electrical elements including but not limited to electrical shielding, diodes, transistors, resistors, capacitors, inductors, ferrites, LEDs, photodiodes, phototransistors, electronic circuitry, etc. as well as materials suitably conductive, insulating, etc. In some optical sensing arrangements (as will be described later), the site or area can further comprise optical elements including but not limited to LEDs, photodiodes, phototransistors, etc. as well as materials suitably opaque, transparent, or translucent at specific wavelengths of electromagnetic radiation, etc. In some optical sensing arrangements (as will be described later), the cap can further comprise optical elements including but not limited to LEDs, photodiodes, phototransistors, etc. as well as materials suitably opaque, transparent, or translucent at specific wavelengths of electromagnetic radiation, etc.

FIG. 39a depicts an example representation showing the "cap" described above (without attention to fluidic ports, electrical connections, mechanical support, etc.) interfacing with a site or area within a removable replaceable media element. In many situations, a particular site or area within a removable replaceable media element would not be populated with a sensor or a reagent—it could be for example not used, used as a mixing chamber, used for optical sensing, etc. The invention provides for caps of this nature to be used to interface individual sites (as suggested in the arrangement depicted in FIG. 35a) or groups of sites (as suggested in the arrangement depicted in FIGS. 35b and 35c). The invention provides for caps to be nested in various hierarchical arrangements and implementations where that is or can be advantageous.

Regarding sensors or sensor components on the removable replaceable media element, FIG. 39b depicts an example representation wherein the "cap" covers a site area within a removable replaceable media element that comprises a sensor (here abstractly represented as a bold rectangular solid).

Regarding reagents, FIG. 39c depicts an example representation wherein the "cap" covers a site or area within a removable replaceable media element that comprises a printed deposition comprising one or more reagents or materials (for example, solvent-soluble, gas-generating, soap, emulsifier, disinfectant, etc.), for example, in the form of a solvent-soluble solid or gel comprising a solvent-soluble reagent or material. The deposition can be functionally structured so as to provide a well-defined dissolution process in the fluid-exchange environment within the cap that does not result in problems such as sedimentation, loose fragments that could clog fluidic ports, clog fluidic valves, provide uncontrolled variations in concentration, or affect sensor operation. For example, the solvent-soluble solid or gel can comprise a polymer lattice, zeolite-like structure, etc. Depending upon the approach taken, the solvent-soluble solid or gel can comprise a solvent-soluble solid reagent, a solvent-mixable or solvent-soluble liquid reagent previously entrapped (macroscopically or microscopically) within the solvent-soluble solid or gel structure, and even a gas (for example entrapped within the structure or resulting from a chemical or enzymic reaction, etc.). FIG. 40a depicts an example representation wherein the "cap" (covering a site or area within a removable replaceable media element that comprises a printed reagent or material deposition) is provided with a fluidic port accepting solvent in and a fluidic port carrying solvent and reagent outward. Although untapered square-opening and round-opening caps are depicted, other cap shapes can be used. FIG. 40b provides a variation on the arrangement depicted in FIG. 40a wherein the removable replaceable media element is of a form comprises wells.

Controllable Valves

The various embodiments of the invention can incorporate fluidics at various scales of physical size, ranging from those that use small-scale convention and fittings, controllable valves, pumps, and fluidic conduit manufacturing techniques to microfluidic scales involving transport of nano-liter volumes of materials. The value of the system would be expected to increase with increasing degrees of miniaturization as less sample, supplies, and power are required, field use is better facilitated, etc. As the scale of physical size decreases, the implementation of valves and pumps becomes less conventional and new emerging approaches and techniques will be used. Further, these less conventional approaches and techniques are expected to continue to evolve.

Some examples of controllable valves suitable for microfluidics systems include but are not limited to those operated by:

pneumatic or hydraulic stimulus (as for example, can be induced by larger scale apparatus driven by and controlled by electrical voltage or current)

thermal processes (induced by electrical resistance or electrically produced infrared radiation)

piezoelectric actuation (as for example, can be driven by electrical voltage or current)

magnetic fields (as for example, can be induced by electrical current)

torque or other mechanical actuation (as for example, can be induced by larger scale apparatus driven by and controlled by electrical voltage or current)

Many of these employ either elastometric materials that response to applied pressure forces or complex polymers that change their physical properties responsive to electricity or heat. These and other know and as yet unknown approaches and techniques are expected to continue to evolve, emerge, and compete. However, as seen in the list above, there are many approaches that ultimately can be controlled by electrical current and/or voltage processes, making theme suitable for control by a microprocessor, other computation system, and/or digital logic circuitry.

As one specific example, piezoelectric actuators can be used to manipulate elastometric materials, either by direct mechanical contact of through intermediate pneumatic or hydraulic transfer. As another specific example, an electrically controlled microvalve leveraging large volumetric phase-change, for example as occurring in polyethylene glycol polymers (PEG), are thermally controlled using thin film resistive elements patterned using standard microfabrication methods, for example as taught in G. Kaigala, V. Hoang, C. Backhouse, "Electrically Controlled Microvalves to Integrate Microchip Polymerase Chain Reaction and Capillary Electrophoresis," Lab on A Chip, 2008, Vol. 8, No. 7, pp. 1071-1078 (whose authors indicate can readily scale down in size and require only electrical connection).

It is noted that thin films, elastometric materials, and polymers can, through various processes and preparation, be functionally printed. Additionally, various practical aspects of the fabrication and operation of microfluidic valves based on elastometric materials can be found, for example, in B. Mosadegh, *Design and Fabrication of Microfluidic Integrated Circuits Using Normally Closed Elastomeric Valves*, UMI Disserrtation Publishing, 2010, ISBN 9781244570306.

Pumps

As will be seen, in many approaches supported by the invention analyte propagates through one or more serial chains of processing and sensing regions, and if there is more than one serial chain at least one fan-out stage is involved; these arranged in a manner that could be adequately managed with a single pump and the operation of valves to control where flow is active or blocked. Accordingly, a single or small number of pumps arranged for transport of small amounts of fluid but having a comparatively considerably larger overall physical size (for example, a miniature motor-driven, solenoid-driven, or piezoelectric-driven diaphragm pump, a miniature motor-driven, solenoid-driven, or piezoelectric-driven peristaltic pump, a miniature motor-driven, solenoid-driven, or piezoelectric-driven syringe pump, etc.).

As to microfluidic pumps, as with microfluidic valves there are many approaches that ultimately can be controlled by electrical current and/or voltage processes to control or induce a mechanical actuation. In many cases the same types of mechanical actuation used to operate a valve can be used to operate a diaphragm pump, actuate a stepping mechanism for a syringe pump, and arranged in a sequenced ensemble or drive a rocker arrangement to create a peristaltic pump. Many examples of these can be found in the literature, and it is expected that these and other know and as yet unknown approaches and techniques are expected to continue to evolve, emerge, and compete. However, as seen in the list above, there are many approaches that ultimately can be controlled by electrical current and/or voltage processes, making theme suitable for control by a microprocessor, other computation system, and/or digital logic circuitry.

Further as to microfluidic pumps, much attention in the microfluidics literature has been directed to electro-osmotic transport. Although the invention provides for the use of electro-osmotic transport where applicable or advantageous, it is noted that the electric fields and introduced voltage potentials involved can affect biomolecules, cells, suspensions, etc, can introduce unwanted or unmanageable electrochemical effects, and can interfere with the intended operation of many types of sensing technologies and processes, Accordingly, in some embodiments electro-osmotic transport is employed where applicable or advantageous to transport materials (or a somewhat restricted class of materials) between fluidic locations but is non-operational when sensing that could be affected by voltages, current, and fields associated with electro-osmotic operation. The invention in a similar manner provides for the use of other similar pump techniques, for example as taught in S. Chang, E. Beaumont, D. Petsev, O. Velev, "Remotely Powered Distributed Microfluidic Pumps and Mixers Based on Miniature Diodes," *Lab on a Chip,* 2008, Vol. 8, pp. 117-124.

Interfacing Removable Replaceable Media Element to Fluidics and Other Infrastructure within or Intermediate to the Base Unit With valves and pumps applicable to the invention now discussed, attention is now directed to interfacing the sites on the removable replaceable media element to fluidics within or intermediate to the base unit, as well as electronics and optics within or intermediate to the base unit, and associated interconnection. Attention is first directed to fluidics interfacing, fluidic control, and fluidics interfacing.

As will be seen via various examples to be provided, in many implementations a fluidic flow arrangement limited to neighbor-to-neighbor fluidic interconnection can be adequate. To begin, FIG. 41*a* depicts an example representation wherein a row of neighboring "caps" are pair-wise connected by an "in-line"-valve-controlled fluidic link associated with that pair, resulting in a "daisy-chain" arrangement.

An "in-line"-valve arrangement can present some issues, ranging from fluids undesirably propagating by pressure or capillary action into fluidic links to complications in the fabrication of the valves in such a location, so in many implementations it can be preferable to use pairs of valves for each fluidic link as in the example case represented in FIG. 41*b*. In such arrangements, the pair of control valves terminating the ends of a specific fluidic link could be operated simultaneously.

The nearest-neighbor connection scheme can be implemented for both dimensions of an array of sites. For example, FIG. 42 depicts an example representation wherein a row of neighboring "caps" are pair-wise connected by a valve-controlled fluidic link associated with that pair, resulting in a two-dimensional "daisy-chain" arrangement. In this case the "in-line" valve arrangement link depicted in FIG. 41*a* is used, although the "endpoint valve pair" arrangement depicted in FIG. 41*b* is in many cases preferable.

In the arrangements depicted in FIGS. 41*a*-41*b* and FIG. 42, a clog in a port, fluidic line, or valve can prevent operation of the sites involved. For this reason it can be advantageous to provide a redundant valve-controlled path for each pair-wise link. For example, FIGS. 43*a*-43*b* depict example representations wherein a row of neighboring "caps" are pair-wise connected by a valve-controlled fluidic link associated with that pair, resulting in a two-dimensional "daisy-chain" arrangement. Such an arrangement can also be used in the two-dimensional nearest-neighbor pair-wise interconnection approach as well, for example by adding similar redundant links to the arrangement depicted in FIG. 42. In FIG. 43*a*, the "in-line" valve arrangement link depicted in FIG. 41*a* is used. As mentioned earlier, the "endpoint valve pair" arrangement depicted in FIG. 41 *b* is in many cases preferable, and this approach is used in FIG. 43*b*. Note here another advantage that now results—should one of the valves in one of the redundant links be stuck in an "on" ("flow-through") mode, the endpoint valve at the other end of that link can be switched off to disable the troubled link until the "stuck-on" valve can be later cleaned, cleared, and restored to normal operation; the redundant line can then take over to link the pair of caps and sites.

As an alternative to the aforedescribed one-dimensional and two-dimensional nearest-neighbor fluidic pair-wise interconnection approach, the sites can be more generally fluidically interconnected with a controllable microfluidic bus (such as that taught in U.S. Pat. No. 8,032,258 and pending U.S. patent application Ser. Nos. 13/251,286 and 13/251,288). This adds a broad range of interconnection possibilities but involved higher fabrication and operational complexity.

In addition to the aforedescribed one-dimensional and two-dimensional pair-wise nearest-neighbor controlled fluidic interconnection approach described in conjunction with FIGS. 41a-41b, FIG. 42, and FIGS. 43a-43b, the fluidic interconnections among caps and associated sites can be supplemented with additional controllable fluidic paths, for example as represented in FIGS. 44a-44c. In some implementations these can be used to carry solvent(s), cleaning fluids and/or clearing gases (such as that taught in pending U.S. patent application Ser. Nos. 11/946,678 and 13/314, 170) and/or can connect to controllable microfluidic bus (such as that taught in U.S. Pat. No. 8,032,258 and pending U.S. patent application Ser. Nos. 13/251,286 and 13/251, 288). The combination of nearest-neighbor pair-wise fluidic interconnection and more general controllable microfluidic bus fluidic interconnection provides many additional advantages in return for the added complexity.

As a reminder, the fluidics arrangements described thus far, including those described in conjunction with FIGS. 41a-41b, FIG. 42, FIGS. 43a-43b, and FIGS. 44a-44c, are again understood to extend to cover additional materials and situations such as suspensions (for example comprising cells), gases dissolved liquids, materials at thermodynamic critical points (such as vapors and gases including vapors), slurries, gases comprising particulates or colloids, emulsions in various stages (flocculation, creaming, coalescence, Ostwald ripening, etc.), micelles, etc. as well as combinations of these. In various aspects of the invention, the fluidics arrangements are arranged to interface to sensor, deposition, and other sites on the removable replaceable media element.

FIG. 45a depicts an example arrangement wherein caps interconnected with fluidics arrangements interface to associated sites on a portion of the removable replaceable media element. FIG. 45b depicts a variation on the example arrangement of FIG. 45a wherein the example arrangement is extended to encompass all possible sites of the removable replaceable media element. In many implementations and usage scenarios it can be advantageous to implement at least the fluidics arrangements in an separate interfacing module, In some embodiments the interfacing module can be comprised by the base unit in either a fixed or replaceable arrangement, In other embodiments the interfacing module can be comprised by the removable replaceable media element in either a fixed or replaceable arrangement, In yet other embodiments the interfacing module can be configured to be inserted into either (at the choice of user or manufacturer product-design) the base unit or attached to the removable replaceable media element in either a fixed or replaceable arrangement, In various embodiments, the interfacing module can additionally comprise one or more of various additional components including but not limited to electronic circuitry, valves or portions of valves, optical elements, electro-optical elements, mechanical actuators, pumps, reservoirs, microprocessors, additional sensors, etc.

In various embodiments, the interfacing module can be fabricated in part or in whole by functional printing. In various embodiments, the interfacing module can be fabricated in part or in whole by injection molding. In various embodiments, the interfacing module can be fabricated in part or in whole by casting.

When the aforedescribed interface module is employed as a removable component for use in the base unit, such an arrangement allows for simplified maintenance, performance upgrades, density upgrades, feature upgrades, means of contamination control within the base unit, etc. When the aforedescribed interface module is employed as an attached or user-attachable component to the removable replaceable media element, such an arrangement allows for containment of contamination, simplified usage, performance customizations, density customizations, feature customizations, etc. FIG. 45c depicts a variation on the example arrangement of FIG. 45a wherein at least the fluidics arrangements are comprised in an interfacing module, FIG. 45d depicts a variation on the example arrangement of FIG. 45c wherein the example arrangement is extended to encompass all possible sites of the removable replaceable media element. FIG. 45e depicts an example wherein the interfacing module can be configured to be inserted into either (at the choice of user or manufacturer product-design) the base unit or attached to the removable replaceable media element in either a fixed or replaceable arrangement, The ports in the caps for fluidic interconnections can be arranged in various configurations depending on the complexity and architecture of the overall system. FIGS. 46a-46c depict representations of some examples, these including controlled valves at each fluidic port (as employed for example in the arrangements depicted in FIGS. 41b, 43b, and 44a-44b).

In an embodiment, at least one solvent reservoir is provided in the base unit. In an embodiment, that solvent reservoir is removable.

In an embodiment, the solvent reservoir is built into the removable replaceable medium element, for example within or beneath the sensor-level substrate removable replaceable medium element.

In an embodiment, at least one disposal reservoir is provided in the base unit. In an embodiment, that disposal reservoir is removable.

In an embodiment, the disposal reservoir is built into the removable replaceable medium element, for example within or beneath the sensor-level substrate removable replaceable medium element.

In an embodiment, the solvent reservoir and disposal reservoir are in a unitary removable configuration.

ROM Aspects of the Base Unit and Removable Replaceable Media Element

As described earlier, the ROM provided by the removable replaceable media stores data (such as configuration data, assignment data, data used by algorithms) and algorithms (such as test algorithms, analysis algorithms, etc.). As indicated earlier, the ROM can take the physical form of printed optical codes (such as printed optical bar codes, printed optical matrix codes, printed holographic codes), printed magnetic code stripe, printed electronic data memory, etc.).

FIGS. 47a-47c depict representations of examples of how optical ROM printed on the removable replaceable media can be read by the base unit. FIG. 47a depicts an example linear (1-dimensional) optical "bar" code that can be printed on instances of the removable replaceable medium and a "reading array" comprising for example a 1-Dimensional Photodiode Array, 1-Dimensional LED Array, 1-Dimensional CCD Array, etc. located in the base unit and configured to lie effectively optically adjacent to the optical bar code printed on the removable replaceable media. No mechanical scanning is needed with this approach. (As described later, LEDs can operate as wavelength-selective photodiodes.) The barcode can be lit by various arrangements, including back lighting, frontal light, via selected LEDs in an LED array, etc. Translational—displacement of the optical bar code with respect to the "reading array" (arising from minor variations in removable replaceable media positioning with respect to the base unit) can be readily handled in software on a microprocessor or other processor chip comprised by the base unit. If the "reading array" comprises LEDs with a number of distinguishable different emission wavelengths, the LED array can be used to implement wavelength division multiplexing arrangements, allowing use of multiple colored inks used in the printing of the optical bar code to increase the information density on the optical bar code.

FIG. 47b depicts an example elongated rectangular 2-dimensional optical "matrix" code that can be printed on instances of the removable replaceable medium and a "reading array" comprising for example an elongated rectangular 2-Dimensional Photodiode Array, 2-Dimensional LED Array, 2-Dimensional CCD Array, etc. located in the base unit and configured to lie effectively optically adjacent to the optical matrix code printed on the removable replaceable media. No mechanical scanning is needed with this approach. The barcode can be lit by various arrangements, including back lighting, frontal light, lighting by LEDs in an LED array, etc. Translational-displacement of the optical bar code with respect to the "reading array" (arising from minor variations in removable replaceable media positioning with respect to the base unit) can be readily handled in software on a microprocessor or other processor chip comprised by the base unit. If the "reading array" comprises LEDs with a number of distinguishable different emission wavelengths, the LED array can be used to implement wavelength division multiplexing arrangements, allowing use of multiple colored inks used in the printing of the optical matrix code to increase the information density on the optical matrix code.

FIG. 47c depicts an example non-elongated rectangular 2-dimensional optical "matrix" code that can be printed on instances of the removable replaceable medium and a "reading array" comprising for example a non-elongated rectangular 2-Dimensional Photodiode Array, 2-Dimensional LED Array, 2-Dimensional CCD Array, etc. located in the base unit and configured to lie effectively optically adjacent to the optical matrix code printed on the removable replaceable media. No mechanical scanning is needed with this approach. The barcode can be lit by various arrangements, including back lighting, frontal light, lighting by LEDs in an LED array, etc. Translational-displacement of the optical bar code with respect to the "reading array" (arising from minor variations in removable replaceable media positioning with respect to the base unit) can be readily handled in software on a microprocessor or other processor chip comprised by the base unit. If the "reading array" comprises LEDs with a number of distinguishable different emission wavelengths, the LED array can be used to implement wavelength division multiplexing arrangements, allowing use of multiple colored inks used in the printing of the optical matrix code to increase the information density on the optical matrix code.

Alternatively, other arrangements for optical ROM, electronic ROM (for example, implemented with printed electronics), magnetic ROM, etc.) can also be used.

In an embodiment, compressed specification languages and procedural languages can be used to minimize the number of characters stored on the ROM.

Measurement and Statistical Process Specification Language

In an embodiment, the invention provides for a measurement specification language that can be used to specify parameters, operations, sequences, event-driven logic, etc. for processes, control and operations to implement specific measurements associated with the particular collection of sensors and reagents on the removable replaceable media element. This will be described first in terms of the data content and organization comprised by data on a ROM element comprised on the removable replaceable media element. However, the same information can also be obtained in part, in whole, or superseded by other data sources such as a network connection, USB port, Bluetooth, cellular data link, or other wireless radio link, infrared or other wireless optical link, etc.

Further, a similar approach can be used to specify statistical processing operations associated with the particular collection of sensors and reagents on the removable replaceable media element.

FIG. 48 depicts a representation of the information stored on the ROM (for example, configuration data, assignment data, data used by algorithms, test algorithms, analysis algorithms, etc.) comprised by the removable replaceable media. The left side of FIG. 48 at the bottom depicts a representation of a site configuration table (comprised by the data portion of the ROM software on the removable replaceable medium) that used to specify what mode each site is to operate in. Moving from left to right in FIG. 48, the next depicted data item comprised by the data portion of the ROM software (on the removable replaceable medium) contains fluidic configuration data that used to configure fluidic elements such as valves (and which can also include pumps. Move right one more step, the next depicted data item comprised by the data portion of the ROM software (on the removable replaceable medium) contains electronic configuration data that used to configure electronic elements such as sensor interface electronics, logic gates, routing of sensor signals to A/D converters, mixed signal integrated circuits, digital processors, microprocessors, etc. The right side of FIG. 48 depicts a representation of algorithms stored on the ROM. Examples include algorithms for operation of tests (including standard or special operation of sensors and fluidics, etc.), as well as algorithms used to produce the statistical analysis of the information provided by the sensors.

In an embodiment, a data medium reader for reading encoded data on a readable medium that is comprised by the removable replaceable media element is implemented in the base unit, wherein the medium reader is responsive to the encoded data and can provide information to a computational processor the base unit as suggested in FIG. 31a and FIG. 31b presented earlier. In some embodiments, it can be advantageous to additionally include an ability to write data onto the data storage element (date used, patient information, test outcomes, etc,) as suggested in the dashed path depicted in FIG. 31b.

In an embodiment, compressed specification languages and procedural languages can be used to minimize the number of characters stored on the ROM.

Reconfigurable Aspects of the Base Unit and Removable Replaceable Media Element In a very general system, every site would have a broad and identical range of capabilities and supported functions. However, this in many cases would largely go unused and would add considerable cost and programming complexity, particularly in early implementations of the device. As the technology matures, however, such broad and identical range of capabilities and supported functions for every site could be approached or attained.

For early implementations of the device, each site can be permitted a restricted one or few capabilities, and the caps would be implemented, electrically connected, and in some cases, fluidically interconnected, accordingly. FIG. 49 depicts a representation of example functional allocations that can be provided for each site. In this case, a column organization is used, although clearly other approaches can clearly be employed instead.

As mentioned above, the left side of FIG. 48 depicts at the bottom a function allocation table. FIG. 50a depicts a representation of a fluidics-based test configuration. FIG. 50b depicts a representation of the function allocation corresponding to the test configuration of FIG. 50a. FIG. 51a depicts a representation of another fluidics-based test configuration. FIG. 51b depicts a representation of the function allocation corresponding to the test configuration of FIG. 51a.

Functional Printing of Sensors, Reagent Reservoirs, and Printed Electronics on the Removable Replaceable Media Element FIGS. 52a-52b depict representations of example functional printed methods that can be used, for example, to print the sensors on the removable replaceable medium. For example, functional printing can be implemented by rendering precision-controlled depositions of one or more types of fluid "inks" onto a surface.

Here the "inks" can comprise one or more of various types of electrical organic conductors, organic insulators, organic semiconductors, reflective materials, antibodies, enzymes, colloidal substances, meta-materials, etc. Such "inks" can dry, polymerize, can be "cured," etc., after deposition by employing various types of drying, heating, evaporating-time pause, vacuum aspiration, photoactivation, and/or other processes. The "inks" can be applied in layers to create layered structures comprising different materials and well-defined interfaces between them. In some arrangements, the inks can be blended in the printing (or other deposition) action. The inks must permit specified functions to properly occur (for example proper immobilization of biologically active materials, electrical conduction, charge carrier injection, etc.), have proper electrical, thermal, and mechanical characteristics, and be non-soluble in the solvent used by the invention to carry the analyte.

In particular, the discovery of conjugated polymers and their development into soluble materials provided the first organic electronics ink materials. Materials from this class of polymers have properties spanning various conducting, semiconducting, electroluminescent, photovoltaic and other forms of electroactive behavior. Other printable polymer inks can serve as insulators and dielectrics. Printed or previously existing inorganic electronic materials and elements can provide better layers, structures, and interfaces, and in many cases electrical performance, than can organic and polymer materials. Accordingly the invention provides for printed or previously existing inorganic electronic materials and elements to be used in conjunction with printed organic electronics and printed biological materials.

While inkjet and screen printing typically imprint rigid substrates like glass and silicon, mass-printing methods nearly exclusively use flexible foil and paper. Poly(Ethylene Terephthalate)-foil (PET) is a common choice, due to its low cost and higher temperature stability. Poly(ethylene naphthalate)—(PEN) and poly(Imide)-foil (PI) are alternatives. Other important substrate criteria in addition to low roughness is suitable wettability, which can be tuned pre-treatment (coating, corona), and low. absorbency. Thus, although in some cases paper can be an attractive substrate, however, its high roughness and large absorbency make many types of paper problematic as a substrate for at least small-scale printed electronics. Further, it is noted that printed electronics methods allow for the use of flexible substrates should that be advantageous in implementations of the invention.

Organic semiconductors that can be printed include the conductive polymers Poly(3,4-Ethylene DiOxiTiophene), doped with Poly(Styrene Sulfonate), (PEDOT:PSS) and poly(aniline) (PANI). Both polymers are commercially available in different formulations and have been printed using inkjet, screen. offset, flexo, and gravure, printing. Polymer semiconductors such as for example poly(thiopene)s such as Poly(3-HexylThiophene) (P3HT)[43] and poly(9,9-dioctylfluorene co-bithiophen) (F8T2), electroluminescent polymers, and other electrically active polymers and materials can be inkjet or gravure printed, as well as organic and inorganic insulators and dielectrics.

Organic field-effect transistors and integrated circuits can be prepared completely by means of mass-printing methods. Printing technologies divide between sheet-based and roll-to-roll-based approaches. Sheet-based techniques, such as inkjet and screen printing are best for low-volume, high-precision work. Gravure, offset and flexographic printing are more common for high-volume production. While offset and flexographic printing are mainly used for inorganic conductors, organic conductors, and dielectrics. Because of its high layer quality and high resolution capabilities, gravure printing is especially suitable for quality-sensitive layers like organic semiconductors and semiconductor/dielectric-interfaces in transistors, and fine-detail printing of inorganic and organic conductor paths.

Example inks include:

Solvent inks: These comprise volatile organic compounds (VOCs), organic chemical compounds that have high vapor pressures.

UV-curable inks: After printing, the ink can be cured by exposure to strong UV-light. Ink is exposed to UV radiation where a chemical reaction takes place where the photo-initiators cause the ink components to cross-link into a solid.

Inks can usually be printed by such methods when $1<Z<10$ where $Z=(a\rho\gamma)^{0.5}/\eta$ (due to J. E. Fromm, *IBM J. Res. Dev.*, 1984, 28, 322.)

a=nozzle diameter
$\rho$=ink density
$\gamma$=ink surface tension
$\eta$=ink viscosity although various exceptions exist. At low values of Z the ejected drop volume falls away from the printing element, and fluids with Z values below 4 are considered to be inappropriate for high-resolution ink-jet printing. In practice, systems where Z is much larger than 10 are printable as long as proximate satellite droplets merge with the main droplet. Schubert et al. found that a number of common solvents whose low viscosities varied from 0.4 to 2 mPa s and surface tensions varied from 23 to 73 mN m$^{-1}$ could be successfully printed (the Z numbers for these printable solvents varied from 21 to 91). The main factor that appeared to affect printability was their vapor pressure, with unstable droplets and no droplets being produced for solvents with vapor pressures higher than approximately 100 mmHg. As additional manufacturing strategy considerations, it is recommended that the printing environment be HEPA filtered and maintained at 6-30° C. with a relative humidity of 40-60%. It is also noted that post-printing conditions can be as important as printing conditions in that post-printing conditions affect the evaporation rates of printed regions which in turn affects the morphology and distribution of the printed semiconductor, conductor, insulator, immobilized protein, etc.

Inkjets are flexible and versatile, and can be set up with relatively low effort. However, inkjets offer lower throughput (currently ~100 m$^2$/hr) and lower resolution (for example, currently ~50 μm). Inkjet printing is well-suited for low-viscosity, soluble materials like organic semiconductors. With high-viscosity materials, like organic dielectrics, and dispersed particles, like inorganic metal inks, difficulties due to nozzle clogging occur. Because ink is deposited via droplets, thickness and dispersion homogeneity is reduced. Simultaneously using many nozzles and pre-structuring the substrate allows improvements in productivity and resolution, respectively. However, in the latter case non-printing methods can be advantageous or even required for the actual patterning step. Inkjet printing is preferable for organic semiconductors in organic field-effect transistors (OFETs) and organic light-emitting diodes (OLEDs), but also OFETs completely prepared by this method have been demonstrated, as have been OLED-displays front-planes/back-planes, entire integrated circuits, as well as many other types of devices and systems.

Another advantage of inkjet printing that useful in the fabrication of parts of the invention is the ability to, layer-by-large, print three-dimensional structures that can provide functions such as mechanical support, optical operations, and fluidic conduits. This is an example of functional printing, of which there are several other available and evolving technologies that depart from classical inkjet printing.

Inkjet printing methods include:

Valve-jet methods using a continuous pressure stream in conjunction with a valve which opens and closes to eject a stream of droplets, Thermal inkjet/bubble-jet methods using the rapid heating of samples to create a pocket of gas to induce the required pressure for droplet ejection, Piezo actuation methods using volumetric change to induce the pressure required for droplet ejection.

The "direct contact" printing method employs micro-machined pins to dispense droplets employing wherein a predefined volume of sample is taken up by capillary action into a reservoir associated with a deposition pin immersed in source material. The pin is then moved to the intended deposition area and a predefined volume of sample is deposited by direct contact with the target printing surface. The primary advantage of the direct contact printing method is in that no thermal or pressure actuation is required for droplet dispensing, the dispensing process does not compromise specialized material properties and antibody activity. However, direct contact methods report a 1-10 nL droplet while non-contact methods such as inkjet printing can dispensing smaller droplets over a wider range of volumes spanning 1 pL to 5 mL (see for example U.S. Pat. No. 6,101,946 and the article J. Delaney, Jr, P. Smith, U. Schubert, "Inkjet Printing of Proteins," *Soft Matter,* 2009, Vol. 5, p. 4866). ArrayIt is a microarray manufacturer and services that utilizes micro-machined pins and processes to implement direct contact printing.

Screen printing is a versatile and comparatively simple method that is known to be useful for printing conductive and dielectric layers, organic semiconductors, and even complete OFETs. Screen printing is appropriate for fabricating electrics and electronics on industrial scales due to its ability to produce thick layers from paste-like materials. This method can produce conducting lines from inorganic materials (e.g. for circuit boards and antennas), insulating layers, passivating layers etc. where layer thickness is more important than fine spatial resolution of the border of the layer. The throughput ('50 m$^2$/hr) and resolution (~100 μm) of screen printing are comparable to that of inkjets "Aerosol Jet Printing" (also known as "Maskless Mesoscale Materials Deposition" (M3D) is another material deposition technology for printed electronics. The process employs ink aerosols, which can be heated up to 80° C., producing droplets on the order of one to two microns in diameter. The atomized droplets are entrained in a gas stream and delivered to the print head. Here, an annular flow of clean gas is introduced around the aerosol stream to focus the droplets into a tightly collimated beam of material. The combined gas streams exit the print head through a converging nozzle that compresses the aerosol stream to a diameter as small as 10 microns. A jet of droplets can exits a print head at high velocity (for example ~50 meters/second) and impinge upon the substrate. Electrical interconnects, passive and active components can be formed by moving the print head, equipped with a mechanical stop/start shutter, relative to the substrate. The resulting patterns can have features ranging from 10 microns wide, with layer thicknesses from tens of nanometers to approximately 10 microns. A wide nozzle print head can enable efficient patterning of millimeter size electronic features and surface coating applications.

All Aerosol Jet Printing or "Maskless Mesoscale Materials Deposition" (M3D) operates without the use of vacuum or pressure chambers and at room temperature. The high exit velocity of the jet enables a relatively large separation between the print head and the substrate, typically 2-5 mm. The droplets remain tightly focused over this distance, resulting in the ability to print conformal patterns over three dimensional substrates. Despite the high velocity, the printing process can be gentle; substrate damage does not occur and there is generally no splatter or overspray from the droplet. Once patterning is complete, the printed ink typically requires post treatment to attain final electrical and mechanical properties. Post-treatment is typically driven more by specific ink and substrate combinations than the printing process. A wide range of materials have been successfully deposited with aerosol jet processes, these materials including diluted thick film pastes, thermosetting polymers such as UV-curable epoxies, and solvent-based polymers like polyurethane and polyimide, and biologic materials.

Other methods with similarities to printing, among them "micro-contact printing," nano-imprint lithography, and "sporadically pad printing" can also be used in fabrication of parts of the invention. Micrometer-to-nanometer thin layers are prepared by methods similar to stamping with soft and hard forms, respectively. Often the actual structures are prepared subtractively, e.g. by deposition of etch masks or by lift-off processes "Transfer printing" methods, where solid layers are transferred from a carrier to the substrate, can also be used in printed electronics and deposition of sensor layers and biologically active materials and can be employed in the manufacturing of aspects or components of the invention.

Electrochemical and BioFET Sensor Fabrication Via Printed Electronics and Functional Printing Electrochemical and bioFET sensor fabrication via printed electronics and functional printing typically involve one or more of:

Printing of electrical conducting (organic or inorganic) electrodes, layers, and traces,
Printing of electrical Insulator layers,
Printing of organic semiconductors,
Printing of selective detection materials.

These and other related topics are discussed below.

Printing of Electrical Conducting Electrodes, Layers, and Traces

Conductive inks comprising inorganic materials have been known for a good while. Polymeric electrodes (source, drain and gate) can be fabricated, for example using a water-based ink of the conducting polymer poly(3,4-ethyl-enedioxythiophene) doped with polystyrene sulfonic acid (PEDOT/PSS). However, using this ink to print electrodes on hydrophilic oxide surfaces can present a problem because water-based conducting polymer ink droplets can completely wet the surface of a substrate and spread uncontrollably, potentially leading to poor printing control of line width, edge definition, and film thickness. This has been addressed in a number of ways, for example using polyimide structures to confine ink droplet spreading on a hydrophilic surface with a pattern of narrow, hydrophobic regions that define critical device dimensions, fabricated for example by photo-patterning and etching a blanket layer of hydrophobic polyimide on the oxide layer prior to ink deposition (for example, see H. Sirringhaus, et al., "High-Resolution Inkjet Printing of All-Polymer Transistor Circuits," *Science.* 2000, Vol. 290, pp. 2123-2126.

Printing of Electrical Insulators and Dielectric Layers

There are a great many materials to draw from for printable electrical insulators and printable dielectric layers. Almost any non-conductive material that is soluble and can reproducibly form thin homogeneous layers when printed can be used, of which there are vast numbers. This allows fabricators to choose among these for a choice of solvents in non-solvent (for example, in engineering the printing of various layers of materials so that one layer does not dissolve a preceding layer) and dielectric constant or relative permittivity. Popular examples particularly useful for fabricating gate structures of organic field effect transistors include poly(methyl methacrylate) ("PMMQA") or polystol.

Printing Organic Semiconductors

Pentacene, for example, is a widely-known carrier-dopable organic semiconductor which can provide highly attractive carrier transport properties. However, pentacene suffers from poor stability in most ambient conditions, and maintaining film stability in aqueous buffer solutions that may have extreme pH and high ionic strength can be challenging. As another example, Poly-3-hexylthiophene (P3HT) is common organic semiconductor that has been widely studied but also suffers from chemical doping by environmental oxygen in ambient conditions.

To address this, the process of "passivation" which deposits organic polymer layers on top of sensitive films (such as a pentacene layer) can be advantageously employed to protect them from degradation (such as oxidative degradation), and as a bonus both maintain device performance and provide a chemically functional layer for subsequent covalent immobilization of organically active materials such as Bovine Serum Abumin (BSA) to its surface. For example it is demonstrated that a pentacene layer can be vacuum-deposited was and subsequently passivated with a 50 nm perfluorinated polymer film (for example, perfluor-1,3-dim-ethyl-cyclohexan, ppPFD-MCH) by plasma-enhanced chemical vapor deposition (PECVD) and a 5 nm maleic anhydride (ppMA) functional layer to covalently attach BSA (*Journal of the American Chemical Society.* 2011, 133, 2170).

Alternatively, poly(9,9-dioctylfluorene-co-bithiophene) (F8T2) can be preferable to P3HT because of its superior stability when compared to P3HT (Sirringhaus et al., *Science,* 2000, 290, 2123). Due to its superior stability, F8T2 can be deposited by spin coating (for example, from a xylene solution) and followed, for example, by deposition of a polyvinylphenol (PVP) layer by spin coating from an iso-propanol solution. Semiconductor devices prepared with F8T2 exhibited higher on-off current ratios exceeding $10^5$ and better operational stability when compared with inkjet-printed P3HT devices. When films are serially deposited from solution whether by inkjet printing, spin coating or otherwise, it is important to carefully choose the sequence of solvents and polymers in order to avoid dissolution and swelling of underlying layers.

Layered Printing Fabrication of Sensors, Organic Electronic Sensors and Devices

As described earlier through many previous examples, a wide variety of sensors, organic electronic sensors, and other printed devices relevant to the removable replaceable medium element aspects of the invention can be created through a layered implementation oriented in a manner suitable for printing. In this section, this matter is considered in more detail.

Discussion will begin with considerations as to the printing of a bioFET, antibody-based "immunotransistor," and the like. FIGS. 53a-53h depict representations of example layered deposition of a bioFET or FET-based electrochemical sensor.

FIG. 53a depicts a representation of a first example conducting layer.

FIG. 53b depicts a representation of a first example functional layer (semiconducting, insulating, dielectric, supporting, etc.), FIG. 53c depicts a representation of a first example side area electrical insulator—the shape and location is merely an example and many other arrangements are possible.

FIG. 53d depicts a representation of a second example conducting layer.

FIG. 53e depicts a representation of a second example functional layer (semiconducting, insulating, dielectric, supporting, etc.), FIG. 53f depicts a representation of a second example side area electrical insulator—the shape and location is merely an example and many other arrangements are possible.

FIG. 53g depicts a representation of a third example conducting layer.

FIG. 53h depicts a representation of a third example functional layer (selective detection material, semiconducting, insulating, dielectric, supporting, etc.).

Each of the above can be sequentially deposited in the order depicted. Printing is one method by which this can be done, although other deposition methods can be used instead or for special needs. In printing-based fabrication of the above, a process design arrangement, choice of materials, use of curing (drying-induced, photo-induced, thermally-induced, chemically-induced), etc. typically must be used so that the printing of a given layer does not dissolve a preceding layer, and that useful interfaces between the layers, for example, providing adequate electrical contact at low enough electrical resistance, adequate carrier injection, appropriate electrical insulation, acceptable dielectric or permittivity constants, mechanical and thermal stability, etc. This spectrum, despite a daunting span and appearance, is fully engaged in the area of printed electronics process and materials development.

Printing of Electrochemical Sensors

Many electrochemical sensors simply deposit selective detection materials on one or more of a group of electrodes. Such electrochemical sensors can readily be printed by first printing the group of conductors with an appropriate conductive ink and then printing selective detection materials on one or more of a group of electrodes.

Some electrochemical sensors can benefit from direct connection of electrochemical electrodes to a field effect transistor and can be fabricated in ways combining the above approach with those involving field effect transistors.

In yet other cases, particularly in the case of the robustly powerful sensing opportunities made possible by carbon paste electrodes (for example as taught in I. Svancara, et al., "Carbon Paste Electrodes in Facts, Numbers, and Notes: A Review on the Occasion of the 50-Years Jubilee of Carbon Paste in Electrochemistry and Electroanalysis," *Electroanalysis*, Vol. 2009, 21, No. 1, pp. 7-28 and I. Svancara, K. Kalcher, A. Walcarius, K. Vytras, *Electroanalysis with Carbon Paste Electrodes*, 2012, CRC Press, ISBN 978-1-4398-3019-2), the selective detection materials are mixed into the materials making up at least one of the electrodes. Efforts have produced extremely small carbon paste electrodes compatible with the scale of microfluidic devices—for example see Y. Sameenoi, et. al., "Poly(dimethylsiloxane) cross-linked carbon paste electrodes for microfluidic electrochemical sensing," *Analyst*. 2011 Aug. 7, 136(15), pp. 3177-84). Such electrochemical sensors can readily be printed, both with the techniques outlined in the Y. Sameenoi, et. al., reference, or by first printing the group of conductors with an appropriate conductive ink and then printing selective detection materials mixed together with carbon paste materials (for example, such as the cross-linked polymer described in the Y. Sameenoi, et. al., reference, as well as polymethyl methacrylate (PMMA), Self-Assembled Monolayer on Mesoporous Supports (SAMMS). etc.) on one or more of a group of electrodes.

Alternative Use of Silicon Semiconductors and Semiconductor Devices

Although printed semiconductor devices such as field effect transistor arrangements suitable for subsequent printing of a layer of selective detection material are expected to become straightforwardly fabricated with optimized materials at low cost with high levels of performance, at the moment traditional silicon semiconductors typically offer higher performance, for example due to carrier mobility issues in organic semiconductors. Accordingly, the invention provides for the use of silicon semiconductors and semiconductor devices.

As a first example, silicon-based semiconducting field effect transistor structures with an exposed insulated gate (the insulated gate subsequently metalized or not, depending on the design of the sensor at the particular site) can be surface mounted on the removable replaceable medium element, and printing of a layer of selective detection material on the exposed gate (or metalized gate contact) can be performed. In this case, the removable replaceable medium element is not itself a silicon wafer, other sensor sites can be freely fabricated by printing of electrodes, organic field effect transistors, etc., and deposited materials such as reagents can be freely fabricated by printing or other deposition processes in other regions of the removable replaceable medium element.

As a second example, such silicon-based semiconducting field effect transistor structures can be surface mounted on every sensor site of the removable replaceable medium element, and printing of a layer of selective detection material on the exposed gate (or metalized gate contact) can be performed. In this case, the removable replaceable medium element is again not itself a silicon wafer, and deposited materials such as reagents can be freely fabricated by printing or other deposition processes in other regions of the removable replaceable medium element.

As a third example, a plurality of such silicon-based semiconducting field effect transistor structures can be rendered and sparsely distributed on a silicon wafer or portion of a silicon wafer that is attached to the removable replaceable medium element, and printing of a layer of selective detection material on the exposed gate (or metalized gate contact) can be performed. In this case, the entire removable replaceable medium element is not a silicon wafer, other sensor sites can be freely fabricated by printing of electrodes, organic field effect transistors, etc. in other regions of the removable replaceable medium element, and deposited materials such as reagents can be freely fabricated by printing or other deposition processes in other regions of the removable replaceable medium element.

As a fourth example, a plurality of such silicon-based semiconducting field effect transistor structures can be rendered and sparsely distributed on a silicon wafer or portion of a silicon wafer that comprises the entire substrate of the removable replaceable medium element, and printing of a layer of selective detection material on the exposed gate (or metalized gate contact) can be performed. In this case, the entire removable replaceable medium element is a silicon wafer, and deposited materials such as reagents can be freely fabricated by printing or other deposition processes in other regions of the removable replaceable medium element.

As a fifth example, the above fourth example, additionally one or more regions of electrodes are provided on the silicon wafer, either in a silicon wafer step or but subsequent printing of conductive material, and other sensor sites can be freely fabricated by printing of organic field effect transistors, etc. in these "electrode only" regions of the removable replaceable medium element, and deposited materials such as reagents can be freely fabricated by printing or other deposition processes in other regions of the removable replaceable medium element.

Other variations are anticipated and provided for by the invention. For example, as described earlier, some electrochemical sensors can benefit from direct connection of electrochemical electrodes to a field effect transistor and can be fabricated in ways combining the above approach with those involving field effect transistors.

Printing of Selective Detection Materials on Semiconductor and Electrode Layer Structures The printing of selective detection materials was considered earlier in the discussion of inks. Once in ink form, inks containing selective detection materials can then be printed atop semiconductor and electrode layer structures. The inks must permit proper immobilization of biologically active materials, have proper electrical, thermal, and mechanical characteristics, and be non-soluble in the solvent used by the invention to carry the analyte.

Inkjet printing is an attractive candidate but is not without concerns, particularly those involving damage to the selective detection materials. The aforementioned article by J. Delaney, Jr, P. Smith, U. Schubert, "Inkjet Printing of Proteins," *Soft Matter*, 2009, Vol. 5, p. 4866 describes successful inkjet printing techniques that can be effective and reliably used. Much of this is driven by the market for microarrays and other forms of assays. Inkjet printing companies that sell equipment to fabricate DNA and protein microarrays include LabCyte and ArrayJet. Sumitomo, Roth-Rau and Kateeva are examples of manufacturers of inkjet printing equipment configured to deposit non-biological organic polymers on a large format array and provide some array fabrication services. Other methods in active use include the "direct contact" printing method employed by ArrayJet wherein no thermal or pressure actuation is used so the dispensing process does not compromise specialized material properties and antibody activity as well as screen printing and flexographic printing.

As described earlier, FIG. 52a depicts a representation of an example arrangement wherein a selection of antibodies can be selectively blended in the printing (or other deposition) action with a blendable bioFET gate material. FIG. 52b depicts a representation of an example arrangement wherein antibodies are blended with bioFET gate material in advance of the printing. It is noted that other arrangement can be supported in a similar way; for example other bioFETs attach antibodies, enzymes, or other materials to gate materials rather than blend these into gate materials—in such a case an arrangement similar or identical to that of FIG. 52b can be used but layering is used rather than blending when creating the gate structures of bioFETs. Layer-structure electrochemical sensors can be created in a similar fashion. Reagent reservoir depositions can also be made in a similar fashion, although in some approaches it can be advantageous to create a more complex deposition strategy so as to create controlled dissolving processes of the reagent material when it is later presented to the solvent.

Functional Printing of Reagent Deposits

As described earlier, The invention provides for sites or other areas on a removable replaceable media element to comprises a printed depositions of one or more reagents or materials (for example, solvent-soluble, gas-generating, soap, emulsifier, disinfectant, etc.). As described earlier, these can be for example in the form of a solvent-soluble solid, a gel comprising a solvent-soluble reagent or material, etc. The solvent-soluble solid or gel can comprise a polymer lattice, zeolite-like structure, etc.

The functional printing of such reagent deposits as inks has been demonstrated and can be done in a number of ways, for example as taught in S. Hossain, et al., "Development of a Bioactive Paper Sensor for Detection of Neurotoxins Using Piezoelectric Inkjet Printing of Sol-Gel-Derived Bio-inks," *Anal. Chem.*, 2009, Vol. 81, pp. 5474-5483. Other approaches to printing reagents in conjunction with sensors can be found in U.S. patent application Ser. No. 12/944,817.

Sensor Interface Electronics for Large Arrays of Electrochemical and BioFET Sensors Typically an electrochemical sensing system comprises only a few electrochemical sensors. In contrast, the present invention can ready require, in various embodiments and usage, a dozen, dozens, hundreds, or even more electrochemical sensors and/or bioFET sensors, and further allows for option use of either of these plus a variety of other types of sensors at sites on the removable replaceable medium element. Accordingly, the invention provides for electrochemical sensor interface electronics arrangements commensurate with these special situations.

To begin, although there are many variations and competing approaches FIG. 54a depicts an example symbolic representation of an electrochemical sensor, and FIG. 54b depicts a representation of an example electrical interface to a bioFET sensor, the interface providing a voltage signal output. In contrast to the simple electrical output provided by the bioFET sensor, FIG. 55a depicts representations of various types of example electronics interfacing and signal exchanges typically used to provide the conditions required to operate an individual electrochemical sensor. FIG. 55b depicts a simplified arrangement provided by the invention wherein the backend of the electrochemical sensor interface arrangement depicted in FIG. 55a is replaced, enhanced, and interpreted by algorithms executing on computational microprocessor or other computing platform (FPLA, embedded controller, remote computer, etc.). For large numbers of electrochemical sensors, even with the arrangement depicted in FIG. 55b there can be a corresponding number of instances of dedicated electrochemical sensor interface electronics as suggested in FIG. 55c, resulting in a potentially massive amount of interface electronics, To reduce this, one or more of multiplexing, shared voltage/current sources, and other shared supporting electronics techniques can be used enable sharing of interface electronics among a significant if not large plurality electrochemical sensors. FIG. 55d depicts an abstracted representation of various types of interface electronics sharing among a plurality of electrochemical sensors.

Optical Sensors, Functional Printing Fabrication, and Interface Electronics

As described earlier, FIGS. 13a-13b depict unified representations of example light florescence and light absorption optical sensors.

In most contemporary laboratory instruments, space consuming expensive precision optical elements, such as diffraction gratings with precise alignments to photodiode arrays, are employed. However, a number of techniques can be used to miniaturize light florescence and light absorption optical sensors. Further, many to most if not all components of these sensors can be fabricated and operated on a site or other portion of a removable replaceable medium element in a manner consistent to various degrees (including completely) consistent with the electrochemical and bioFET, and OECT sensors described earlier.

Additionally, many types of optically-based detection technologies such as those employed in microplate/microarray technologies and techniques can be modified or adapted for useful miniaturized implementation.

Most optical techniques employing optically-based technology for biochemical applications have been developed in the product and technology context of large laboratory instruments, and thus the comprehensive miniaturized implementations taught later in the specification differ from current trends in industry and academic research. For example, some of the modifications and adaptations to be presented leverage small ultraviolet LEDs, while other modifications and adaptations leverage a family of wavelength-selective LED-based sensing technologies as taught later in this and associated patent applications that remove with the need for large and/or expensive precision optical components and precise alignment needs requiring expensive manufacturing processes.

To begin, a variety of example arrangements for light absorption sensing are described. FIG. 56a depicts a representation of a miniature absorption optical sensor arrangement wherein both light emitted and light detecting elements are provided in the base unit. Here, an optical reflective coating can be provided on the removable replaceable medium element by functional printing. FIG. 56b depicts a representation of another miniature absorption optical sensor arrangement. Here, a photodiode or (wavelength selective) LED is provided on the removable replaceable medium element, for example rendered by functional printing. FIG. 56c depicts a representation of yet another miniature absorption optical sensor arrangement. Here, an emitted LED is provided on the removable replaceable medium element, for example rendered by functional printing. FIG. 56d depicts a representation of another miniature absorption optical sensor arrangement. Here, a photodiode or (wavelength selective) LED is provided in the lid of the base unit. FIG. 56e depicts a representation of still another miniature absorption optical sensor arrangement. Here, an emitted LED is provided in the lid of the base unit.

Next, a variety of example arrangements for example fluorescence optical sensing are described. FIG. 56f depicts a representation of an example fluorescence optical sensor wherein both light emitted and light detecting elements are provided in the base unit and optical reflective coating is provided on the removable replaceable medium element by functional printing. FIG. 56g depicts a representation of another miniature absorption optical sensor arrangement. Here, both an emitting LED and a photodiode or (wavelength selective) LED is provided on the removable replaceable medium element by functional printing. Other related arrangements, including many with LED emission and photodetection layouts of FIGS. 56a-56e, are also possible and provided for by the invention. Polarization optics, curved or flat reflective services, and other specialized optical elements and materials can also be included.

Arrangements such as those of FIG. 56e and FIG. 56f (as of course others) further provide a means for performing ranges and degrees of fluorescent-lifetime spectroscopy, time-resolved fluorescent spectroscopy, phase-resolved fluorescent spectroscopy, and other forms of time-resolved spectroscopy. On the emission side, switching rates for various LEDs can range from $10^{-8}$ seconds to as short as $10^{-11}$ seconds depending on the LED and electronic circuitry, but can be increased towards and above $10^{-12}$ using voltage control and other techniques (for example, see A. Brailovsky, V. Mitin, "Fast switching of light-emitting diodes," *Solid-State Electronics* 44 (2000) pp. 713-718), and similarly contemporary high-speed photodiode can respond in roughly the same switching rate (for example, operating in the 75 to 110 GHz W-band in communications systems). Such performance limits and their associated cost points are likely to advantageously evolve, putting the optoelectrical infrastructure in at least the $10^{-8}$ to $10^{-11}$ second resolution range. Example common ranges of faster-side fluorescent lifetimes are in the 0.4 to 12 nanoseconds (i.e, $1.2 \times 10^{-8}$ to $4 \times 10^{-10}$ seconds) range, so the $10^{-8}$ to $10^{-11}$ second resolution range is already quite adequate and can provide at least a useful if not valuable capability (although by way of comparison today's highest speed lasers employed in commercial time-resolved spectroscopy systems can operate with switching speeds as high as $10^{-16}$ seconds).

Microprocessor clock-speeds at their highest are in the low GHz, so external high-speed electronic circuitry, at least in near-term implementations, can advantageously be used to measure the time different between emission pulse events and fluorescent lifetime events. Examples of such external high-speed electronic circuitry include (a) digital fast binary counters whose extremely high clock signal and reset inputs are gated by known emission pulse events and measured fluorescent lifetime events respectively, and (b) analog RC circuit stimulated by known emission pulse events and sampling a resultant exponential decay by high-speed sample-hold circuits triggered by measured fluorescent lifetime events, the sampled electrical quantity then presented to an analog-to-digital converter whose digital output is presented at the leisure of the far slower microprocessor. Other arrangements are of course possible as is clear to one skilled in the art of high-speed electronics design and signal acquisition.

The resulting measurements, together with other information such as known dynamic transient behaviors, solvent cage effects (which can vary lifetimes by a factor of three or more), chemical influences, etc. can then be used in algorithms (running after the fluorescent lifetime event and executing comparatively slowly) to subsequently compute accurate fluorescent lifetime signatures.

Next, by providing a collection of LEDs or other narrowband light-emitting devices or arrangements in a cap, site, or combination of these, a range of stimulus wavelengths can be available or provided for various sensing operations depending on the type of test or measurement the site is configured to implement. Also by providing a collection of LEDs or other narrowband light-emitting devices or arrangements in a cap, site, or combination of these, marker/probe "stimulus multiplexing" can be supported for cases where a sensor comprises a plurality of fluorophores, each fluorophores selectively and separately stimulated by light of a uniquely associated wavelength.

Sensing of reflected or emitted light typically requires a range of wavelengths and at least a moderate, sometimes fine differentiation among individual wavelength sensing reneges. Many optical sensor methods involving multiple wavelength sensing employ precision optical elements that involve cost, space, and spatial arrangement that are challenging to miniaturize. However, the present invention can use adaptations of these that facilitate miniaturization, and additionally or alternatively can use the wavelength-selectivity (energy "high-pass"/wavelength "lowpass" filtering) and linear amplitude response of ultraviolet, visible-range, infrared LEDs or other precise band-gap photodetectors when deployed as light sensors.

Although other precise band-gap photodetectors can be used in a similar fashion, the discussion below will be provided with reference to LEDs. It is to be understood that the methods and systems below extend to include Organic Light Emitting Diodes (OLEDs) and other types of precise band-gap photodetectors.

FIG. 57 depicts a representation of an example response of an LED used as a light source (top graph) and as a light sensor (bottom graph). With regards to light emission, only a (typically narrow) band of light wavelengths are energies are emitted, the peak of which is typically closely associated with the band gap of the LED junction arrangement. With regards to light sensing, however, the LED acts as a "high-pass filter" with respect to the energy spectrum and as a "lowpass filter" with respect to the wavelength spectrum (as required since wavelength is inversely proportional to energy for usual relevant conditions). Further, the amplitude response between incoming light amplitude and the amplitude of many measurable photo-induced electrical quantities (photovoltage, photocurrent, etc.) is at least for a wide usable range is linear.

Various interface circuits can be used to measure photo-induced electrical quantities (photovoltage, photocurrent, etc.), but one with a minimum of electronic components and directly electrically connected to raw I/O pins of a microprocessor or data bus expander is sketched in FIG. 58. In fact, depending on the voltage levels set at the I/O pins, timing, duty-cycles of pulse-width modulation and multiplexing, etc, the simple circuit sketched in FIG. 58 (adapted from U.S. Pat. No. 8,305,480 of one of the inventors) depicts a representation of an example electrical interface allowing a given LED to be used as an on/off or dimmable light source, as a light sensor, or (using time-division multiplexing) a time-interleaving of both modalities. Further, as described in the aforementioned U.S. Pat. No. 8,305,480 and associated patent applications, the energy-spectrum "high-pass filter"/wavelength-spectrum "lowpass filter" and linear photo-induced electrical amplitude response properties of LEDs (and other types of precise band-gap photodetectors) to create energy-band/wavelength-band selective sensing with an extensive range of capabilities and resolutions.

FIGS. 59-60 (also adapted from U.S. Pat. No. 8,305,480) depict representations of example signal processing of received multiple-LED light sensor signals to produce wavelength-selective optical detectors without precision optical elements that involve cost, space, and spatial arrangement that otherwise have been and remain quite challenging to miniaturize. In more detail, FIG. 59 depicts the general principle where cumulative subtractions of normalized measured amplitudes of co-incident LEDs, OLEDs, and/or other types of precise band-gap photodetectors, beginning with the lowest energy/longest wavelength LED, OLED, or other types of precise band-gap photodetector can create minimally-overlapping passbands. Reorganizing the subtractions and including other mathematical operations can create other types of passbands or other wavelength-differentiated responses as advantageous. FIG. 60 depicts a refinement of the general principle depicted in FIG. 59 wherein calibrated (active, passive, preset, etc.) amplitude adjustments are used to normalize the individual wavelength-dependent photoelectric measurement signal amplitudes.

Such an arrangement can provide many useful sensing functions. For example, by providing such multiple-wavelength sensing arrangements in a cap, site, or combination of these, together with collection of LEDs or other narrowband light-emitting devices or arrangements in a cap, site, or combination of these, a rich optical measurement capability can be crafted suitable for a wide range of selective detection materials and processes, useful for absorption, fluorescence, chemical luminescence, and other optical detection and measurement capabilities.

As another type of example, by providing such multiple-wavelength sensing arrangements in a cap, site, or combination of these, marker/probe "emission multiplexing" can be supported for cases where a sensor comprises a plurality of fluorophores, each fluorophores selectively and separately emitting light of a uniquely associated wavelength. providing such multiple-wavelength sensing arrangements in a cap, site, or combination of these can also be combined with providing a collection of LEDs or other narrowband light-emitting devices or arrangements in a cap, site, or combination of these so as to implement more general forms of probe/marker "multiplexing" where each of a plurality of probes/markers can be provided an optimal stimulus wavelength and be monitored for emissions at their associated emission wavelength. Further, these and other wavelength-selective sensing processes described can be combined, for example combining wavelength-selective stimulus and measurement capabilities with time-resolved spectroscopy capabilities.

Finally, by including such multiple-wavelength light emission and multiple-wavelength light detection utilities in the same cap that can also host electrochemical and/or bioFET sensors, each site can readily be allocated a wide range of sensor types. Further, such an arrangement also permits interesting new hybrid sensing capabilities, for example combining optical processes with probe/marker processes involved with electrochemical sensors and bioFET sensors, electrochemical processes, bioFET processes, etc.

The LEDs employed in the above arrangements can be implemented as Organic Light Emitting Diodes (OLEDs) which in turn be fabricated from printed electronics semiconductors. Other types of spectrally selective light sources and/or other types of precise band-gap photodetectors can also be used. In various example embodiments, the LEDs, OLEDs, and/or other types of precise band-gap photodetectors can be located on the caps in the base unit (as shown in FIGS. 56*a*-56*f*) and/or on the removable replaceable media element in various combinations.

Statistical Processing of Sensor Measurement Data

The range of possible diverse and redundant sensor arrays made possible by the invention give rise to statistical enhancing of measurement through novel statistical processing approaches.

For example, as discussed earlier, the table provided in FIGS. 16*a*-16*b* depicts example commercially-available antibodies (for example, as provided by Santa Cruz Biotechnologies) that can be used in sensors to detect the most prominent food and water pathogens. It is noted that several different antibodies are responsive to the same pathogen.

As will be described, the invention provides for the leveraged use of multiple diverse detectors (in this case, a plurality of different antibodies) that are responsive to the same target (in this case, the same pathogen) so as to obtain parallel reinforcing results than can be used in statistical processing to provide improved reliability as well as other capabilities (for example, statistically handle nuances of pathogen variants, etc.).

The invention also provides for the leveraged use of multiple identical detectors (that are responsive to the same target but operating under different measurement conditions (pH, alternate solvent, presence of ions, exogenous stimulus, etc.) so as to obtain parallel reinforcing results than can be used in statistical processing to provide improved reliability as well as other capabilities.

To begin, FIG. 61*a* depicts an example illustrative scenario wherein seven selective detector materials (designated A through G) are responsive or non-responsive to a sought target as well as various ones of N other non-target materials. In the figure, the lines graphically represent responsiveness, so for example only selective detector materials B, C, D, and E are responsive to the sought target, while selective detector material B is also responsive to other materials 1 and 2, selective detector material C is also responsive to other materials 2, K, and K+1, selective detector material D is also responsive to other materials 2, K, and K+2, and selective detector material E is also responsive to other materials K+2 and K+3, etc. FIG. 61*b* presents a table summarizing each of the graphically represented response and non-response relationships represented in FIG. 61*a*.

In reviewing the table of FIG. 61*b* it is clear that if each of four properly functioning sensors respectively comprising selective detector materials B, C, D, and E respond to a commonly provided analyte while sensors as A, F, and G selective detector materials do not, there is a strong likelihood that the target is found. Of course it is also possible to obtain the same outcome if instead materials 2 and K+2 are both present but the material 2 concentration, measurement condition, sensor failure, or system failure (such might result from a clogged fluidic path, stuck valve, etc.) prevents sensors with selective detector material A from responding to the presence of material 2 in the analyte as sensors with selective detector material A otherwise would. More subtly, if all sensors employing selective detector materials A, B, C but no others are responsive to an analyte, this would suggest Material 2 is more likely to be present than Material 1, but the accuracy of this inference is completely dependent on the proper functioning of sensors employing selective detector material C. Similarly, if all sensors employing selective detector materials A and B but no others are responsive to an analyte, this would suggest Material 1 is more likely to be present than Material 2, but here again the accuracy of this inference is once again completely dependent on the proper functioning of sensors employing selective detector material C.

This and many other interesting cases can be identified from the example gross-behavior detection table, but overall it should be clear that:

The patterns of what sensors respond to an analyte and which do not can be matched to the presence of a specific individual materials and/or the presence of a combination of specific individual materials;

With poor planning and organization of the collection of sensing materials, some discerning identifications are more dependent on the accuracy of a single selective detector material than would otherwise be desired;

With good planning and organization of the collection of sensing materials, discerning identifications can be made far more robust and far less dependent on the accuracy of a single selective detector material.

Accordingly, the choice of the collection of sensors populating the replaceable removable medium element, together with the particular detailed statistical analysis procedures that is to be advantageously performed on the results so as to provide probabilistic (likelihood, probability, etc.) or statistical (statistical confidence level, statistical inference, etc.) relating to the presence of one or more specific targets (pathogens, toxins, proteins, biomarkers, chemicals, etc.) can be structured as a type of formal "experiment design."

Further, the specific collection of sensors populating the replaceable removable medium element, the associated reagents provided on the replaceable removable medium element, the specification of the interfacing and operation procedures of the sensors for testing an applied analyte (for example in data on a ROM comprised by the replaceable removable medium element and/or provided through networking), and the associated detailed statistical analysis procedures (for example in data on a ROM comprised by the replaceable removable medium element and/or provided through networking) together form a powerful package for testing for the presence of one or more specific targets (pathogens, toxins, proteins, biomarkers, chemicals, etc.). The arrangement and approached described permits a very flexible single-target or multi-target detection device that is practical, readily customizable, and evolvable.

Accordingly, the invention provides for statistical analysis procedures and/or algorithms to be provided by or specified by data comprised by the ROM in the removable replaceable medium element and/or provided through networking. In some implementations, statistical analysis procedures and/or algorithms provided by the ROM can be upgraded over a network. Additionally, in some implementations algorithms executing on computation resources in the base unit such as microprocessors can work together with connected devices such as laptop computers, tablet computers, Personal Digital Assistants (PDAs), desktop computers, cellular phones, smartphones. Further, in some implementations, algorithms executing on computation resources in the base unit such as microprocessors can work together with high-performance servers computers and/or computing clouds over a network.

The arrangements described can be configured to support optical sensing multiplexing as described earlier. Additionally, and more subtly, the arrangements described can be configured to work with unusual advantageous arrangements wherein more than one selective detection material is comprised by a given electrochemical sensor, bioFET, etc. As to this, recall the example represented graphically in FIG. 61*a* and by the table presented in FIG. 61*b* comprised selective detection materials that could be used to create sensor but inherently were responsive to more than one material. Typically such multiple response behavior is regarded as a limitation of the selectivity of the selective detection material, and statistical procedures can be devised to work around these. However, by creating sensors comprising more than one selective detection material, response table such as that presented in FIG. 61*b* can be designed and engineered. This can be used to create more complex sensing array designs and arrangements wherein redundancy and diversity are multiplexed together in a manner advantageously extractable by statistical methods albeit muddled for direct interpretation. The statistical design for such a novel arrangement can be structured in a manner somewhat similar to that employed in a fractional factorial design and also somewhat similar to that of an error correcting code (including the advantageous use of Hamming Distance)— desired measurement information is "spread" over a data set as in (although not precisely!) a hologram, spread-spectrum communications systems, "Magic Eye" pictorials, etc., but the purpose for the information spread is to more optimally integrate redundant measurements (for greater error performance) and measurement diversity (for wider sensing options, multiple targets, alternative corroborating measurements, etc.).

Another capability of the invention is to use a plurality of sensors from the sensor array to create various types of "meta-sensors" that deliver higher performance with respect to combined co-optimized selectivity and sensitivity than an individual sensor can. A simple version of this was presented earlier in conjunction with FIG. 61*a* and FIG. 61*b*, but there are additional formalisms and variations possible that are advantageous to the invention and other applications. To begin this, first the notion of a "binary classifier" detector arrangement and its "Receiver Operating Characteristic" (also called "Relative Operating Characteristic" by some and in either case denoted as "ROC"). FIG. 62*a* depicts an example binary classifier" detector arrangement comprising a sensor or test providing a measurement quantity taking on a value from a range of values, the range comprising more than two values (that is the range have more than two possible values). A binary classifier uses pre-described knowledge of the measurement process and/or other considerations to convert the measurement quantity value to a binary classification (for example "yes" or "no" outcome or interpretation). An example of a such an arrangement is the combination of a test/sensor strip that turns one color or another as a result of a pregnancy test, HIV test, etc. and the "binary classifier" color guide that indicates what color ranges infer "yes" and which infer "no."

The binary classifier will statistically produce "True Positive," "False Positive," "True Negative," and "False Negative" performance with various probabilities (or rates) for some series of experimental trials. The rate (or probability) of a "True Positive" is formally the "sensitivity" of the test/sensor, while the rate (or probability) of a "False Positive" is the opposite or complement of "specificity." The plot of the tradeoffs between a "True Positive" rate and "False Positive" rate for a given parameter (for example, a parameter for assigning a yes/no threshold to values of incoming measurement quantities) for the binary classifier is its "Receiver Operating Characteristic"/"Relative Operating Characteristic"/"ROC". The ROC comprises an analytical continuous curve or statistical data point plot similar to a curve; these are referred to as an "ROC curve." FIG. 62b depicts an example Receiver Operating Characteristic/Relative Operating Characteristic/ROC comprising an example ROC curve. In general each pair of sensor or test with an associated binary classifier detector has its own ROC curve. ROC curves have various properties, but of casual note is that the closer the ROC curve comes to the upper left corner of the plot, the higher the rate of True Positives and lower the rate of False Positives, hence higher performance. An ideal pair of sensor or test with associated binary classifier detector makes only True Positives and zero False Positives and this has an ROC curve consisting of a single point in the upper left corner of the ROC.

Returning again to the example provided in FIG. 61a and FIG. 61b, each sensor associated with selective detection materials denoted A through G, when coupled to a binary ("yes/no" classifier) has an associated ROC curve for the materials it is responsive to, For example, test/sensor strip that turns one color or another as a result of a pregnancy test, HIV test, etc. and the "binary classifier" color guide that indicates what color ranges infer "yes" and which infer "no" has an associated underlying ROC curve reflecting the trade-offs between the True Positive rate (probability of True Positive) and the False Positive rate (probability of False Positive) for the choice of color that divides "yes" interpretations and "no" interpretations of the test. Regarding the example provided in FIG. 61a and FIG. 61b, FIG. 63 depicts a representation of this by taking the table provided in FIG. 61b and replacing the "X" entries signifying responsiveness with the associated underlying ROC curve reflecting the detection performance.

If each of the sensor/binary-classifiers are used as is for a particular column of the table presented in FIG. 61b provide their yes/no outcomes, if any, to logic operations like that described when introducing FIG. 61a and FIG. 61b, the result would be an arrangement represented by FIG. 64a. Here if the sensors are non-responsive for a particular analyte material, the classifier output can be included or ignored by the logic operation. For example, regarding a version of the arrangement of FIG. 64a for the sought target, the outcomes of sensors comprising selective detection materials B, C, D, and E are included while the regarding a version of the arrangement of FIG. 64a for the sought target, the outcomes of sensors comprising selective detection materials A, F, and G can be included or ignored by the logic operation. For a larger number of "yes" outcomes from sensors comprising B, C, D, and E, the likelihood that the analyte comprises the sought target increases, while for a larger number of "yes" outcomes from sensors comprising A, F, and G, the likelihood that the analyte comprises the sought target decreases. From this, the logic operations described and depicted in FIG. 64a can usually produce a superior "yes/no" outcome performance than any one particular sensor. Additionally, even if one sensor is near ideal the logic operations described and depicted in FIG. 64a can compensate for sensor malfunction, system malfunction preventing proper sensor operation, etc. Further, since larger number of "yes" outcomes from sensors comprising B, C, D, and E, and larger number of "no" outcomes from sensors comprising A, F, and G, all increase the likelihood that the analyte comprises the sought target, the logic operations described and depicted in FIG. 64a can additionally produce additional information such as likelihood, confidence level, probabilities of "yes" being true, etc.

The arrangements described above can be replicated for some or all of the N materials as advantageous. One such illustrative arrangement is depicted in FIG. 64b wherein various superior "yes/no" outcomes, additional information such as likelihood, confidence level, probabilities of "yes" being true, etc. can be produced for multiple materials and targets.

However, as suggested by comparing the entries in each row for a given column the table presented in FIG. 63, typically different classifiers are involved or required for each pairing of target and selective detection material. Accordingly, FIG. 64c depicts a variation on the arrangement depicted in FIG. 64b wherein different classifiers are provided for each pairing of target and selective detection material.

The example logical processing architectures depicted in FIG. 64b through FIG. 64c process each measurement separately with the associated binary classifier, the binary classifier typically acting as a thresholding scalar quantizer. However, as the sensor array associated with the invention comprises so many correlated sensor outcomes, better performance (and other functions to be described) can be implemented when vector quantizing is employed. FIG. 64d depicts one approach to implementing vector quantizing useful to statistical processing for the invention although many other approaches are possible and anticipated. Here, actual measurement values from a plurality of sensors are provided to multiple-input function that each respectively produce, for example, a scalar result (i.e., a scalar-valued vector function) that is presented to an associated binary classifier. The outcomes of these classifiers are then processed by logical operations to produce various superior "yes/no" outcomes, additional information such as likelihood, confidence level, probabilities of "yes" being true, etc for one or more materials and targets. As another example, FIG. 64e depicts a simplified arrangement wherein the logical operations represented in FIG. 64d are omitted.

The example arrangements represented in FIG. 64d and FIG. 64e can also be used to provide another entirely different capability, i.e., compensation for measurement conditions. For example, the operation and performance of various sensors described are affected by many measurement condition factors (temperature, pH, ambient ion concentrations, etc.). Additional measurement condition sensors can be provided at sites, in caps, or elsewhere, to measure one or more of these measurement condition factors. The measurement quantities from these measurement condition sensors can also be provided to the multiple-input functions such as depicted in FIG. 64d and FIG. 64e, and the multiple-input function can be chosen or specified to provide compensation for the one or more of these measurement condition factors.

The multiple-input functions depicted in FIG. 64d and FIG. 64e can comprise one or more of actual mathematical functions resulting from a theoretical analysis, actual mathematical functions resulting from an interpolation, surfacefitting, curve-fitting, etc., piecewise-linear functions, piecewise-linear interpolation of data, splines/B-splines, etc.

With statistical processing addressed, attention is now directed to test and analysis algorithms that can be employed by the invention.

Test and Analysis Algorithms

The invention provides for test and analysis algorithms to be provided by or specified by data comprised by the ROM in the removable replaceable medium element and/or provided through networking. In some implementations, test and analysis algorithms provided by the ROM can be upgraded over a network. Additionally, in some implementations, algorithms executing on computation resources in the base unit such as microprocessors can work together with connected devices such as laptop computers, tablet computers, Personal Digital Assistants (PDAs), desktop computers, cellular phones, smartphones Further, in some implementations, algorithms executing on computation resources in the base unit such as microprocessors can work together with high-performance servers computers and/or computing clouds over a network.

The invention provides for the concurrent operation of one or more test sequences as specified by the by the data comprised by the ROM in the removable replaceable medium element and/or provided through networking. FIG. 65 depicts an example representation of an example collection of parallel sequences of tests and/or test steps used to create measurement situations (for example via fluidic operations, sensor operations, sensor data processing operations, user interface operations, and potentially other operations). Each measurement situation can produce one or more test outcomes that are directed to statistical analysis operations. The invention additionally provides for conditional arrangements in test procedures, for example using the results of fluidic operations, sensor operations, sensor data processing operations, user interface operations, statistical analysis operations, system self-test and self-diagnostic operations, etc. to affect subsequent steps in a multi-step test procedure. The invention further provides for feedback arrangements and recursive arrangements, for example using the results of fluidic operations, sensor operations, sensor data processing operations, user interface operations, statistical analysis operations, system self-test and self-diagnostic operations, etc. to affect controlled measurement conditions, provide alternate tests, provide alternate fluidic routing, skip or modify steps in a multi-step test procedure, etc. In some cases, the invention can provides for such conditional, feedback, and/or recursive arrangements of one sequential sequence of test steps to affect the execution of another parallel sequential sequence of test steps.

Each test typical produces a measurement, an outcome, additional information, or combinations of these. In some situations these have stand-alone value and are reported out to the user, reporting agency, as outcome information. In other cases, these outcomes are input to one or more subsequent analysis steps, operations, procedures, etc. In such cases, a given test outcome could be used by a plurality of subsequent analysis steps, operations, procedures, etc. Accordingly, the invention provides for as-specified, as-needed, as-relevant, or other controlled routing of test outcomes to a collection of subsequent analysis steps, operations, procedures, etc. As an example, FIG. 66 depicts a representation of an example approach wherein test outcomes are provided, via a test outcome routing arrangement, to a plurality of analysis actions implemented in software. Each analysis action can, for example, use at least one measurement and produces at least one probabilistic outcome conveying probabilities of various candidate determinations. In some implementations, embodiments, situations, and specific instances all of these analysis actions can be executed within the base unit. In other implementations, embodiments, situations, and specific instances only some of the analysis actions are executed within the base unit, while others are executed on other platforms such as networked or other data-transfer-linked (thumb drive transfer) computation platforms in devices such as laptop computers, tablet computers, Personal Digital Assistants (PDAs), desktop computers, cellular phones, smartphones, high-performance servers computers and/or computing clouds.

User Operation and Reporting

In some embodiments the invention provides for user operation and outcome reporting to be supported, provided, and implemented completely within the base unit. In other embodiments the invention provides for at least some user operation and outcome reporting to be supported, provided, and implemented outside the base unit, for example employing connected devices such as laptop computers, tablet computers, Personal Digital Assistants (PDAs), desktop computers, cellular phones, smartphones. For the latter, user interfaces can be implemented as application software, via a web browser, or other arrangement. In yet other embodiments the invention provides for flexible allocation of specific user operation and outcome reporting aspects, computations, and aspects to be supported, provided, and implemented either on the base unit or outside the base unit (for example employing connected devices such as laptop computers, tablet computers, Personal Digital Assistants (PDAs), desktop computers, cellular phones, smartphones).

In some implementations, algorithms executing on computation resources in the base unit such as microprocessors can work together with connected devices such as laptop computers, tablet computers, Personal Digital Assistants (PDAs), desktop computers, cellular phones, smartphones Further, in some implementations, algorithms executing on computation resources in the base unit such as microprocessors can work together with high-performance servers computers and/or computing clouds over a network.

In an embodiment, the invention supports partial or full remote operation over the network by one or more remote physicians, experts, institutions, etc.

User Experience

FIG. 67 depicts a representation of an overall example user experience scenario using an example implementation of the technology. The depicted steps, features, elements, event sequence, clustering, and flow are merely illustrative and are in no way limiting. Further, the invention provides for the example user experience scenario illustrated in FIG. 67 to support various degrees or variability, exchange of orders, roles, and domains, and to support broadened operation such as repeated use while powered one, operation with additional connected devices, remote operation over the network by remote physicians, experts, institutions, etc.

Example Applications

As mentioned earlier, various component methods, technologies, and approaches as well as additional natural extensions of the invention provide for a wide range of other applications including:

Water safety field testing, monitoring, and process testing,
Food safety field testing, monitoring, and production process testing,
Consumer product (toothpaste, cosmetics, over-the-counter medication, etc.) safety field testing, monitoring, and production process testing,
Clinical and home medical testing and diagnostics testing,
Environmental (indoor, outdoor, remediation, home, building, manufacturing plant) field-use testing/monitoring and laboratory-based testing/monitoring, Homeland security, conflict-zone, and terrorism prevention field testing and monitoring, Industrial manufacturing process monitoring, Laboratory instruments for advanced cell incubation, Laboratory instruments for infectious disease studies, Laboratory instruments for monitoring gene expression molecules, Biotechnology for advanced life-process systems (fermentation, protein manufacture, etc.), In-body drug delivery, metabolite-synthesis, biochemical prosthesis, or artificial organ applications.

Previously presented FIG. 24 motivates the opportunities for a combined platform combining pathogen sensors, biomarker sensors, and chemical sensors. Within FIG. 24 the sensing opportunities span by the bracket currently lie within the reachable scope of low-cost forms of the invention. However, with anticipated technology evolution and the open architecture of the invention it is anticipated that eventually sensing opportunities not spanned by the bracket as well as other not depicted will lie within the reachable scope of low-cost forms of the present invention.

As described earlier, FIG. 3a depicts an example representation of how pathogens borne by food and/or water can be ingested by, absorbed by, and/or exposed to an organism (such as a human, animal, plant, etc.). In such a situation, a sample of the food or water can be presented to the aforedescribed technologies, wherein the antibody or other types of pathogen sensors are used to directly and rapidly identify pathogens present in the food and/or water sample.

As described earlier, FIG. 3b depicts an example representation wherein pathogens borne by food and/or have already can be ingested by, absorbed by, and/or exposed to an organism and are now present in the organism. In some cases the pathogen can be present in easily obtained bodily fluids or tissues of the organism, while in other cases biomarkers can be highly localized within tissues or confined fluids of the organism. If a sample containing the pathogen can be obtained from the organism, that sample can be presented to the aforedescribed technologies, wherein the antibody or other types of pathogen sensors are used to directly and rapidly identify pathogens present in that sample.

In many cases, however, the approach of FIG. 3b is not possible or realistic. The pathogen can have already been wiped out by the immune system, or can be in a part of the organism from which obtaining a sample is difficult, or the pathogen can be too rarefied within the organism to be adequately captured in the sample. In such cases, the pathogen could have induced a change in the biological state of the organism which can be identified by testing for biomarkers.

FIG. 68a depicts an example representation of a biomarker created by an organism in response to the ingestion, absorption, or exposure to a pathogen present in air, food, and water, wherein the biomarker is present in a sample that can be obtained from the organism and provided to a corresponding biomarker detection process.

FIG. 68b depicts an example representation of a biomarker created by a disease invoked within an organism in response to the ingestion, absorption, or exposure to a pathogen, wherein the biomarker is present in a sample that can be obtained from the organism and provided to a corresponding biomarker detection process.

FIG. 68c depicts an example representation of a biomarker created more generally by a disease within an organism (for example kidney disease, cancer, Alzheimer's disease, etc., wherein the biomarker is present in a sample that can be obtained from the organism and provided to a corresponding biomarker detection process.

Accordingly, FIG. 69 (in contrast to FIG. 3b) depicts an example representation wherein an organism that has ingested, absorbed, and/or been exposed to a pathogen present in air, food, or water causes the organism to produce associated biomarkers that can be present in a sample provided to a biomarker detector. FIG. 70 depicts a more general example representation wherein an organism that has ingested, absorbed, been exposed, and/or experienced a pathogen, toxin, radiation, high temperature, or other harmful substance or harmful situation causes the organism to produce associated biomarkers that can be present in a sample provided to a biomarker detector.

The invention further provides for some of the sensors to be configured for pathogen sensing and other sensors to be configured for biomarker sensing. FIG. 71 depicts an example representation of an adaptation of the arrangement depicted in FIG. 69 wherein a sample is provided to pathogen and/or biomarker detection processes. Similarly, FIG. 72 depicts an example representation of an adaptation of the arrangement depicted in FIG. 70 wherein a sample is provided to pathogen sensors and/or biomarker detection processes.

Example Food and Water Testing Applications in the Field, Home, Site, Farm, Manufacturer, and Distribution Chains The invention provides for food and water testing in the field, home, site, farm, manufacturer, and distribution chains.

Figure 2A:
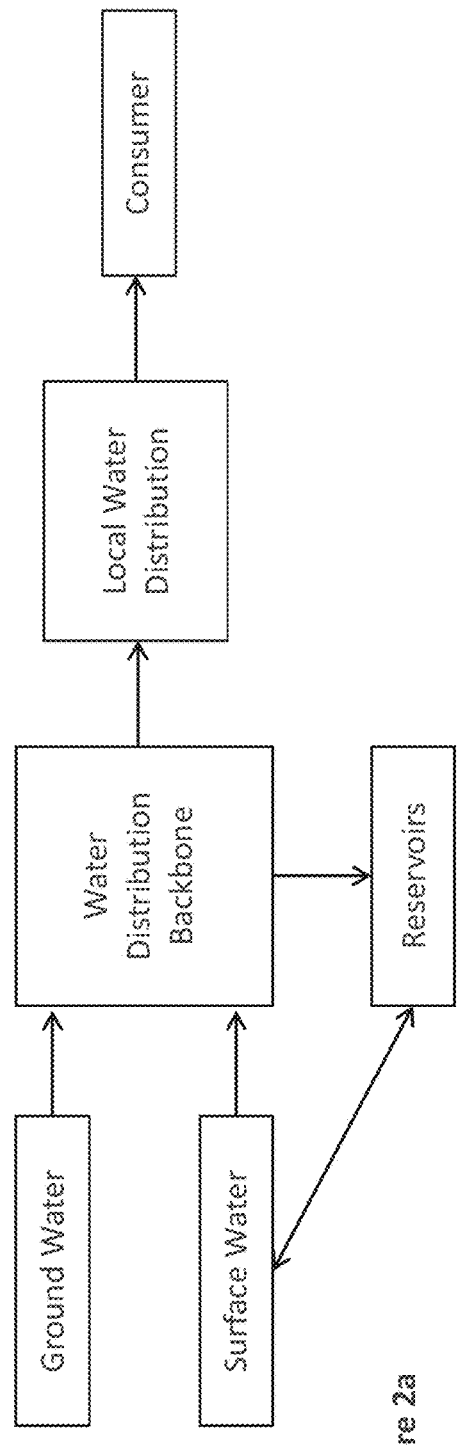
FIG. 2a depicts example large-scale water aggregation and distribution arrangements typically found at municipal, county, state, interstate, and in many cases (for example, shared rivers and lakes) international levels.
Figure 2B:
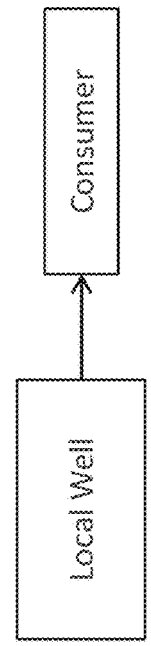
FIG. 2b depicts the smaller scale distribution arrangements associated with village, rural areas, individual farms, and homes found worldwide at all levels of economic development.

As described earlier, FIG. 1a depicts a simplified representation of large-scale commercial food distribution chains, and FIG. 1b depicts the smaller scale distribution arrangements associated with both "local food" trends in developed nations as well as the long-established systems and arrangements in rural areas and developing countries. Also as described earlier, FIG. 2a depicts example large-scale water aggregation and distribution arrangements typically found at municipal, county, state, interstate, and in many cases (for example, shared rivers and lakes) international levels, and FIG. 2b depicts the smaller scale distribution arrangements associated with village, rural areas, individual farms, and homes found worldwide at all levels of economic development.

Ideally, the technology would be used preventatively, that is prior to the ingestion, absorption, or exposure of pathogens borne by food and/or water by an organism (such as a human, animal, plant, etc.) as suggested by FIG. 3a. Alternatively (for example after an outbreak), the technology can be used after to the ingestion, absorption, or exposure of pathogens borne by food and/or water by an organism (such as a human, animal, plant, etc.) as suggested by FIG. 3b.

The most dominant food and water pathogens typically encountered include *S.* spp., *Clostridium Perfirngens, Pseudomonas* spp., *Bacillus Cereus, Campylobacter Jejuni, L. Monocytogenes, Salmonella* spp., *E. coli* 0157:H7, *Shigella*, Norovirus, Norwalk-like viruses, *Legionella, Clostidium Botulinum, Yesinia Enterocolitica*, and *Vibrio* spp. As an example, the table provided in FIGS. 16a-16b list some example commercially-available antibodies (for example, as provided by Santa Cruz Biotechnologies) that can be used in the aforedescribed electrochemical bioFETs, and optical sensors to detect these pathogens with high selectivity. As described earlier, several antibodies are responsive to the same pathogen. The invention provides for leveraged use of multiple antibodies responsive to the same pathogen so as to obtain parallel redundant results than can be used to improve reliability and/or handle nuances of pathogen variants.

Example for Contagious Disease Applications

The invention can be used to test for or track contagious diseases, for example as suggested by FIG. 3b. For example, previously described FIG. 17 provides a table of example antibodies for the detection of various example strains of Influenza.

In an embodiment, the removable replaceable medium element invention can be made inexpensively and widespread available with sensors that comprise selective detection materials selectively responsive to pathogens and/or biomarkers for the latest epidemic outbreak.

In another embodiment, the removable replaceable medium element invention can be made inexpensively and widespread available with sensors that comprise not only selective detection materials selectively responsive to pathogens and/or biomarkers for the latest epidemic outbreak but additionally selective detection materials selectively responsive to pathogens and/or biomarkers for other ailments and conditions with similar or identical symptoms.

Accordingly, the invention provides for and anticipates a wide range of applications in the monitoring and diagnosis of contagious diseases.

In an example embodiment, the sample can be provided directly to a material import port on the embodiment of the present invention. In another example embodiment, the sample can be provided via an easily-mixed fluidic form utilizing an applicable convenient solvent (for example alcohol, sterile deionized distilled water, etc.). In an embodiment, a surfactant, wetting agent, emulsifier, or other agent can additionally be incorporated into the mixture. In an embodiment, a buffer can additionally be incorporated into the mixture.

Accordingly, the invention provides for and anticipates a wide range of clinical and field medical applications.

Example Medical and Pharmaceutical Research Applications

Because of the wide range of sensing capabilities and technologies provided by the invention, including the invention's advanced statistical processing approaches, versatility, anticipated low cost, small size, and open architecture, the invention is well suited for a plethora of medical and pharmaceutical research applications. The invention can be used in a laboratory setting, in hospital rooms, in outpatient clinics, in medical trial facilities, and other settings.

As a first example, various new generation "-omic" technologies have been employed in the discovery of biomarkers and their use in medical and pharmaceutical research. Some examples are provided in the Table 6 below, adapted from K. K. Jain, *The Handbook of Biomarkers*, ISBN 160761684X, Springer, 2010.

TABLE 6

| Analysis Level | Tissue Sample Source | Detection Technologies | Application |
| --- | --- | --- | --- |
| Genomics | Nucleated cells | Positional cloning | Mapping of disease loci |
|  | Nucleated cells | SNP genotyping | Identification of disease gene |
|  | Nucleated cells | Microsatellites | Mapping of disease loci |
|  | Pathologically affected cells | Expression arrays | Identification of dysregulated genes |
|  | Pathologically affected cells | Comparative genomic hybridization arrays | Detection of gene amplification and loss of heterozygosity |
| Proteomics | Affected tissues | 2D gel electrophoresis | Identification of protein biomarkers |
|  | Body fluids: urine, blood, saliva | Liquid chromatography - mass spectrometry (MS) ICAT-MS |  |
| Metabolomics | Body fluids: urine, blood, saliva | Nuclear magnetic resonance (NMR) MS | Identification of small molecules |
| Glycomics | Body fluids: urine, blood, saliva | NMR | Identification of carbohydrates |
|  |  | Oligosaccharide arrays | Identification of glycoproteins |

Example Clinical and Field Medical Applications

In an example clinical application employing the present invention, an implementation of the present invention is located in the clinic and therein is provided with a selected removable replaceable medium element. A small sample of blood, saliva, tears, urine, earwax, secretions, etc. obtained in the clinical setting is presented to an implementation of the present invention. Information produced by the sensors is processed by algorithms to produce outputs such as disease or pathogen probability and confidence levels. The invention performs measurement and analysis operations on the sample. The invention can be used in doctor's offices, testing clinics, hospitals, pharmacies, first-aid areas, ambulances, field hospitals, travelling medical situations, etc.

Through the use of antibody-basing sensing, the full range of these can be detected and analyzed by the invention.

As another example, many human diseases are the result of autoimmune attack, presumably related to a loss of tolerance to self. Autoimmune disorders that are under study for autoantibodies as predictors of disease are shown in the Table provided in FIG. 18, adapted from Table 1.4 of K. K. Jain, *The Handbook of Biomarkers*, ISBN 160761684X, Springer, 2010.

As yet another example, there is an established need to assess DNA damage because of the impact that damaged genetic material can have on human health. Gene expression can in many circumstances create observable biomarkers, and accordingly some gene mutations can affect observable biomarkers. In some arrangements and applications, for example in the laboratory, genes themselves, DNA, various forms of RNA, and peptides themselves can be used as biomarkers recognizable by antibody-based or enzyme-based selective detection materials. Various examples, materials, and fabrication techniques for miniaturized sensors applicable to the detection of DNA damage relevant to the invention are taught by N. Perera, *Fabricating Miniatured Sensors—Detection of DNA Damage and DNA Base Alterations*, Verlag D. Muller, 2009, ISBN 978-3-639-22335-4.

Many other examples are possible, including usage in translational medicine and clinical trial applications as briefly considered in the two sections to follow.

Example Translational Medicine Applications

Biomarkers have proven to be extremely useful in translational medicine studies and are expected to become even more so. For example, the book by K. K. Jain, *The Handbook of Biomarkers*, ISBN 160761684X, Springer, 2010 lists examples such as (and similar to):

Translational toxicology using biomarkers
Steps in drug validation and development
Transition of preclinical methods to clinical methods
Consistent monitoring vehicle spanning from preclinical to phase III
Consistent biomarker instrumentation and analysis for preclinical and clinical studies Additionally, in that translational medicine also provides a platform for:

Biomarker discovery
Biomarker scoring systems for grading accuracy and predictive value.
Development of biomarker tests into reliable diagnostic protocols and technologies
translational medicine provides both an R&D setting plus a hard-core proving ground for identification and/or confirmation of new biomarkers and creative new uses of biomarkers.

Accordingly, the invention provides for and anticipates a wide range of applications in translational medicine.

Example Clinical Trial Applications

Again because of the wide range of sensing capabilities and technologies provided by the invention, including the invention's advanced statistical processing approaches, versatility, anticipated low cost, small size, and open architecture, the invention is well suited for many applications in clinical trial settings. The invention can be used in a laboratory environment, at the bedside, in outpatient clinics, in medical trial facilities, and other settings. As an indication of the breadth of applicability, Table 7 below, adapted from K. K. Jain, *The Handbook of Biomarkers, ISBN* 160761684X, Springer, 2010, identifies seven functional classes of biomarkers relevant to clinical development of disease processes.

TABLE 7

| Example Class Terminology | Example Applications |
| --- | --- |
| Predisposition biomarker | Identify predisposition to a disease, |
| Screening biomarker | Identify those suffering from a disease |
| Staging biomarker | Identify the stage of progression of a disease |
| Prediction biomarker | Predict the course of the disease |
| Prognostic biomarker | Assess disease progression and outcome |
| Recurrence monitoring biomarker | Identify recurrence of the disease |

As another indication of the breadth of applicability, it is noted that biomarkers have become useful in the analyses of biological pathways, providing new insight into the understanding of disease processes, developing improved biomarkers, better understanding of the effects of administered drugs, and an important step towards individualized and personalized medicine.

Accordingly, the invention provides for and anticipates a wide range of applications in clinical trial applications.

Example Drug Testing Applications

A significant portion of the commercial biomarker industry interest is in the area of biomarkers for drug testing applications. As a part of this, a variety of antibodies are commercially available for detecting the presence of biomarkers responsive to the presence or previous usage illicit drugs drug and other banned substances which are used in "routine" clinical-based testing. The invention provides for these and other selective detection materials responsive to biomarkers that are responsive to the presence or previous usage illicit drugs drug and other banned substances to be used in the removable replaceable medium element, thus providing the invention with capabilities valuable for routine testing for the presence or previous usage illicit drugs drug and other banned substances, not only in clinics but also in the field (for example in the workplace, transportation depots, gymnasiums in schools or colleges, sporting events, law enforcement scenarios, etc.).

Example Homeland Security and Anti-Terrorism Applications

As described earlier, the sensor assay systems described can be used for detection of chemicals, contaminations, pathogens, toxins, and environmental biomarkers present on or in a sample obtained from the environment. Accordingly, the invention can be used for highly selective monitoring useful for a wide range of national security applications. The invention can be used for these applications in testing relevant to security concerns and matters at airport, water reservoirs, police stations, police vehicles, military bases, public health facilities, etc.

Example Environmental Monitoring Applications

As described earlier, the sensor assay systems described can be used for detection of chemicals, contaminations, pathogens, toxins, and environmental biomarkers present on or in a sample obtained from the environment. Accordingly, the invention can be used for highly selective monitoring of these ecological, environmental, national security, public health, agriculture, and other rapidly emerging opportunities and imperatives.

As described earlier, environmental and ecological researchers and policy makers have come to appreciate the role of biomarkers as important tools for monitoring many aspects of ecology, environment, national security, public health, agriculture, with new realizations of the opportunities and imperatives rapidly emerging. By sampling or monitoring appropriate environmental or ecological elements, components, and members, such air, ground water, surface water, soils, natural flora, crops, wildlife, domesticated animals, ocean regions, fish, other aquatic organisms, etc. early warnings of great consequence to humans, economies, urban areas, countryside, fisheries, etc. can be had. By employing antibodies responsive to environmental and ecological biomarkers, sensor technologies can be made that could be useful for many aspects of ecology, environment, national security, public health, agriculture, and new rapidly emerging opportunities and imperatives.

In various situations the invention can be used as a field instrument, arranged for operation as a remote sensing device for water, soil, and air, as a site-based tool for forest rangers, wildlife management teams, and environmental protection teams, as well as a lab-based device for evaluation of collected samples.

Additional Example Agriculture Industry Applications

Several food safety, (irrigation and livestock) water safety, and environmental monitoring applications have described above and throughout this document that are relevant to agricultural applications. Additionally, the sensing capabilities of the invention can be used to monitor fertilizer and pesticide runoff, fertilizer and pesticide residues on crops, fertilizer and pesticide ingestion by livestock, as well as to monitor or test for the presence of crop and livestock disease, crop pathology, crop soil contamination, presence and levels of specific types of crop soil bacteria and fungi, signifiers of the presence and levels of crop or livestock damage from extreme drought, rain, heat, or cold, crop vitamin and mineral levels, etc. Some example methods, considerations, and applications are described, for example, in P. Bansal, *Bioanalysis & Sensors in Agricultural Science*, Gene-Tech Books (New Deli), 2006, ISBN 81-89729-00-4.

Example Laboratory Instruments and Applications

In addition to laboratory instruments related to, derived from, and generalized from the above applications, the invention further provides a foundation that can be enhanced and expanded in many additional directions. By way of representational illustration, below six example categories of biological cell and cell-related extensions to the invention are considered.

Cell Incubator and Laboratory Testbed

The cap and site arrangement provided by the invention can be adapted and/or modified to support living cells, either individually or in culture. For example, the fluidics arrangements can be programmed, adapted, augmented, and/or redesigned in various ways so as to provided controlled fluidic delivery of nutrients and needed dissolved needed gases as well as the controlled fluidic removal of waste materials so as to support life processes one or more cells in an adapted and/or modified cap and site arrangement. Additionally, the adapted and/or modified cap and site arrangement can be configured with fixed sensors (for example temperature, $O_2$, and $CO_2$ sensors) in the cap and special purpose sensors (for example monitoring biomarkers, other excreted proteins, and waste products) on the removable replaceable media element. The fluid baths or cap can also be configured to provide regulated thermal control, and arrangements can be used to dispense protective materials to prevent or fight infections from various phages, pathogens, parasites, and competing intruder cell types. The fluidic environment can also be used to introduce materials to be exposed to the cells, for example drugs, photosensitizers, fluorophore probes/markers, etc.

Accordingly, the invention provides for the inclusion of features, adaptations, and modifications so as to serve as a cell incubator. In addition to those described above, imaging camera arrangements can be added.

The incubated cells supported in the aforedescribed environment can be then used in various experiments. Some example experiments include:

Controlled regulation of oxygen to invoke various types of oxygen stress,
Controlled regulation of nitric oxide to study concentration effects on cell processes,
Controlled dispending of pharmaceutical agents to the cells,
Controlled optical stimulation of native cells or cells prepared with photosensitizers, etc.,
Controlled dispending of infectious agents to the cells,
Controlled dispending of chemical or biochemical compounds to the cells,
Controlled dispending of toxins and non-infectious agents to the cells.

In the experiments, various sensors (and imaging cameras if used) can be employed to monitor the status, condition, and response of the living cells. Other types of experiments, features, enhancements modifications, and design variations are anticipated and provided for by the invention.

Cell-Based Pathogen and Toxin Detection

As mentioned earlier, changes in cells themselves can be used as biomarkers for the presence of pathogens and toxins in an analyte. Cell-based sensors range in approach from early form (for example as taught in J. Racek, *Cell-Based Sensors*, Technomic Publishing, 1995, ISBN 1-56676-190-5) to cells producing materials arranged to be sensed by proximate sensors to startling hybrids of cells and electronics, for example as described in S. Ingerbrant, A. Offenhauser, "Cell-Transistor Hybrid Systems—Electrogenic Cells as Signal Transducing Elements Coupled to Microfluidic Devices," in W-L. Xing, J. Cheng (eds.), *Frontiers in Biochip Technology*, Springer, 2006, ISBN 0-387-25568-0.

Accordingly, the invention provides for living cells to be used as a selective detection material. In an embodiment, living cells can be kept alive using features such as those described in the "Cell Incubator and Laboratory Testbed" example just above. The fluidic environment is used to provide analyte to the living cells, and the response of the cells can be monitored through various types of sensors, including those configured to respond to biomarkers. Alternatively, the invention provides for the use of sensors comprising hybrids of cells and electronics.

Cell-Based Bioreactor

The invention additionally provides for features, modifications, and adaptations such as those described in the "Cell Incubator and Laboratory Testbed" example above to support living cells to be used in a highly organized bioreactor or bioreactor network. Here fluidics are used to harvest proteins or other substances excreted by cells in living cell cultures. The array approach permits variations in cell culture maturity, living conditions, or cell type, The array approach inherent in the removable replaceable medium element and base unit also permits implementations of highly monitored and regulated cascading multistage bioreactors and/or bioprocessors, for example wherein the product outcome of one bioreaction stage is provided, perhaps after separation or other refinement, under controlled conditions to a subsequent bioreaction stage.

Controlled Cell Ecosystem Emulation Testbed

The invention additionally provides for features, modifications, and adaptations such as those described in the "Cell-Based Bioreactor" example above to support controlled-condition emulation of ecosystems of pluralities of cells, The array approach inherent in the removable replaceable medium element and base unit also permits implementations of highly monitored and highly controlled exchange among pluralities of segregated communities of cells, each community segregated by cell type, and wherein each cell community's living conditions are closely controlled and monitored.

Cell Signaling Monitoring

The invention further provides for features, modifications, and adaptations such as those described in the "Cell Incubator and Laboratory Testbed" example to be used to create a tightly monitored environment for study of intracellular signaling and membrane signal transduction. The fluidic environment can be used to introduce fluorophore probes/markers to, for example, monitor signaling-related biochemical events within the cell or at the cell membrane. Fluorophore multiplexing can be used so as to monitor multiple signaling-related biochemical processes and events simultaneously in the same cell. Multiple wavelength optical sensing can be used to measure gross fluorophore response, or alternatively imaging camera features provided in the cap can be used to monitor the spatial distribution of signaling-related biochemical processes and events.

Cell Process Emulation Experimental Breadboard

Each of the five examples above incorporated living cells into the site and cap arrangements provided by the invention. In an example radically different from these, the invention further provides for the array arrangements inherent in the removable replaceable medium element and base unit to implement a highly controlled and monitored chemical reaction network involving proteins and ions associated with cell processes (such as metabolism, signaling, apoptosis, cell division, transcription, repair, etc.). The cap and site array arrangements formed by the removable replaceable medium element and base unit can be used to create segregated reaction chambers in which proteins and ions can be co-introduced to create bindings, complexes, etc. that can be closely monitored within the cap/site environment and then directed to a subsequent cap/site environment for a subsequent biochemical reaction step or process that again can be closely controlled and monitored.

The fluidic environment can be used to introduce fluorophore probes/markers. Fluorophore multiplexing can be used so as to monitor multiple biochemical processes and events simultaneously in the cap/site environment. Multiple wavelength optical sensing can be used to measure gross fluorophore response, or alternatively imaging camera features provided in the cap can be used to monitor fluorophore response in more detail.

Closing

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

While the invention has been described in detail with reference to disclosed embodiments, various modifications within the scope of the invention will be apparent to those of ordinary skill in this technological field. It is to be appreciated that features described with respect to one embodiment typically can be applied to other embodiments.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Although exemplary embodiments have been provided in detail, various changes, substitutions and alternations could be made thereto without departing from spirit and scope of the disclosed subject matter as defined by the appended claims. Variations described for the embodiments may be realized in any combination desirable for each particular application. Thus particular limitations and embodiment enhancements described herein, which may have particular advantages to a particular application, need not be used for all applications. Also, not all limitations need be implemented in methods, systems, and apparatuses including one or more concepts described with relation to the provided embodiments. Therefore, the invention properly is to be construed with reference to the claims.

SUMMARY OF THE EMBODIMENTS OF THE INVENTION

In one aspect, the invention provides a removable medium apparatus for providing replaceable sensing function to an external base unit, the apparatus comprising a plurality of isolated selective sensors on the surface of a substrate, the isolated selective sensors each comprising at least one layer of a selective detection material, wherein each selective sensor is configured to provide a variation in a detectable signal responsive to a target agent in a fluid analyte provided to the selective sensor, wherein the removable medium apparatus further comprises a readable medium attached to the substrate and an alignment arrangement for aligning the substrate into a receiving arrangement within the base unit.

In certain embodiments, the isolated sensors each comprise at least one layer of a semiconducting material, wherein the semiconducting material and the selective detection material form at least a portion of each selective sensor, and wherein each selective sensor is configured to provide a variation in an electrical signal responsive to the target agent. In certain embodiments, each of the isolated selective sensors is connected to an electrical connection. In certain embodiments, the removable medium apparatus further comprises an electrical interface arrangement on the substrate, wherein the electrical interface arrangement is electrically linked to the electrical connections of each of the isolated electrical sensors and is further configured for electrically linking to a host electrical interface within the base unit.

In certain embodiments, at least two of the selective sensors respond to different target agents in the analyte. In certain embodiments, at least two of the selective sensors comprise a different selective detection material from each other, and wherein the different selective detection materials respond to the same target agent in the analyte. In certain embodiments, the selective sensors are of the same nature. In certain embodiments, at least two of the selective sensors are of different nature. In certain embodiments, the removable medium apparatus comprises at least one optical sensor.

In certain embodiments, the substrate allows optical propagation through it for a range of wavelengths usable by at least one optical sensing arrangement. In certain embodiments, the substrate does not allow optical propagation through it for a range of wavelengths employed by at least one optical sensing arrangement. In certain embodiments, the substrate further comprises an optical filter. In certain embodiments, the substrate further comprises an optical element. In certain embodiments, the fluid analyte is a raw or processed sample. In certain embodiments, the analyte is selective from the group consisting of a food sample, an environmental sample, or a human sample. In certain embodiments, the target agent is one or a plurality of agents selected from the group consisting of biomarkers, proteins, pathogens, or chemical toxins.

In certain embodiments, at least one of the selective sensors is an electrochemical sensor, part of a field effector transistor, or a photodiode. In certain embodiments, at least one of the selective sensor materials comprises an antibody. In certain embodiments, the antibody is a synthetic antibody. In certain embodiments at least one of the selective sensor materials comprises a molecularly imprinted material. In certain embodiments, the molecularly imprinted material is a molecularly imprinted polymer. In certain embodiments, at least one of the selective sensor materials comprises an enzyme or a membrane.

In certain embodiments, the removable medium apparatus further comprises a deposit of a reagent. In certain embodiments, the reagent is a pH buffer material. In certain embodiments, the readable medium is attached to the substrate by printing at least one material on the substrate. In certain embodiments, the readable medium is a separately manufactured label that is adhered to the substrate. In certain embodiments, the readable medium comprises one or more of: information usable to operate a testing procedure, information usable to perform a statistical analysis, data information, serial number information, information specifying at least one algorithm, parameters used by at least one algorithm, optical encoded data, or magnetic strip.

In certain embodiments, the removable medium apparatus further comprises a fluidic interface arranged for providing fluid transfer for the receiving arrangement within the base unit. In certain embodiments, the substrate is attached to a second substrate so that the resulting arrangement is configured to comprise a fluid channel. In certain embodiments, the second substrate further comprises arrangements associated with at least one optical sensor. In certain embodiments, the second substrate provides a fluidic interface arranged for providing fluid transfer for the receiving arrangement within the base unit. In certain embodiments, the second substrate allows optical propagation through it for a range of wavelengths usable by at least one optical sensing arrangement. In certain embodiments, the second substrate does not allow optical propagation through it for a range of wavelengths employed by at least one optical sensing arrangement. In certain embodiments, the second substrate further comprises an optical filter. In certain embodiments, the second substrate further comprises an optical element. In certain embodiments, the fluid analyte comprises cells, viruses, suspensions, slurries, emulsions, micelles, or dissolved gases.

The invention provides a sensor device comprising any removable medium apparatus of the invention. In certain embodiments, the base unit of the sensor device comprises at least one computational processor for executing software and a receiving arrangement for receiving, aligning, or physically supporting the removable medium apparatus. In certain embodiments, the base unit further comprising an electrical interface arrangement for electrically connecting to the removable medium apparatus. In certain embodiments, the base unit further comprises interface electronics for connecting to the electrical interface arrangement for producing sensor measurement signals, each sensor measurement signal comprising a measurement value, the measurement value being one from a range of collection of permitted values.

In certain embodiments, the sensor device further comprises a medium reader for reading encoded data on a readable medium on the removable medium apparatus. In certain embodiments, the sensor device further comprises a fluidic interface arrangement for connecting to the removable medium apparatus. In certain embodiments, the sensor device further comprises a fluid system comprising controllable valves that can be controlled by the computational processor and connected to the fluidic interface arrangement. In certain embodiments, the sensor device further comprising a statistical analysis capability responsive to the measurement values and providing statistical output.

In certain embodiments of the sensor device, the statistical analysis capability is implemented in a software. In certain embodiments, the software is executed on a computational processor comprised by the base unit, an external computational processor, a laptop computer, a table computer, a desk computer, or a mobile phone. In certain embodiments, the sensor device further comprises a fluidic bus. In certain embodiments, the fluidic bus comprises a connection topology that comprises an N-dimensional lattice, wherein N is an integer greater than 1.

The invention also provides a method of using any one of the sensor devices described herein for detecting a target agent in a fluid analyte, comprising 1) allowing the fluid analyte to be in contact with the selective detection material on the removable medium apparatus; and 2) detecting a detectable signal from the selective sensor on the removable medium apparatus, wherein a variation of the detectable signal prior to and after the contact of the fluid analyte is indicative of the presence of the target analyte. Also provided by the invention is a method of using any one of the sensor devices described herein for determining the amount of a target agent in a fluid analyte, comprising: 1) allowing the fluid analyte to be in contact with the selective detection material on the removable medium apparatus, and 2) detecting a detectable signal from the selective sensors on the removable medium apparatus, wherein the change of the detectable signal after the contact of the fluid analyte correlates with the amount of the target agent in the fluid analyte.

In certain embodiments, the methods further comprising replacing the removable medium apparatus with a different removable medium apparatus and repeating steps 1) and 2). In certain embodiments, the methods are used for detecting a pathogen or toxin in a food sample. In certain embodiments, the methods are used for detecting a human biomarker in a human sample. In certain embodiments, the methods are used for detecting an environmental biomarker in an environmental sample. In certain embodiments, the environmental sample is a water sample. In certain embodiments, the methods are used for a biochemical or chemical assay. In certain embodiments, the biochemical or chemical assay is for filed or clinical use. In certain embodiments, biochemical or chemical assay is used for laboratory analysis. In certain embodiments, the biochemical or chemical assay is used for diagnosis.

The invention also provides a method of making a removable medium apparatus for providing replaceable sensing function to an external base unit, the apparatus comprising a plurality of isolated selective sensors on the surface of a substrate, wherein each of the isolated regions the semiconducting material and selective detection material form at least portions of a selective sensor, the method comprising: depositing an array of isolated regions of semiconducting material on the surface of a substrate, the isolated regions comprising at least one layer of semiconducting material; depositing at least one layer of a selective detection material on each of the isolated regions in the array. In certain embodiments, the method further comprises providing an electrical connection to each of the isolated regions of semiconducting material. In certain embodiments, the deposition is accomplished by inkjet-printing. In certain embodiments, the deposition is accomplished by functional printing.

The invention also provides a method for implementing statistical processing of sensor measurements produced by sensor assay system comprising a plurality of selective sensors, the method comprising: (a) obtaining a collection of measurements, the collection comprising at least one measurement from a plurality of selective sensors, the measurements responsive to a target agent in an analyte, and the plurality of selective sensors comprising at least a collection of sensors, each responsive to a different attribute of the sample, and at least a collection of different types of sensors responsive to the same attribute of the sample; (b) performing first mathematical operations on at least some of the measurements of the collection to produce a plurality of first mathematical outcomes, each first mathematical outcome comprising an associated value; (c) performing a second mathematical operation on at least some of the first mathematical outcomes to produce at least one second mathematical outcome, each second mathematical outcome comprising an associated result value; wherein the result value is used to represent the outcome of a test to which the sample is interrogated, and wherein the first mathematical operations and second mathematical operation are chosen so that the statistical accuracy of the test is greater than the statistical accuracy of each individual sensor.

The invention claimed is:

1. A removable medium apparatus for providing replaceable sensing function to an external base unit, the apparatus comprising a plurality of isolated selective sensors on the surface of a substrate, the isolated selective sensors each comprising at least one layer of a selective detection material,
   wherein each selective sensor is configured to provide a variation in a detectable signal responsive to a target agent in a fluid analyte provided to the selective sensor,
   wherein the removable medium apparatus further comprises a readable medium attached to the substrate and an alignment arrangement for aligning the substrate into a receiving arrangement within the base unit,
   wherein each of the isolated selective sensor is connected to an electrical connection, and
   wherein the removable medium apparatus further comprises an electrical interface arrangement on the substrate, wherein the electrical interface arrangement is electrically linked to the electrical connections of each of the isolated electrical sensors and is further configured for electrically linking to a host electrical interface within the base unit.

2. The removable medium apparatus of claim 1, wherein the isolated sensors each comprise at least one layer of a semiconducting material, wherein the semiconducting material and the selective detection material form at least a portion of each selective sensor, and wherein each selective sensor is configured to provide a variation in an electrical signal responsive to the target agent.

3. The removable medium apparatus of claim 1, wherein at least two of the selective sensors respond to a different target agent in the analyte.

4. The removable medium apparatus of claim 1, wherein at least two of the selective sensors comprises a different selective detection material from each other, and wherein the different selective detection materials respond to the same target agent in the analyte.

5. The removable medium apparatus of claim 1, wherein the selective sensors are of the same nature.

6. The removable medium apparatus of claim 1, wherein at least two of the selective sensors are of different nature.

7. The removable medium apparatus of claim 1, wherein the removable medium apparatus comprises at least one optical sensor.

8. The removable medium apparatus of claim 1, wherein the analyte is selective from the group consisting of a food sample, an environmental sample, or a human sample.

9. The removable medium apparatus of claim 1, wherein the target agent is one or a plurality of agents selected from the group consisting of biomarkers, proteins, pathogens, or chemical toxins.

10. The removable medium apparatus of claim 1, wherein at least one of the selective sensor materials comprises an antibody.

11. The removable medium apparatus of claim 1, further comprising a fluidic interface arranged for providing fluid transfer for the receiving arrangement within the base unit.

12. The removable medium apparatus of claim 1, wherein the substrate is attached to a second substrate so that the resulting arrangement is configured to comprise a fluid channel.

13. The removable medium apparatus of claim 1, wherein the fluid analyte comprises cells, viruses, suspensions, slurries, emulsions, micelles, or dissolved gases.

14. A sensor device comprising the removable medium apparatus of claim 1 and a base unit.

15. The sensor device of claim 14, wherein the base unit comprises at least one computational processor for executing software and a receiving arrangement for receiving, aligning, or physically supporting the removable medium apparatus.

16. The sensor device of claim 15, wherein the base unit further comprises an electrical interface arrangement for electrically connecting to the removable medium apparatus.

17. The sensor device of claim 16, wherein the base unit further comprises interface electronics for connecting to the electrical interface arrangement for producing sensor measurement signals, each sensor measurement signal comprising a measurement value, the measurement value being one from a range of collection of permitted values.

* * * * *